(12) United States Patent
Giasolli et al.

(10) Patent No.: US 11,369,779 B2
(45) Date of Patent: Jun. 28, 2022

(54) MEDICAL BALLOON CATHETERS WITH ENHANCED PUSHABILITY

(71) Applicant: Cagent Vascular, Inc., Wayne, PA (US)

(72) Inventors: Robert M. Giasolli, Orange, CA (US); Peter Schneider, Honolulu, HI (US); Peter Johansson, Wayne, PA (US); Carol Burns, Wayne, PA (US)

(73) Assignee: Cagent Vascular, Inc., Wayne, PA (US)

( * ) Notice: Subject to any disclaimer, the term of this patent is extended or adjusted under 35 U.S.C. 154(b) by 0 days.

(21) Appl. No.: 17/390,122

(22) Filed: Jul. 30, 2021

(65) Prior Publication Data

US 2021/0353918 A1 Nov. 18, 2021

Related U.S. Application Data

(63) Continuation of application No. 16/522,238, filed on Jul. 25, 2019.
(Continued)

(51) Int. Cl.
| | |
|---|---|
| *A61M 31/00* | (2006.01) |
| *A61M 37/00* | (2006.01) |
| *A61M 29/00* | (2006.01) |
| *A61M 25/10* | (2013.01) |
| *A61M 25/00* | (2006.01) |
| *B29C 65/14* | (2006.01) |
| *B29C 65/48* | (2006.01) |

(52) U.S. Cl.
CPC ...... *A61M 25/104* (2013.01); *A61M 25/0012* (2013.01); *A61M 25/1029* (2013.01); *B29C 65/14* (2013.01); *B29C 65/4805* (2013.01); *A61M 2025/1056* (2013.01); *A61M 2207/00* (2013.01)

(58) Field of Classification Search
CPC .... A61M 2025/105; A61M 2025/1086; A61M 2025/109; A61M 25/0012; A61M 25/005; A61M 25/10; A61M 25/1011; A61M 2025/1013
See application file for complete search history.

(56) References Cited

U.S. PATENT DOCUMENTS

| | | |
|---|---|---|
| 3,221,746 A | 12/1965 | Noble |
| 3,635,223 A | 1/1972 | Klieman |
| (Continued) | | |

FOREIGN PATENT DOCUMENTS

| | | |
|---|---|---|
| AU | 2009226025 | 9/2009 |
| AU | 2015343272 | 7/2020 |
| (Continued) | | |

OTHER PUBLICATIONS

International Search Report and Written Opinion for International Application No. PCT/US2009/001786, dated Sep. 28, 2009 in 8 pages.
(Continued)

*Primary Examiner* — Rebecca E Eisenberg
(74) *Attorney, Agent, or Firm* — Knobbe, Martens, Olson & Bear, LLP

(57) ABSTRACT

Systems and methods can involve wedge dissectors attached to strips in turn attached to medical balloons, for forming serrations within vascular wall tissue for angioplasty as well as drug delivery.

20 Claims, 116 Drawing Sheets

Related U.S. Application Data

(60) Provisional application No. 62/827,124, filed on Mar. 31, 2019, provisional application No. 62/703,419, filed on Jul. 25, 2018.

(56) References Cited

U.S. PATENT DOCUMENTS

| | | |
|---|---|---|
| 4,465,072 A | 8/1984 | Taheri |
| 4,665,906 A | 5/1987 | Jervis |
| 4,699,611 A | 10/1987 | Bowden |
| 4,795,458 A | 1/1989 | Regan |
| 4,856,516 A | 8/1989 | Hillstead |
| 5,009,659 A | 4/1991 | Hamlin |
| 5,042,707 A | 8/1991 | Taheri |
| 5,078,736 A | 1/1992 | Behl |
| 5,192,291 A | 3/1993 | Pannek, Jr. |
| 5,196,024 A | 3/1993 | Barath |
| 5,209,799 A | 5/1993 | Vigil |
| 5,320,634 A | 6/1994 | Vigil et al. |
| 5,336,234 A | 8/1994 | Vigil |
| 5,397,355 A | 3/1995 | Marin et al. |
| 5,411,478 A | 5/1995 | Stillabower |
| 5,417,707 A | 5/1995 | Parkola |
| 5,423,851 A | 6/1995 | Samuels |
| 5,484,411 A | 1/1996 | Inderbitzen et al. |
| 5,501,689 A | 3/1996 | Green |
| 5,514,154 A | 5/1996 | Lau et al. |
| 5,569,272 A | 10/1996 | Reed |
| 5,591,197 A | 1/1997 | Orth et al. |
| 5,593,434 A | 1/1997 | Williams |
| 5,616,149 A | 4/1997 | Barath |
| 5,665,116 A | 9/1997 | Chaisson |
| 5,681,346 A | 10/1997 | Orth |
| 5,713,860 A | 2/1998 | Kaplan et al. |
| 5,713,863 A | 2/1998 | Vigil et al. |
| 5,718,684 A | 2/1998 | Gupta |
| 5,720,726 A | 2/1998 | Marcadis et al. |
| 5,797,935 A | 8/1998 | Barath et al. |
| 5,797,951 A | 8/1998 | Mueller |
| 5,800,526 A | 9/1998 | Anderson |
| 5,824,053 A | 10/1998 | Khosravi et al. |
| 5,868,779 A | 2/1999 | Ruiz |
| 5,957,949 A | 9/1999 | Leonhardt et al. |
| 6,007,543 A | 12/1999 | Ellis |
| 6,036,725 A | 3/2000 | Avellanet |
| 6,048,332 A | 4/2000 | Duffy et al. |
| 6,053,943 A | 4/2000 | Edwin |
| 6,102,904 A | 8/2000 | Vigil et al. |
| 6,126,685 A | 10/2000 | Lenker |
| 6,197,013 B1 | 3/2001 | Reed |
| 6,221,102 B1 | 4/2001 | Baker |
| 6,254,642 B1 | 7/2001 | Taylor |
| 6,280,414 B1 | 8/2001 | Shah et al. |
| 6,290,728 B1 | 9/2001 | Phelps |
| 6,371,962 B1 | 4/2002 | Ellis |
| 6,450,989 B2 | 9/2002 | Dubrul et al. |
| 6,485,496 B1 | 10/2002 | Suyker et al. |
| 6,475,237 B2 | 11/2002 | Drasler |
| 6,562,062 B2 | 5/2003 | Jenusaitis et al. |
| 6,623,452 B2 | 9/2003 | Chien et al. |
| 6,626,861 B1 | 9/2003 | Hart et al. |
| 6,632,231 B2 | 10/2003 | Radisch, Jr. |
| 6,638,246 B1 | 10/2003 | Naimark et al. |
| 6,692,504 B2 | 2/2004 | Kurz |
| 6,719,775 B2 | 4/2004 | Slaker |
| 6,808,518 B2 | 10/2004 | Wellman et al. |
| 6,942,680 B2 | 9/2005 | Grayzel et al. |
| 7,007,698 B2 | 3/2006 | Thornton |
| 7,011,670 B2 | 3/2006 | Radisch, Jr. |
| 7,087,088 B2 | 8/2006 | Berg |
| 7,172,609 B2 | 2/2007 | Radisch, Jr. |
| 7,179,284 B2 | 2/2007 | Khosravi |
| 7,179,345 B2 | 2/2007 | Shkolnik |
| 7,186,237 B2 | 3/2007 | Meyer et al. |
| 7,204,847 B1 | 4/2007 | Gambale |
| 7,211,101 B2 | 5/2007 | Carley |
| 7,252,674 B2 | 8/2007 | Wyzgala et al. |
| 7,270,673 B2 | 9/2007 | Yee |
| 7,279,002 B2 | 10/2007 | Shaw et al. |
| 7,291,158 B2 | 11/2007 | Crow |
| 7,303,572 B2 | 12/2007 | Meisheimer |
| 7,326,245 B2 | 2/2008 | Rosenthal et al. |
| 7,331,992 B2 | 2/2008 | Randall |
| 7,413,558 B2 | 8/2008 | Kelley et al. |
| 7,500,986 B2 | 3/2009 | Lye et al. |
| 7,611,484 B2 | 11/2009 | Wellman et al. |
| 7,662,163 B2 | 2/2010 | Grayzel et al. |
| 7,686,824 B2 | 3/2010 | Konstantino |
| 7,691,116 B2 | 4/2010 | Goodin |
| 7,691,119 B2 | 4/2010 | Farnan |
| 7,771,447 B2 | 8/2010 | Kunis |
| 7,883,537 B2 | 2/2011 | Grayzel et al. |
| 7,931,663 B2 | 4/2011 | Farnan |
| 7,933,660 B2 | 4/2011 | Carr |
| 7,947,015 B2 | 5/2011 | Herweck et al. |
| 7,972,351 B2 | 7/2011 | Trinidad |
| 7,985,234 B2 | 7/2011 | Wang et al. |
| 7,993,358 B2 | 8/2011 | O'Brien |
| 8,002,725 B2 | 8/2011 | Hogendijk |
| 8,038,691 B2 | 10/2011 | Bence et al. |
| 8,052,703 B2 | 11/2011 | St. Martin et al. |
| 8,114,049 B2 | 2/2012 | Freyman et al. |
| 8,192,675 B2 | 6/2012 | Burton et al. |
| 8,211,354 B2 | 7/2012 | Burton |
| 8,323,243 B2 | 12/2012 | Schneider et al. |
| 8,361,096 B2 | 1/2013 | Bence et al. |
| 8,454,637 B2 | 6/2013 | Aggerholm et al. |
| 8,491,615 B2 | 7/2013 | Manderfeld et al. |
| 8,523,887 B2 | 9/2013 | Grayzel et al. |
| 8,557,271 B2 | 10/2013 | Kimble et al. |
| 8,574,248 B2 | 11/2013 | Kassab |
| 8,690,903 B2 | 4/2014 | Bence et al. |
| 9,017,353 B2 | 4/2015 | Bence et al. |
| 9,061,127 B2 | 6/2015 | Weber et al. |
| 9,066,749 B2 | 6/2015 | Burton et al. |
| 9,095,688 B2 | 8/2015 | Burton |
| 9,119,944 B2 | 9/2015 | Chambers et al. |
| 9,179,936 B2 | 11/2015 | Feld et al. |
| 9,199,066 B2 | 12/2015 | Konstantino et al. |
| 9,204,893 B2 | 12/2015 | Rizk et al. |
| 9,216,033 B2 | 12/2015 | Feld et al. |
| 9,226,768 B2 | 1/2016 | Gunderson et al. |
| 9,242,076 B2 | 1/2016 | Burton et al. |
| 9,302,071 B2 | 4/2016 | Manderfeld et al. |
| 9,320,530 B2 | 4/2016 | Grace |
| 9,339,291 B2 | 5/2016 | Aggerholm et al. |
| 9,393,386 B2 | 7/2016 | Schneider et al. |
| 9,415,193 B2 | 8/2016 | Campbell et al. |
| 9,480,526 B2 | 11/2016 | Singh |
| 9,480,826 B2 | 11/2016 | Schneider et al. |
| 9,586,031 B2 | 3/2017 | Konstantino et al. |
| 9,592,119 B2 | 3/2017 | Tilson et al. |
| 9,603,619 B2 | 3/2017 | Bence et al. |
| 9,604,036 B2 | 3/2017 | Burton et al. |
| 10,166,374 B2 | 1/2019 | Giasolli et al. |
| 10,172,729 B2 | 1/2019 | Fulkerson et al. |
| 10,258,487 B2 | 4/2019 | Fulkerson et al. |
| 10,300,253 B2 | 5/2019 | Pederson |
| 10,463,842 B2 | 11/2019 | Giasolli et al. |
| 10,471,238 B2 | 11/2019 | Schneider et al. |
| 10,689,154 B2 | 6/2020 | Giasolli et al. |
| 10,729,892 B2 | 8/2020 | Yamazaki |
| 10,905,863 B2 | 2/2021 | Giasolli et al. |
| 11,040,178 B2 | 6/2021 | Schneider et al. |
| 11,123,527 B2 | 9/2021 | Giasolli et al. |
| 11,141,573 B2 | 10/2021 | Schneider et al. |
| 11,166,742 B2 | 11/2021 | Schneider et al. |
| 2001/0016726 A1 | 8/2001 | Dubrul et al. |
| 2001/0020151 A1 | 9/2001 | Reed et al. |
| 2002/0010489 A1* | 1/2002 | Grayzel ........... A61F 2/958 606/194 |
| 2002/0077594 A1 | 6/2002 | Chien et al. |
| 2003/0065303 A1 | 4/2003 | Wellman et al. |
| 2003/0153870 A1 | 8/2003 | Meyer et al. |

(56) References Cited

U.S. PATENT DOCUMENTS

| | | |
|---|---|---|
| 2003/0158595 A1 | 8/2003 | Randall |
| 2003/0163148 A1 | 8/2003 | Wang et al. |
| 2003/0229370 A1 | 12/2003 | Miller |
| 2004/0098014 A1 | 5/2004 | Flugelman et al. |
| 2004/0106904 A1 | 6/2004 | Gonnelli et al. |
| 2004/0143287 A1 | 7/2004 | Konstantino et al. |
| 2004/0158270 A1 | 8/2004 | Wyzgala et al. |
| 2004/0186551 A1 | 9/2004 | Kao |
| 2004/0249445 A1 | 12/2004 | Rosenthal et al. |
| 2005/0021070 A1 | 1/2005 | Feld et al. |
| 2005/0137618 A1 | 6/2005 | Kunis |
| 2005/0149082 A1 | 7/2005 | Yee et al. |
| 2005/0177130 A1 | 8/2005 | Konstantino et al. |
| 2005/0203388 A1 | 9/2005 | Carr |
| 2005/0228343 A1 | 10/2005 | Kelley |
| 2005/0251164 A1 | 11/2005 | Gifford |
| 2005/0267409 A1 | 12/2005 | Shkolnik |
| 2005/0288764 A1 | 12/2005 | Snow |
| 2006/0015134 A1 | 1/2006 | Trinidad |
| 2006/0085023 A1 | 4/2006 | Davies et al. |
| 2006/0122684 A1 | 6/2006 | Lye et al. |
| 2006/0129093 A1 | 6/2006 | Jackson |
| 2006/0184191 A1 | 6/2006 | Lye et al. |
| 2006/0149308 A1 | 7/2006 | Melsheimer |
| 2006/0271093 A1 | 11/2006 | Holman |
| 2007/0016232 A1 | 1/2007 | Martin et al. |
| 2007/0021774 A1 | 1/2007 | Hogendijk |
| 2007/0060863 A1 | 3/2007 | Goeken et al. |
| 2007/0093744 A1 | 4/2007 | Elmaleh |
| 2007/0191766 A1 | 8/2007 | McMorrow |
| 2007/0191811 A1 | 8/2007 | Berglund |
| 2007/0213761 A1 | 9/2007 | Murphy et al. |
| 2008/0015500 A1 | 1/2008 | Herweck et al. |
| 2008/0275483 A1 | 11/2008 | Makower et al. |
| 2009/0157159 A1 | 6/2009 | Schneider et al. |
| 2009/0214615 A1 | 8/2009 | Zhao |
| 2009/0227949 A1 | 9/2009 | Knapp et al. |
| 2009/0240270 A1 | 9/2009 | Schneider et al. |
| 2010/0015196 A1 | 1/2010 | Kimble et al. |
| 2010/0042121 A1 | 2/2010 | Schneider et al. |
| 2010/0087783 A1 | 4/2010 | Weber et al. |
| 2010/0274188 A1 | 10/2010 | Chang et al. |
| 2010/0274271 A1 | 10/2010 | Kelly |
| 2011/0178503 A1 | 7/2011 | Kangas |
| 2011/0213401 A1 | 9/2011 | Grayzel et al. |
| 2012/0041412 A1 | 2/2012 | Roth et al. |
| 2012/0059401 A1 | 3/2012 | Konstantino et al. |
| 2012/0172901 A1 | 7/2012 | Manderfled et al. |
| 2012/0277843 A1 | 11/2012 | Weber et al. |
| 2013/0018396 A1 | 1/2013 | Gunderson et al. |
| 2013/0066346 A1 | 3/2013 | Pigott |
| 2013/0110142 A1 | 5/2013 | Bence et al. |
| 2013/0165958 A1 | 6/2013 | Schneider et al. |
| 2013/0190725 A1 | 7/2013 | Pacetti et al. |
| 2013/0211381 A1 | 8/2013 | Feld |
| 2013/0218181 A1 | 8/2013 | Feld et al. |
| 2013/0253426 A1 | 9/2013 | Campbell et al. |
| 2013/0261545 A1 | 10/2013 | Osypka |
| 2014/0066898 A1 | 3/2014 | Cully et al. |
| 2014/0066960 A1 | 3/2014 | Feld et al. |
| 2016/0081711 A1 | 3/2016 | Gunderson et al. |
| 2016/0175568 A1 | 6/2016 | Manderfeld et al. |
| 2016/0324538 A1 | 11/2016 | Schneider et al. |
| 2016/0346506 A1 | 12/2016 | Jackson et al. |
| 2017/0080192 A1 | 3/2017 | Giasolli et al. |
| 2017/0100570 A1 | 4/2017 | Giasolli et al. |
| 2017/0106174 A1 | 4/2017 | Schneider et al. |
| 2017/0112526 A1 | 4/2017 | Burton et al. |
| 2017/0150988 A1 | 6/2017 | Konstantino et al. |
| 2017/0333686 A1 | 11/2017 | Schneider et al. |
| 2018/0140804 A1 | 5/2018 | Tsukamoto et al. |
| 2018/0200491 A1 | 7/2018 | Giasolli et al. |
| 2018/0304052 A1 | 10/2018 | Schneider et al. |
| 2019/0240464 A1 | 8/2019 | Giasolli et al. |
| 2019/0262595 A1 | 8/2019 | Ryu et al. |
| 2019/0282789 A1 | 9/2019 | Mayda |
| 2020/0140141 A1 | 5/2020 | Giasolli et al. |
| 2020/0155815 A1 | 5/2020 | Giasolli et al. |
| 2020/0188641 A1 | 6/2020 | Giasolli et al. |
| 2021/0213259 A1 | 7/2021 | Giasolli et al. |
| 2021/0299418 A1 | 9/2021 | Schneider et al. |
| 2021/0353915 A1 | 11/2021 | Schneider et al. |
| 2021/0353916 A1 | 11/2021 | Giasolli et al. |
| 2021/0353917 A1 | 11/2021 | Schneider et al. |
| 2021/0353919 A1 | 11/2021 | Giasolli et al. |

FOREIGN PATENT DOCUMENTS

| | | | |
|---|---|---|---|
| CN | | 1642593 | 7/2005 |
| CN | | 101420913 | 3/2012 |
| CN | | 102512747 | 6/2012 |
| CN | | 102781508 | 11/2012 |
| CN | | 102939125 | 2/2013 |
| CN | | 203379465 | 1/2014 |
| CN | | 103582508 | 2/2014 |
| CN | | 103764218 | 4/2014 |
| CN | | 203564643 | 4/2014 |
| CN | | 103948972 | 6/2016 |
| CN | | 103930158 | 8/2016 |
| CN | | 107405158 | 11/2017 |
| CN | | 107405475 | 11/2017 |
| CN | | 108348734 | 7/2018 |
| CN | | 110114108 | 8/2019 |
| CN | ZL 201080051844.9 | | 7/2020 |
| CN | ZL 201580071624.5 | | 9/2020 |
| EP | | 1604704 | 12/2005 |
| EP | | 1809361 | 7/2007 |
| EP | | 2254641 | 9/2016 |
| EP | | 3215030 | 9/2017 |
| EP | | 3215212 | 9/2017 |
| EP | | 3349837 | 7/2018 |
| EP | | 3541464 | 9/2019 |
| JP | | H05-293176 | 11/1993 |
| JP | | H09-108358 | 4/1997 |
| JP | | H09-192226 | 7/1997 |
| JP | | 2004-504111 | 2/2004 |
| JP | | 2006-501869 | 1/2006 |
| JP | | 2007-527740 | 10/2007 |
| JP | | 2008-519654 | 6/2008 |
| JP | | 2008-526312 | 7/2008 |
| JP | | 2008-529658 | 8/2008 |
| WO | WO 2002/043796 | | 6/2002 |
| WO | WO 2002/078511 | | 10/2002 |
| WO | WO 2003/051442 | | 6/2003 |
| WO | WO 2003/068307 | | 8/2003 |
| WO | WO 2003/101310 | | 12/2003 |
| WO | WO 2005/076833 | | 8/2005 |
| WO | WO 2006/130194 | | 12/2006 |
| WO | WO 2008/020980 | | 2/2008 |
| WO | WO 2009/117158 | | 9/2009 |
| WO | WO 2011/035132 | | 3/2011 |
| WO | WO 2013/012714 | | 1/2013 |
| WO | WO 2015/187872 | | 12/2015 |
| WO | WO 2016/073490 | | 5/2016 |
| WO | WO 2016/073511 | | 5/2016 |
| WO | WO-2016073490 A1 * | | 5/2016 ............ B29C 70/72 |
| WO | WO 2016/116821 | | 7/2016 |
| WO | WO 2018/094077 | | 5/2018 |
| WO | WO 2020/023749 | | 1/2020 |

OTHER PUBLICATIONS

International Search Report and Written Opinion for International Application No. PCT/US2010/049297, dated Jun. 21, 2011 in 9 pages.

Supplemental Search Report for European Application No. 09722111.3, dated Jun. 29, 2011 in 2 pages.

Australian Office Action for Application No. 2009226025 dated Oct. 31, 2011 in 4 pages.

Japanese Notice of Rejection in Japanese Patent Application 2011-500815 dated Jun. 26, 2012 in 7 pages.

Japanese Notice of Rejection in Japanese Patent Application 2011-500815 dated Feb. 1, 2013 in 16 pages.

(56) References Cited

OTHER PUBLICATIONS

Supplemental European Search Report for European Application No. 10817896.3 dated Jun. 19, 2013 in 8 pages.
European Search Report dated Jun. 7, 2018 in EP application No. 15857951.6 in 7 pages.
Supplemental Search Report for European Application No. 16847495, dated Apr. 30, 2019 in 9 pages.
International Search Report and Written Opinion for International Application No. PCT/US2019/043443, dated Oct. 1, 2019 in 14 pages.
International Search Report and Written Opinion for International Application No. PCT/US2015/034060, dated Nov. 5, 2015 in 23 pages.
International Search Report and Written Opinion for International Application No. PCT/US2015/058847, dated Feb. 23, 2016 in 12 pages.
International Search Report and Written Opinion for International Application No. PCT/US2015/058874, dated Mar. 30, 2016 in 22 pages.
International Search Report for Application No. PCT/US2017/062060 dated Mar. 15, 2018 in 11 pages.
European Extended Search Report dated Jun. 13, 2018 in EP application No. 15856760.2 in 9 pages.
Office Action for Chinese Patent Application No. 201580071707.4 dated Jun. 28, 2019 in 8 pages.
Australian Office Action for Application No. 2015343272 dated Jul. 24, 2019 in 4 pages.
Australian Office Action for Application No. 2016324292 dated Jun. 1, 2020 in 6 pages.
Office Action for Chinese Patent Application No. 201680059509.0 dated Jun. 2, 2020 in 21 pages.
European Extended Search Report dated Jun. 17, 2020 in EP application No. 17872835.8 in 7 pages.
Invitation to Pay Additional Search Fees in PCT Application No. PCT/US2021/071644, dated Dec. 2, 2021, in 3 pages.

* cited by examiner

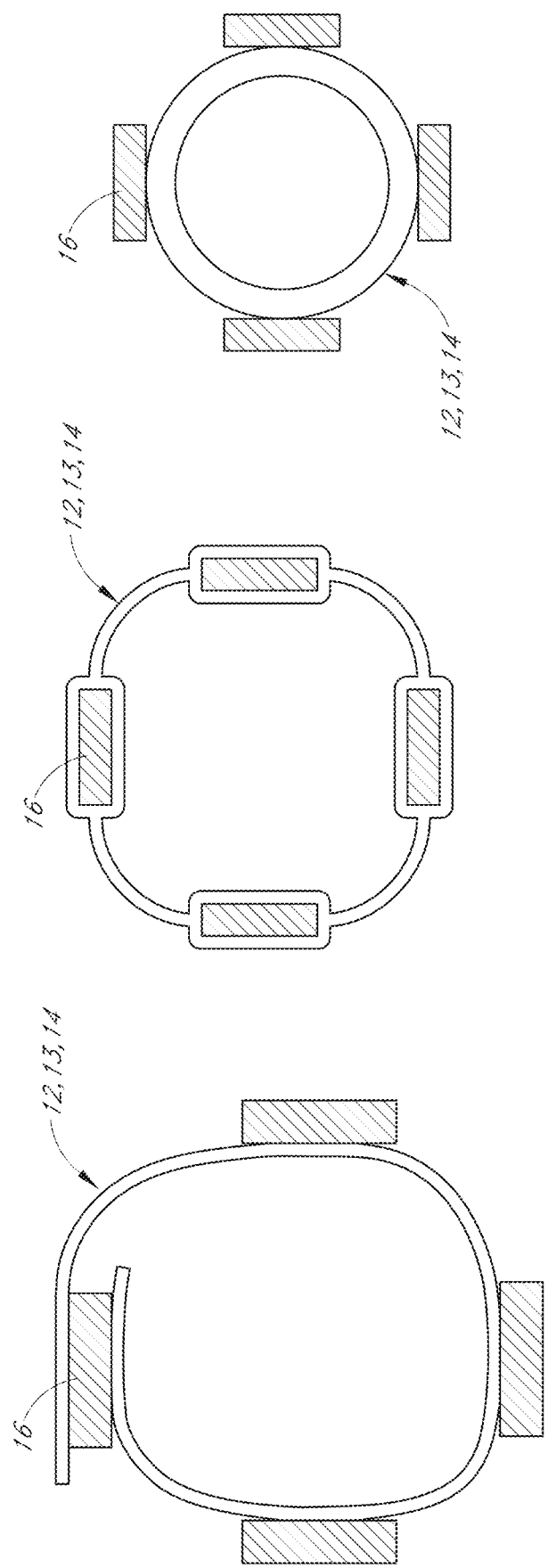

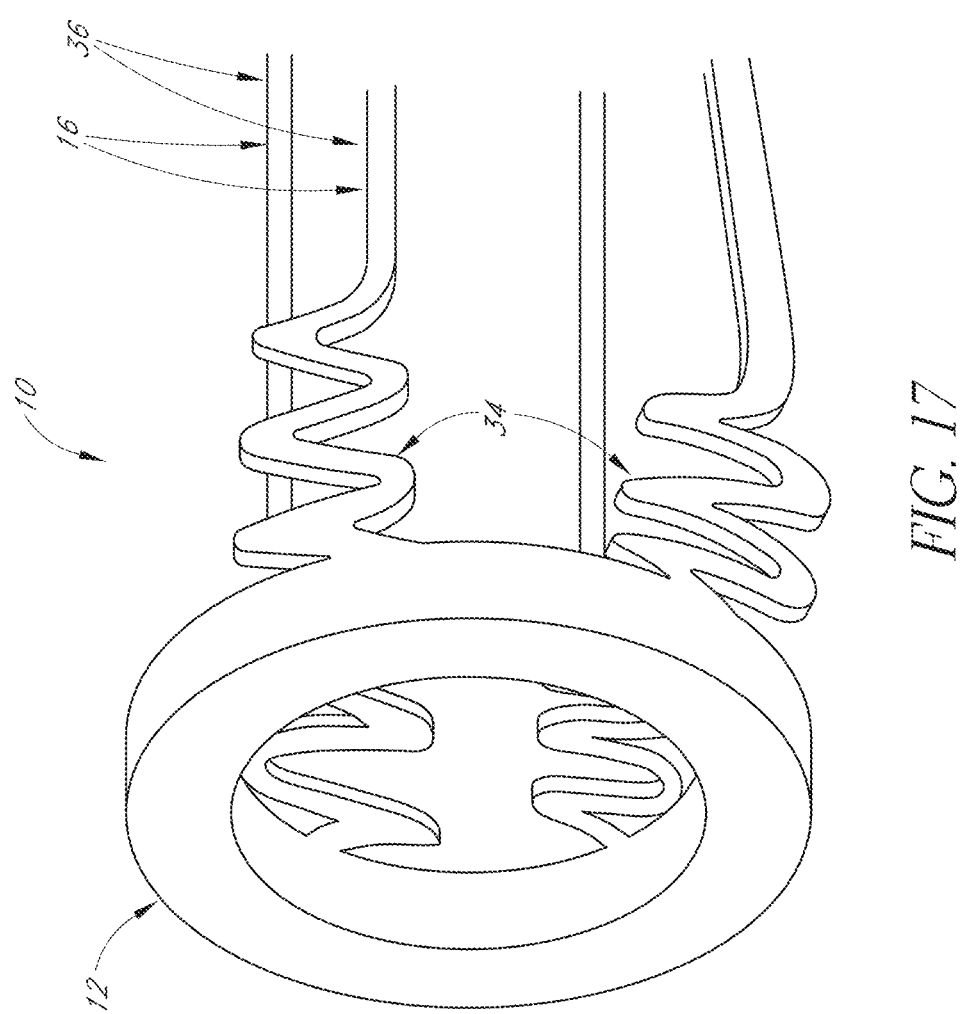

Scanning Electron Microscopy Porcine tissue at 7-days*

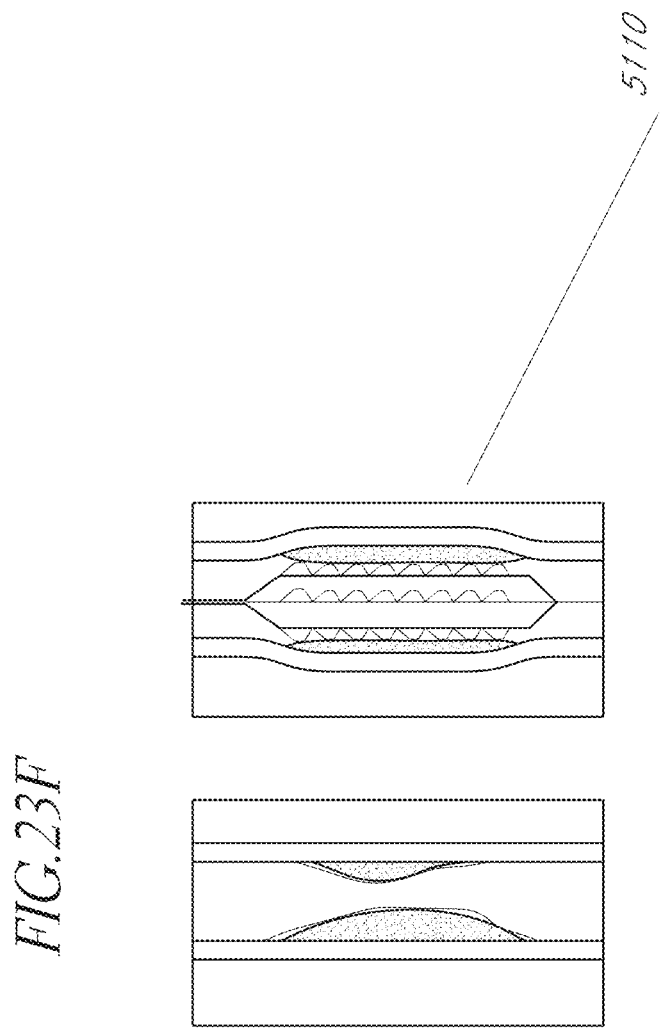
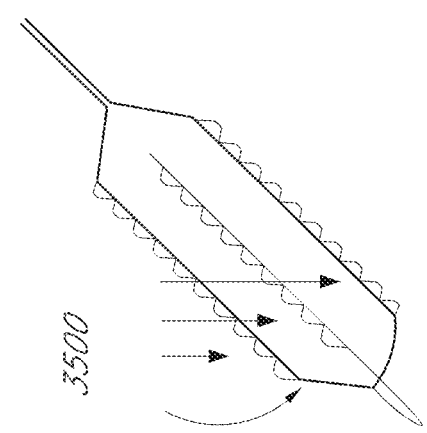
FIG. 23F

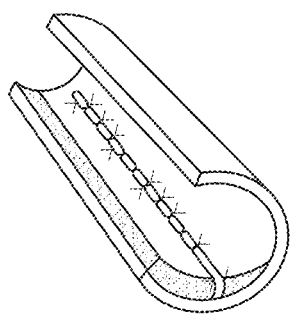
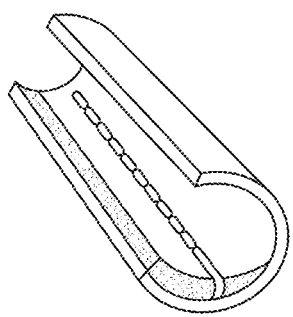
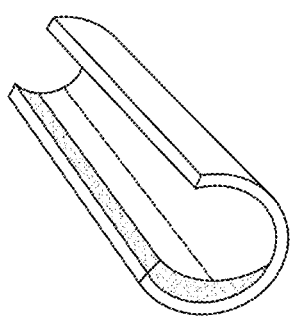
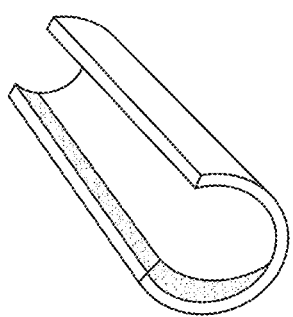
FIG. 23F.1

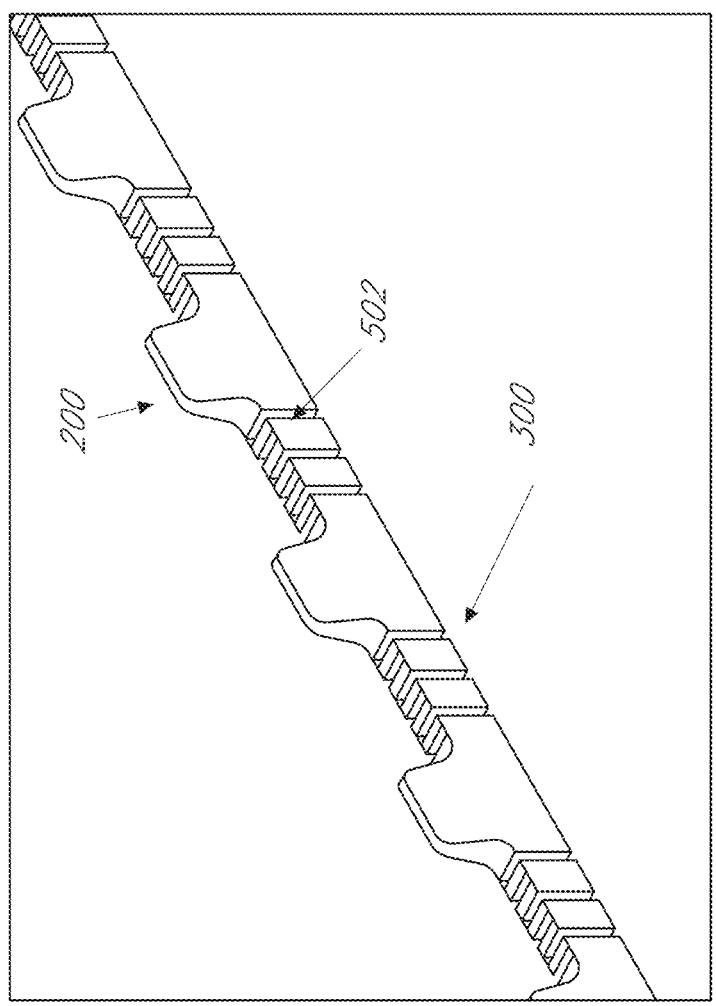

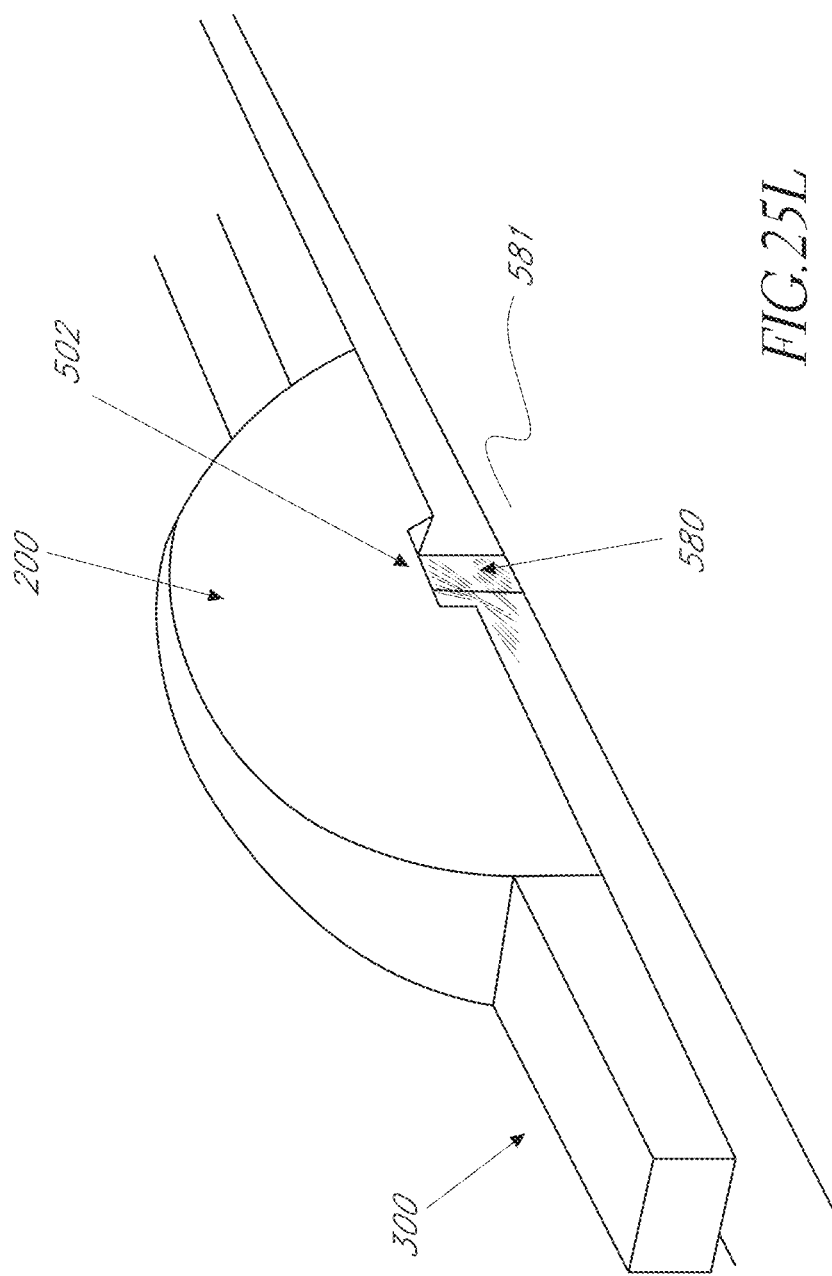

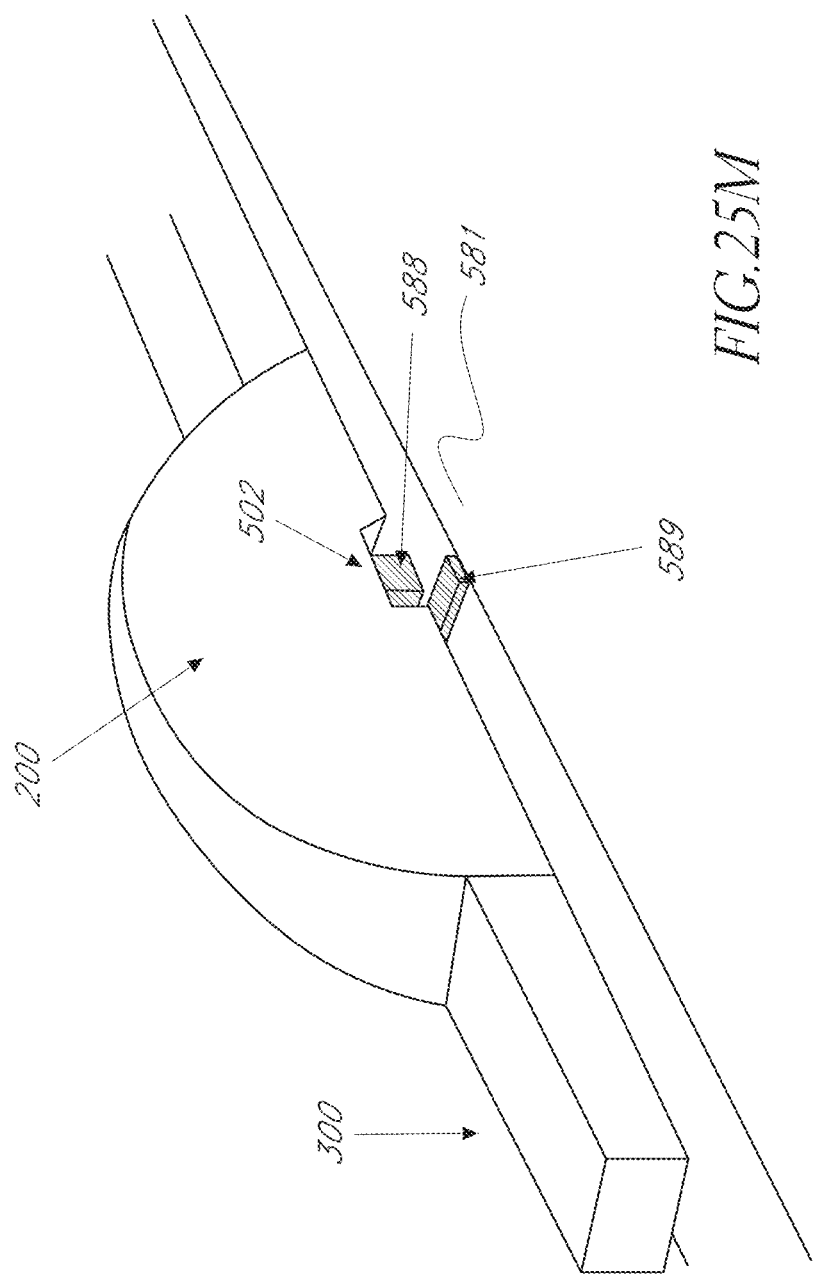

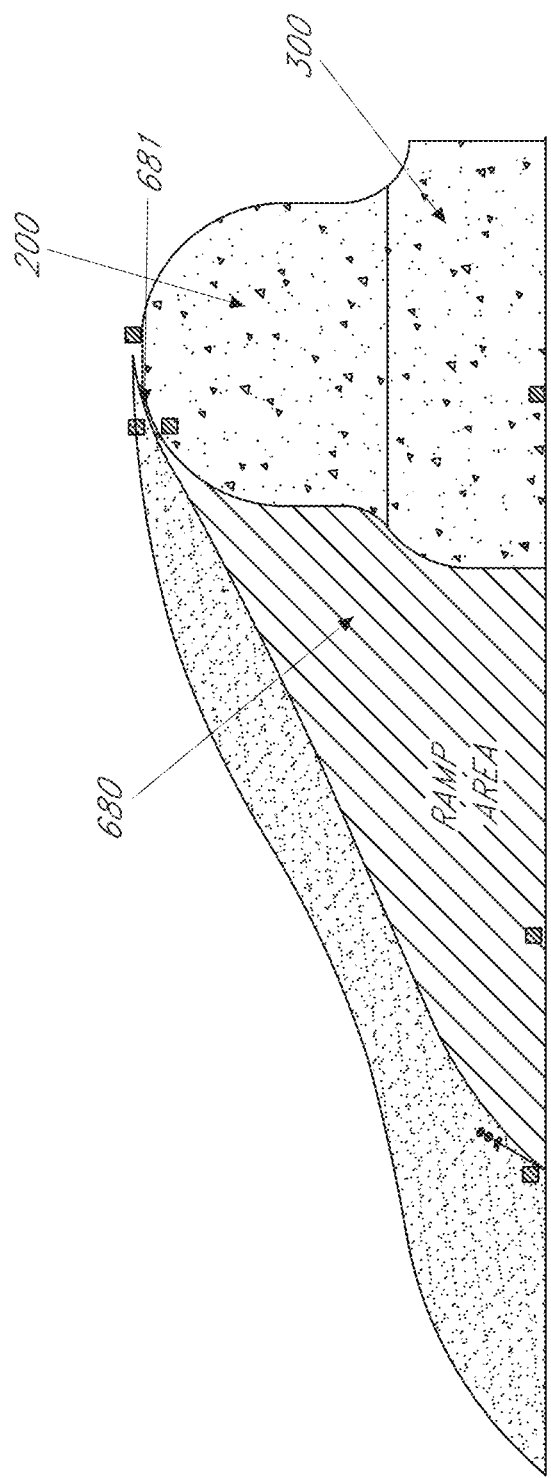
FIG.25N.1

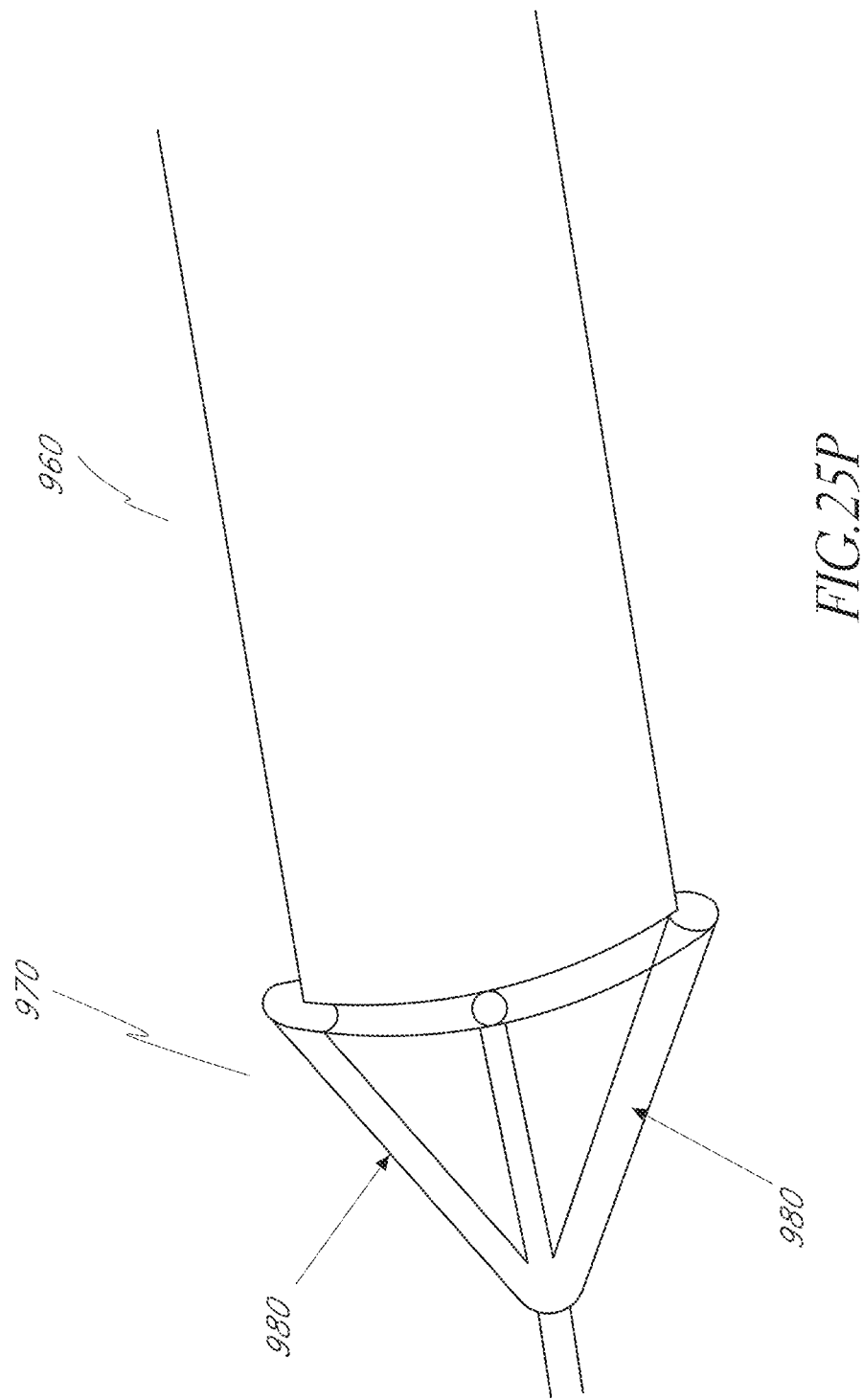

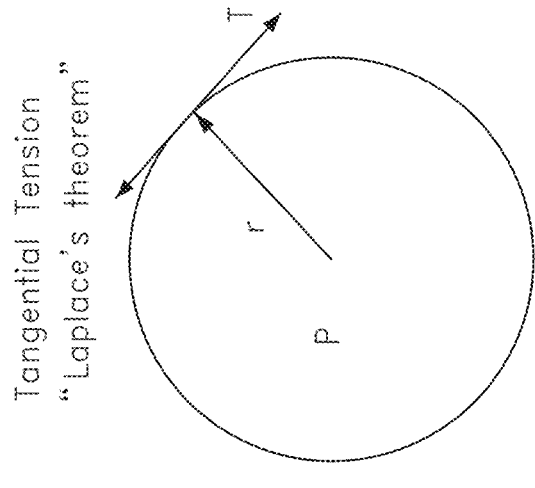
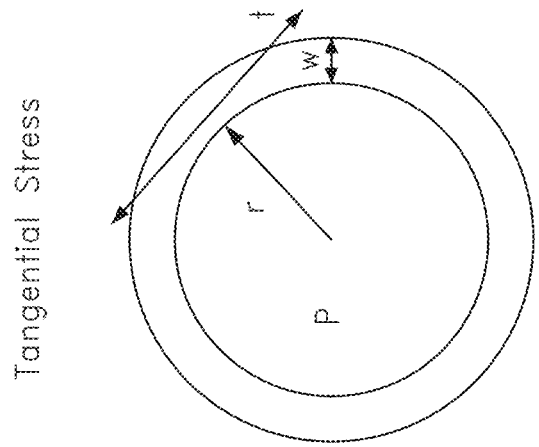
FIG. 29

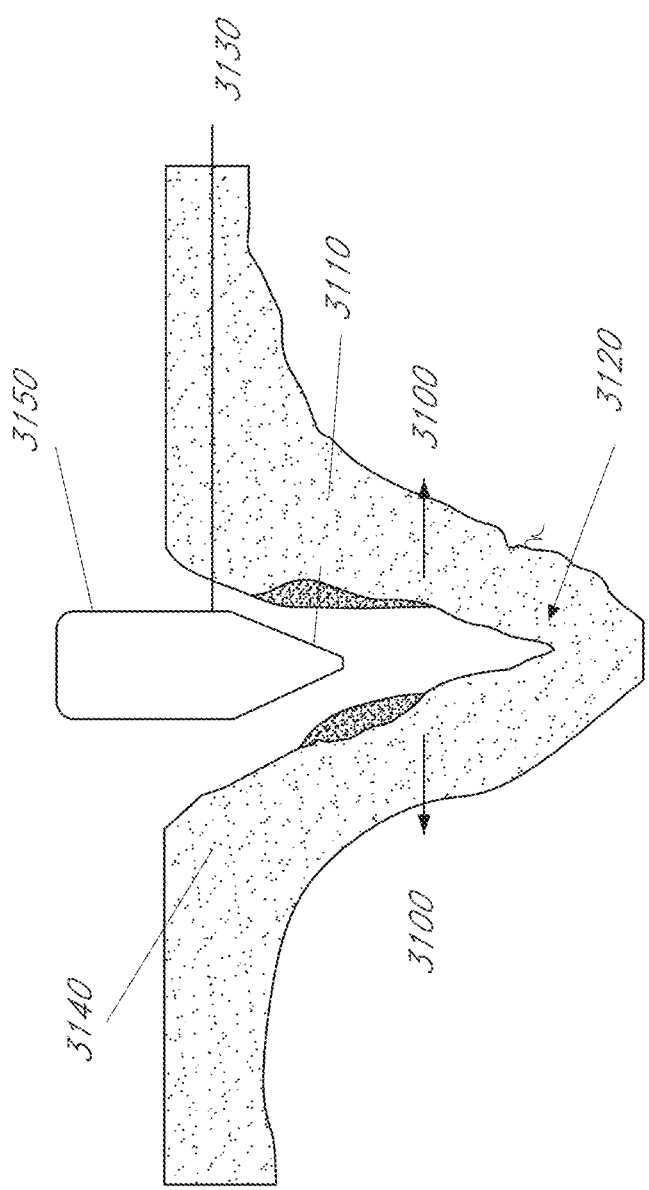

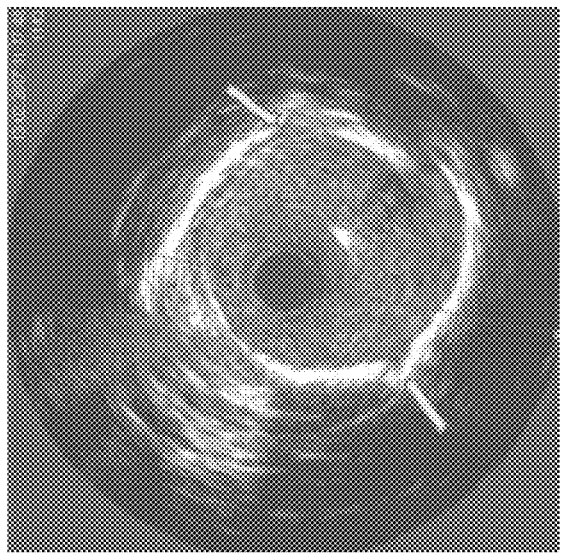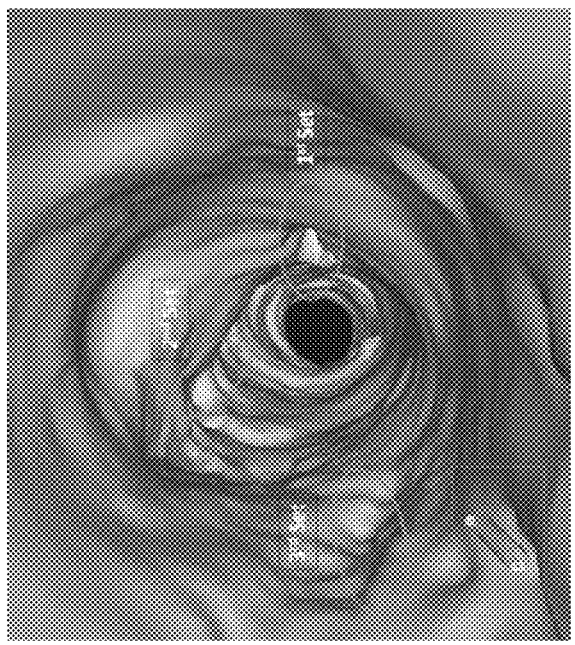
FIG.31D

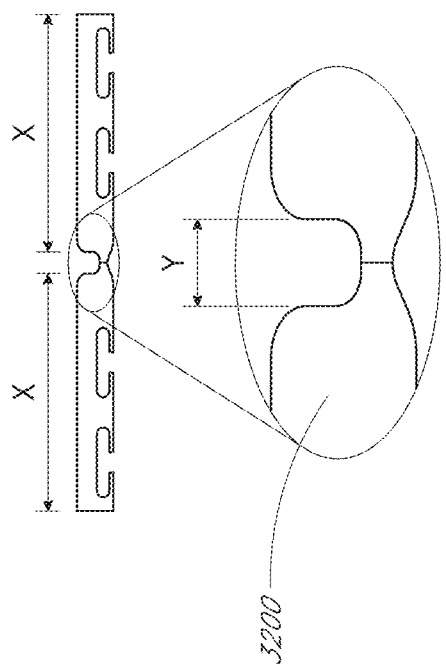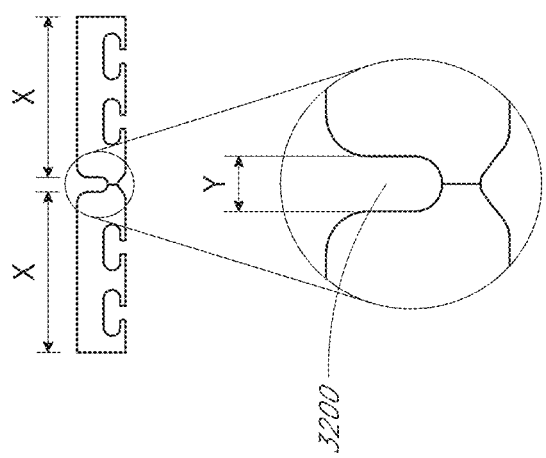
FIG. 32

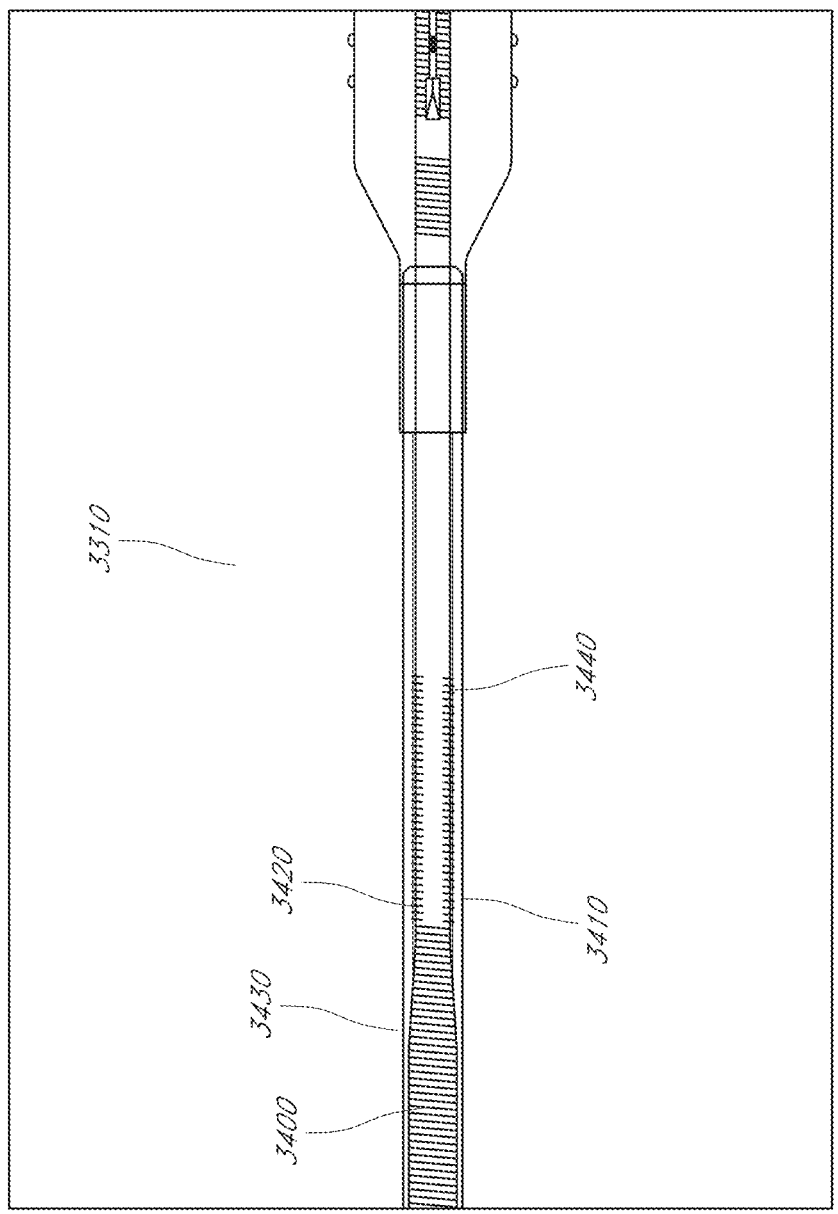

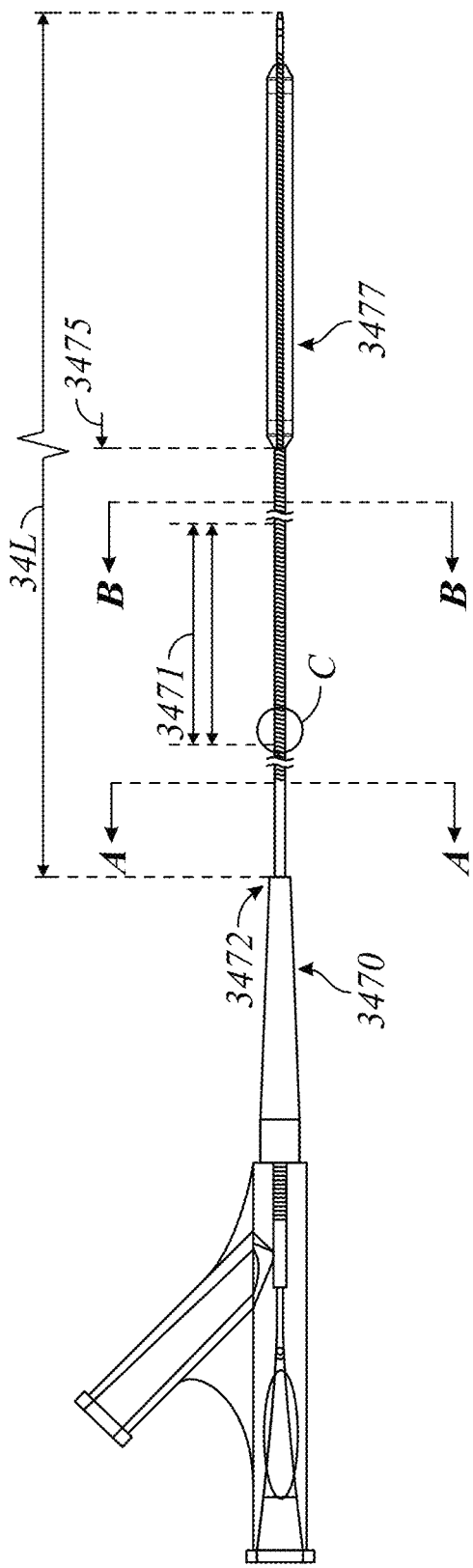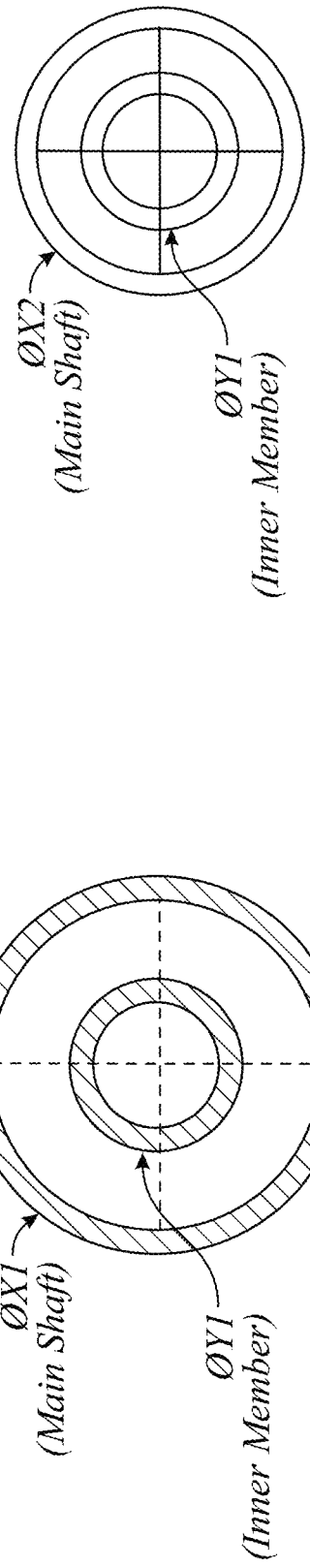
FIG. 34A
FIG. 34B
Section A-A
(Coil (A) not shown)
FIG. 34C
Section B-B
(Coil (A) not shown)

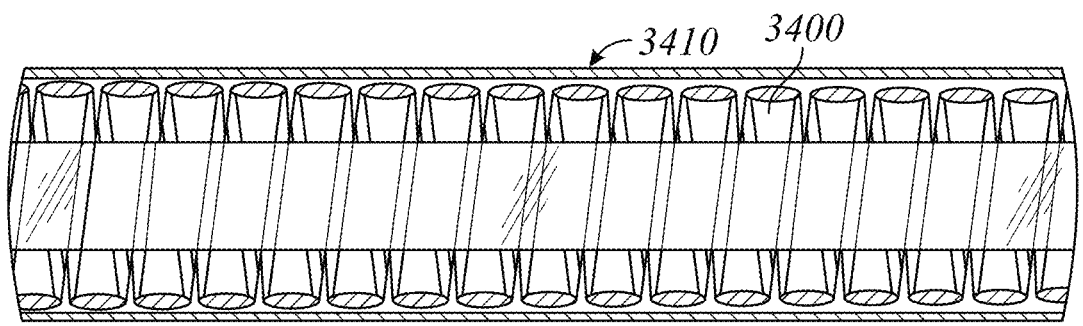
DETAIL C
FIG. 34D
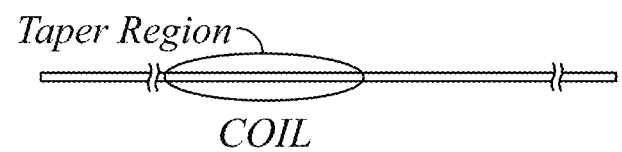
COIL
MAIN SHAFT
FIG. 34E

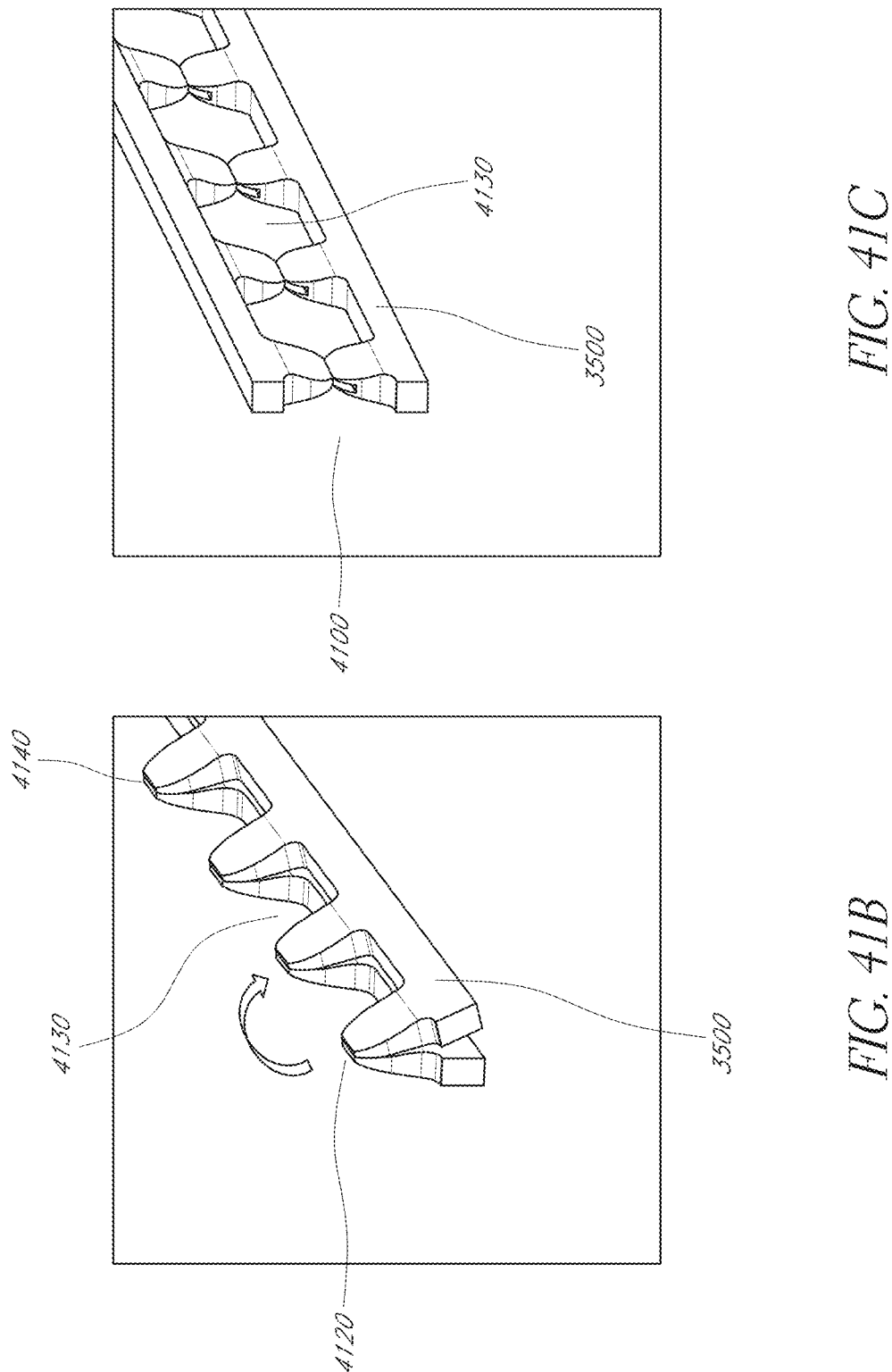

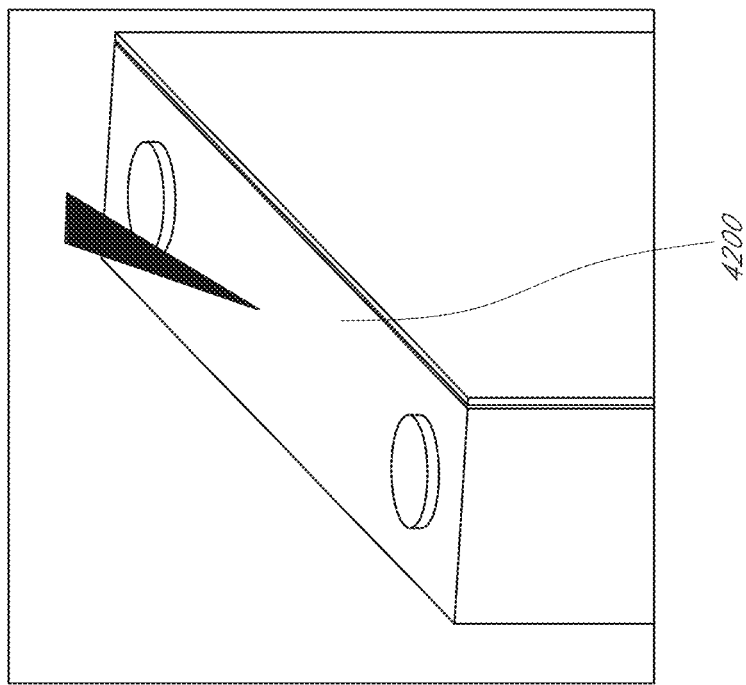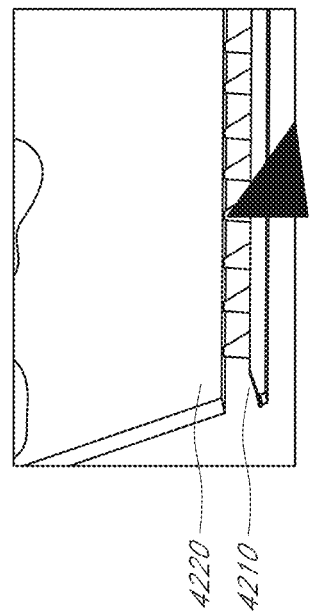
FIG. 42

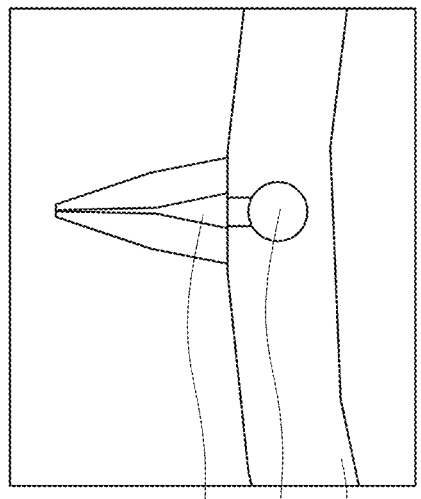
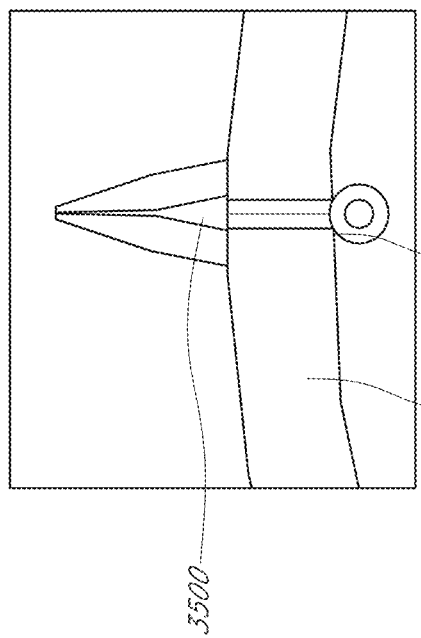
FIG. 45B
FIG. 45A

MEDICAL BALLOON CATHETERS WITH ENHANCED PUSHABILITY

CROSS-REFERENCE TO RELATED APPLICATIONS

This application claims the benefit under 35 U.S.C. § 120 as a continuation application of U.S. patent application Ser. No. 16/522,238 filed on Jul. 25, 2019, which in turn claims the benefit under 35 U.S.C. § 119(e) as a nonprovisional application of U.S. Prov. App. Nos. 62/703,419 filed on Jul. 25, 2018 and 62/827,124 filed on Mar. 31, 2019. Each of the foregoing applications are hereby incorporated by reference in its entirety. Any and all applications for which a foreign or domestic priority claim is identified in the Application Data Sheet as filed with the present application are hereby incorporated by reference under 37 CFR 1.57. This application also incorporates by reference U.S. Pub. No. 2018/0200491 to Giasolli et al., which in turn claims the benefit under 35 U.S.C. § 119(e) as a nonprovisional application of U.S. Prov. App. Nos. 62/423,117 filed on Nov. 16, 2016 and 62/522,482 filed on Jun. 20, 2017, each of which is hereby incorporated by reference in its entirety. This application is also related to U.S. patent application Ser. No. 15/268,407 filed on Sep. 16, 2016 and is hereby incorporated by reference under 37 CFR 1.57 in its entirety.

BACKGROUND

Field of the Invention

Certain embodiments disclosed herein relate generally to a cage for use with a medical balloon, such as an angioplasty balloon and methods of depositing drug into tissue via serrations. Methods of manufacturing the cage and treatment methods involving the cage are also disclosed, as well as various wedge dissectors and features of splines that can be used with the cages. Among other things, the wedge dissectors can be used to create perforations in plaque in a blood vessel in an effort to control crack propagation and to reduce flow limiting dissections.

Description of the Related Art

Atherosclerotic occlusive disease is the primary cause of stroke, heart attack, limb loss, and death in the United States and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is a method of opening blocked or narrowed blood vessels in the body. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is generally inflated to a size that is consistent with the original diameter of the artery prior to developing occlusive disease.

When the balloon is inflated, the plaque is stretched, compressed, fractured, or broken, depending on its composition, location, and the amount of pressure exerted by the balloon. The plaque is heterogeneous and may be soft in some areas or hard in others causing unpredictable cleavage planes to form under standard balloon angioplasty. Balloon angioplasty can cause plaque disruption and sometimes even arterial injury at the angioplasty site.

SUMMARY

There is continuous need to improve the methods for treating occlusive disease, including balloon angioplasty and other related treatment systems. In some embodiments, drug uptake from a drug eluting balloon at a treatment site in a vessel can be improved by a method of pretreating a site in a vessel by expanding a pretreatment balloon at the site to create a plurality of micro fissures into the media layer of the vessel wall. The pretreatment balloon has a plurality of strips with each strip containing a plurality of wedge dissectors spaced apart along a surface of each strip. These strips extend longitudinally along an outer surface of the pretreatment balloon. The pretreatment balloon would then be removed and a drug eluting balloon would be placed at the site. The drug eluting balloon would be expanded to contact with the vessel wall and allow drug to elute from the surface of the drug eluting balloon into the micro fissures, through the intima and into the media. In some embodiments, the plurality of wedge dissectors are spaced equally or the plurality of strips of wedge dissectors all have the same length.

In some embodiments, drug uptake from a drug eluting balloon at a treatment site in a vessel can be improved by a method of pretreating a site in a vessel by expanding a pretreatment balloon at the site to create a plurality of micro fissures into the media layer of the vessel wall. The pretreatment balloon have a plurality of strips with each strip containing a plurality of wedge dissectors spaced apart along a surface of each strip. These strips extend longitudinally along an outer surface of the pretreatment balloon. The pretreatment balloon would then be deflated and rotated by a fraction of an angle, that in some cases is different from the spacing of each strip along the circumference of the balloon. As one non-limiting example, if there are 4 wedge dissectors are spaced 90 degrees apart along the circumference of the balloon, the balloon can be rotated, for example, 45 degrees and then reinflated to create new serrations along the vessel wall where there were none previously. The pretreatment balloon would then be re-inflated so that the strips on the pretreatment balloon are at different positions from than the original inflation, and the wedge dissectors are in a position to create serrations in areas of the vessel wall that were previously free of serrations. The pretreatment balloon would then be removed and a drug eluting balloon would be placed at the site. The drug eluting balloon would be expanded to contact with the vessel wall and allow drug to elute from the surface of the drug eluting balloon into the micro fissures, through the intima and into the media. The plurality of wedge dissectors can be spaced equally or the plurality of strips of wedge dissectors can all have the same length. The fraction of the angle can be, in some cases, about 5, 10, 15, 20, 25, 30, 35, 40, 45, 50, 55, 60, 65, 70, 75, 80, 85, 90 degrees or more or less, or ranges including any two of the foregoing values. In some embodiments, the balloon can be rotated between about 1 degree and about 30 degrees or the fraction of the angle is between about 5 degrees and about 20 degrees. In some embodiments, the balloon can be rotated once in a first direction, and then repeated 1, 2, 3, 4, 5, or more times in the same or an opposite direction to increase the number of serrations in the vessel wall.

In some embodiments, the method of pretreatment of the site is achieved with wedge dissectors that have radially-outward facing surfaces with a rectangular shape.

In some embodiments, the method of depositing drugs through the tissue serration uses a pretreatment balloon that has an elongate member having an inner lumen which defines a longitudinal axis, an expandable balloon connected to the elongate member at a distal end of the elongate member, a plurality of strip with each strip of the plurality of strips having a plurality of wedge dissectors spaced apart along a surface of each strip and each strip extends longitudinally along an outer surface of the balloon. The wedge dissectors in this example have strip-facing base surface directly adjacent a surface of each of the strips, an unhoned radially outward facing surface having a length between a proximal edge of the radially outward facing surface and a distal edge of the radially outward facing surface and defining a height of each wedge dissector, and lateral surfaces between the strip-facing base surface and the radially outward facing surface. The radially outward facing surface have a first width at the proximal edge, a second width smaller than the first width between the proximal edge and the distal edge, and a third width at the distal edge larger than the second width. The second width can correspond to a single point along the length of the radially outward facing surface or the second width can correspond to a central segment having a central length in between the proximal edge and the distal edge. The length of each strip can be less than a length of the outer surface of the balloon coaxial to the length of each strip or the length of each strip can be between about 3% and about 6% less than the length of the outer surface of the balloon coaxial to the length of each strip. The total length of the radially outward facing surface of each wedge dissector can be less than a total length of the strip-facing base surface of each wedge dissector. In another example, the radially outward facing surface has a curved surface or has least one chamfered surface or a first height at the proximal edge and a second height between the proximal edge and the distal edge where the second height is greater than the first height. In some embodiments, the maximal height of the radially outward facing surface is at a midpoint between the first unbounded edge and the second unbounded edge. The maximal height of the unbounded surface can be offset from a midpoint between the proximal edge and the distal edge. The lateral surface segment of the wedge dissector from the strip-facing base surface to the proximal edge can have a first segment with a first slope and a second segment with a second slope different from the first slope. The strip could have a textured surface. The strip could also have a plurality of reliefs. The method could also have a pretreatment balloon with a plurality of strips having an elongate length having first and second lateral edges where the first and second lateral edges of the plurality of strips are circumscribed by an adhesive. The method could also use a hydrophilic slip layer surrounding the outer surface of the balloon, the strips, and the wedge dissectors. In another example, the method uses at least one polymer retention layer surrounding the outer surface of the balloon, the strips, and the wedge dissectors. The balloon of this method could have cones about the lateral ends of the balloon where the cones have a maximal outer diameter that is greater than about 5% of the maximal outer diameter of the balloon. The cones could comprise rails oriented with longitudinal axes of the strips.

In some embodiments, the method of attaching wedge dissectors to a medical balloon can be achieved by providing a strip including a plurality of wedge dissectors spaced longitudinally apart along a surface of the strip. Each of the wedge dissectors has a strip-facing base surface directly adjacent a first surface of the strip, an unhoned radially outward facing surface having a length between a proximal edge of the radially outward facing surface and a distal edge of the radially outward facing surface and defining a height of each wedge dissector, and lateral surfaces between the strip-facing base surface and the radially outward facing surface. Each unhoned radially outward facing surface of each of the wedge dissectors are attached to a linear free edge of a strip carrier at attachment zones, where the areas between attachment zones define voids and the strip has a second surface opposing the first surface of the strip. Then, the second surface of the strip is attached to a surface of the medical balloon and is detached from the strip carrier from the strip after the second surface of the strip is attached to the medical balloon. The second surface of the strip could be bonded to the surface of the medical balloon with an adhesive. The detaching the strip carrier from the strip could be accomplished using a mechanical force. The strip carrier could also be integrally formed with the strip. In some cases, the strip carrier and the strip are created using chemical etching.

In some embodiments, a carrier system for attaching wedge dissectors to a medical balloon has a strip including a plurality of wedge dissectors spaced longitudinally apart along a surface of the strip. Each of the wedge dissectors has a strip-facing base surface directly adjacent a first surface of the strip, an unhoned radially outward facing surface having a length between a proximal edge of the radially outward facing surface and a distal edge of the radially outward facing surface and defining a height of each wedge dissector, and lateral surfaces between the strip-facing base surface and the radially outward facing surface. The strip has a second surface opposing the first surface of the strip, and the strip carrier has a free edge. The unhoned radially outward facing surface of each wedge dissectors is attached to the free edge of a strip carrier at attachment zones. There are voids between attachment zones, and the attachment zones configured to be detached upon application of a mechanical force. In some cases, the carrier system strip is made out of a metal. The strips can be made from stainless steel or the carrier system can be the same material as that of the strip.

In some embodiments, a method of creating serrations at a treatment site in a vessel has a serration balloon with a plurality of strips. Each strip of the plurality includes a plurality of wedge dissectors spaced apart along a surface of each strip and each strip extends longitudinally along an outer surface of the serration balloon. Each wedge dissector has radially outward facing surfaces and lateral surfaces. The serration balloon is expanded at the site such that the radially outward facing surfaces of the plurality of wedge dissectors directly contact tissue of the intima layer of the vessel wall creating cleavage planes into a media layer of the vessel wall. Then continued expansion of the serration balloon is conducted so the radially outward facing surfaces of the plurality of wedge dissectors no longer contact tissue of the media layer of the vessel wall, and the lateral surfaces of the wedge dissector contact tissue of the media layer of the vessel wall to expand the cleavage planes. The cleavage planes can have a depth of between about 0.3 mm and about 1.5 mm or the cleavage planes can have a depth of between about 0.5 mm and about 1.2 mm.

In some embodiments, disclosed herein is a medical balloon catheter with enhanced pushability. The catheter can include any number of the following: an outer shaft comprising an elongate member comprising an inner diameter and an outer diameter; an inner member; and an elongate coil positioned between the outer shaft and the inner member, the coil extending substantially the entire length of the outer shaft. In some embodiments, the elongate coil comprises one or more tapered portions that tapers from a first larger diameter to a second smaller diameter. In some embodiments, the outer shaft comprises one or more tapered portions that tapers from a first larger diameter to a second smaller diameter. In some embodiments, the one or more tapered portions of the elongate coil substantially correlates with the one or more tapered portions of the outer shaft.

In some configurations, the coil comprises at least two tapered portions.

In some configurations, the one or more tapered portions of the coil comprise a pitch of between about 0 degrees and about 15 degrees.

In some configurations, the one or more tapered portions of the coil are all present only between about 5 cm and about 50 cm from a distal tip of the catheter.

In some configurations, the coil is fused to the outer shaft at least at a proximal end of the catheter and/or a distal end of the catheter.

In some configurations, the inner member comprises a guidewire.

In some configurations, the catheter further comprises an expandable member associated with the catheter, wherein the elongate coil extends through the expandable member.

In some configurations, the expandable member comprises a balloon.

In some configurations, the expandable balloon comprises a plurality of strips, each strip comprising a plurality of wedge dissectors thereon.

In some configurations, the wedge dissectors are configured to create serrations in a vessel without cutting the vessel.

In some configurations, the wedge dissectors are configured to cut through a portion of a vessel.

Also disclosed herein are methods of creating serrations in a treatment site in a vessel, comprising providing a balloon catheter comprising a balloon comprising a plurality of strips, each strip comprising a plurality of wedge dissectors, the balloon catheter further comprising an inner member, an outer sheath, and an elongate tapered coil between the matched tapered outer sheath and the non-tapered inner member, the elongate coil running substantially the entire length of the balloon catheter and through the balloon; expanding the balloon at the site to create a plurality of microfissures into the media layer of the vessel wall without cutting the vessel wall; and removing the balloon from the site.

In some configurations, the method further comprises performing an index procedure at the site.

In some configurations the index procedure is selected from the group consisting of: endovascular aortic repair (EVAR), fenestrated endovascular aortic repair (FEVAR), transcatheter aortic valve replacement (TAVR), transcatheter mitral valve repair or replacement, and thoracic endovascular aortic repair (TEVAR).

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIGS. 16A-C show a plurality of embodiments of strips secured by a ring.

FIG. 17 illustrates a schematic view showing a detail of an embodiment of a cage with a spring.

Figure 23A:
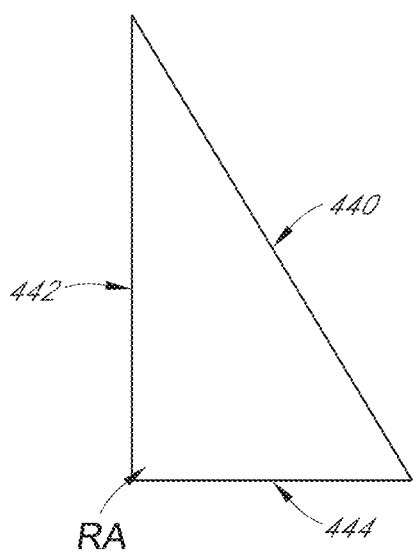
FIGS. 23A-23D illustrate respective end and isometric views of various asymmetric wedge dissector geometries, according to some embodiments.
Figure 23B:
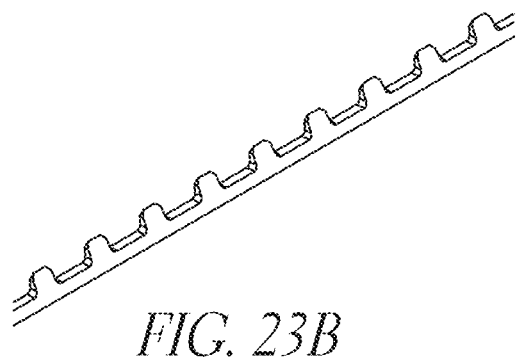
Figure 23C:
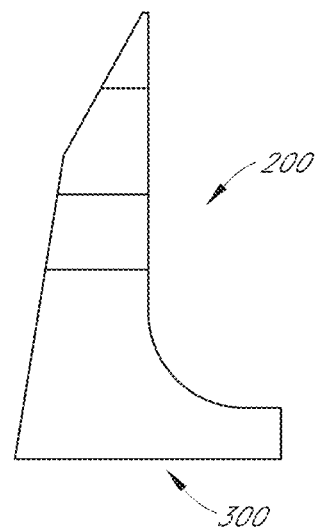
Figure 23D:
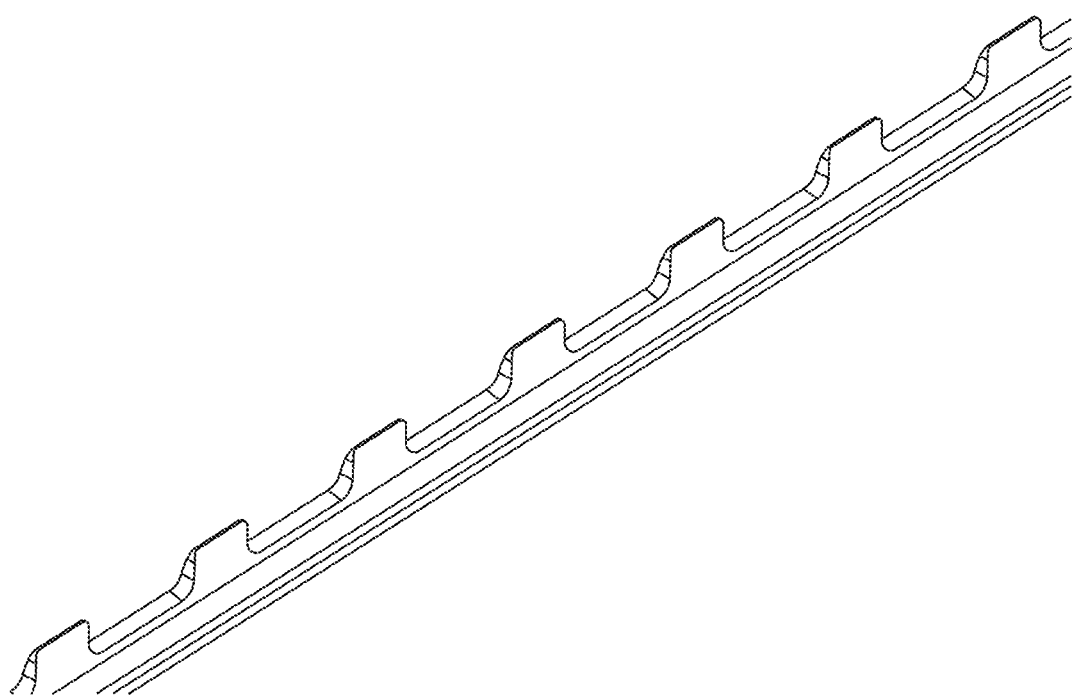
Figure 23E:
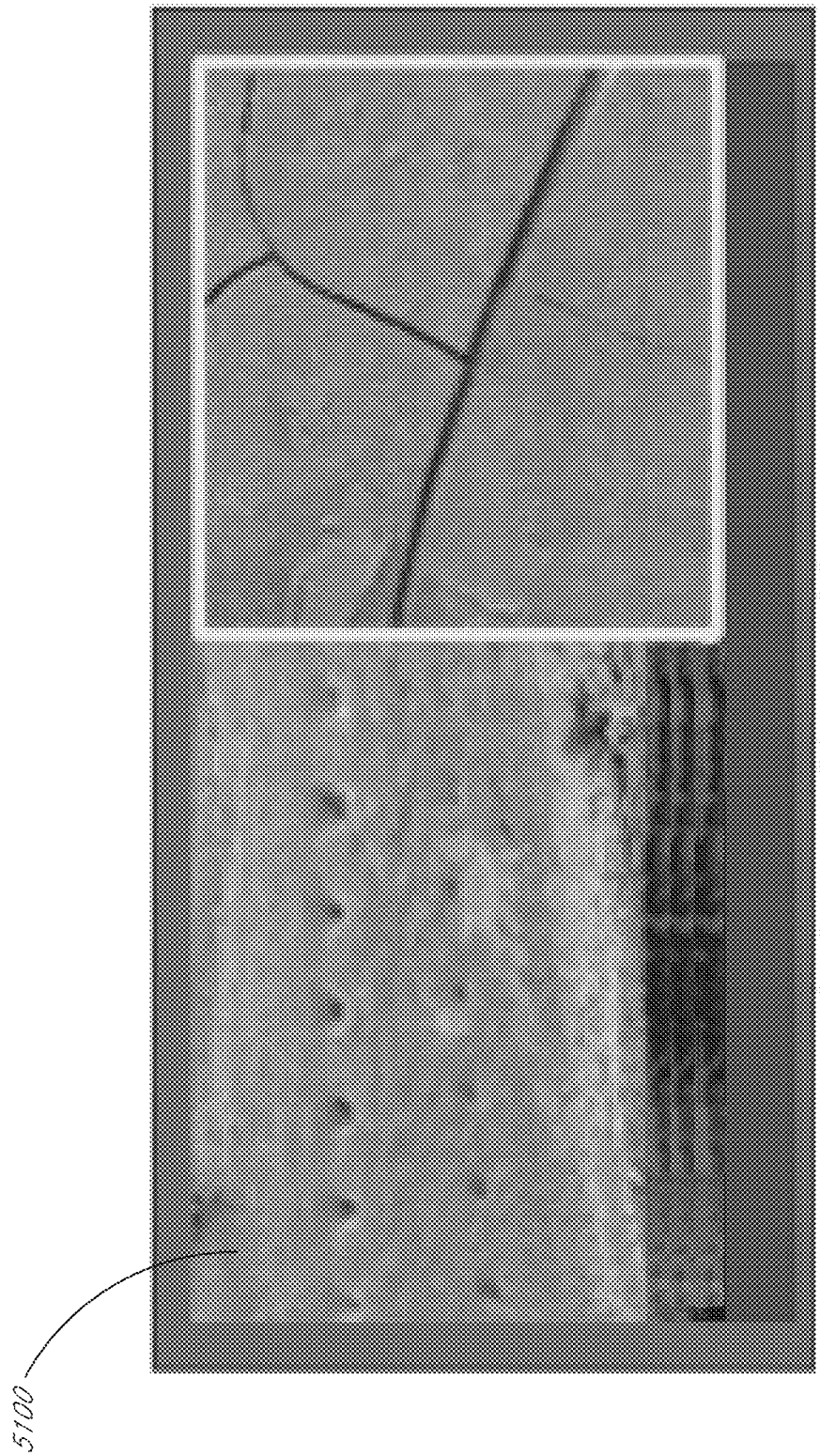

Not to be limited by theory, FIGS. 23E, 23F, and 23F.1 show potential mechanisms of actions of a serration device.

Figure 24:
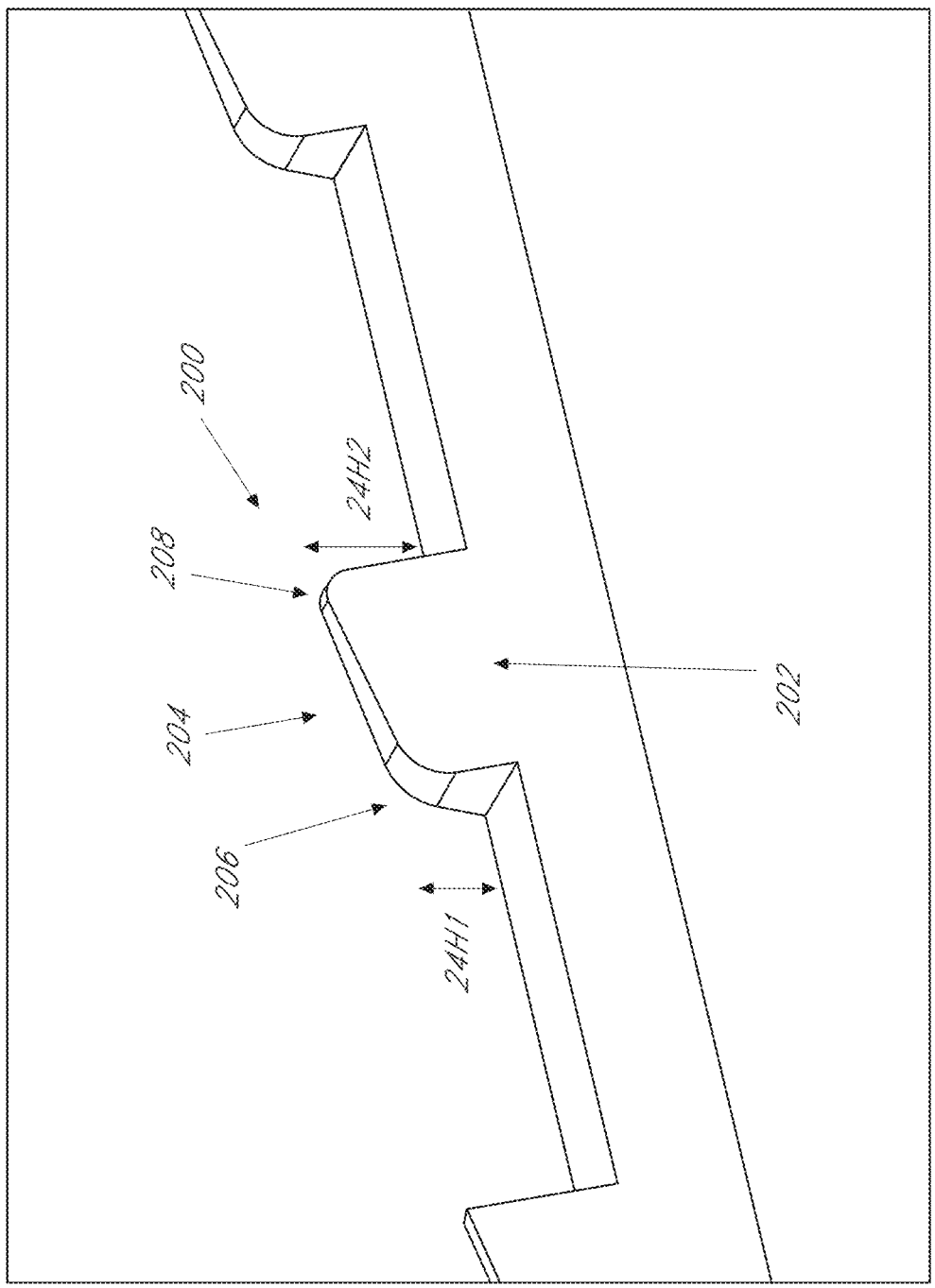

FIG. 24 illustrates an embodiment illustrating how the unbounded surface 204 may have a varying height, according to some embodiments.

FIGS. 25A-25K illustrate various embodiments of strips with reliefs in various locations.

FIGS. 25L and 25M illustrate embodiments of method of stabilizing strips during the laser cutting manufacturing process and involving temporary tabs, according to some embodiments.

Figure 25A:
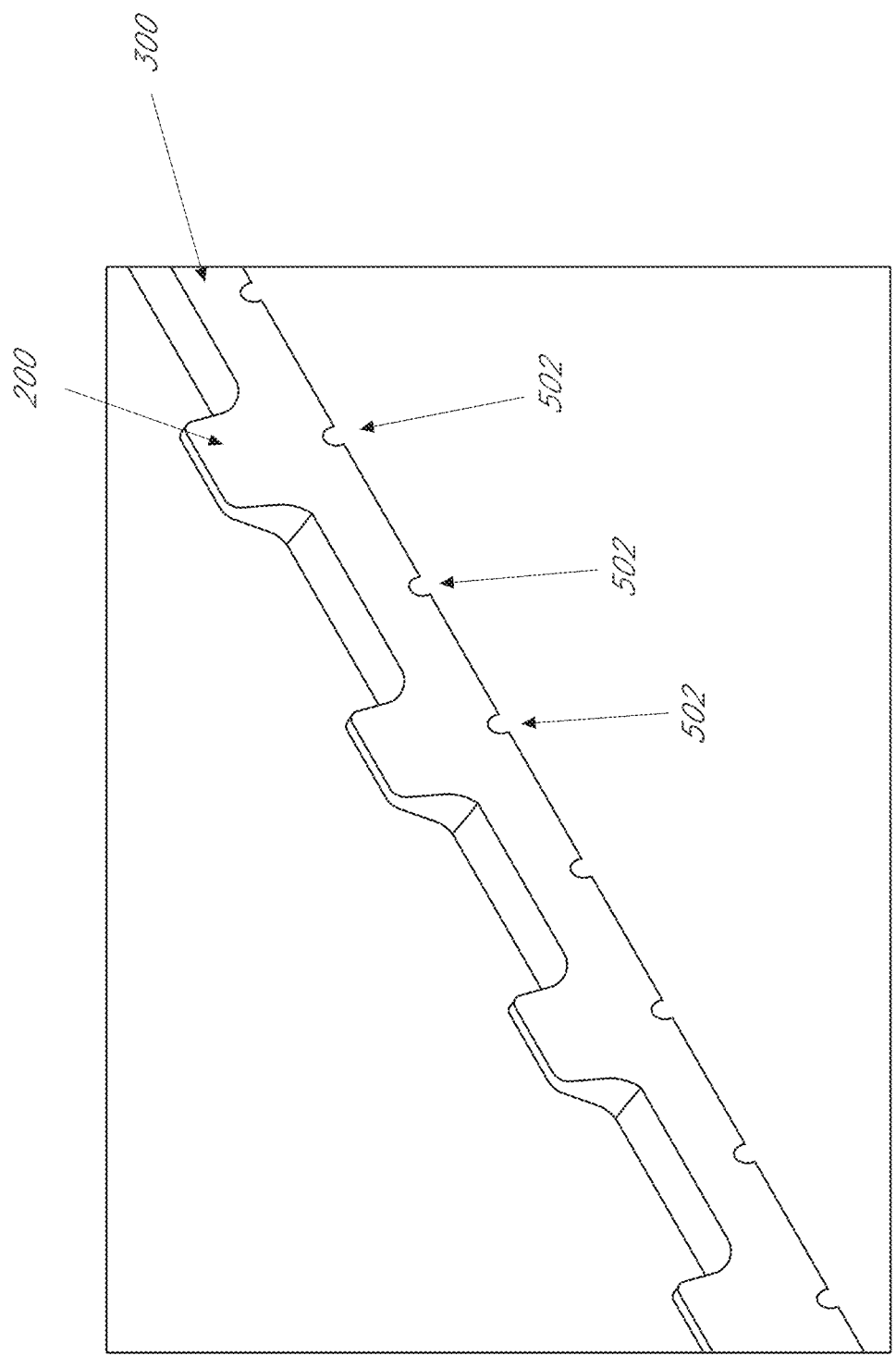
Figure 25B:
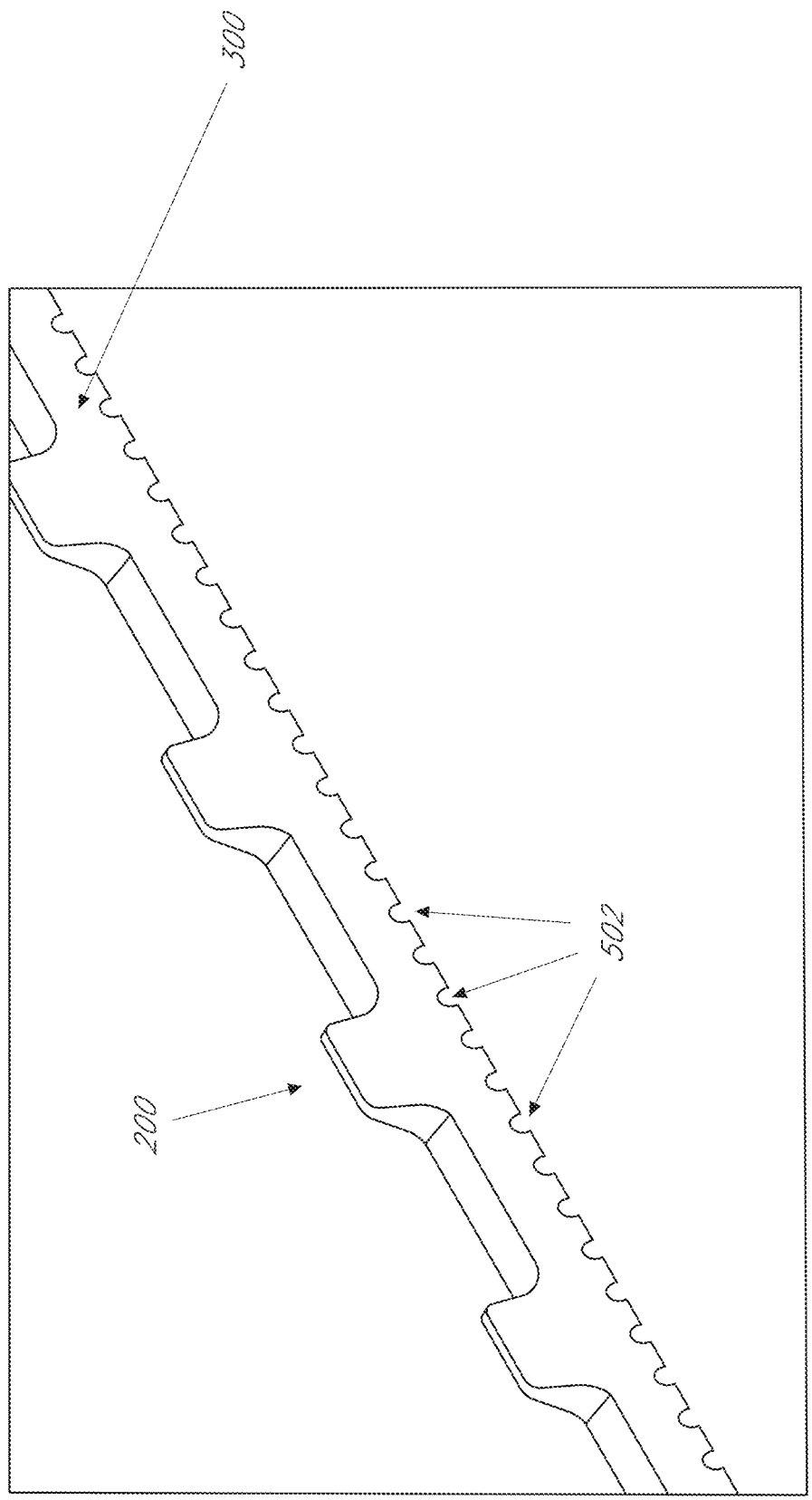
Figure 25C:
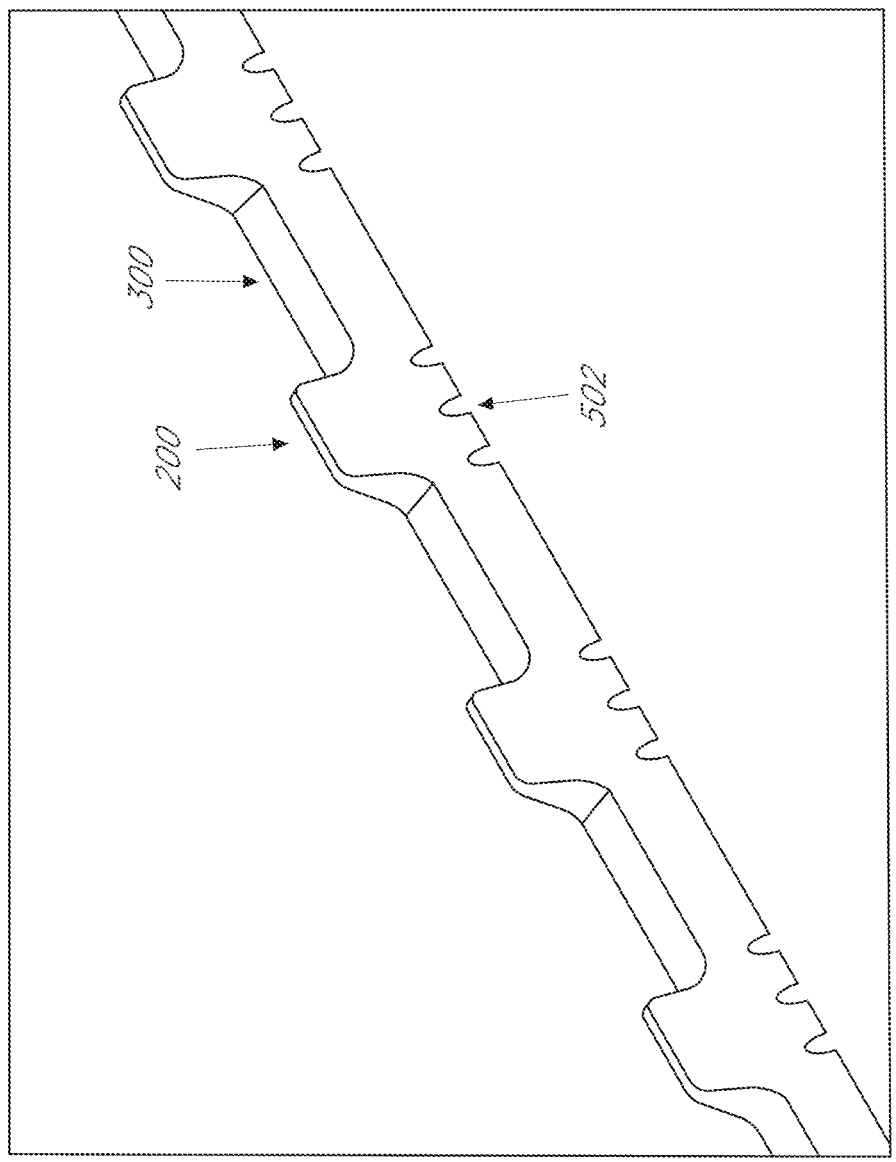
Figure 25D:
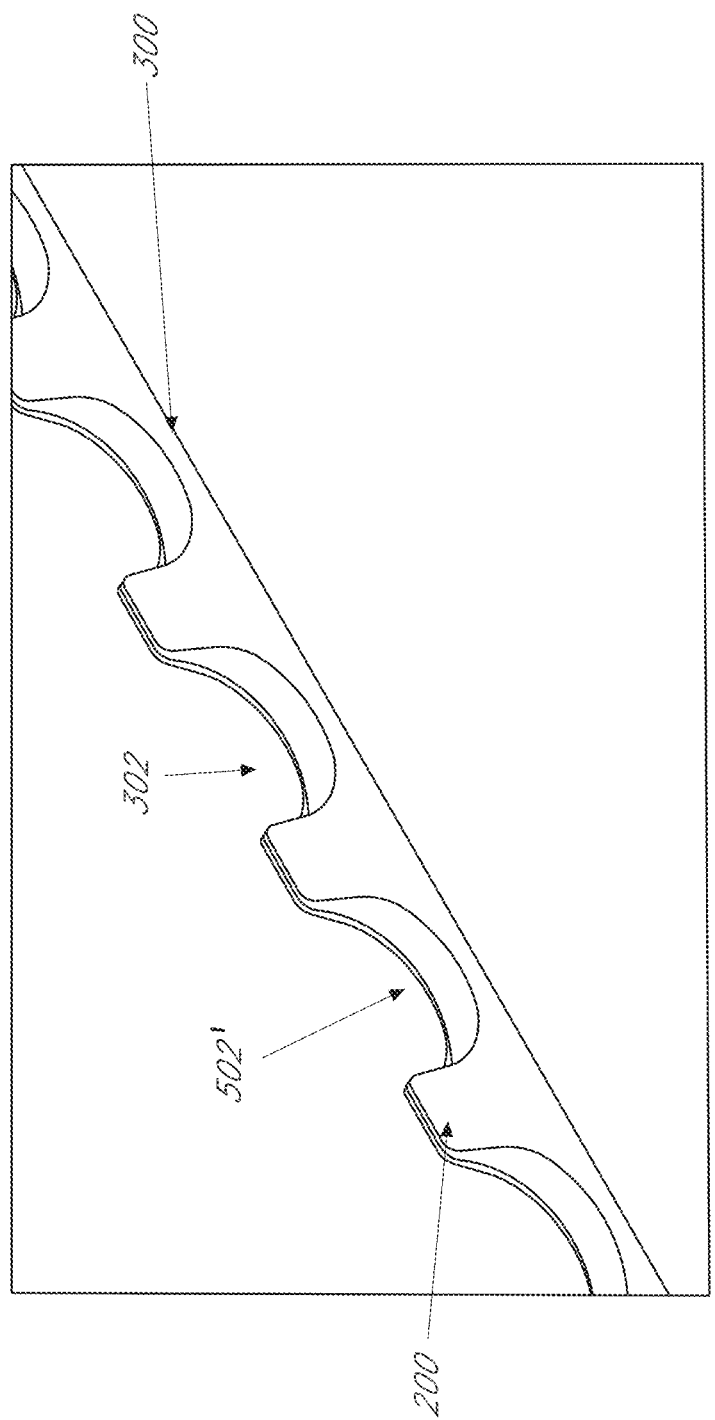
Figure 25E:
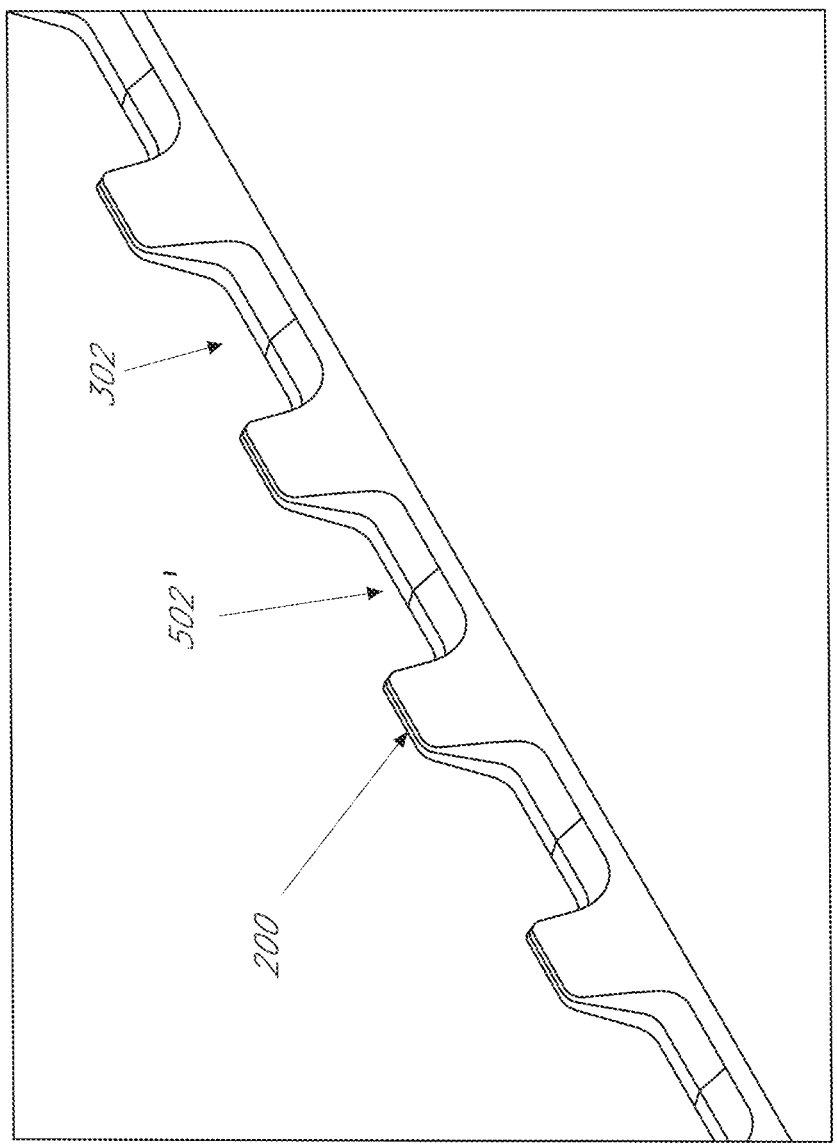
Figure 25F:
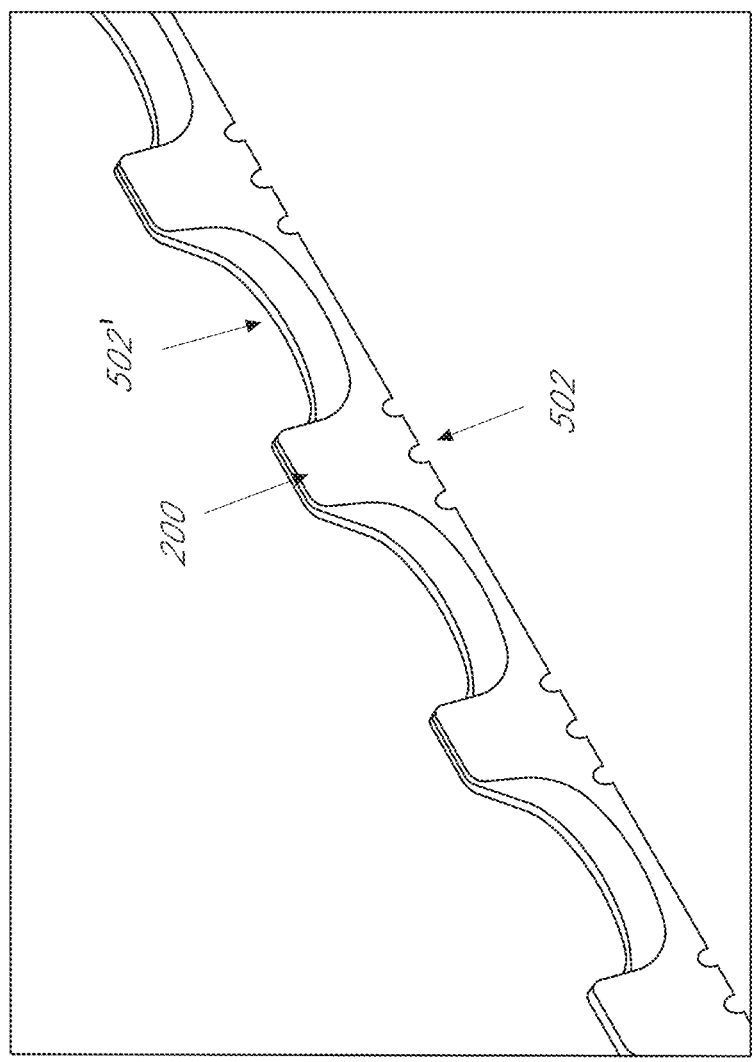
Figure 25G:
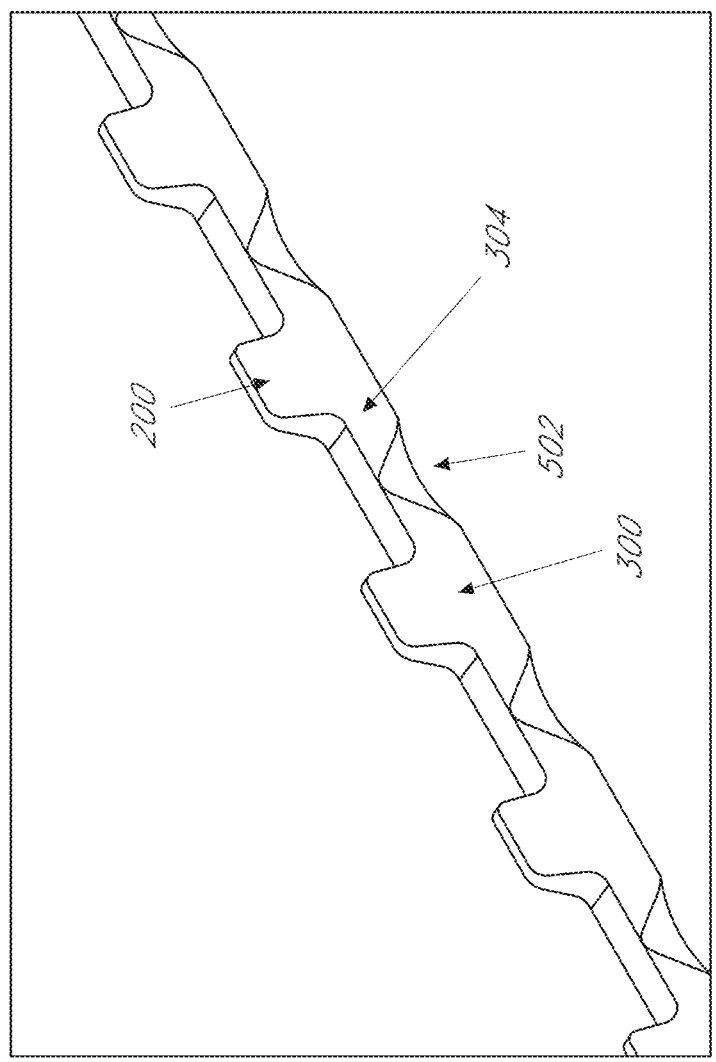
Figure 25H:
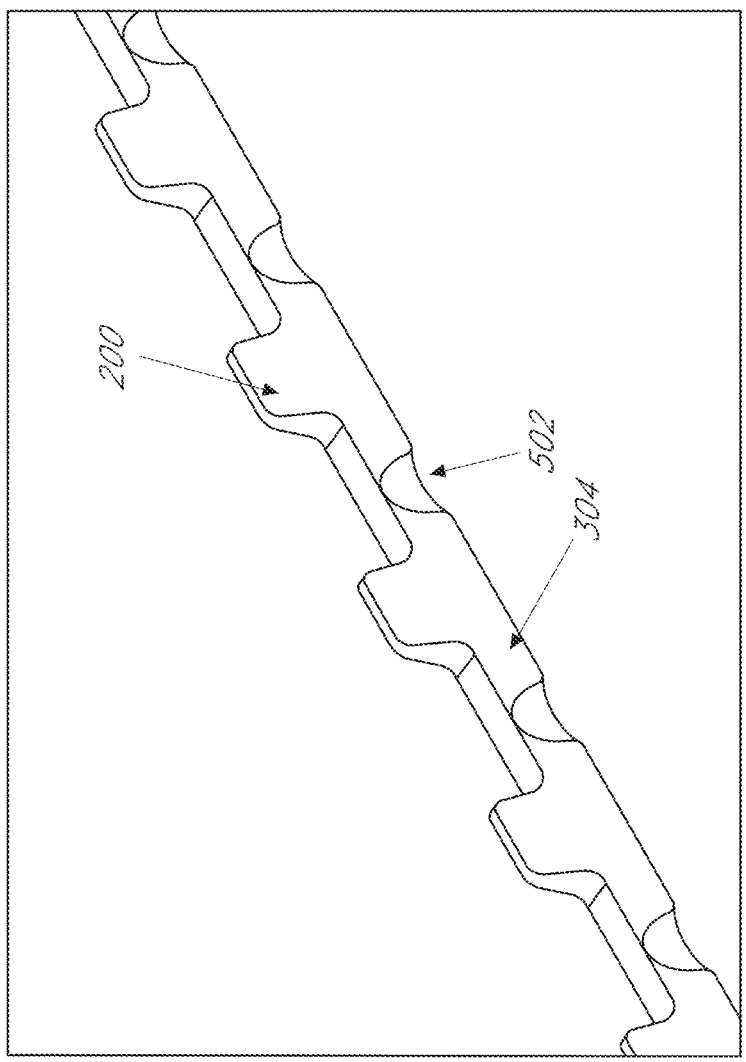
Figure 25I:
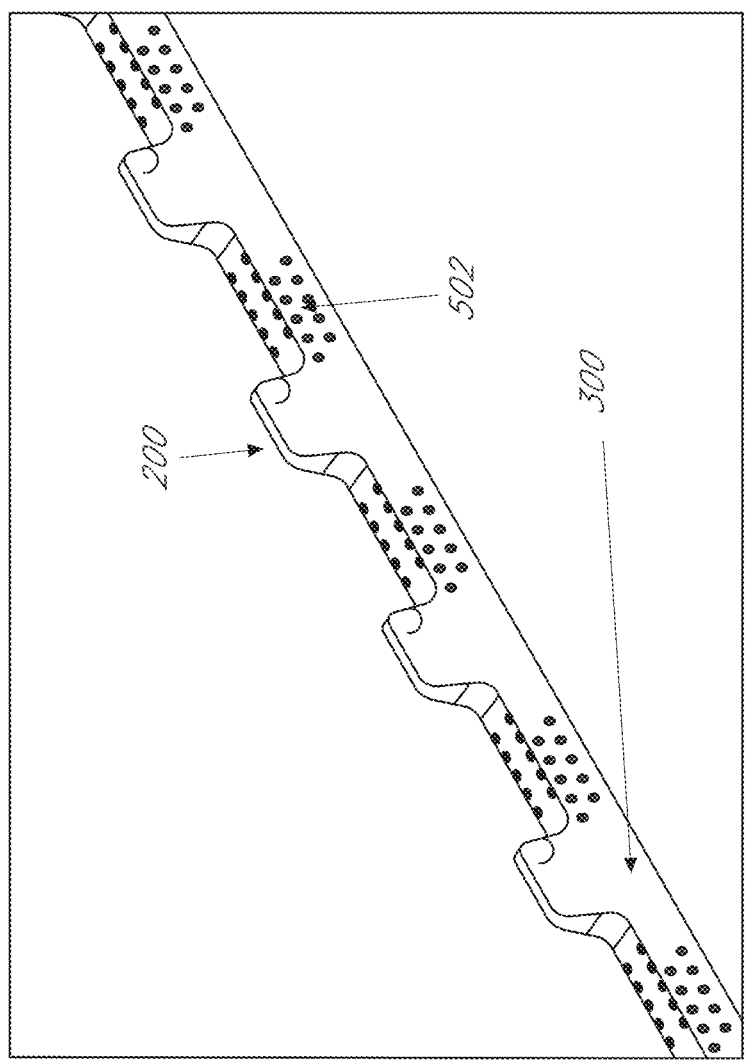
Figure 25J:
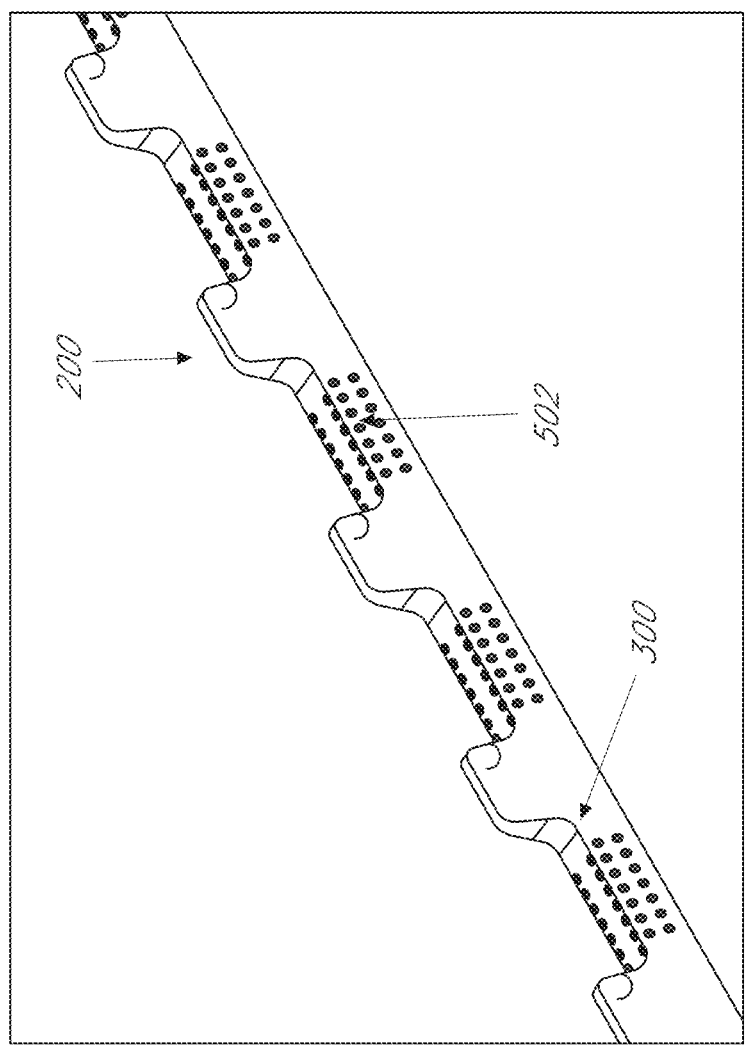
Figure 25N:
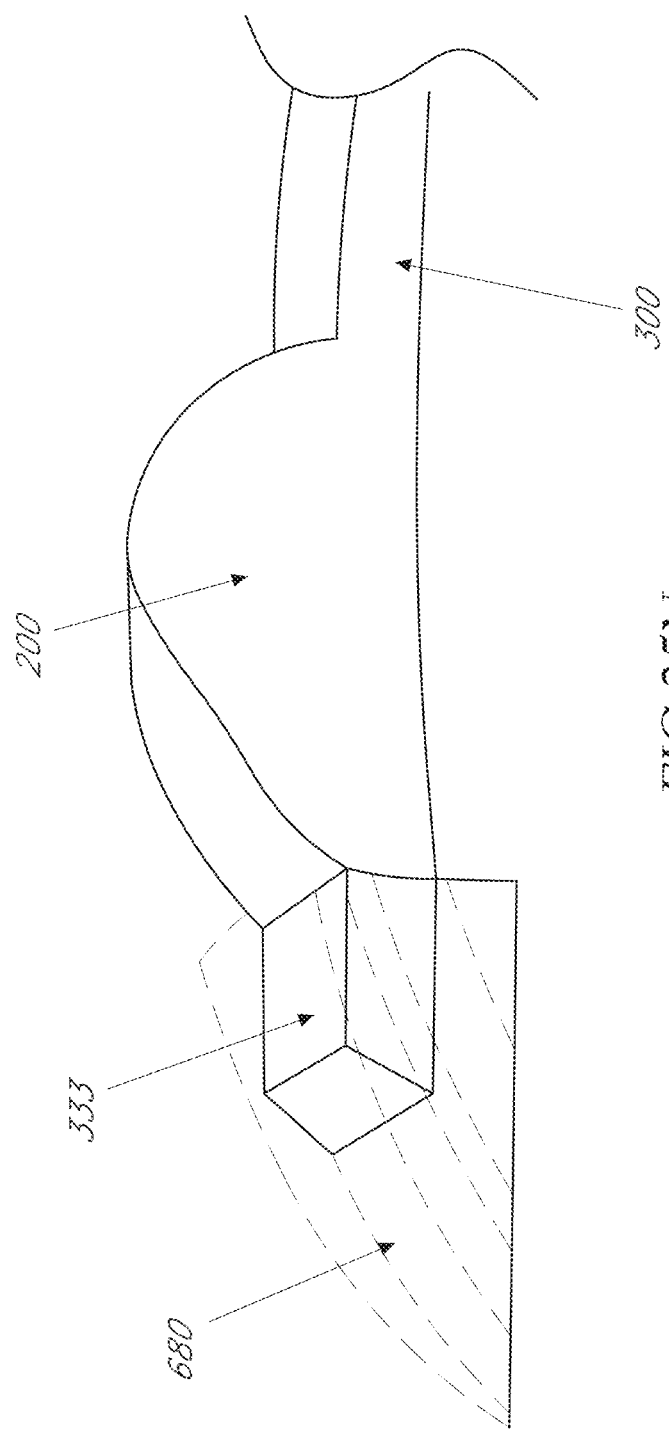
Figure 250:
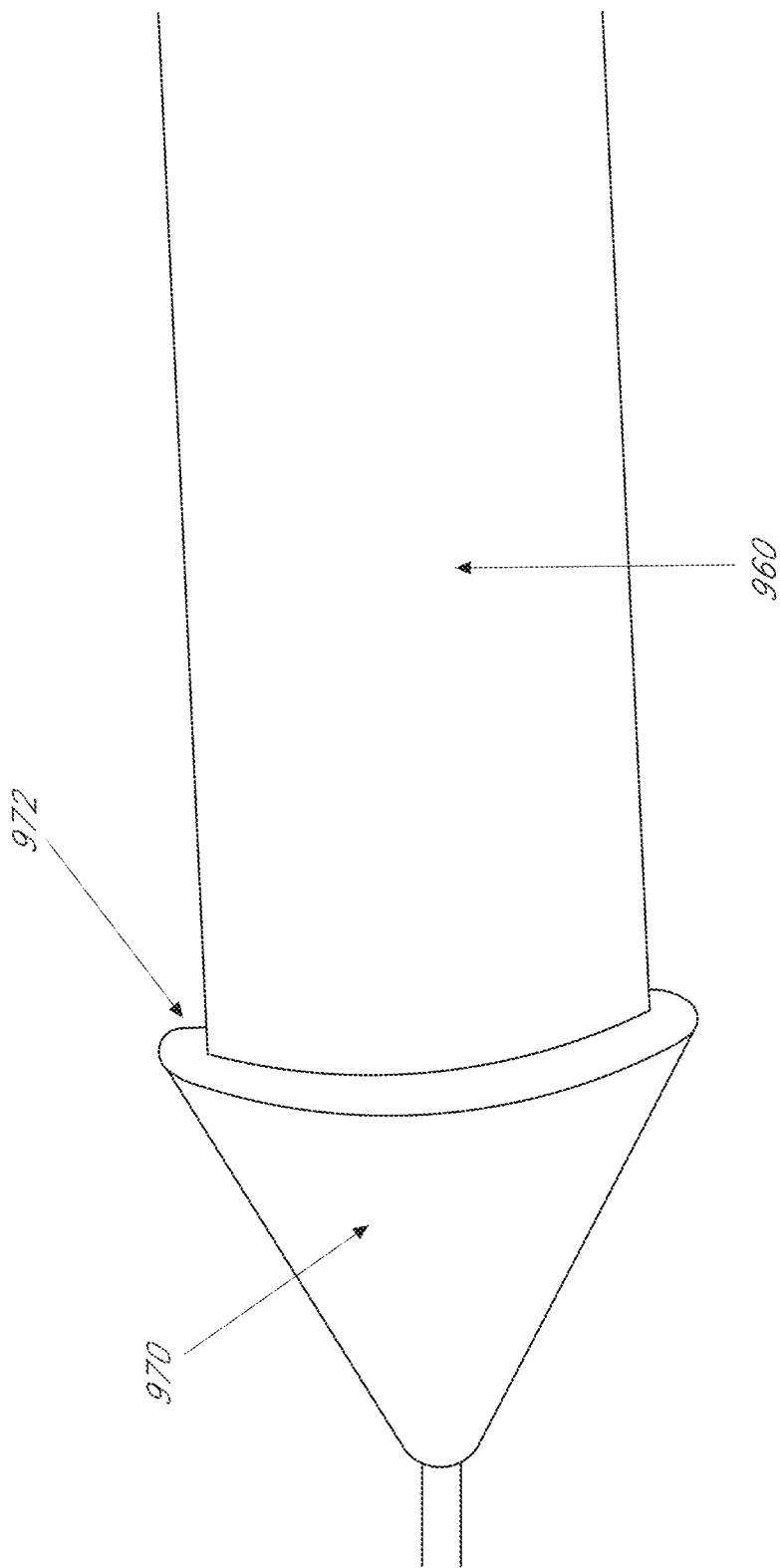

FIG. 25N illustrates embodiments of an adhesive ramp for bonding lateral ends of a strip to the balloon surface, according to some embodiments. FIG. 25N.1 shows another image of a ramp feature shown in a side view to illustrate the distance away from the strip edge where a ramp extends.

FIG. 25O illustrates a cone ramp for a balloon, according to some embodiments.

FIG. 25P illustrates a series of cone rails or struts, according to some embodiments.

Figure 26:
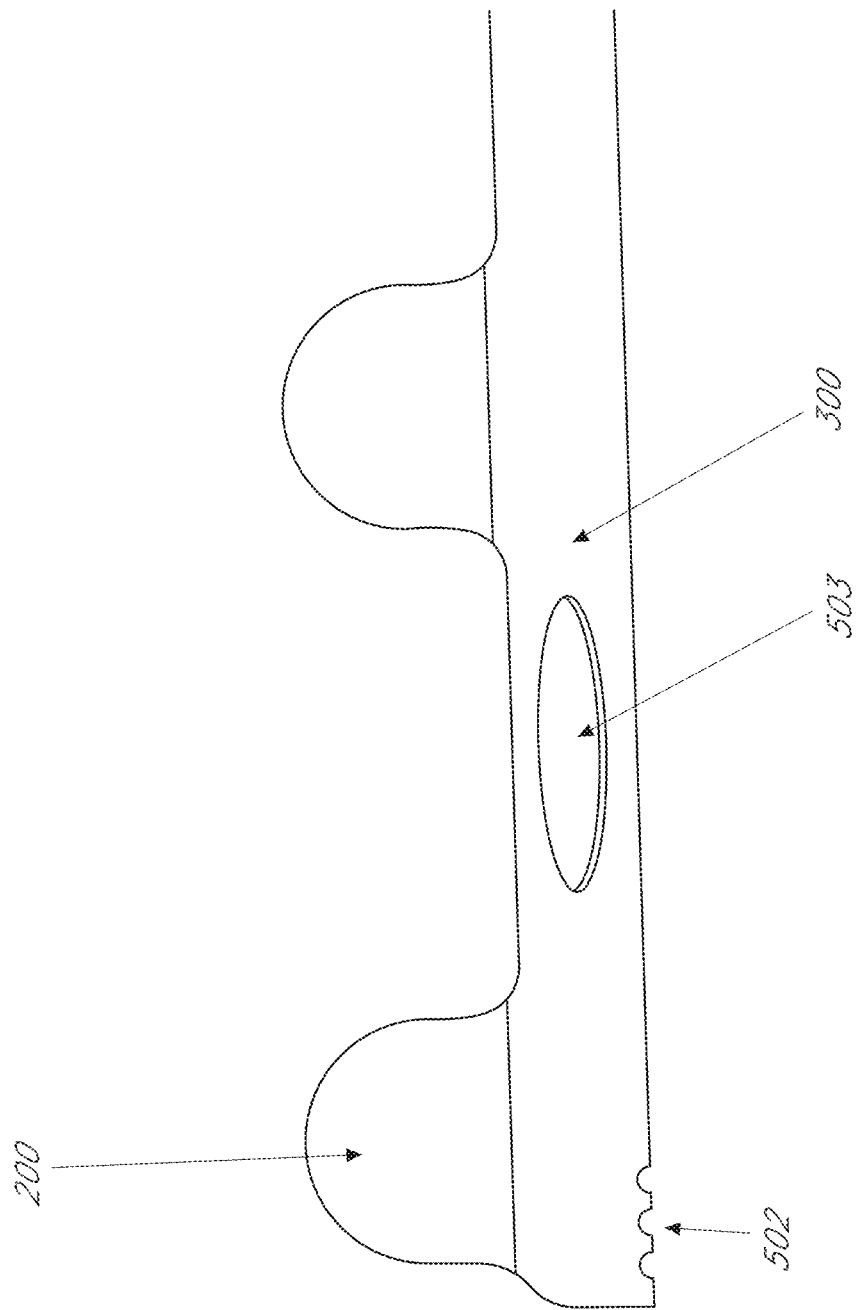

FIG. 26 illustrates another embodiment of strips having reliefs, according to some embodiments.

Figure 27:
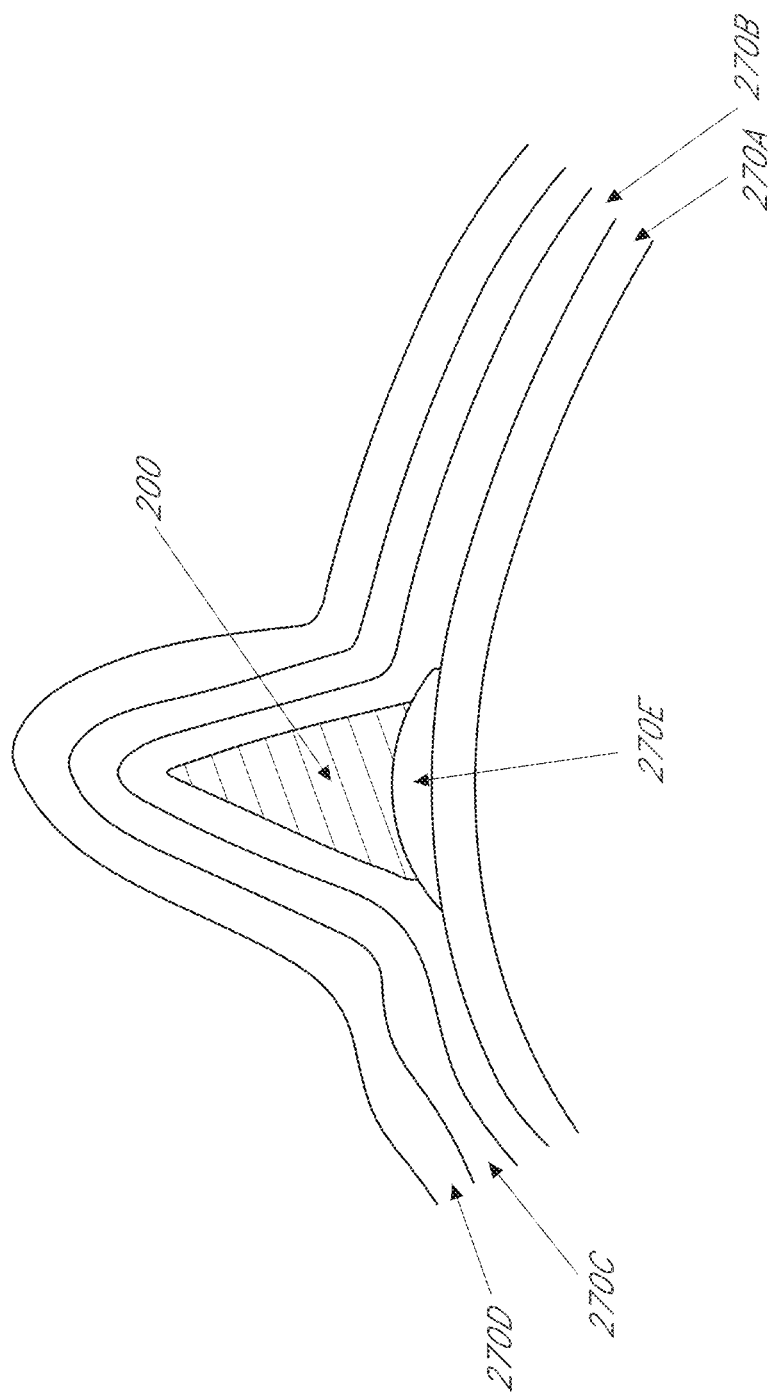

FIG. 27 illustrates a schematic cross-section of a balloon with wedge dissector and intervening layers.

Figure 28:
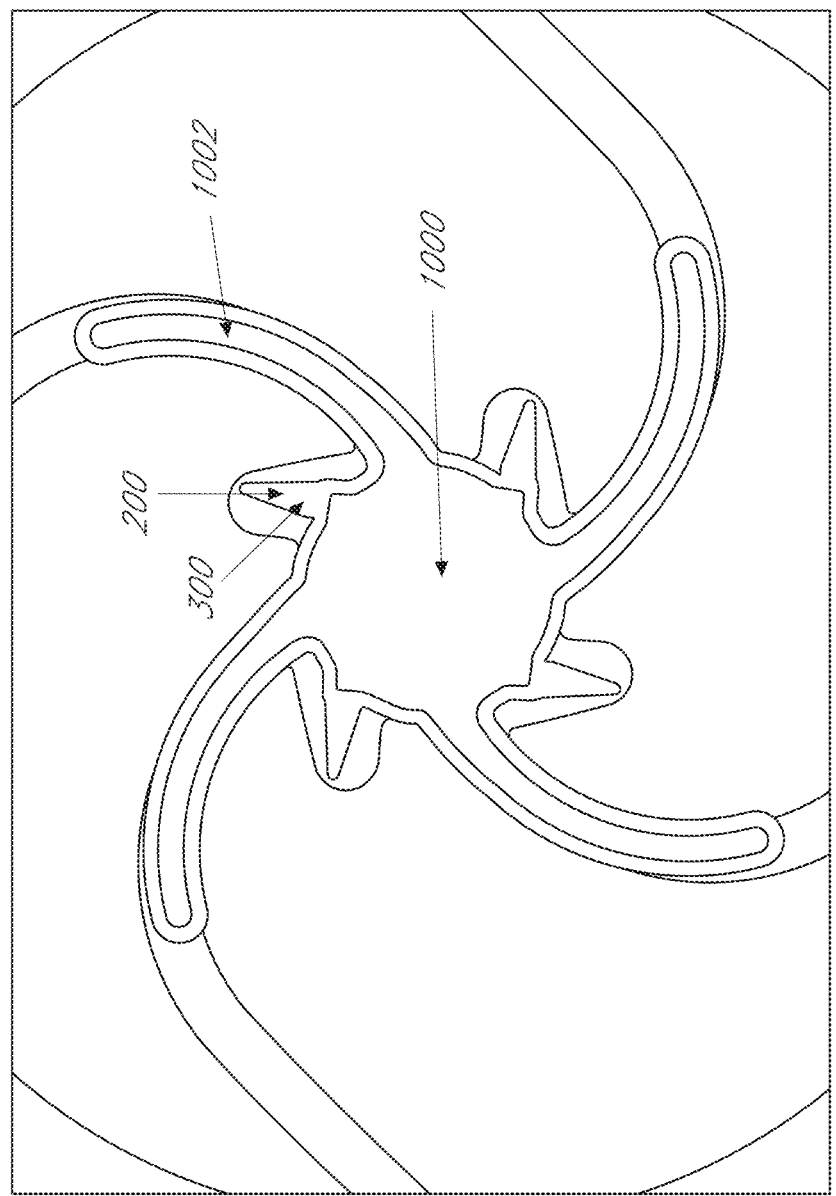
Figure 28A:
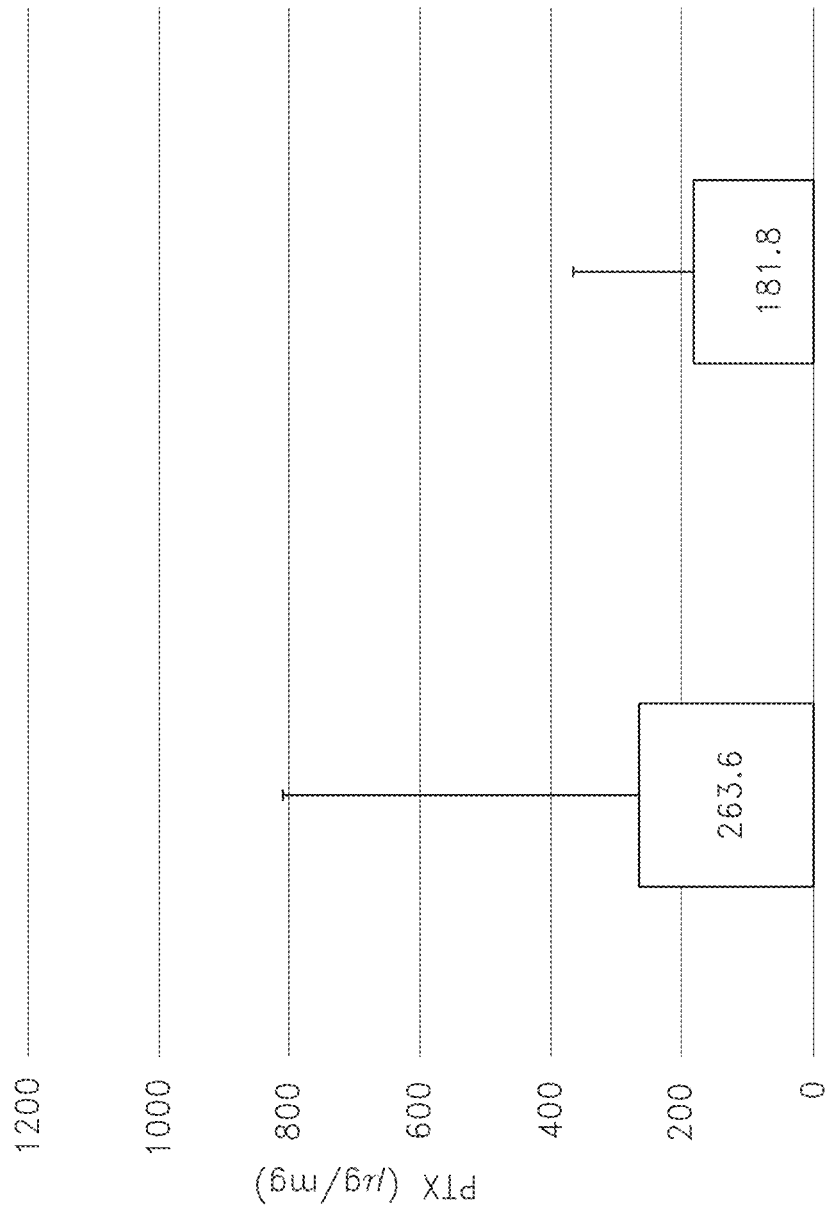
Figure 28B:
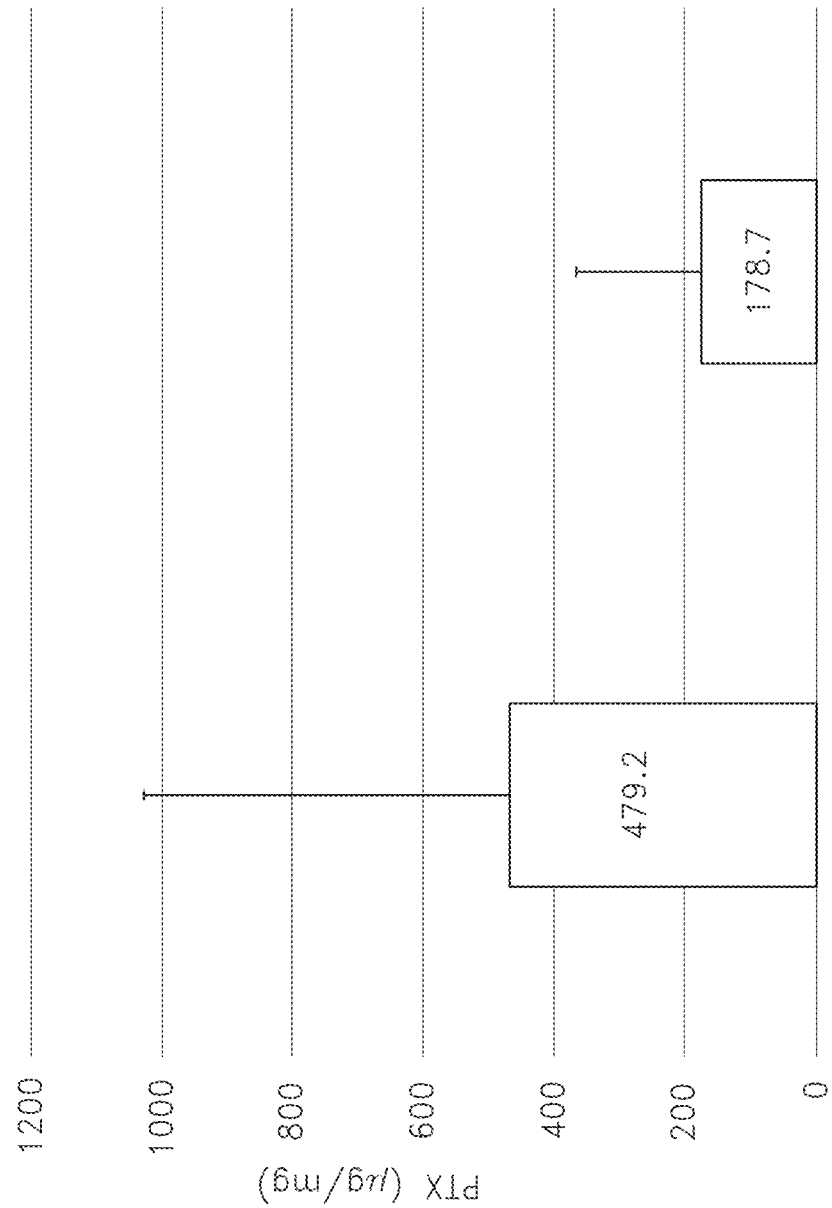

FIG. 28 illustrates an embodiment of a pleated balloon with strips and wedge dissectors in between pleats. FIGS. 28A and 28B illustrate drug retention data in tissue with serration systems followed by DCB vs. POBA followed by DCB.

FIG. 29 is an illustration of Tangential Stress of a cylinder with a known wall thickness and the simplified equation of Tangential Tension of a cylinder assuming no wall thickness.

Figure 30:
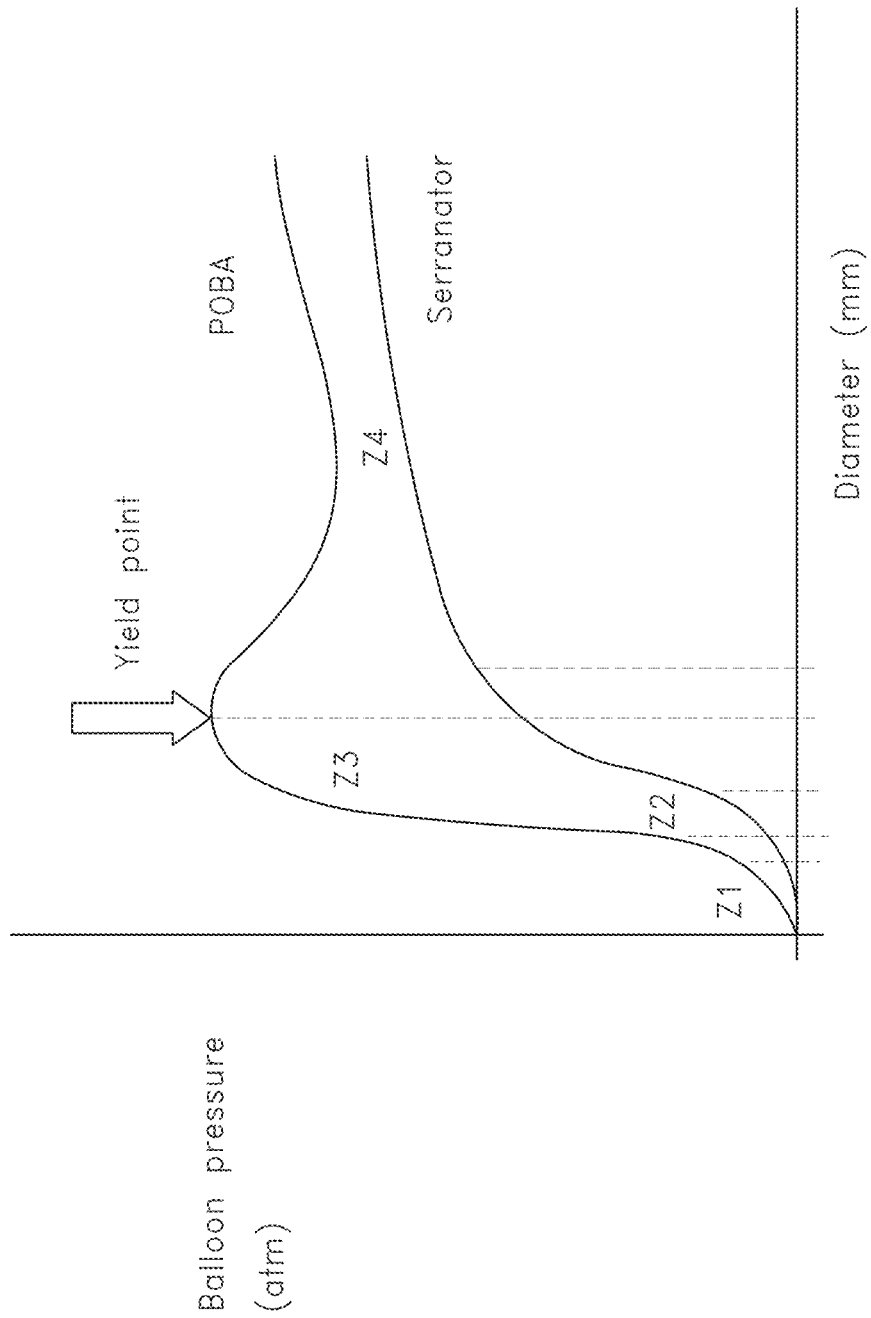

FIG. 30 illustrates balloon pressure vs. diameter enlargement.

Figure 31B:
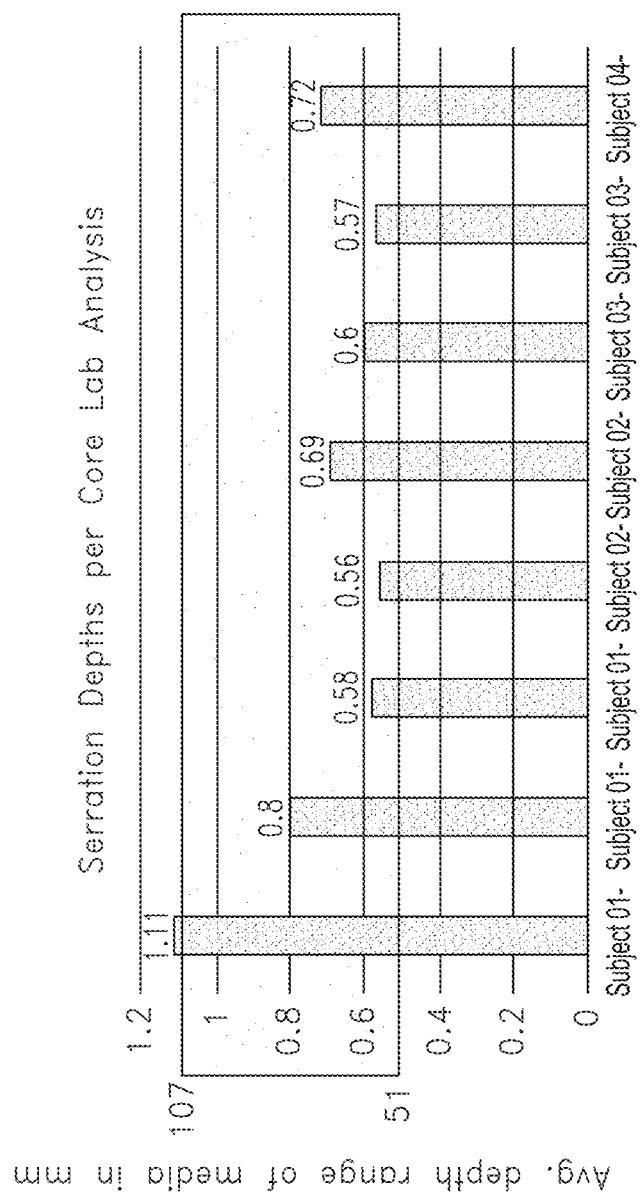
Figure 31C:
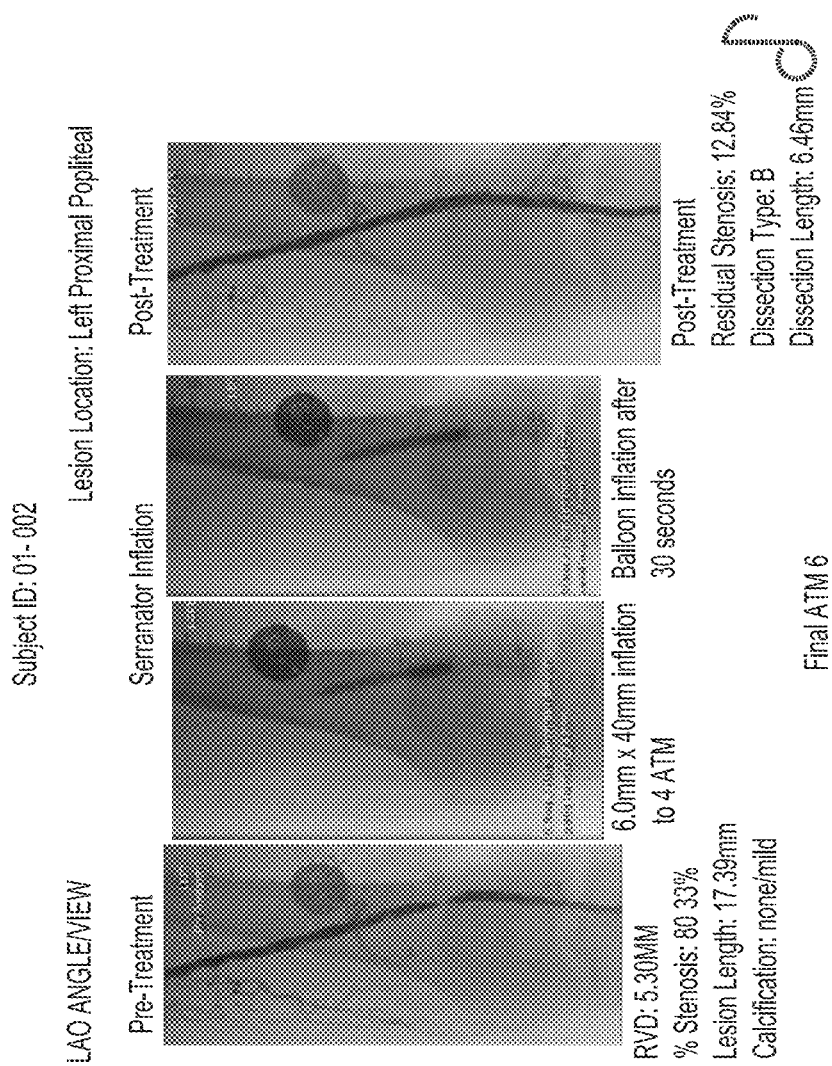

FIG. 31A illustrates that the tip does not contact the full surface of the crack generated by the tip. FIG. 31B illustrates the serrations were able to penetrate into the medial tissue in every patient that was examined with OCT imaging. FIG. 31C illustrates the waist when the balloon is inflated to 4 ATM in the left middle image. FIG. 31D illustrates an OCT image on the left showing intima dissection.

FIG. 32 illustrates an embodiment of a modified cutting balloon to produce serrations.

Figure 33:
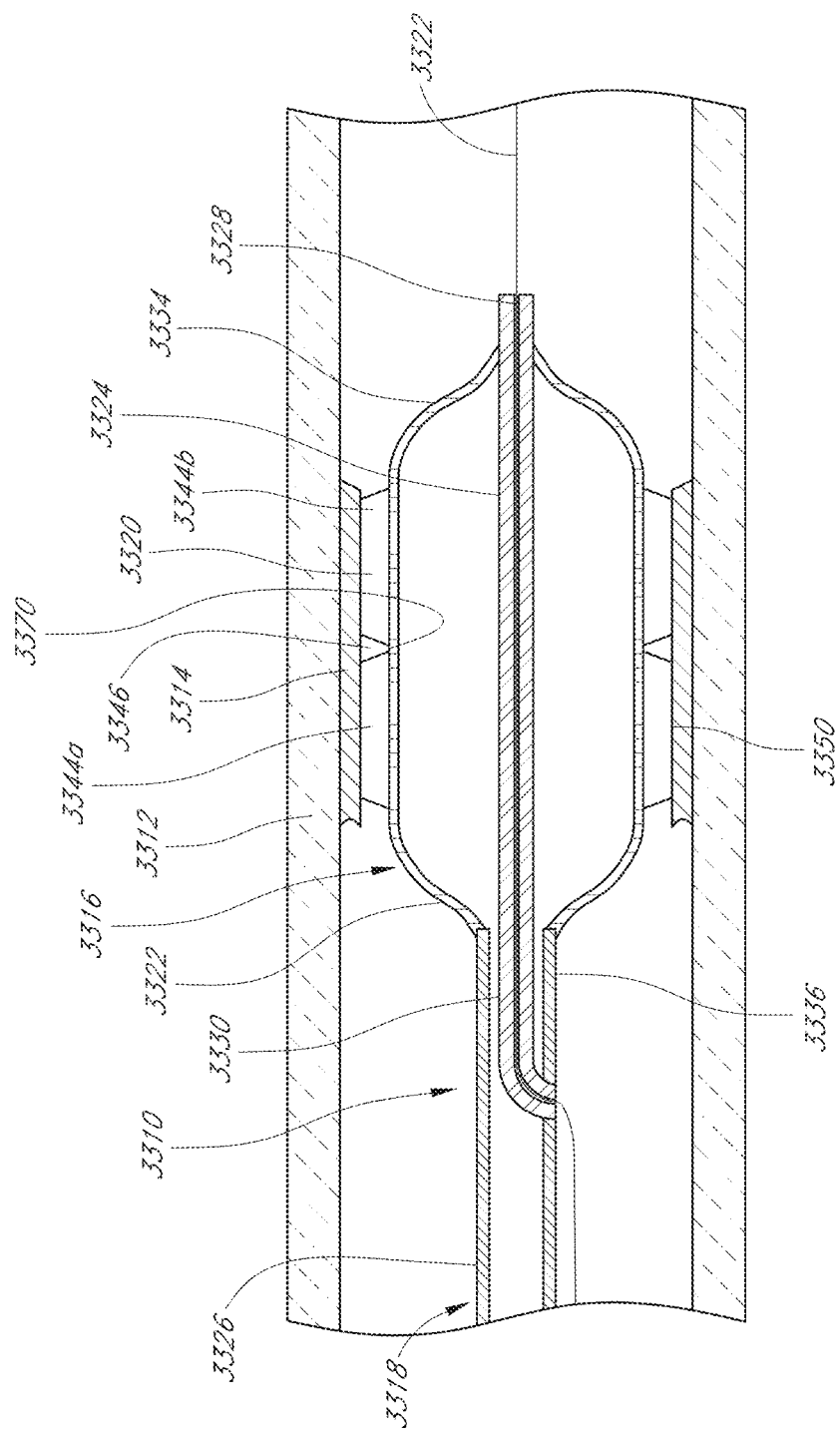
Figure 34F:
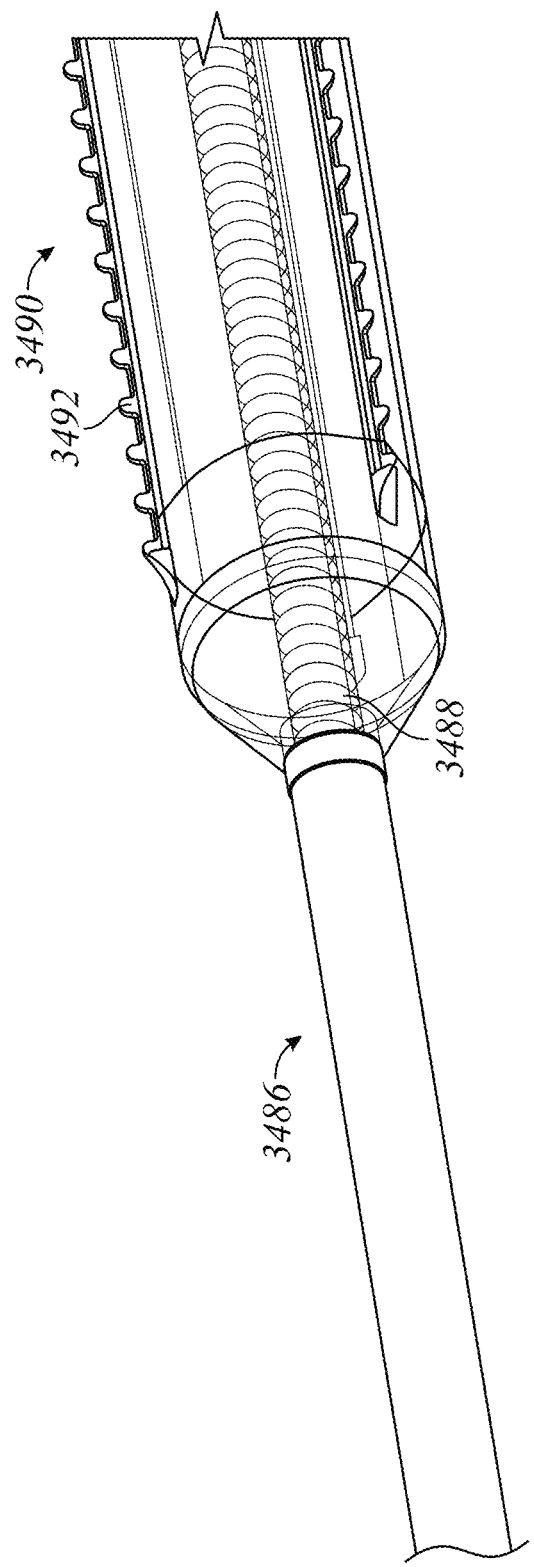
Figure 34G:
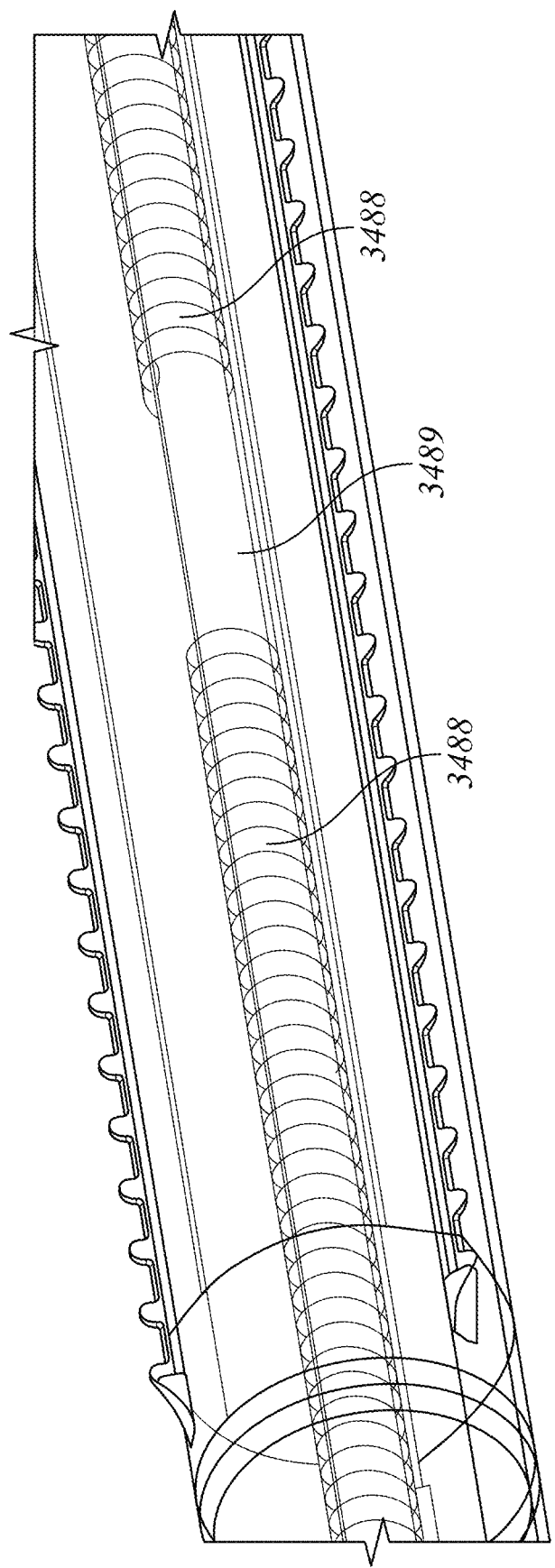
Figure 34H:
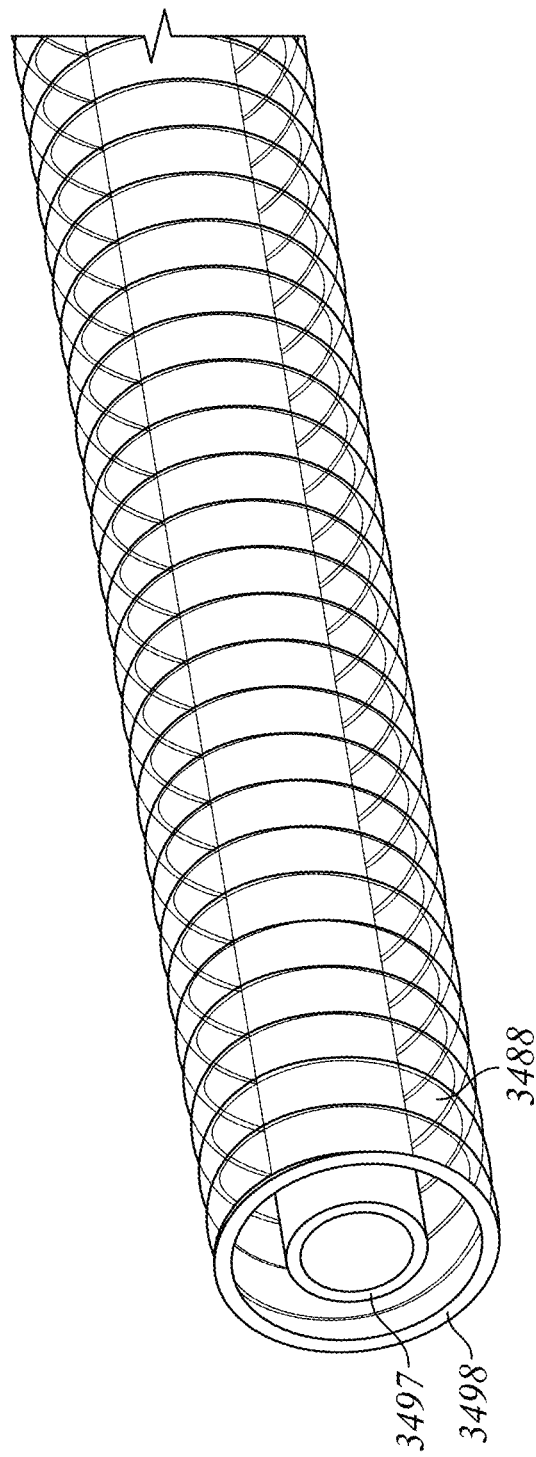
Figure 34I:
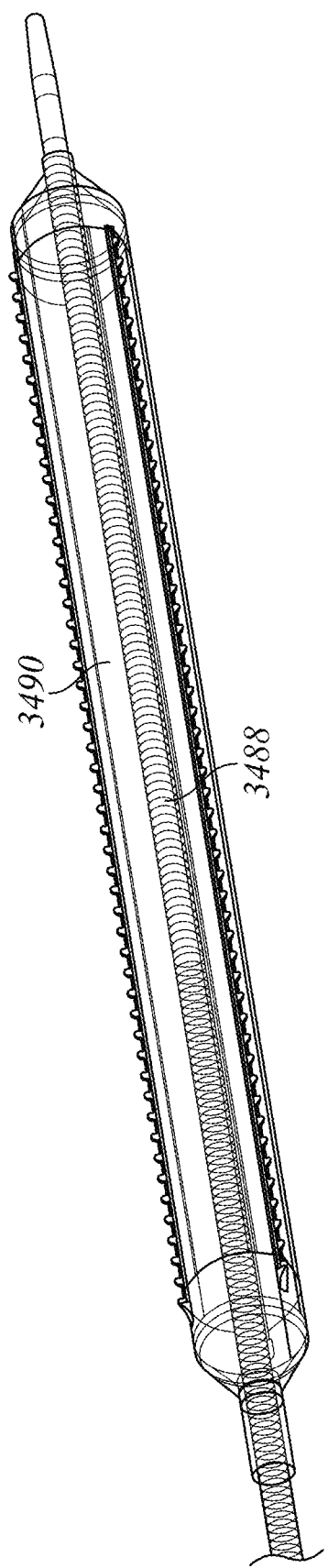
Figure 34J:
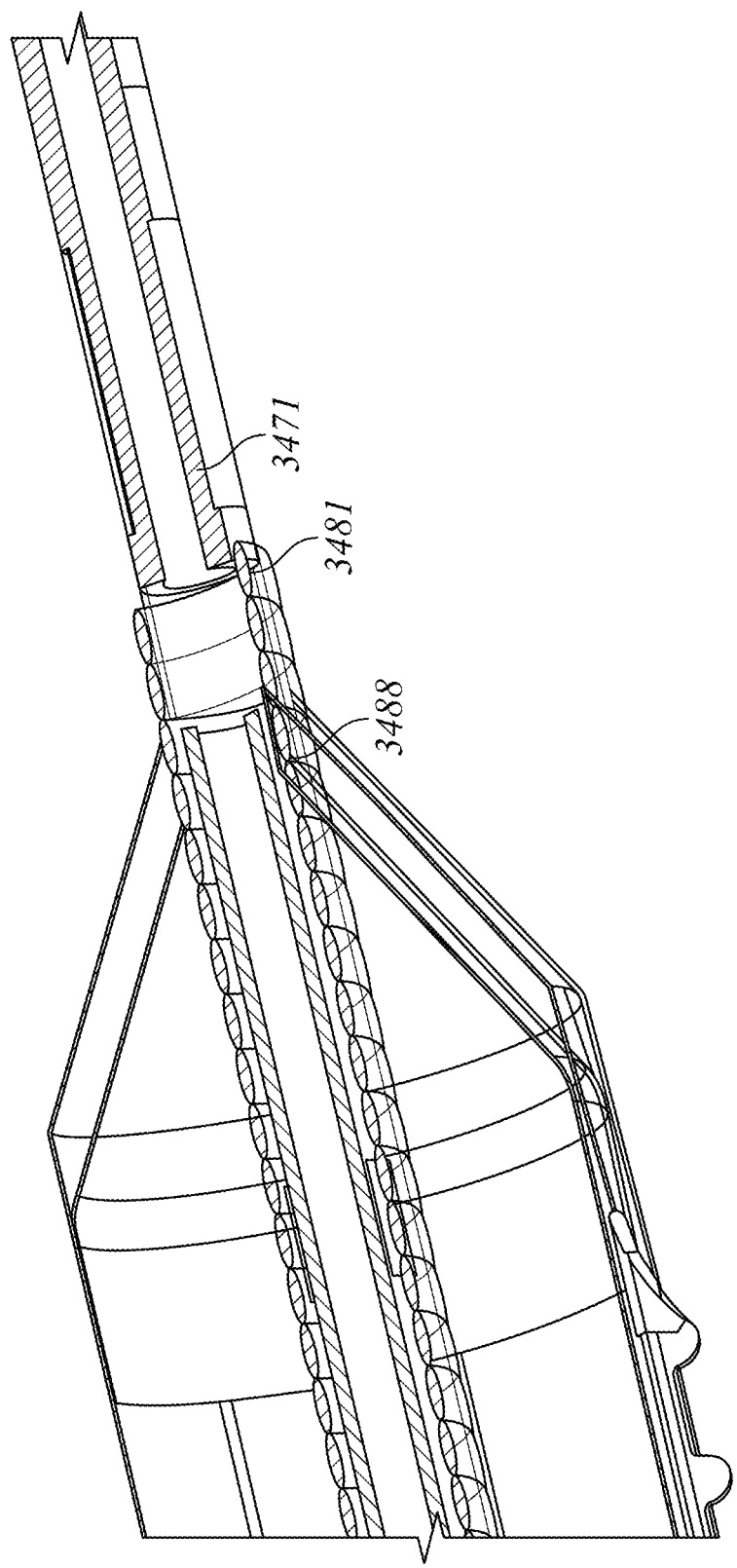
Figure 34K:
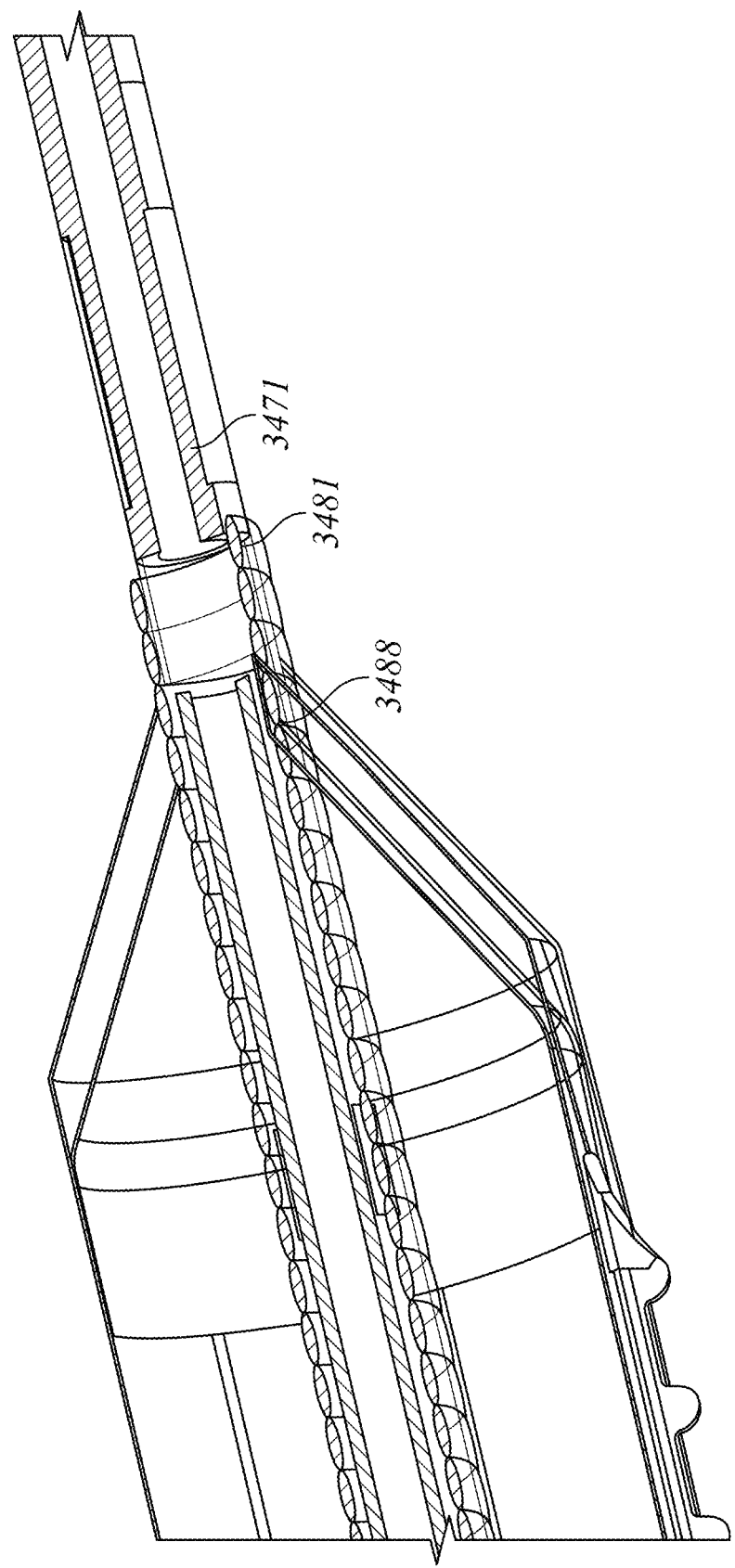
Figure 34L:
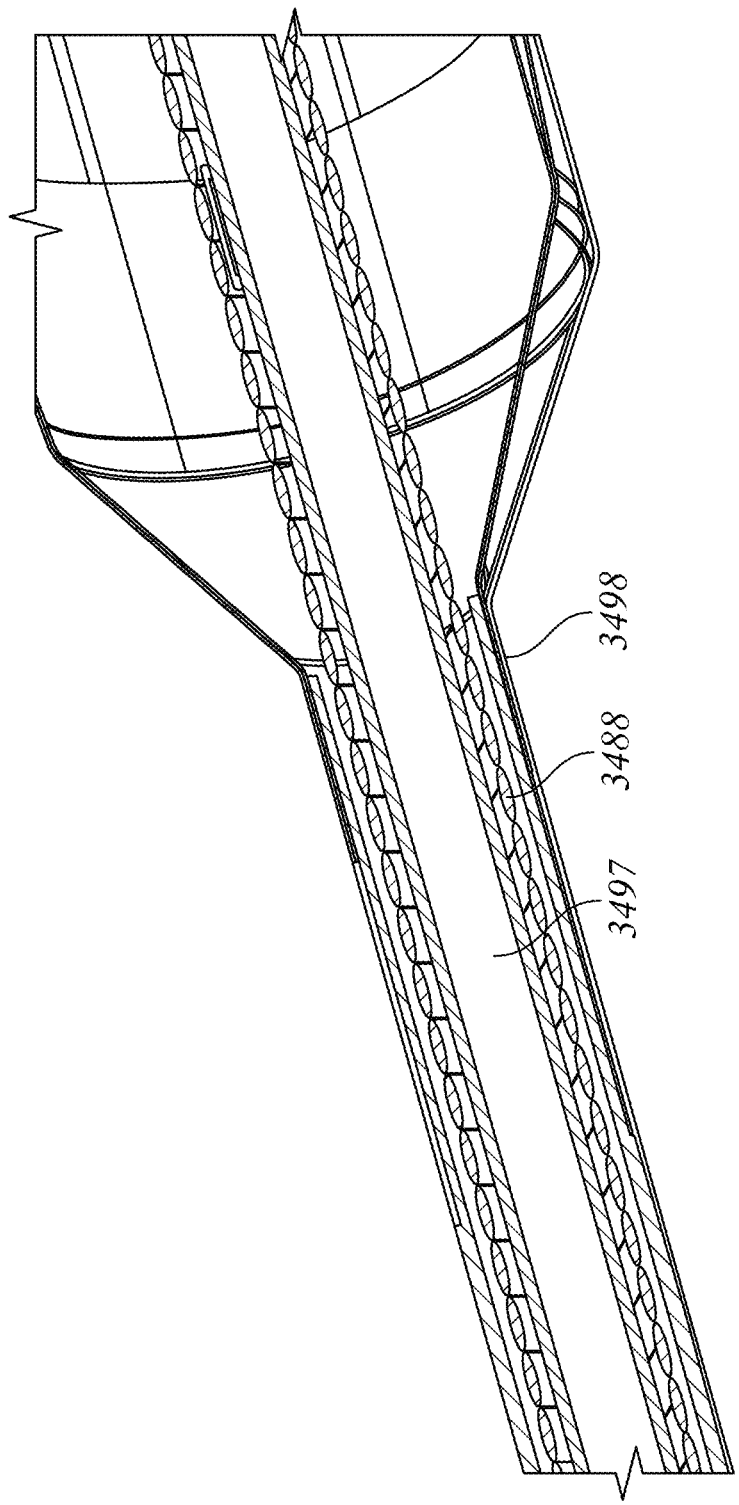
Figure 34M:
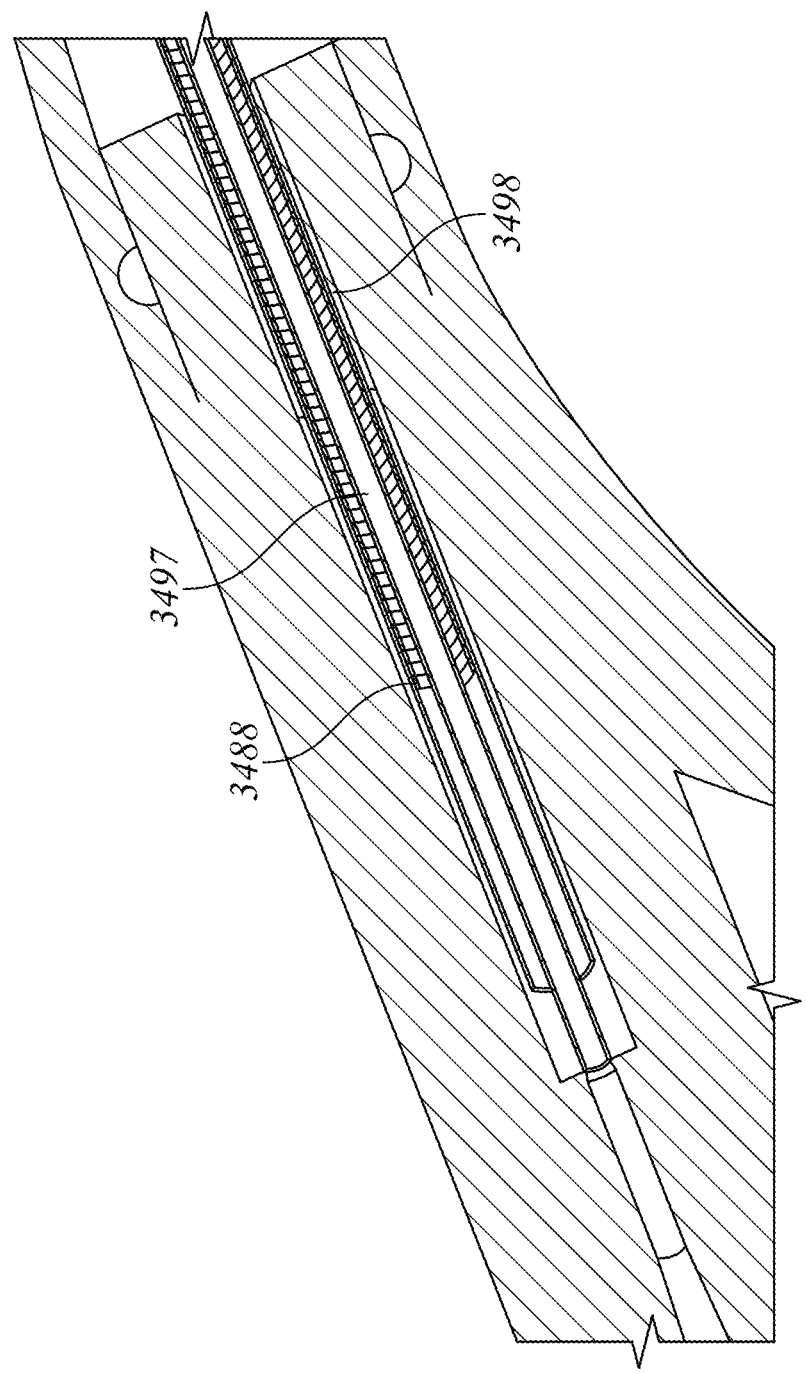

FIG. 33 shows an illustration of a modified cutting balloon where flexibility is further enhanced and the cutting is either completely or partially replaced with a serrated blade pattern FIGS. 34-34M illustrate embodiments of a catheter that can include a coil in the space between the outer catheter shaft and the inner member (guide wire shaft), as well as tortuous anatomy that can be navigated via the catheter.

Figure 34N:
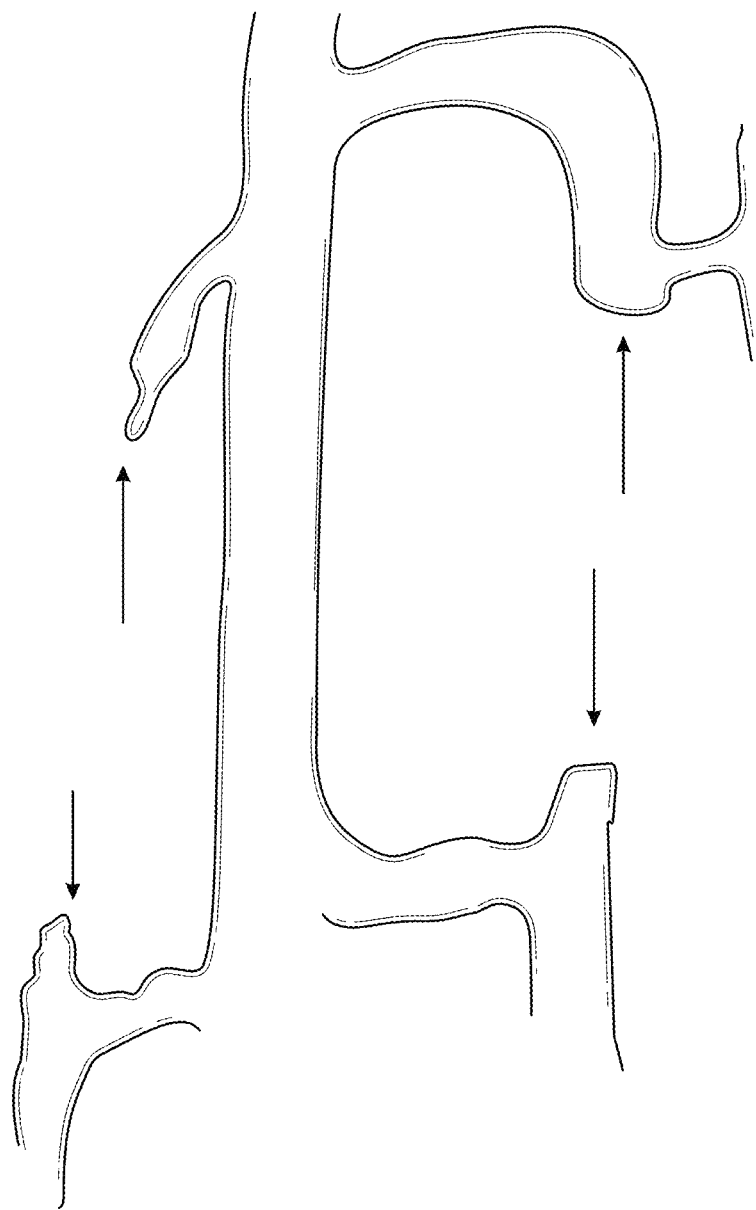

FIG. 34N illustrates a simplified view of the arteries in the tibia that typically occlude for long lengths. Occlusions of greater than 200 mm are not uncommon in the posterior and anterior tibial arteries.

Figure 34O:
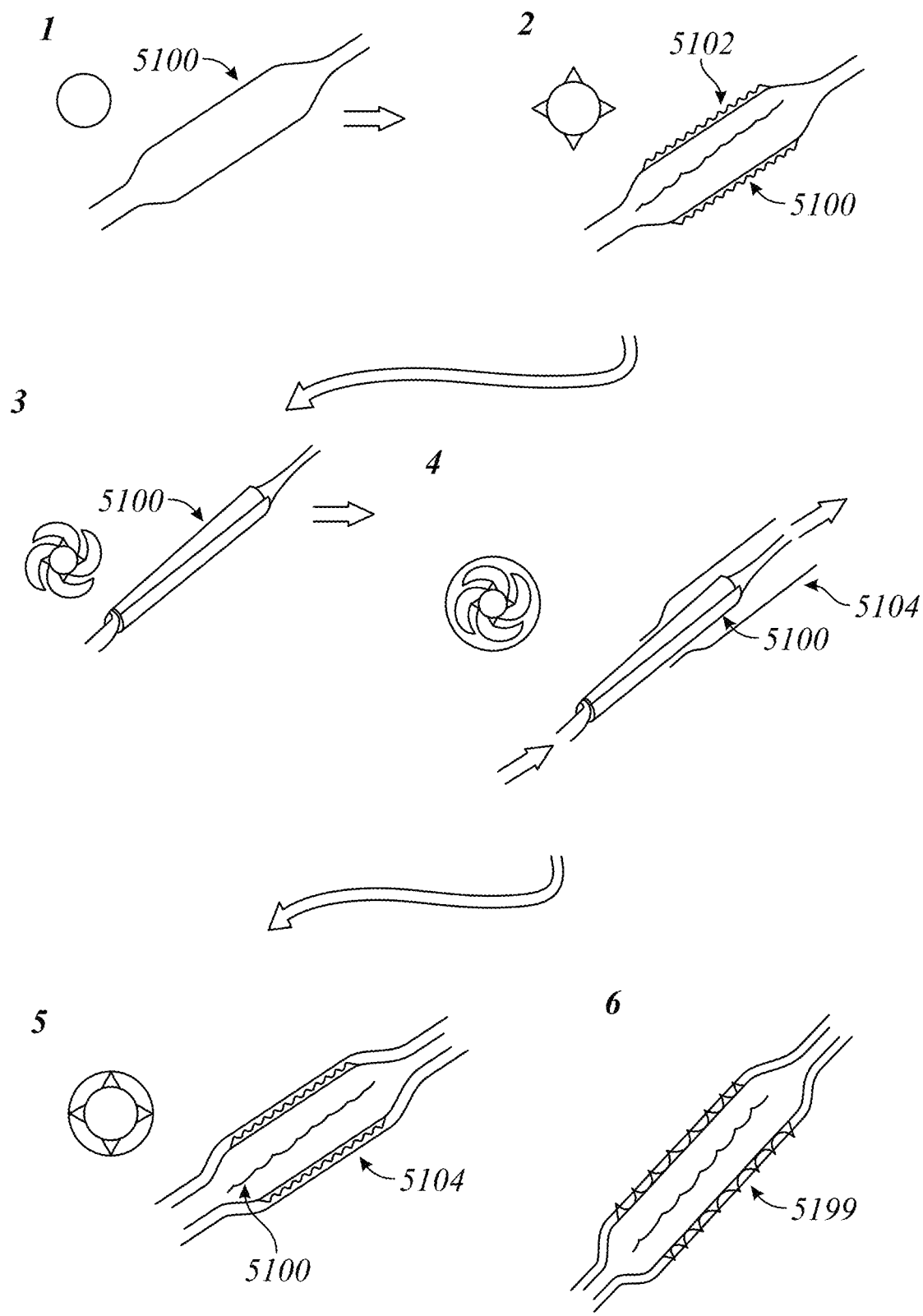

FIG. 34O illustrates schematically an embodiment of a method for producing a balloon-in-balloon design.

Figures 35A, 35B:
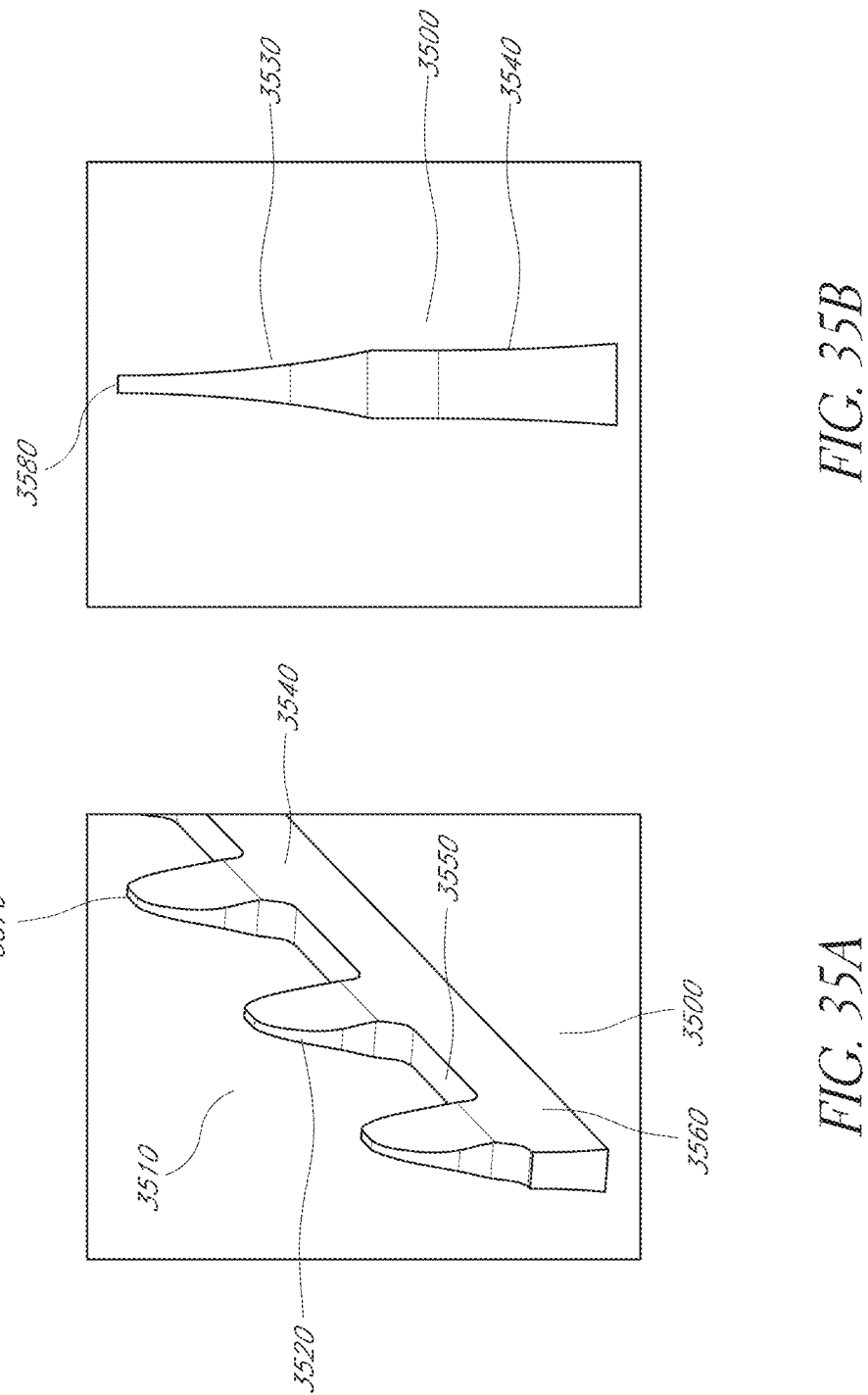

FIGS. 35A-B illustrates an embodiment of a strip with wedge dissectors where the wedge dissector has a sloped non-linear edges.

Figure 36:
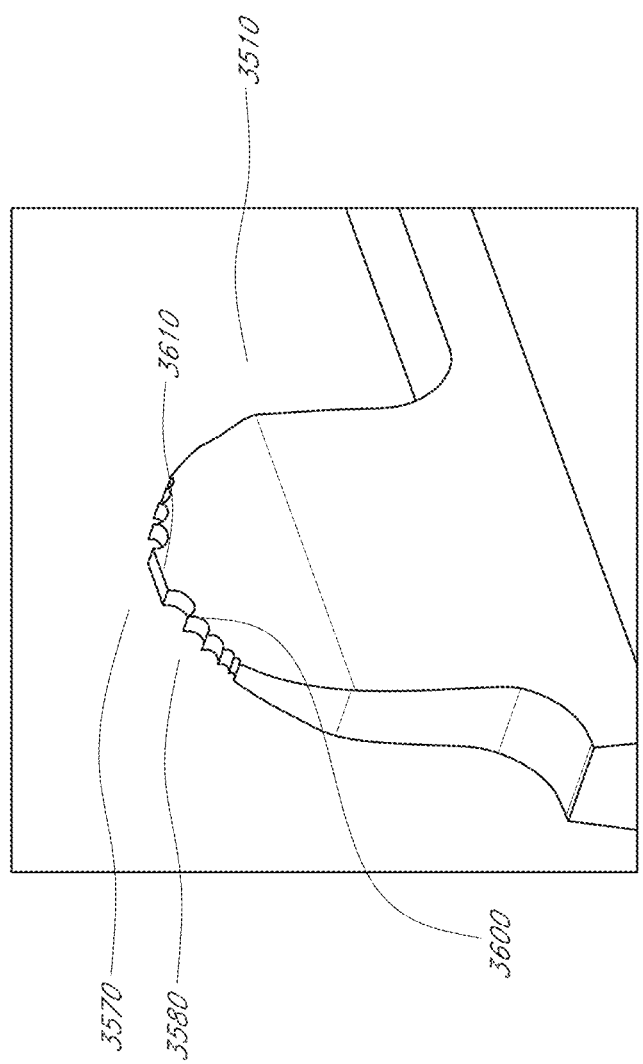

FIG. 36 illustrates the top of the wedge dissector can have a variety of the unique features on the tip (e.g., radially outward facing surface) that contacts the tissue.

Figure 37:
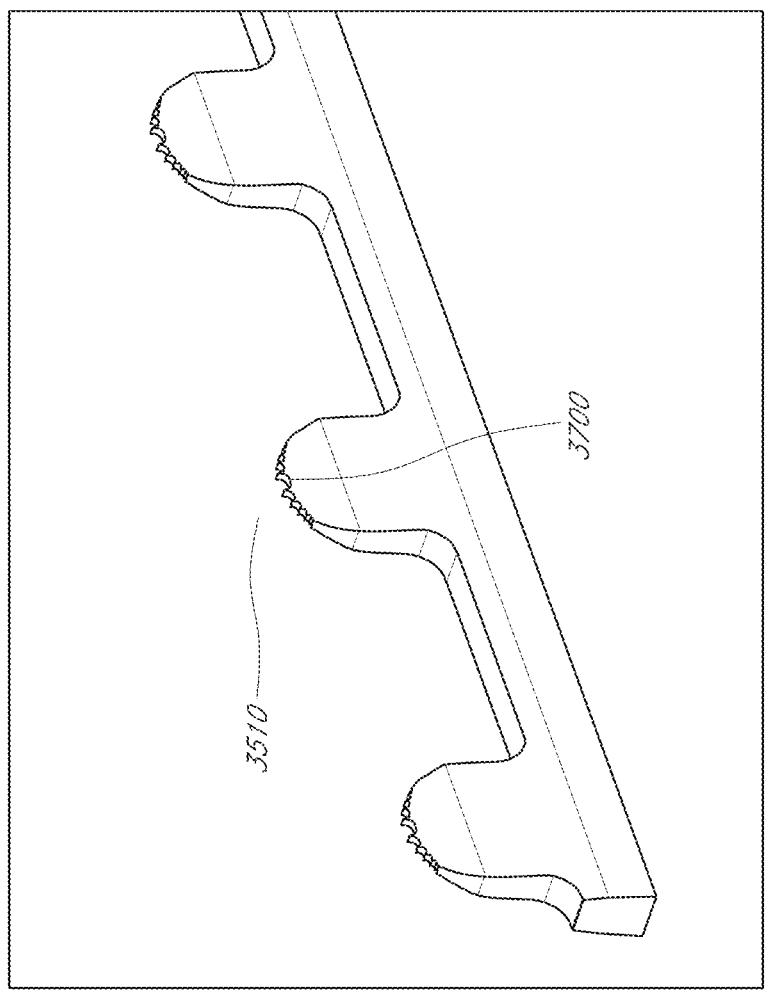

FIG. 37 is another design illustrating an alternate variation of the serrated edge of the wedge dissector, where the central segment can include a small depression as shown.

Figure 38:
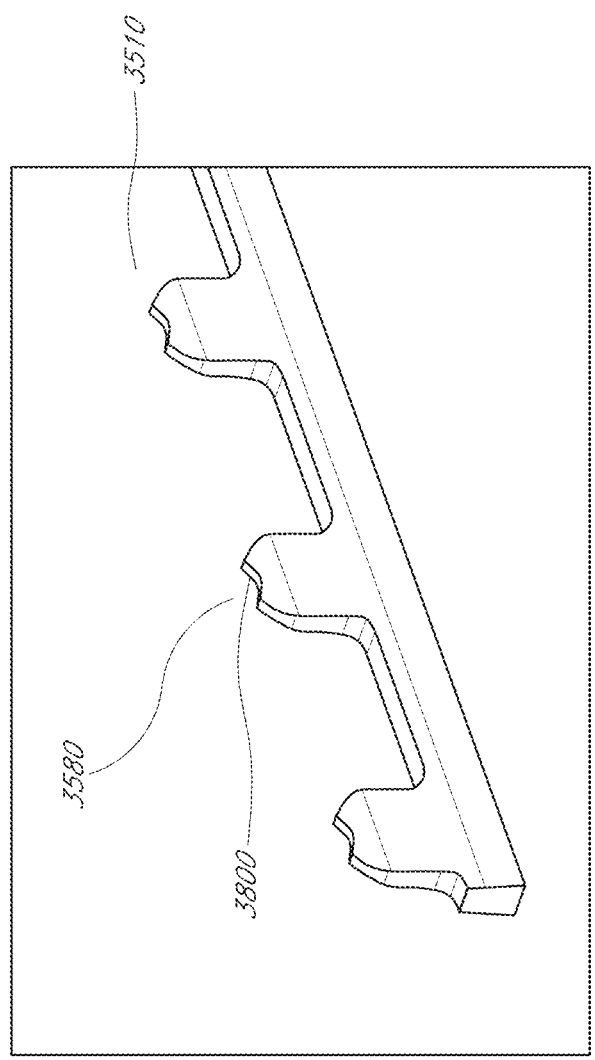

FIG. 38 illustrates the wedge dissectors having rounded double-hump like contacting surfaces at the tip that can provide effective tissue penetration.

Figure 39:
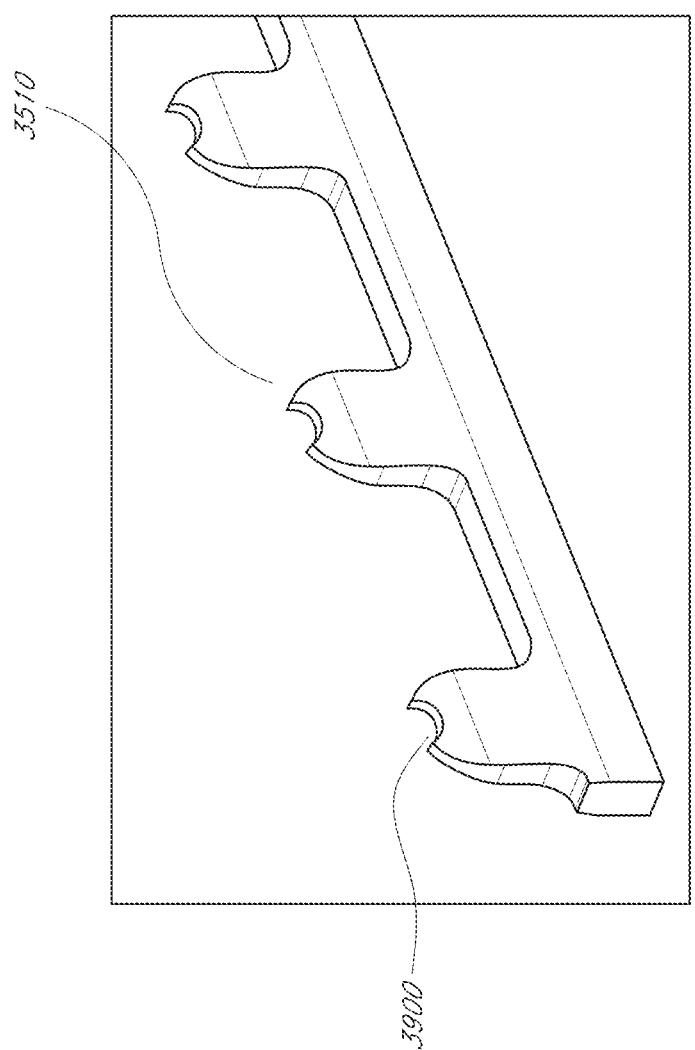

FIG. 39 illustrates variations on a design that provides a relatively sharp, pointed double contacting surface at the tip of each wedge dissector providing effective tissue penetration.

Figure 40:
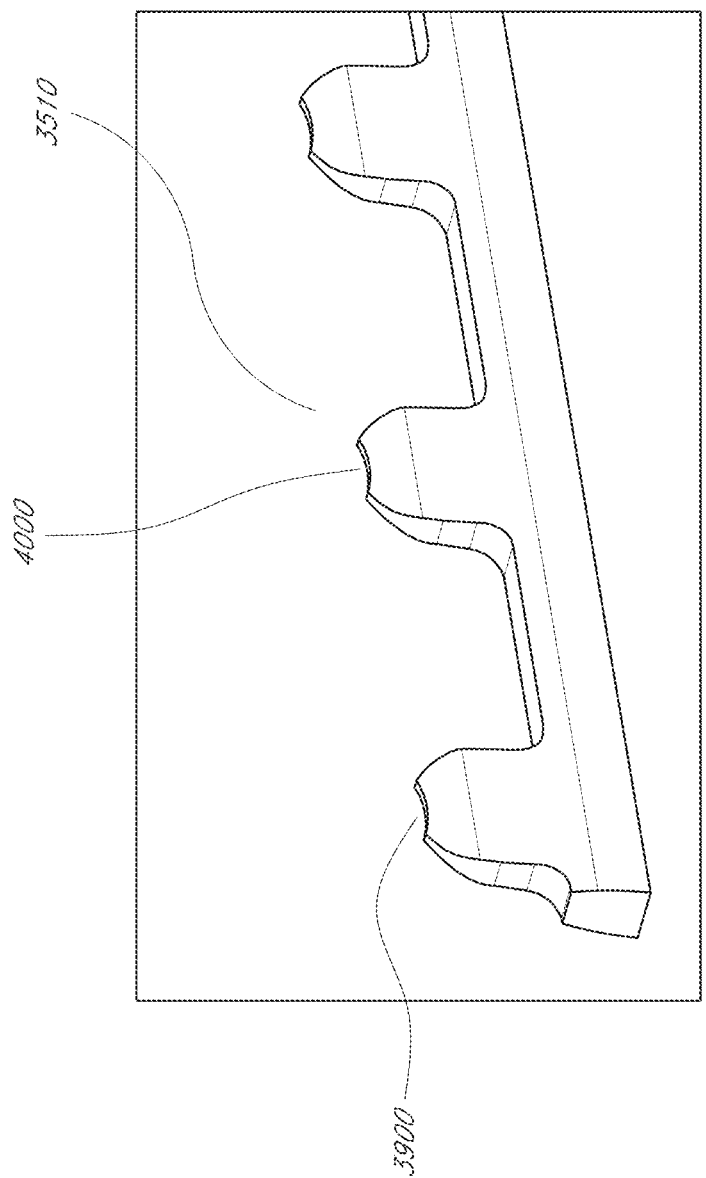

FIG. 40 illustrates a similar design that provides a relatively sharp, pointed double contacting surface at the tip of each wedge dissector which provides effective tissue penetration, that abut a central deeper, and more shallow valley/depression respectively.

Figure 41A:
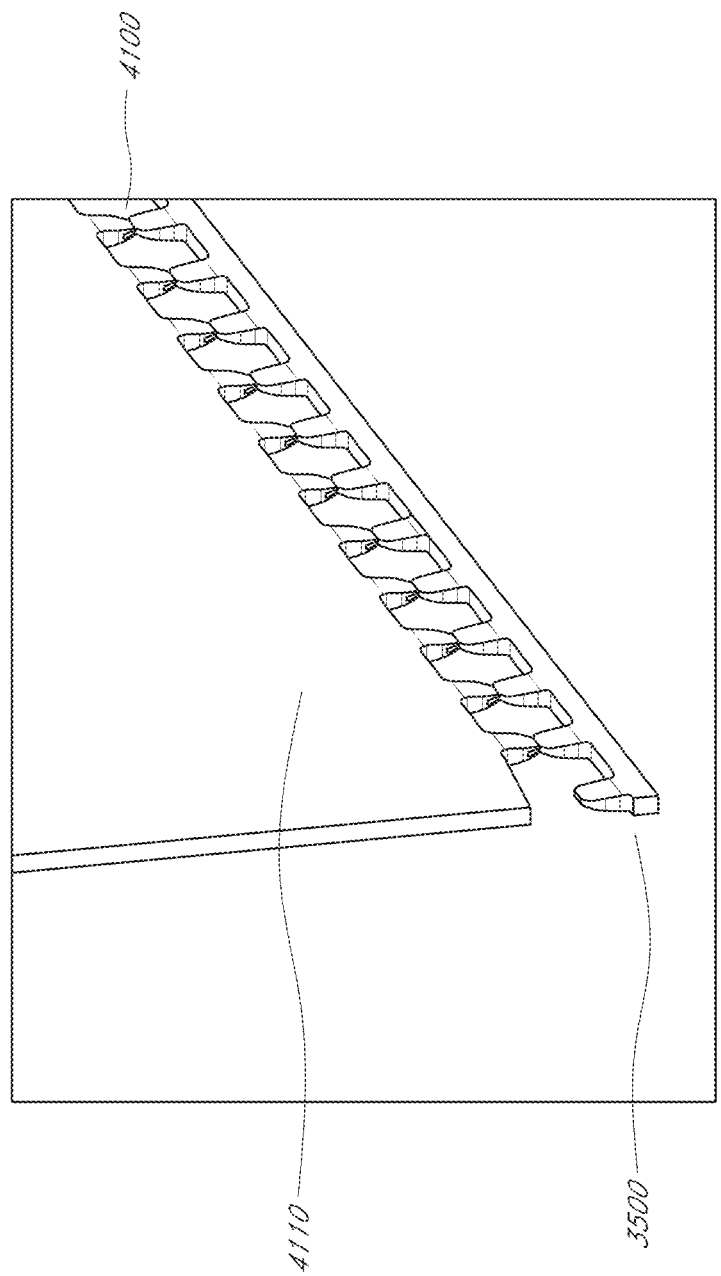

FIG. 41A illustrates that a strip can be fabricated that includes a plurality of strips (e.g., two identical strips) touching tip to tip in a wedge dissector frame.

FIGS. 41B and 41C illustrate that in some embodiments, a plurality of strips can be bent or folded over into a bent form.

Figure 41E:
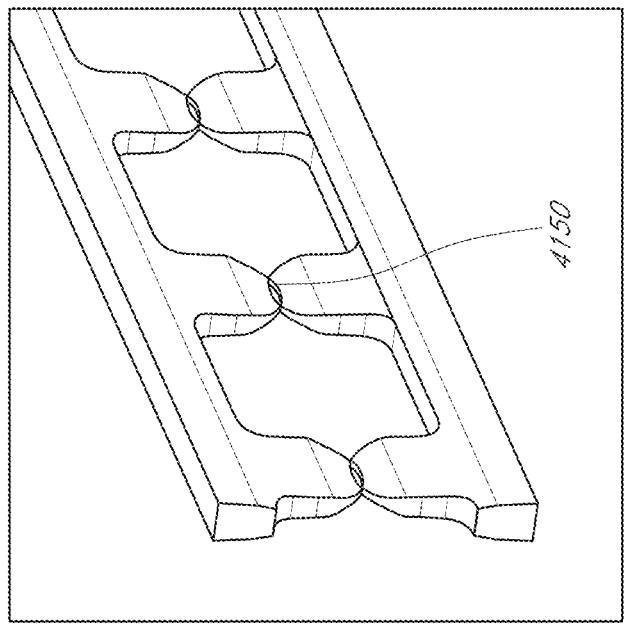
Figure 41D:
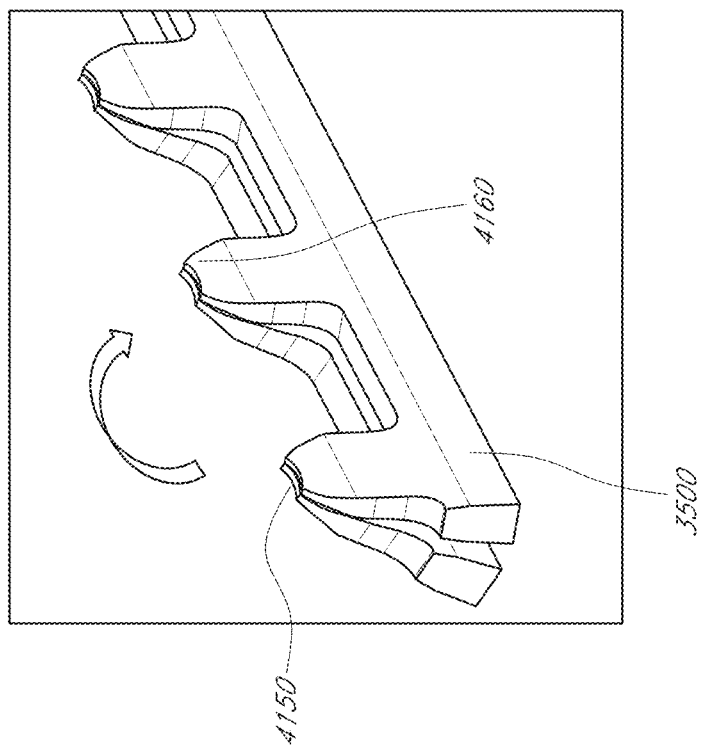

FIGS. 41D and 41E illustrate an alternative embodiment with serrated tips that include a plurality of pointed surfaces with a central concave segment there between.

FIG. 42 illustrates an illustration series that shows the ability to take a stack of strips connected to a blank that can be discarded at any point in the strip attachment process. The radial distal tips are abutted against continuous edge for easy breaking off.

Figure 43:
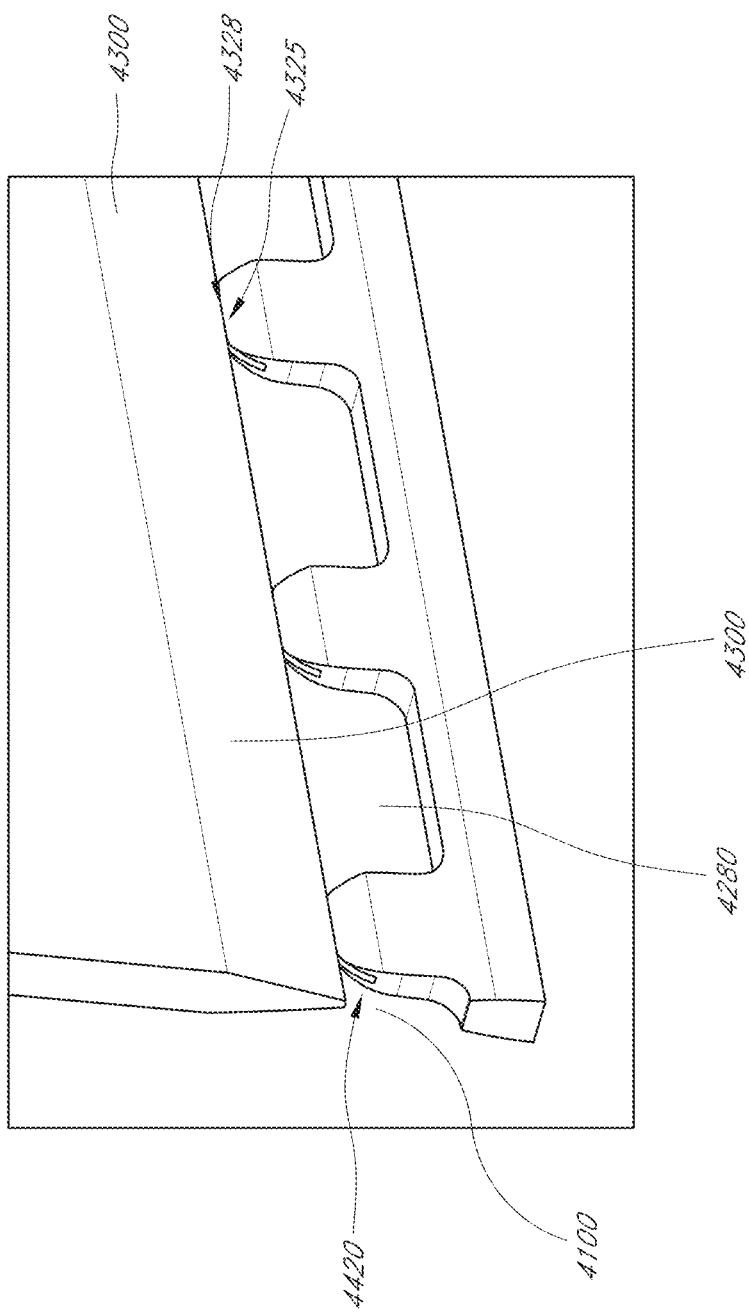

FIG. 43 illustrates an embodiment of a close-up drawing of the attachment of the strip tip to the blank.

Figure 44A:
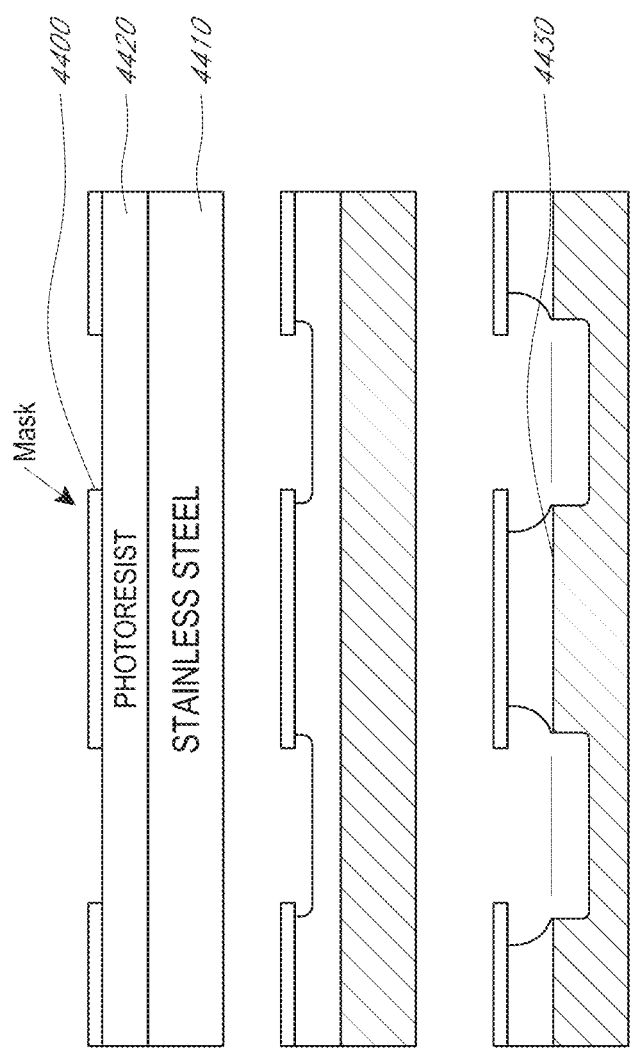
Figure 44B:
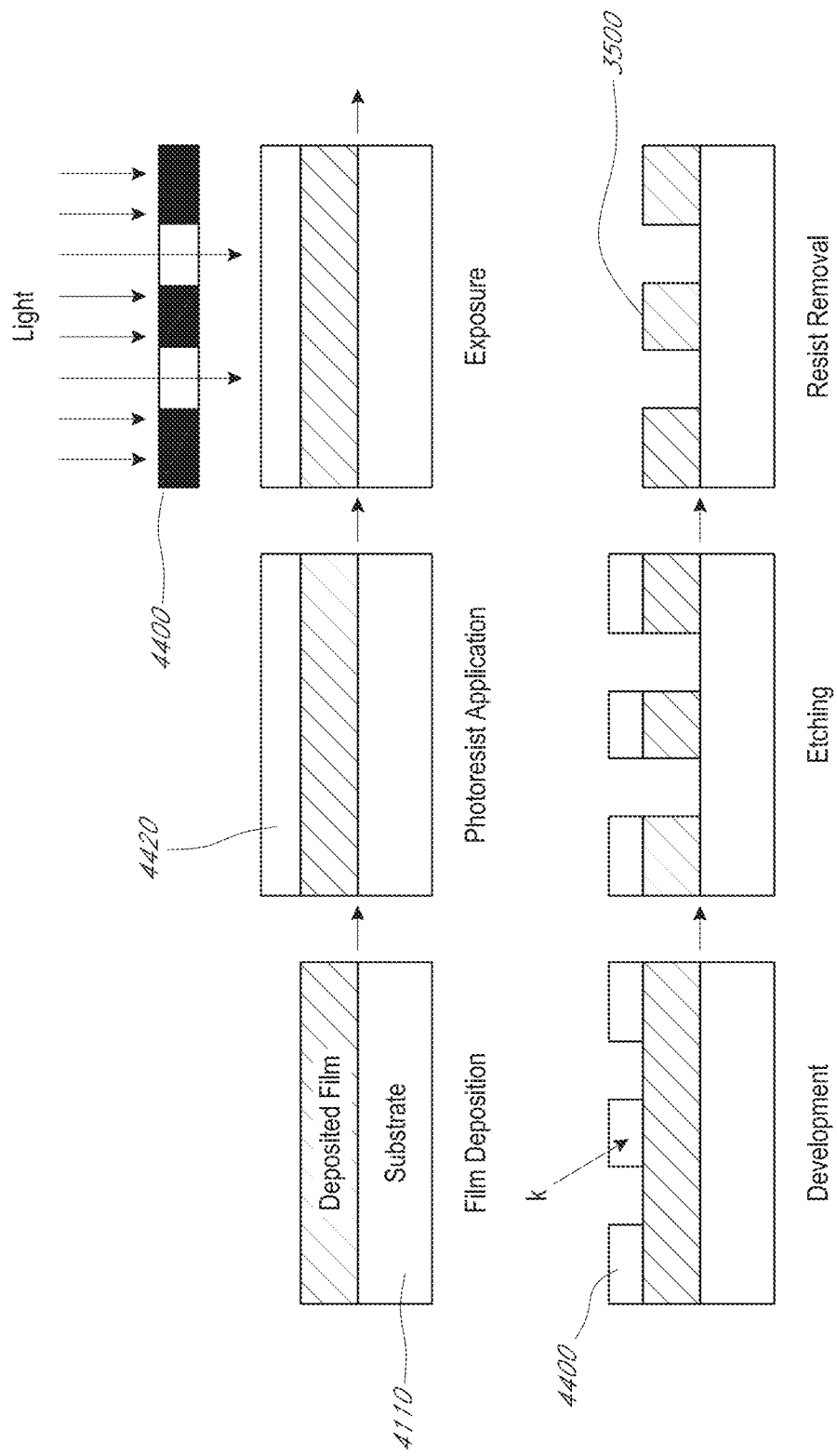

FIGS. 44A and 44B illustrate an isotropic etching where the etch occurs in more than one direction (both vertically and horizontally under the mask).

Figure 46:
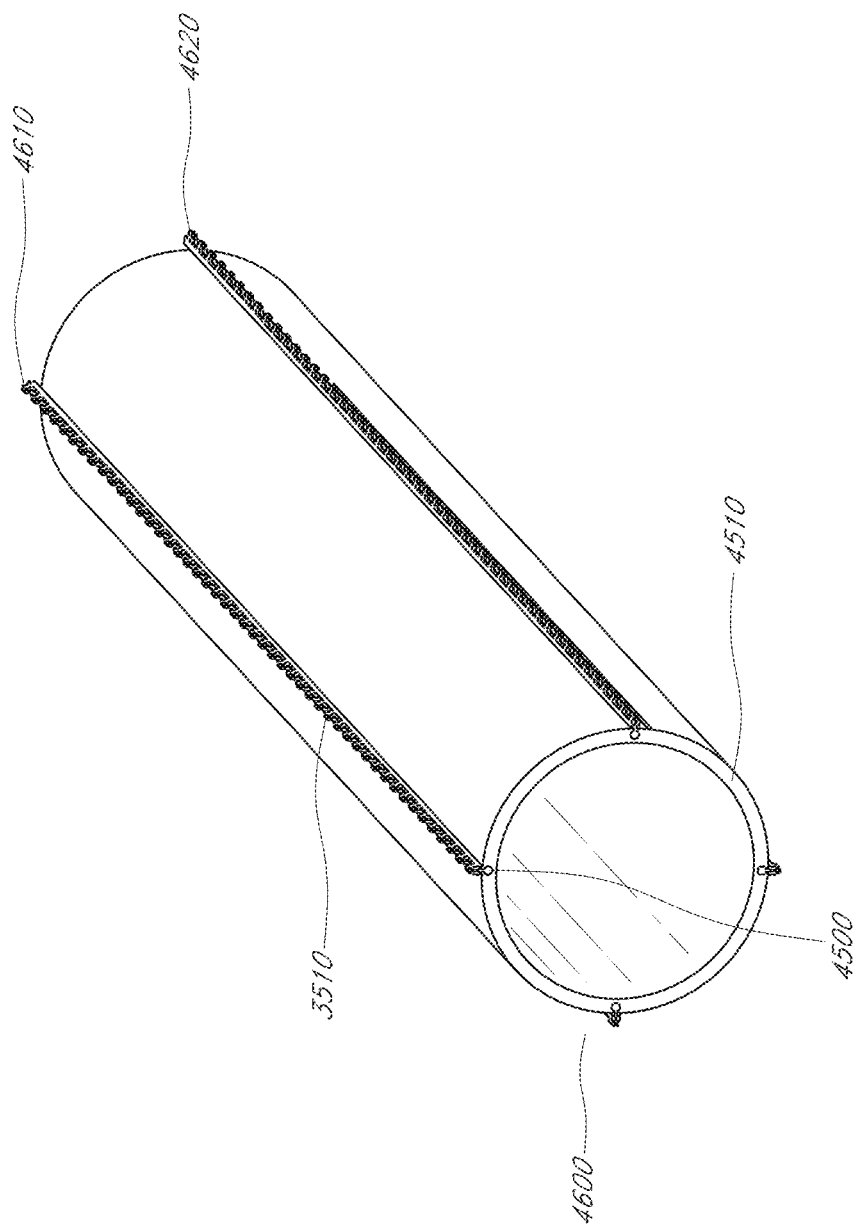

FIG. 45A shows the strip can be placed over a through hole embedded in the balloon. FIG. 45B shows the strip can be placed over a through hole embedded in the balloon wall FIG. 46 illustrates in some embodiments, a series of 4 A-frame strips can be placed over through holes embedded in the balloon wall.

Figure 47:
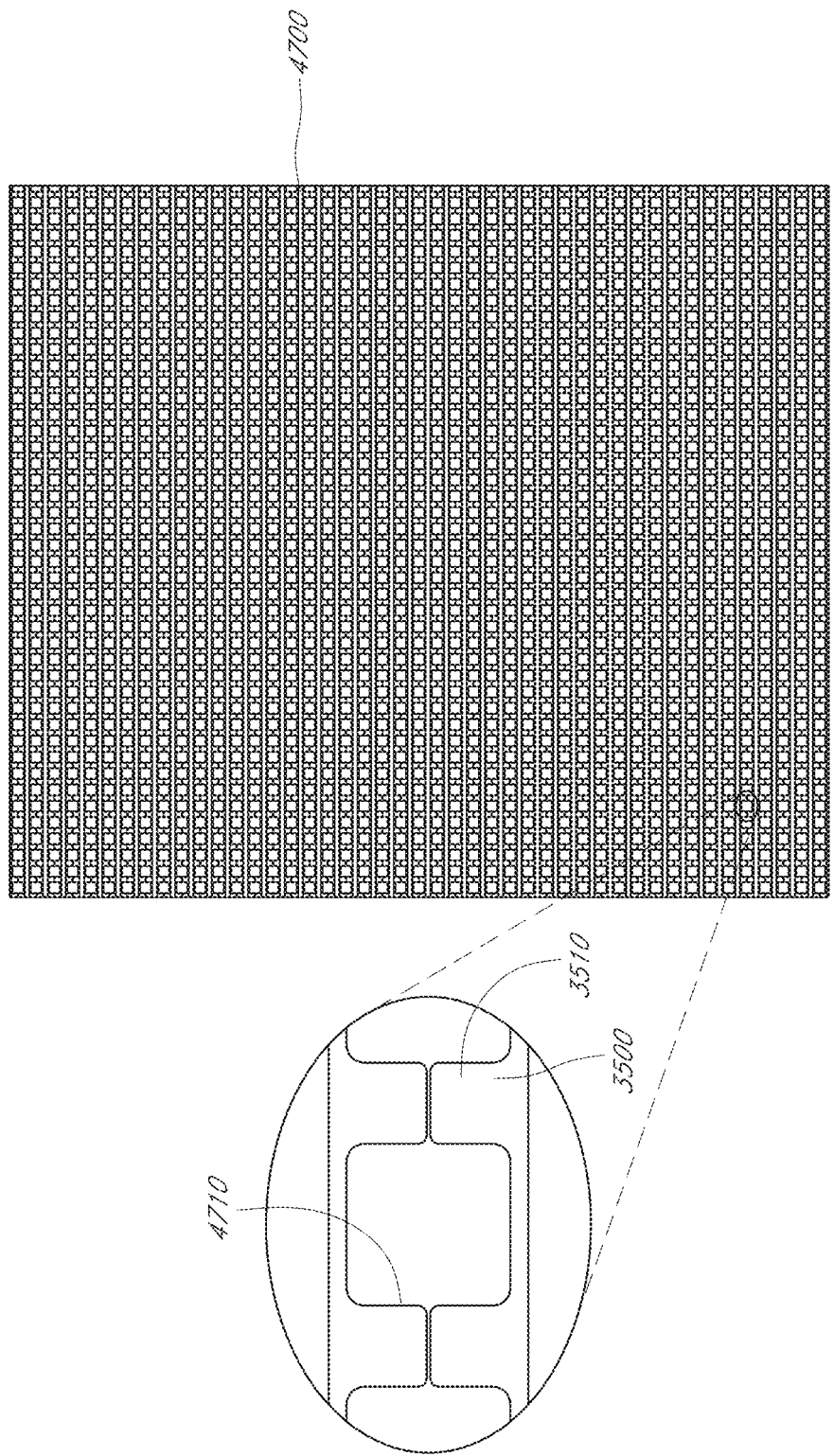

FIG. 47 illustrates an embodiment (with a close-up insert) of what an array of strips might look like on a mask set prior to chemical etching.

Figure 48B:
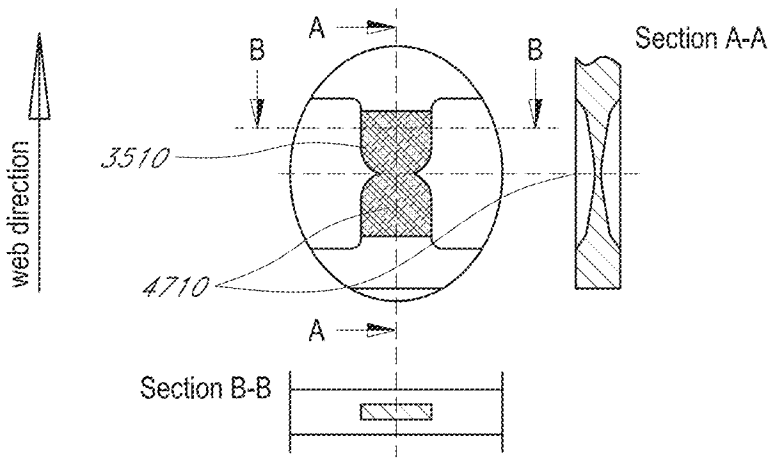
Figure 48A:
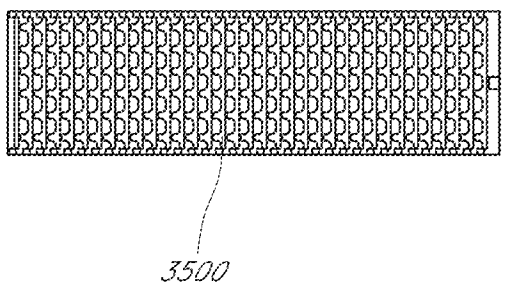
Figure 48C:
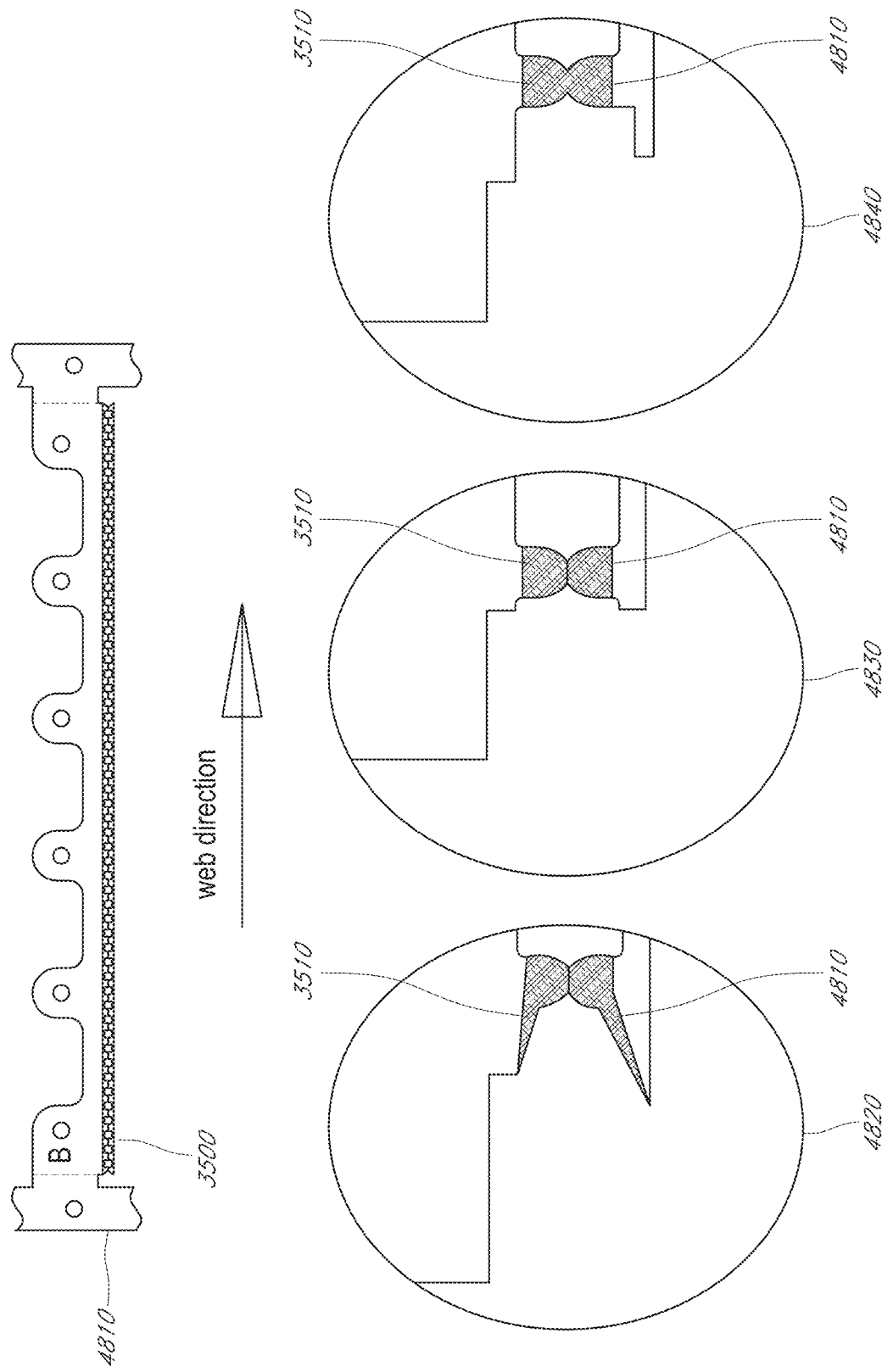
Figure 48D:
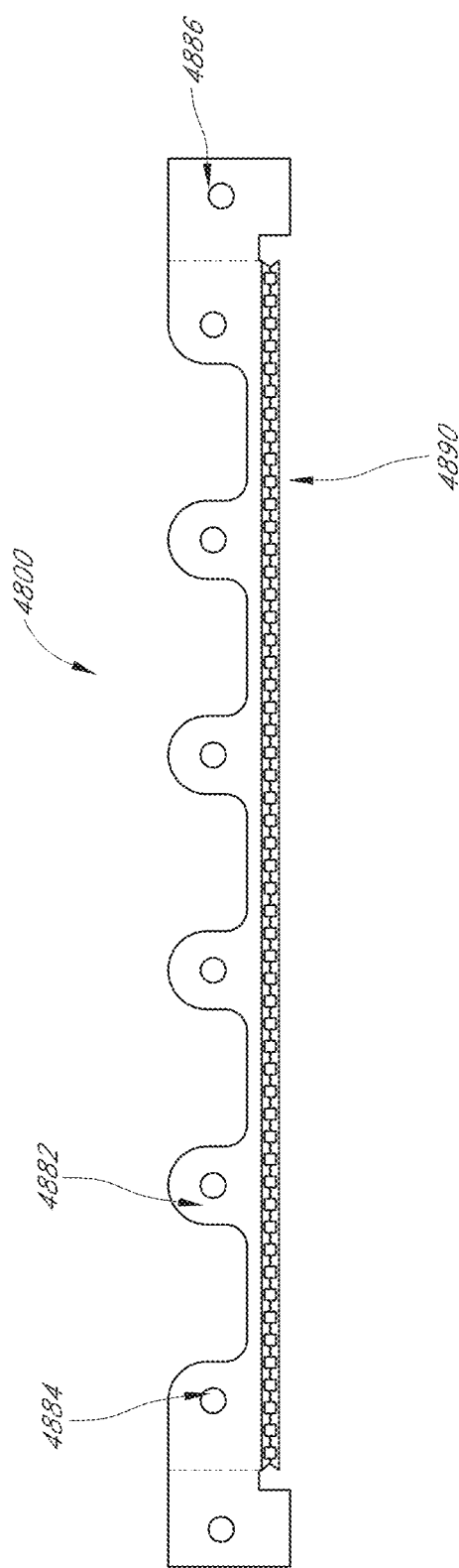

FIG. 48a shows a strip array. FIG. 48b shows a detailed close up image of the adjacent wedge dissectors with detachable zones. FIG. 48c shows serration strips connected to a strip carrier for alignment, control, placement, and ease of manufacturing. FIG. 48d illustrates an embodiment of a strip carrier reversibly attached to a strip.

Figure 49:
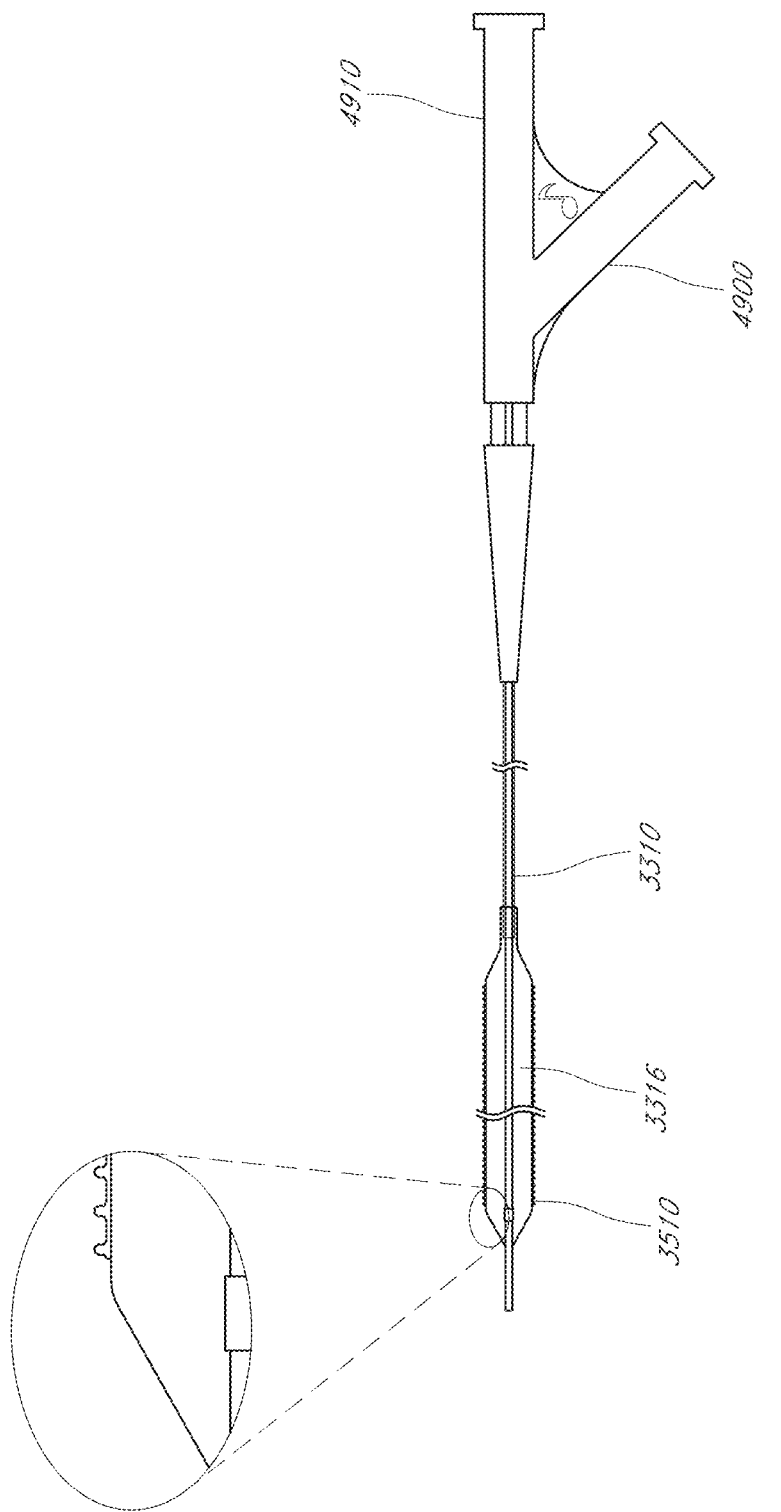
Figure 49A:
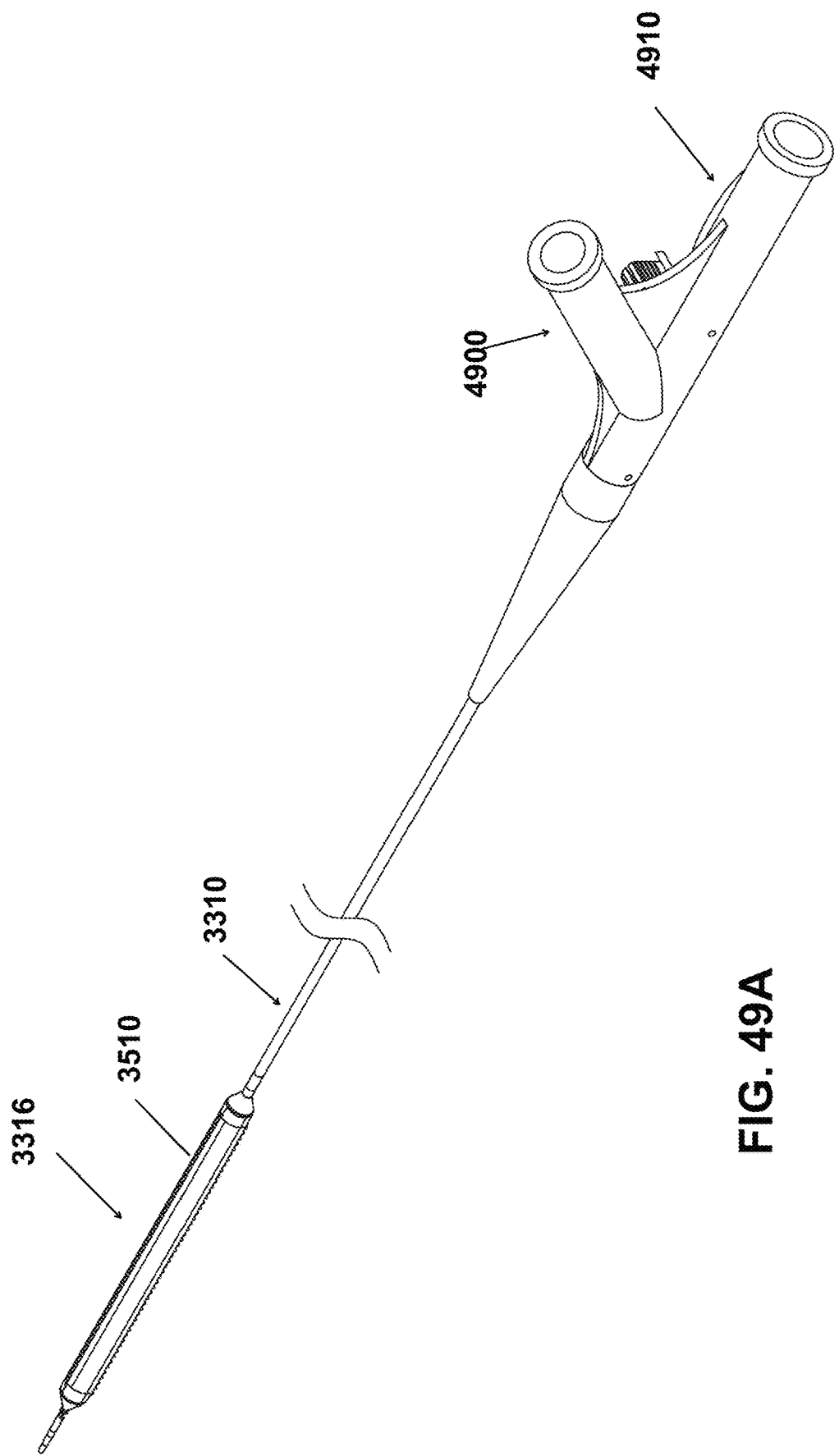
Figure 49B:
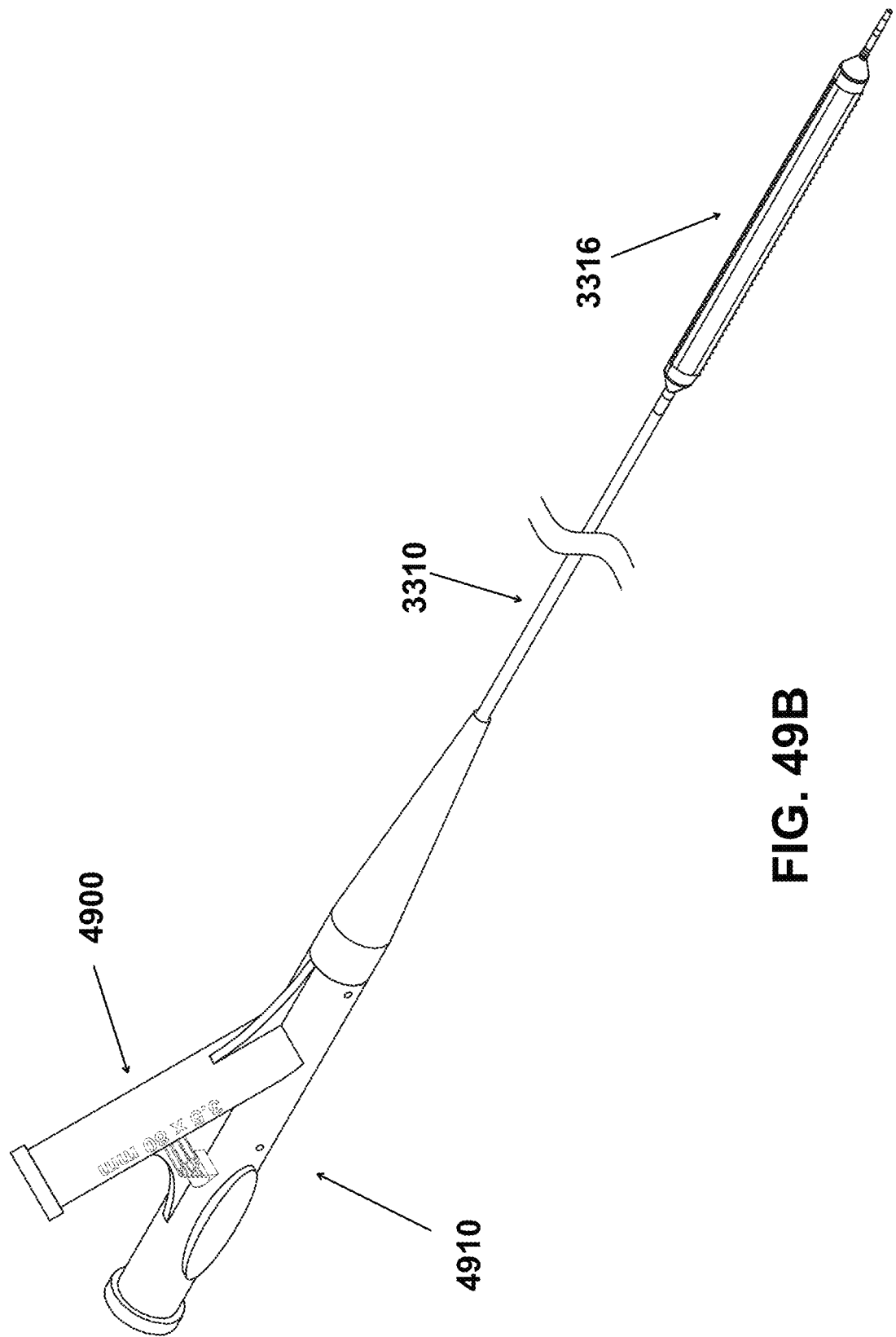
Figure 49C:
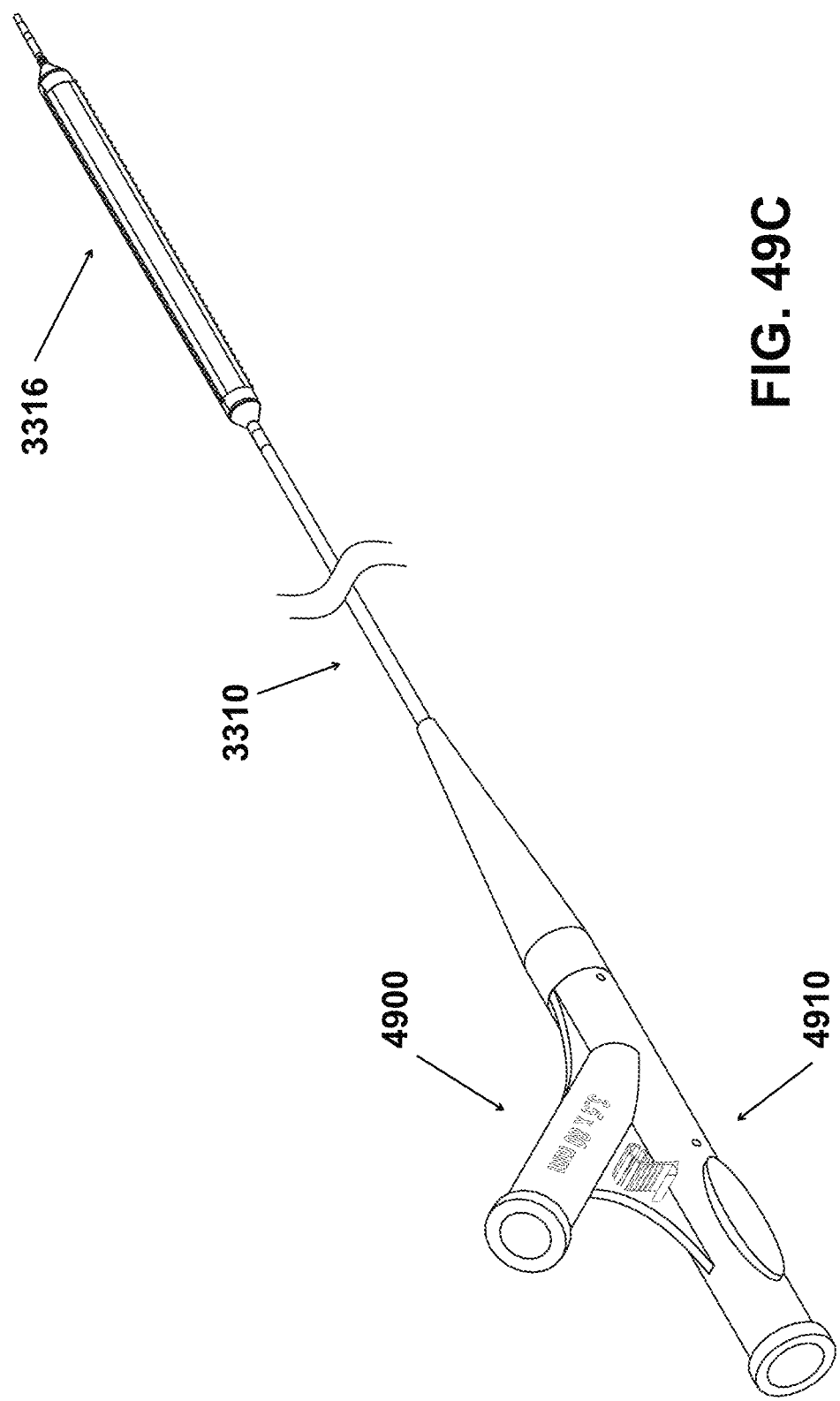
Figure 49D:
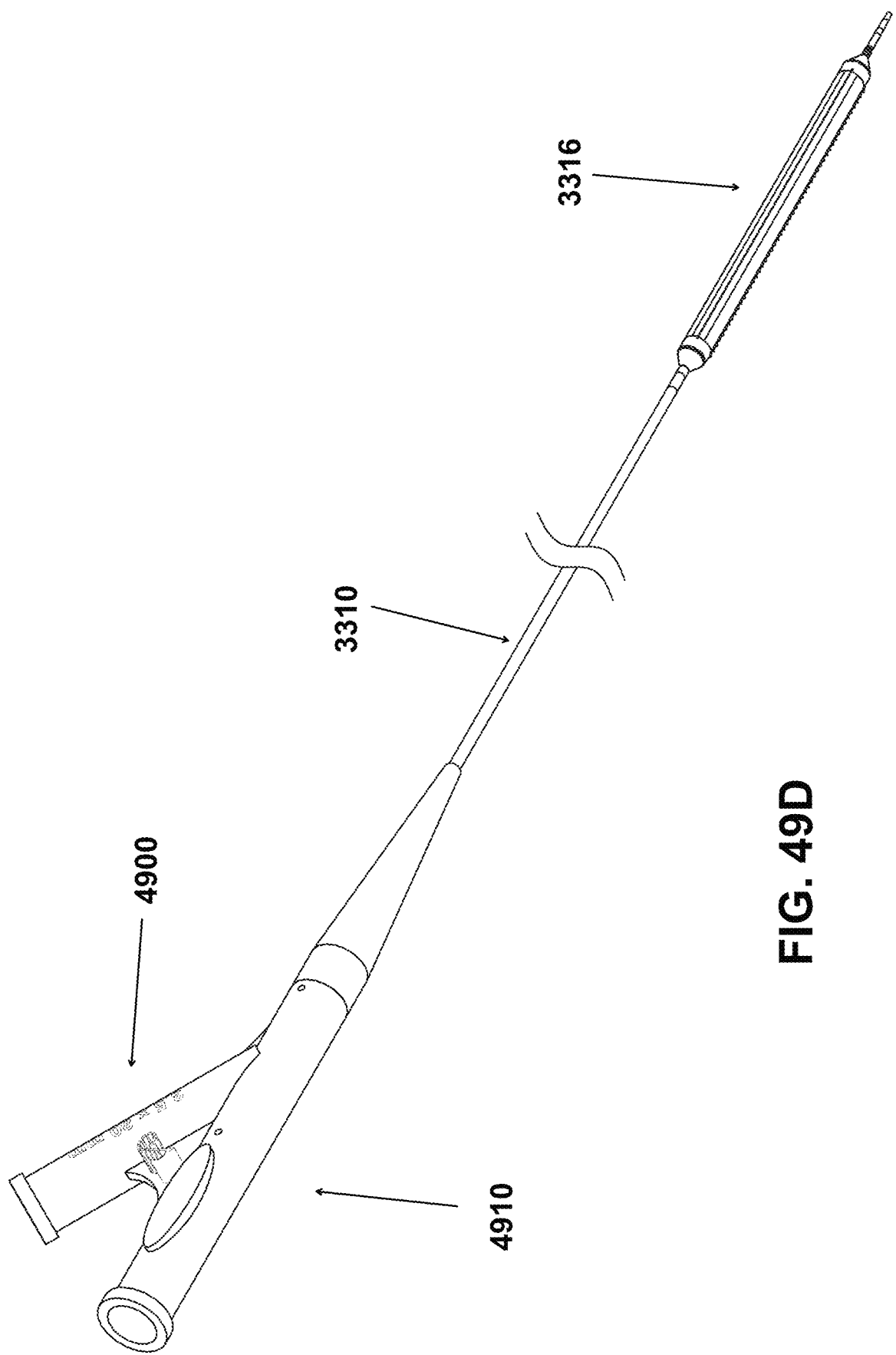
Figure 49E:
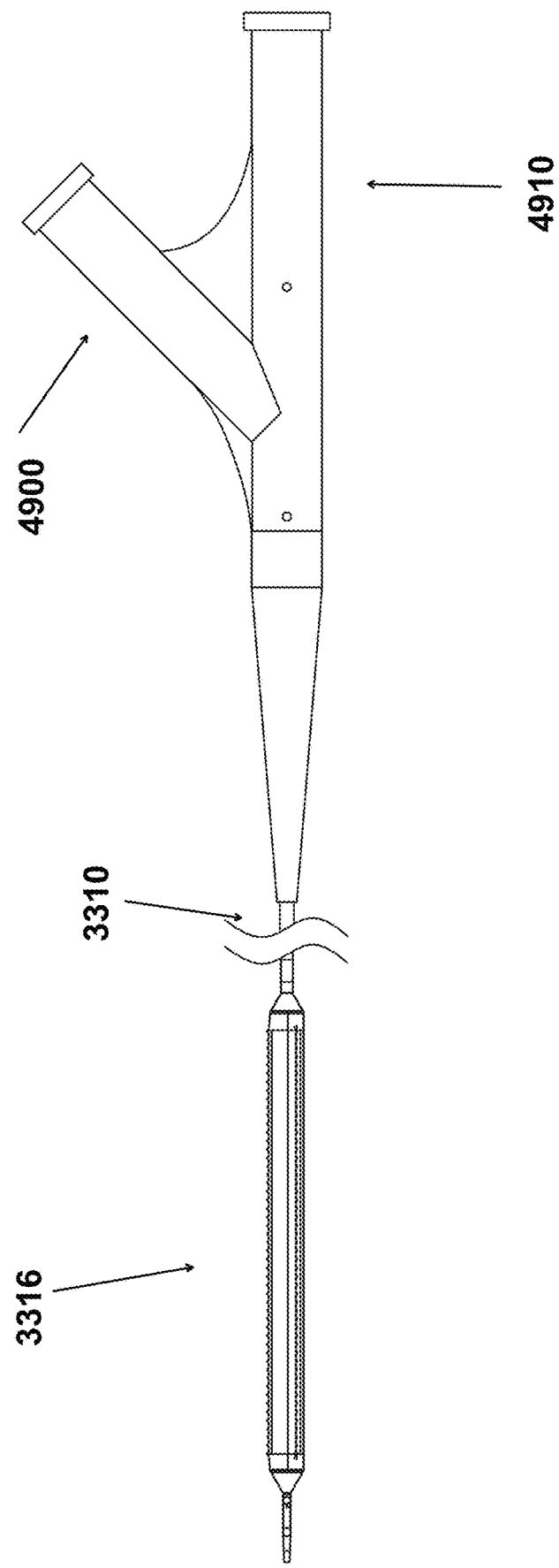
Figure 49F:
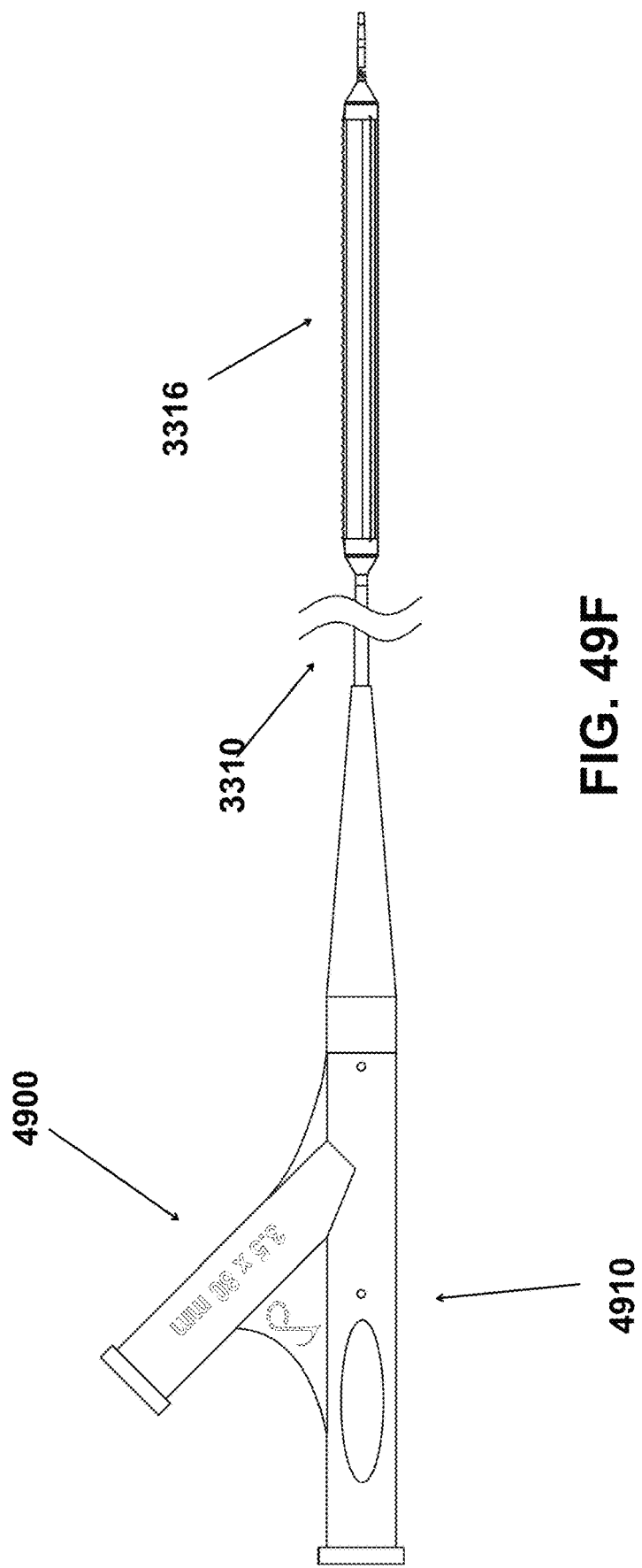
Figure 49G:
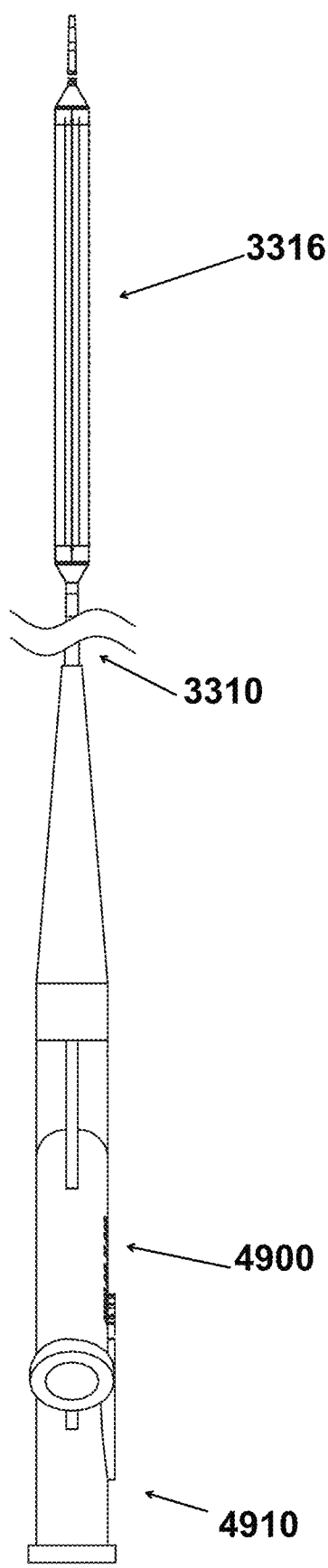
Figure 49H:
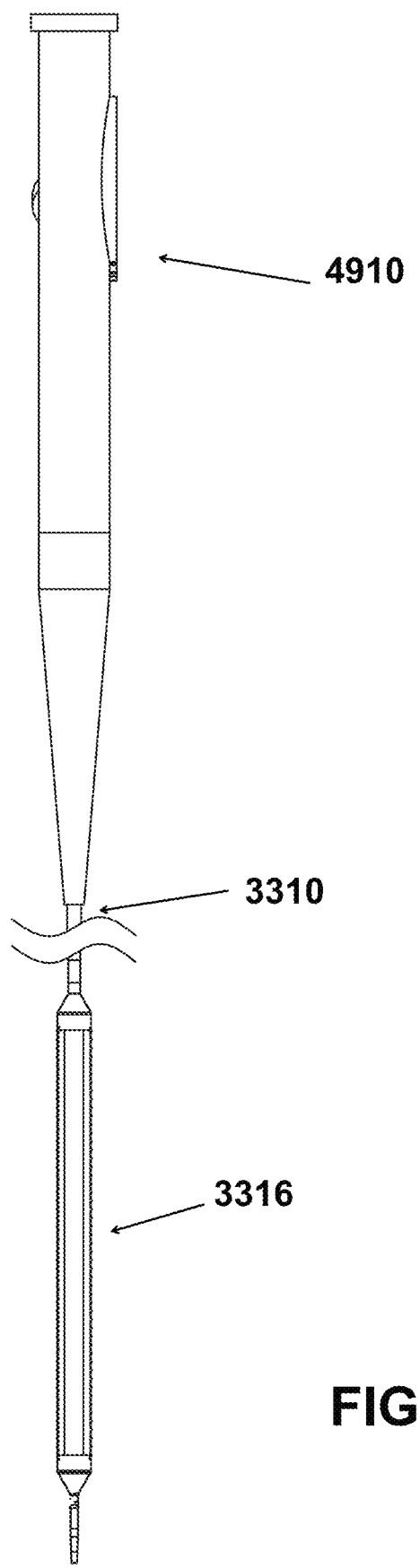
Figure 49J:
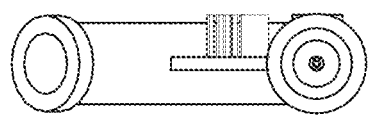
Figure 49I:
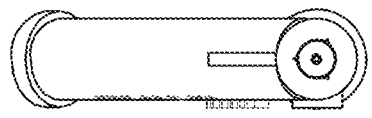

FIGS. 49-49J illustrate various views of one embodiment of an overall system for producing serratoplasty showing a series of serrating or scoring wedge dissectors on the outer diameter of the catheter attached to a catheter with a guidewire hub and balloon inflation hub.

DETAILED DESCRIPTION

Figure 1A:
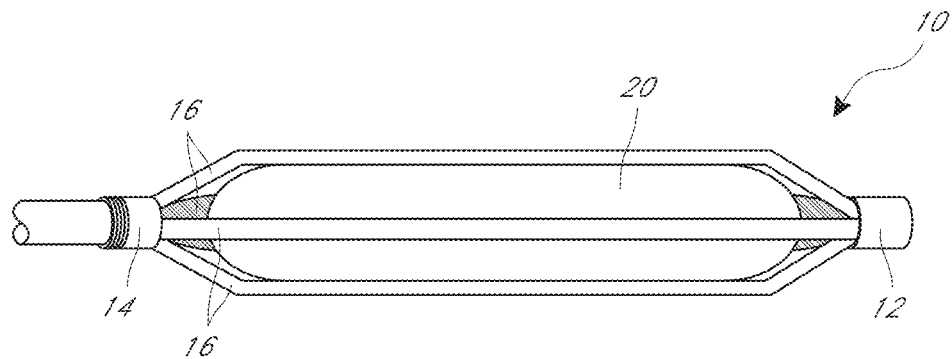
FIG. 1A illustrates a cage positioned on an angioplasty balloon in an expanded position.
Figure 1B:
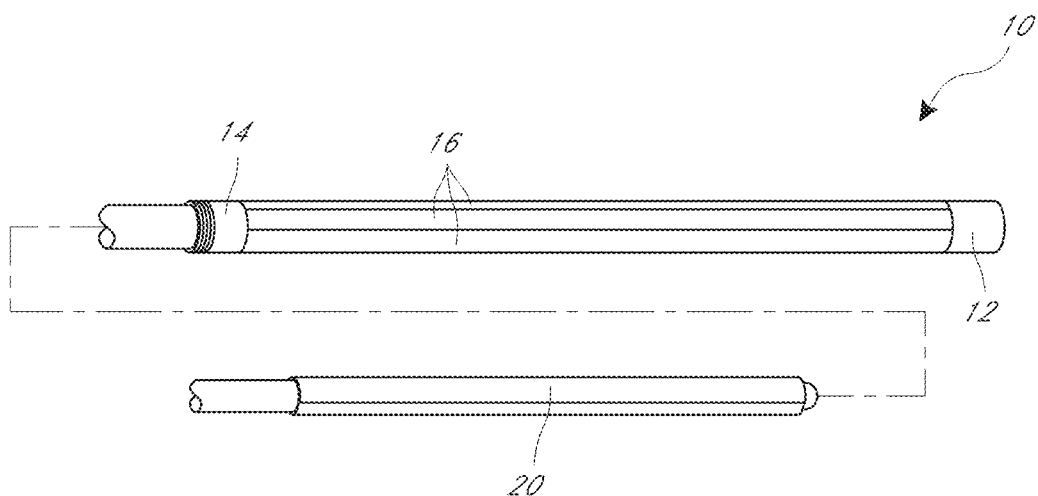
FIG. 1B shows an exploded view of an angioplasty balloon that can be positioned within a cage, both being shown in a pre-expanded position.

FIGS. 1A and 1B illustrate an embodiment of a cage 10 positioned on an angioplasty balloon 20. FIG. 1A shows an expanded position and FIG. 1B shows how the angioplasty balloon can be advanced into the cage. The cage 10 is described herein primarily with respect to an angioplasty balloon 20 and an angioplasty procedure. It is to be understood that the cage 10 can be used with other types of medical balloons and in other procedures.

The cage 10 can include a first ring 12 and second ring 14, and a plurality of strips 16. Each strip can extend longitudinally between the first ring 12 and the second ring 14. The strips and rings can be made of a monolithic part formed from a single piece of material. Thus, the first and second rings can be the ends of a cut tube, for example. The strips and rings can also be made of separate materials and be connected together. As shown the illustrated cage of FIGS. 1A and 1B has five strips 16, though other numbers of strips can be used such as 2, 3, 4, 5, 6, 7, 8, 9, 10, etc.

Figure 2:
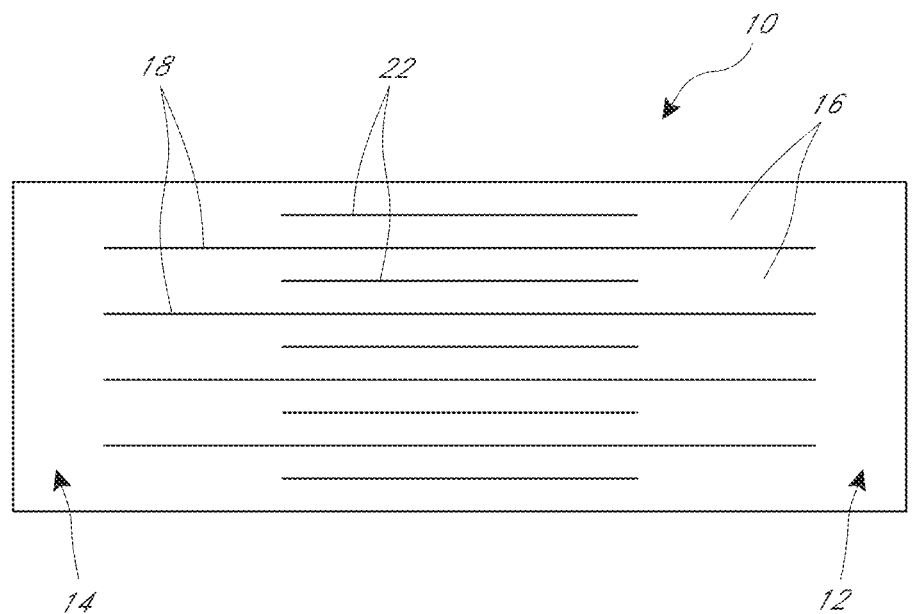
FIG. 2 shows a schematic representation of a cage laid flat showing both long and short slits.

FIG. 2 shows a plan view of a cut tube embodiment of cage, though some embodiments of cage can alternatively be made of a single flat piece of material. The material can be elastic or semi-elastic and made from a polymer, copolymer, a metal, alloy or combination of these. The strips are typically designed to enable the balloon 20 to be inflated multiple times. As well, the strips 16 can be configured such that the cage 10 can apply forces both longitudinally and axially or in orientations that enable the strips 16 to return to this original position.

In some embodiments the cage 10 is prefabricated, packaged, and sterilized separately from the balloon 20, allowing the physician to position the cage 10 around a medical balloon 20, such as an angioplasty balloon, to assist in a medical procedure at the time of the procedure. FIG. 1B shows the balloon 20 in a folded state prior to deployment and prior to placement within the cage 10. The folded balloon 20 can be advanced into the cage 10 without requiring expansion or change in shape of the cage 10. The cage 10 can completely surround and enclose the balloon 20 prior to balloon deployment or expansion. The cage 10 in the pre-expanded state can be longer than the balloon 20. This can allow for movement of one or both ends of the cage 10 towards each other while the device (e.g. balloon 20) expands. The cage 10 can be free floating over the balloon 20. One or both ends 12, 14 of the cage 10 may be fixed to the balloon 20 or another part of the delivery device. In some embodiments the cage 10 is not attached to any portion of the balloon 20 that expands. This can prevent the cage 10 from interfering with the balloon 20 as it expands.

In some examples, a cage 10 can be used with an angioplasty balloon 20 with a drug coating to can protect the drug coating. The cage 10 can prevent or reduce the premature exposure of the drug to the blood vessel. As will be understood with reference to FIG. 1B, the cage 10 can be positioned over a drug coated angioplasty balloon 20 in the pre-expansion state to prevent premature exposure of the drug to the blood vessel. The cage 10 can cover the balloon 20 radially such that a minimal amount, or substantially none, of the surface of the angioplasty balloon 20 with the drug coating is exposed. The balloon 20 and cage 10 can be advanced to a treatment location in this configuration. Though not shown, the system may be advanced over a guidewire within the vasculature.

As illustrated in FIG. 1A, the cage 10 can be moved to an expanded position. In the expanded position the first 12 and second rings 14 are closer together and the strips are expanded thereby exposing the angioplasty balloon surface. In this position, the drug can be placed into contact with diseased tissue in the blood vessel.

In currently available systems, it is generally difficult to predict how much drug will reach the diseased tissue. There are many factors that limit the ability to accurately predict how much drug will be transferred to the diseased tissue. For example, blood flow can dilute the drug on the balloon 20 as it is advanced to the treatment site. Furthermore, navigating the device through the blood vessel can cause the balloon 20 to rub against the endoluminal surface thereby removing some of the drug as the balloon 20 is being advanced to the treatment location. Therefore, in some examples, the cage 10 can offer a physical barrier to protect the drug covering of the balloon 20 during advancement to the treatment location. In this way the cage 10 can be used such that balloon 20 and drug covering are exposed to blood flow in a vessel only during expansion of the balloon 20 as the space between the strips increases. In this way, the cage 10 can prevent or reduce the chances that the drug will become diluted or that the drug will treat areas of the body that are not meant for treatment. In some variants, this can allow for more controlled delivery of the drug with a reduction in the amount of drug necessary to be coated on the balloon 20.

In some embodiments, the folded balloon 20 can be positioned entirely within the cage 10. As is illustrated in FIG. 1A, the cage 10 can have slits between each of the strips 16. In some variants, the slits can be formed by cutting between each of the strips 16 to separate them from a single piece of material. In other embodiments, the slits are really just the space between adjacent strips. The space between strips can be a minuscule amount, such as would formed by a laser cut, or much larger, such as equal to or greater than a width of the strip itself. Depending on the size of the slits, the exposed surface of the balloon 20 in the pre-expansion position is not more than 50% and can be as low as 25%, 10%, 5%, 1%, or less.

As has been described previously, expansion of the balloon 20 moves the first 12 and second rings 14 closer together while moving the strips 16 further apart radially. With the strips 16 in an expanded position, the balloon 20 is more exposed to and can interact with the vessel wall. In the expanded position, the balloon 20 can deliver a drug, stem cells, or other treatment to the vessel wall or to a diseased area of the vessel wall. When the balloon 20 is fully expanded, the exposed surface of the balloon 20 not covered by the strips 16 can be between 65% and 99%, 75% and 99%, more commonly 80% and 99%, or most commonly 90% and 99%, among other ranges.

Drug delivery using the cage 10 can be employed before, during, or after an angioplasty procedure. At the same time, it is not required that the cage cover the entire balloon, or be used to control or assist with drug delivery.

Figure 3:
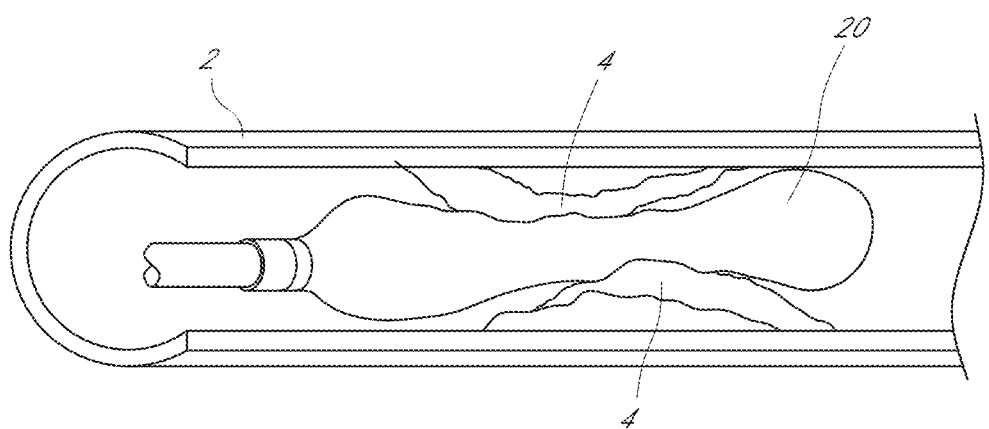
FIG. 3 shows an angioplasty balloon within a vessel at a treatment site that is experiencing dog boning.

In some embodiments, a cage 10 can be used to prevent or reduce dog boning of the balloon 20 in an angioplasty procedure. This may be in addition to, or instead of assisting with drug delivery. FIG. 3 shows an angioplasty balloon 20 within a blood vessel 2 at a treatment site. As illustrated, the angioplasty balloon 20 is experiencing dog boning as it is expanding. The plaque buildup 4 resists expansion of the balloon 20, forcing both ends of the balloon 20 to expand first, rather than focusing the expansion energy in the center of the balloon 20 at the plaque 4 where it is needed most.

To prevent dog boning, the cage 10 as shown in FIG. 1A, can constrain the balloon 20 upon expansion to encourage the middle of balloon 20 to expand first. This is because the middle area of the cage 10 can be designed to have the least resistance to expansion, being farthest away from the ends where the strips are confined by rings. This can prevent or reduce dog boning of the balloon 20 independent of the disease morphology or arterial topography the balloon 20 is expanding within.

Dog boning usually occurs where a balloon 20 expands in a vessel with plaque where the plaque resists expansion, forcing the ends of the balloon 20 to expand first (due to lack of resistance) such that the balloon 20 takes the shape of a dog bone. By enveloping a balloon 20 with a cage 10 and configuring the rings to display different expansion resistance, the ends of the balloon 20 can have the highest resistance and the center of the balloon 20 have the lowest resistance. Therefore, the cage 10 can help control and limit expansion of the balloon 20, as the balloon 20 will tend to expand more readily in the center which is typically the area of disease.

The pattern and orientation of the strips 16 can influence expansion and dog boning. Returning to FIG. 2, the short slits 22 positioned in the center of the strips 16 can reduce rigidity in the center of each of the strips 16. This can help reduce the likelihood of dog boning by further reducing resistance to expansion in the center of the cage 10.

The cage may further include spikes or wedge dissectors on the strips. The spikes can be used as a vessel preparation tool before a secondary treatment, or during a primary treatment. For example, the spikes can assist with cutting and/or perforating plaque before or during an angioplasty procedure. This may be in addition to, or instead of assisting with drug delivery and/or preventing dog boning. It will be understood that any of the embodiments described herein can provide any of these benefits and/or be used in any of these procedures, as well as the other benefits and procedures described herein.

Spikes can be positioned on the strips in any number of different orientations and configurations as will be described further below. The spikes can be any of the spikes discussed in U.S. Pat. No. 8,323,243 to Schneider et al., issued Dec. 4, 2012 and incorporated by reference herein in its entirety. The spikes and cage can also be used in accordance with the plaque serration methods and other methods also described therein.

Figure 4A:
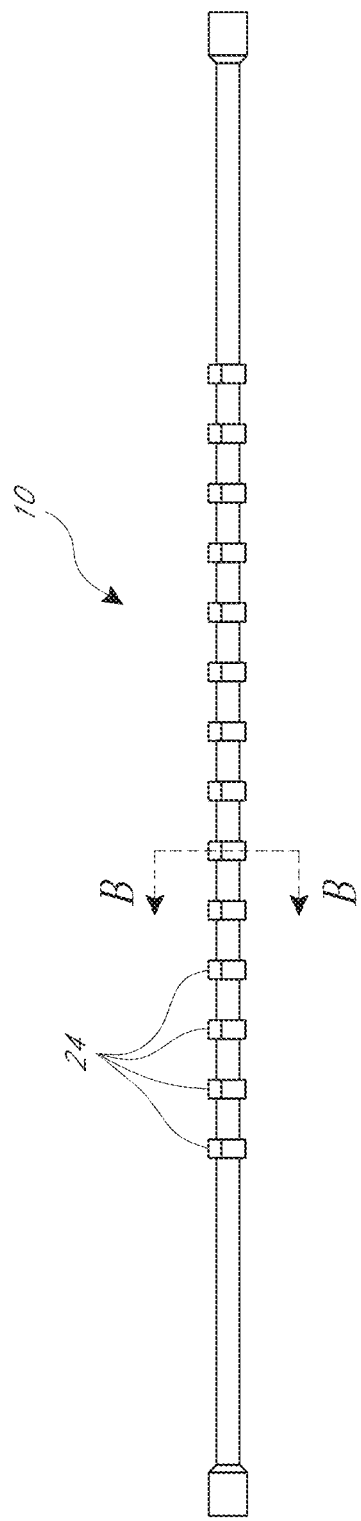
FIG. 4A shows an unfinished cage during manufacturing being cut from a tube.
Figure 4B:
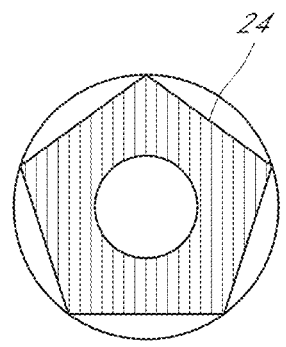
FIG. 4B is a cross-section of the unfinished cage of FIG. 4A taken along line B-B.
Figure 4C:
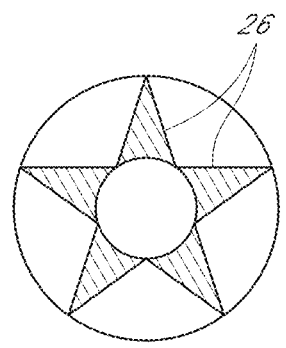
FIG. 4C shows the cross-section of FIG. 4B after an additional manufacturing step.
Figure 4D:
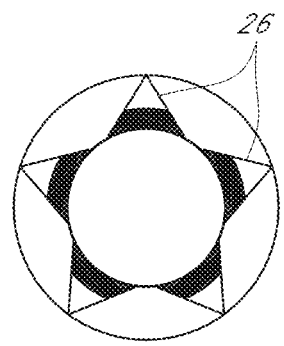
FIG. 4D illustrates a cross-section of another embodiment with a larger interior lumen.

The cage 10 can be made in many ways. For example, an extrusion process may be used, a tube may be cut, and/or a wire split as will be described in more detail below. Beginning with FIGS. 4A-5B, various embodiments of cages will be described. FIGS. 4A and 5A show embodiments of cages 10 during the manufacturing process. The cages 10 are each in the form of a tube with a plurality of splines 24 spaced apart on the tube. In some embodiments, the tube can be pre-formed and then machined to the illustrated shape. The tube can be made of metal or plastic among other materials. In other embodiments, the tube is extruded to form the illustrated shape. For example, a method of making the tube can include extruding a plastic tube with a plurality of spaced apart splines 24 positioned longitudinally along the tube. Cross-sections of the cages are shown in FIGS. 4B-D and 5A.

After forming the tube with the splines 24, material from the tube can be removed to form the slits and strips 16. Either as part of removal process, or before creating the slits, the splines may be shaped to form different shaped spikes or wedge dissectors 26. For example, the splines 24 illustrated in FIG. 4B can be machined to form the sharp wedge dissectors 26 as shown in FIGS. 4C and 4D. In some embodiments, the splines 24 can be manufactured with an additive process and shaped initially like the illustrated wedge dissectors 26 without requiring additional machining or other work.

Figure 4E:
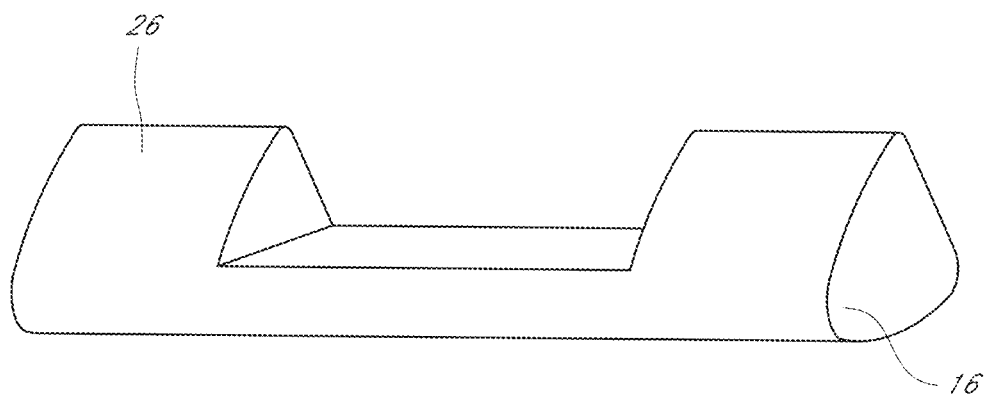
FIG. 4E shows a detail view of a portion of another embodiment of cage.
Figure 5A:
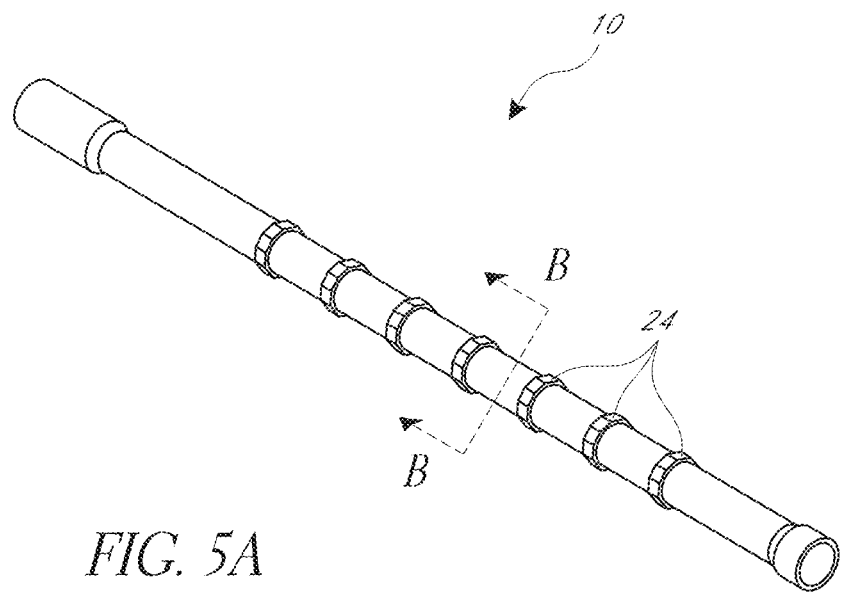
FIG. 5A shows another embodiment of an unfinished cage during manufacturing.
Figure 5B:
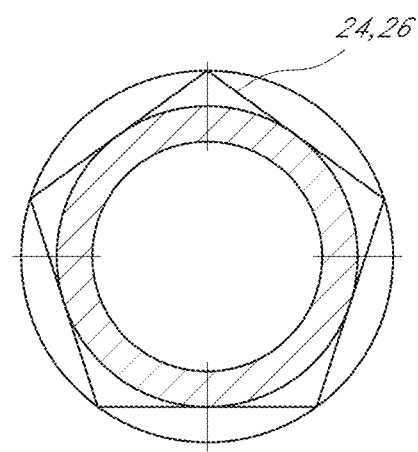
FIG. 5B shows a cross-section of the unfinished cage of FIG. 5A taken along line B-B.

Looking now to FIG. 4E, an enlarged detail view of a portion of a cage is shown. In this embodiment, the strip 16 has been formed with a plurality of spikes or wedge dissectors 26. In some embodiments, from the base of the unfinished cage of FIGS. 4A and 4B, a slit can be cut in the tube to form adjacent strips. The wedge dissectors 26 can be shaped like a tent or axe head with an elongated tip and base, both of which extend longitudinally, along the longitudinal axis of the tube. The wedge dissectors 26 can assist with cutting and/or perforating plaque before or during an angioplasty procedure. The space between the wedge dissectors 26 can be machined or otherwise formed to remove material and increase the flexibility of the strip. The space between the wedge dissectors 26 is shown as being twice the length of the wedge dissector 26, though other spacing can also be used. Typically spacing length can be 4:1 to 3:1 space to length and more commonly 3:1 to 1:1 space to length.

Turning to manufacturing of the splines, in some embodiments, the splines 26 are fabricated from a tube of material, where the cage 10 is a plastic extruded tube with splines that are cut, ground, electrical discharge machined, or molded to form the wedge dissectors 26. The tube can be manufactured with slits along its length. In some examples, the ends of the tube remain intact in order to forming rings. In some variants, the strips 16 are spaced apart with some or all the strips 16 having spikes or wedge dissectors 26. As will be understood from the above discussion, in the embodiments shown in FIGS. 4A-5B five slits would be made to form outward points.

In some embodiments, a method of making a cage 10 for an angioplasty balloon 20 can comprise first extruding a plastic tube with a plurality of spaced apart splines positioned longitudinally along the tube. In some examples, the method can then include cutting at least one of the splines of the plurality of splines to form a plurality of spikes or wedge dissectors 26 positioned circumferentially around the tube. In some variants, the method can further include cutting the tube to form a plurality of longitudinally extending strips 16, each strip including at least one spike of the plurality of wedge dissectors 26.

Figure 6A:
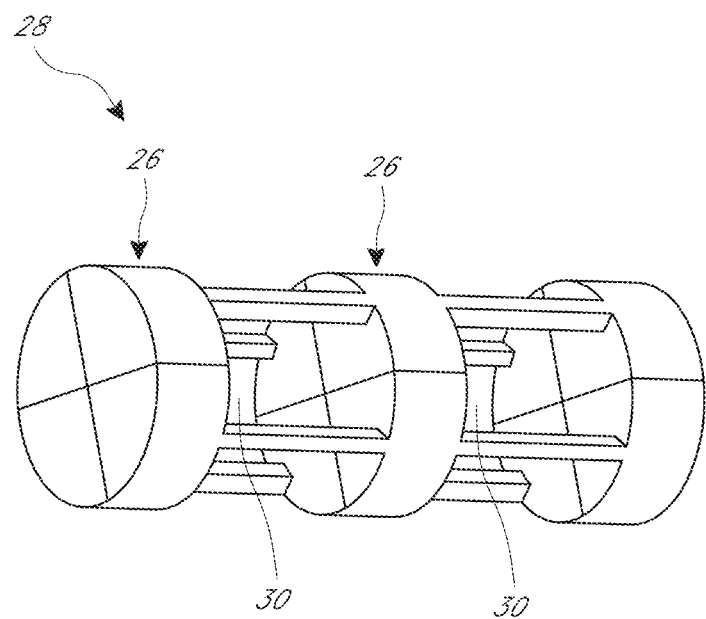
FIG. 6A shows a wire cut to form strips and wedge dissectors for an embodiment of a cage.
Figure 6B:
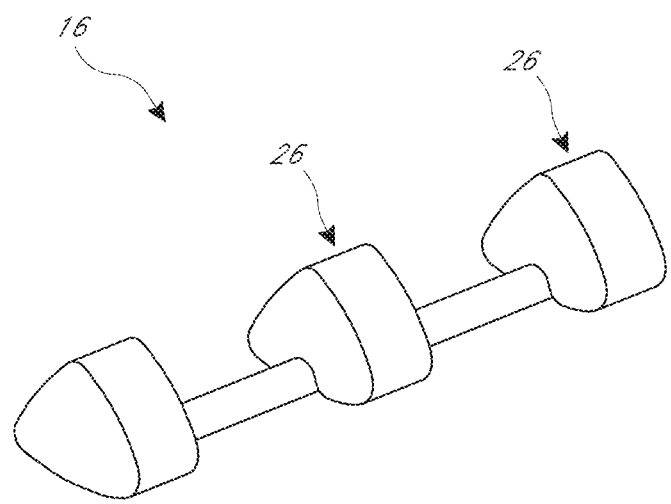
FIG. 6B shows a section of the cut wire of FIG. 6A.

Looking now to FIGS. 6A-6B, another method of manufacturing a cage 10 will be described. A wire 28 can be split or cut to form three or more strips 16 that can be used as part of forming a cage 10. In some examples, the wire 28 is constructed of an alloy, or polymeric material. Any number of different manufacturing methods can be used including laser cutting and electrical discharge machining. In some variants, the wire 28 can be divided into sections, such as four quarters. In some embodiments, square or other shaped holes 30 can be cut into the wire 28 to form spaces between the wedge dissectors 26. Each of the sections of wire can then be separated to form the strips 16 of the cage 10. A cage 10 can be assembled with a plurality of rings and include any number of strips 16. In some examples, a cage 10 can be assembled from 1, 2, 3, 4, 5, 6, 7, 8 or more strips 16.

Strips 16 can be attached in many ways to form the cage 10. In addition, to forming the strips from a wire, they can also be extruded and/or formed from a flat piece of material and/or a tube. For example, it will be understood that the embodiments described with reference to FIGS. 2, 4A-5B can be modified to provide individual strips that can then be connected to form a cage.

Figure 7:
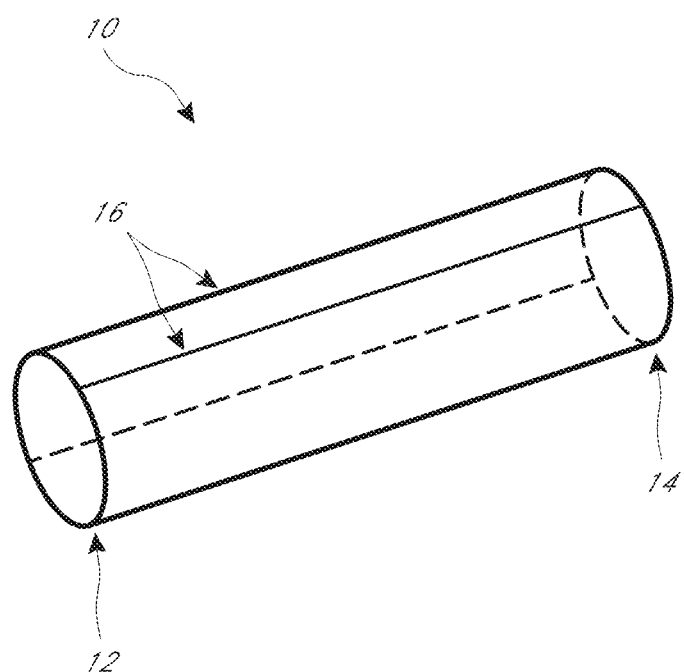
FIG. 7 shows a schematic view of a plurality of strips that are connected by two rings to form a cage.

In some embodiments, strips can be connected with two or more rings 12, 14 to form a cage 10. For instance, the individual strips of the cage 10 may be bonded to rings on either end. As illustrated in FIG. 7, each individual strip 16 is secured on either end by rings 12, 14. In constructing the cage 10, the strips 16 can be attached to the rings 12, 14 first before positioning around a balloon, or the cage can be assembled around a balloon. For example, one or more strips can be placed onto the surface of the balloon 20 before connecting to the rings. The cage 10 may be permanently fixed to one or both ends of the balloon 20 or to the balloon catheter. In some embodiments, the rings 12, 14 can hold the strips against a portion of the balloon or the balloon catheter. The strips 16 can also help to keep the balloon 20 in a compressed state prior to deployment and can assist in deflating the balloon after expansion.

The rings 12, 14 are typically circular bands, though they can be a band of any number of shapes including oval, square, elliptical, rectangular, etc. The rings can also be capable of producing a binding and/or restraining force. The rings 12, 14 can be any number of different materials including one or more of a metal, polymer, copolymer, elastomer, thermoplastic elastomer, glue, or hydrogel. The rings can be rigid or flexible.

In some examples, the rings 12, 14 can be composed of a heat shrink material or a material with elastic properties that binds, captures, or restrains the plurality of strips 16 and prevents or limits the strips 16 from moving, sliding, tilting or twisting at any point along the length of the strips but especially at either end of the balloon 20. When the rings are elastic, super elastic, or thermally active, the rings can be placed about the strips and allowed to shrink onto the strips such that the strips 16 are retained against the outer diameter of the balloon 20. Preferably, the rings and strips are positioned around a balloon in a fully expanded state and then heat is applied to the heat shrink type rings. In other embodiments, the heat shrink type rings are applied with the balloon in a deflated state.

As discussed with respect to FIGS. 1A and 1B the cage can be performed and slid onto the balloon. But, in some embodiments, assembling the cage around the balloon can allow for a smaller cage design. In retrofitting the balloon 20, the rings can be advanced onto the balloon catheter from either side which may allow for a smaller ring inner dimension as compared to a cage with one ring that is advanced over a balloon.

The rings 12, 14 of the cage 10 can be configured to accommodate the balloon 20 as it transitions from a deflated to an inflated shape. Not unlike the configuration of the cage with balloon illustrated in FIG. 1B, the strips 16 of the cage 10 can be in contact with the balloon 20 when the balloon 20 is in a deflated configuration. As the balloon 20 inflates, each strip 16 bows in a concave orientation with the balloon 20 (FIG. 1A). In some examples, the strips 16 are free-floating and not bound to the balloon surface.

As the balloon 20 begins deflating, the material properties of the strips 16 can allow it to begin to return to their original position. This may be a completely flat position. As the strips 16 return to their original position, this can provide an additional force to assist the deflation of the balloon 20. As the strips move from the concave position to a flat linear position, the strips 16 move from an expanded length ("$L_e$") to a deflated length ("$L_d$") where $L_d$ is longer than $L_e$. The straightening of the strips 16 from $L_e$ to $L_d$ in the axial direction elongates the balloon 20 and assists in more complete balloon 20 deflation.

The rings 12, 14 can come in a variety of shapes and sizes that can secure the plurality of strips 16. The following discussion of certain illustrated embodiments, are but a few such examples.

Figure 8:
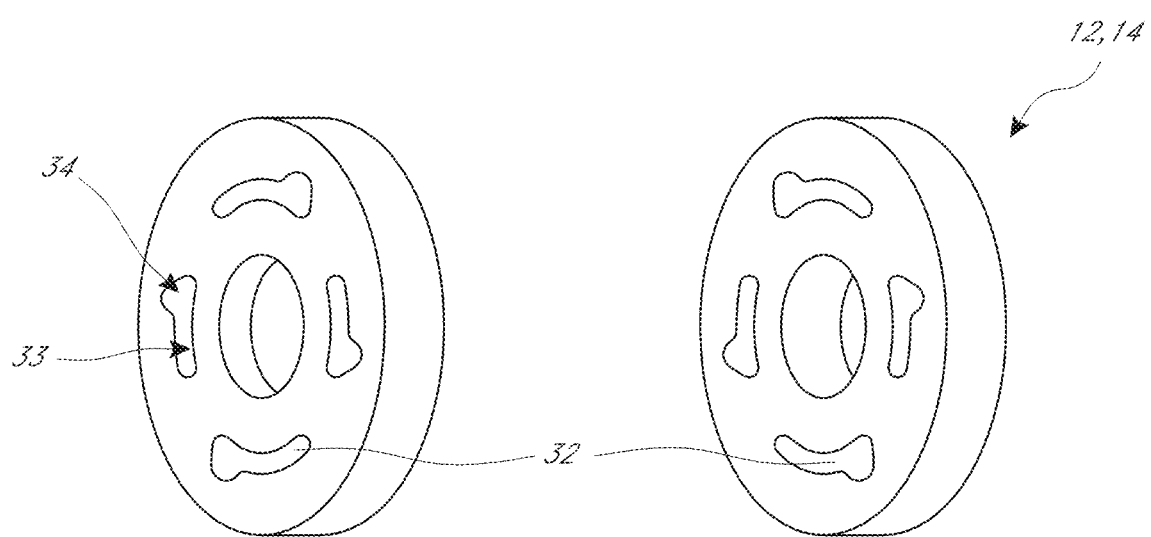
FIG. 8 illustrates a two-part ring that can be used to capture strips to form part of a cage.

The rings 12, 14 can connect to the strips 16 in a number of different ways. The rings can be mechanically attached to the strips 16 through a friction fit for example, or can be connected with an ultrasonic weld, adhesive, etc. Turning to FIG. 8, each ring 12, 14 can be a two-part ring that can connect to one or more strips 16 of the cage 10 by rotating the rings in opposite directions (e.g. clockwise and counterclockwise). The rings 12, 14 can include holes 32, through which the strips 16 can be advanced to connect to the ring. In particular, the asymmetrical shape of the holes 32 can be configured to accommodate a strip 16 with periodically spaced wedge dissectors 26 such as that illustrated in FIG. 6B.

As illustrated, the holes 32 can have a narrowed portion 33 and a wider portion 34. The wider portion 34 can be configured to accommodate the wedge dissector 26 while the narrowed portion 33 can be configured to accommodate the width of the strip 16 (i.e. the space between wedge dissectors). The strips 16 can be advanced through the holes 32 by fitting a wedge dissector 26 through the wider portion 34. In some examples, the strip 16 can then be secured by turning the rings 12, 14 such that the strip 16 is moved into the narrowed portion 33. This can secure the strips 16 to the rings 12, 14 as the wedge dissector 26 cannot move past the narrowed portion 33. As described above, both rings 12, 14 can be present at either end of the cage 10. Additionally, as illustrated in FIG. 8, because the holes 32 of the ring 12 and the holes 32 of the ring 14 are opposed, by rotating the two parts of the ring in opposite directions, this further prevents movement of the strips 16.

Figure 9A:
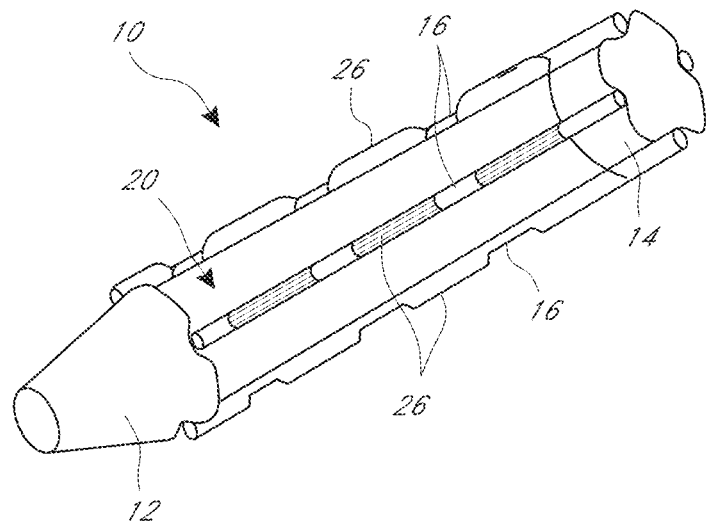
FIG. 9A is another embodiment of cage with a conical ring.

The strips 16 can be secured by rings 12, 14 that are formed from a variety of shapes. For example, FIG. 9A illustrates an embodiment of the cage 10 where the strips 16 are secured with a conical ring 12 at the distal end. The conical end can be the distal end of the balloon catheter and can provide an atraumatic end of the device.

Figure 9B:
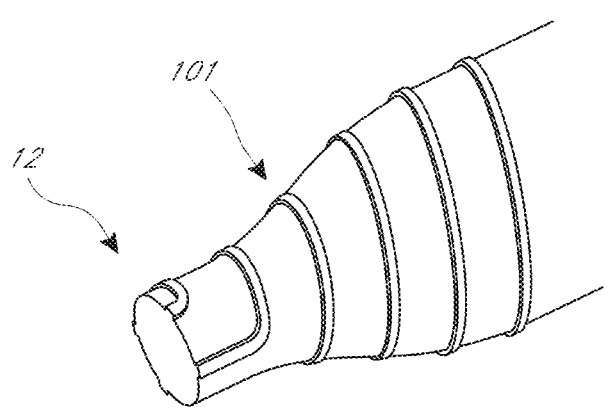
FIG. 9B is a perspective view of a ring with a tapered outer diameter wherein the ring includes a screw-like feature on its outer surface.

Similarly, FIG. 9B shows a ring 12 with a tapered outer diameter with a screw feature 101 on its outer surface. This screw feature 101 can provide either a negative or positive impression about the outer surface of the distal ring.

The ring 12 illustrated in FIG. 9B can serve a treatment purpose as well. In some examples, the tapered and screw features on the ring can assist the balloon 20 in navigating and entering a narrow lesion. The coiled outer surface 101 can be configured to provide a gripping or tunneling mechanism. This feature can allow the ring to aid the operator in navigating through occluded lesions (either totally or partially) and enable passage of the balloon 20 therein. The negative or positive impression 101 can be circumferential or patterned like a cork screw. In some embodiments, the negative or positive impression 101 can be macro in scale or have micro features that offer an enhanced surface to enable passage through a narrowing in a vessel. In some examples, the function of the outer surface 101 of the ring can be described as acting like a lubricant although the feature is mechanical in nature. This function can be further enhanced with hydrophilic, hydrophobic coating. The surface texture can also be modified to aid in passages with less penetration energy. In some embodiments, this can be accomplished by adding micro scales (as seen in porcupine quills) or enhanced surface roughness (as used in nature by mosquitos).

The ring 12 illustrated in FIG. 9B can be secured to strips 16 that are disposed about the surface of the balloon circumferentially in a helical fashion. In contrast to the linear strips 16 illustrated in FIG. 9A, the strips 16 attached to the tapered ring 12 can be wound around the balloon. A tapered or untampered ring 14 can be used at the proximal end of the balloon. In some examples, the configuration of the attached strips 16 can follow the same pattern as the negative or positive impression 101 on the ring 12.

Figure 10:
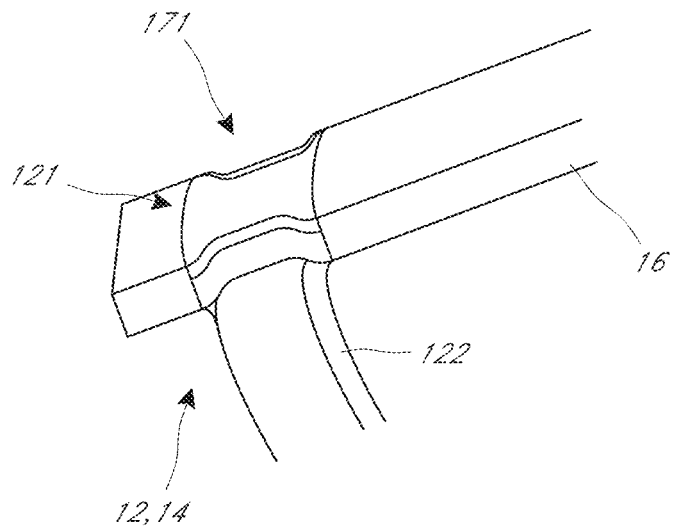
FIG. 10 shows the end of a strip configured to accommodate and be secured by a multi-layer ring to form an end of the cage.
Figure 11:
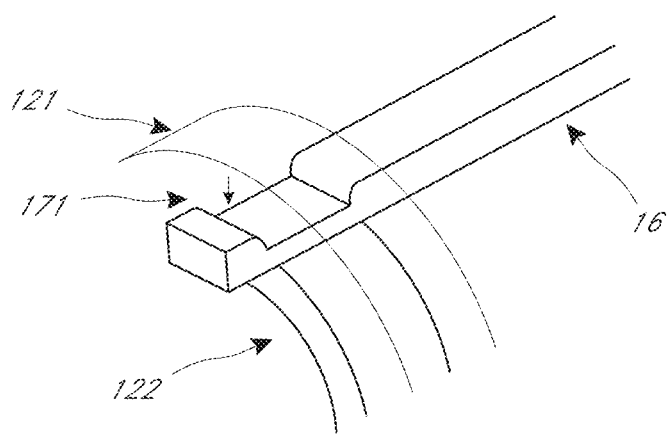
FIG. 11 illustrates another embodiment of the end of a strip configured to accommodate and be secured by a multi-layer ring to form an end of the cage.

Turning now to FIGS. 10-11, multiple layer rings will be discussed. A ring with multiple layers can be used to hold the strips between the layers. The ring can have at least a base layer 122 and a top layer 121. As seen in FIGS. 10-11, the ring 12, 14 can have a non-compressible bottom layer 122 and a compressible, thermally or electrostatically compressible layer 121. The top layer 121 can be configured of a compressible material while the base layer 122 can be configured of a non-compressible material and the strips 16 can be captured between them. In some examples, the top layer or the top and base layers can be made from a heat shrink material. In some embodiments, the ring 12, 14 can be formed from lengths of materials that are wound around themselves to form a layer of ring.

The rings can be made of a layer of composite materials where the base layer 122 is less compressible or elastic than the top layer 121. Energy can be added to the top layer 121 to produce a reduction in the top layer's diameter until the top layer compresses and captures the strips between the base layer 122. For example, the top layer 121 can be a heat shrink material. In this way, the top layer 121, base layer 122 and strips 16 can form a cage 10 as seen in FIGS. 10 and 11. In some embodiments, the strips can be attached to the balloon and/or balloon catheter with the rings that are made of a single layer of heat shrink material positioned over the strips similar to just the top layer.

The strips or rings can include indentations to facilitate attachment to the other. The strip 16 can include an indentation 171 on either side of the strip 16 (as illustrated in FIG. 10) or an indentation 171 on one surface of the strip 16 that can form a groove (as illustrated in FIG. 11). Though in FIG. 11, the top layer 121 is shown as a heat shrink material, it will be understood that in other embodiments a rigid ring could be press fit into the indentation 171. Such a rigid ring could be part of a single or multiple layer ring, thus there may or may not be a corresponding base layer 122.

Figure 12:
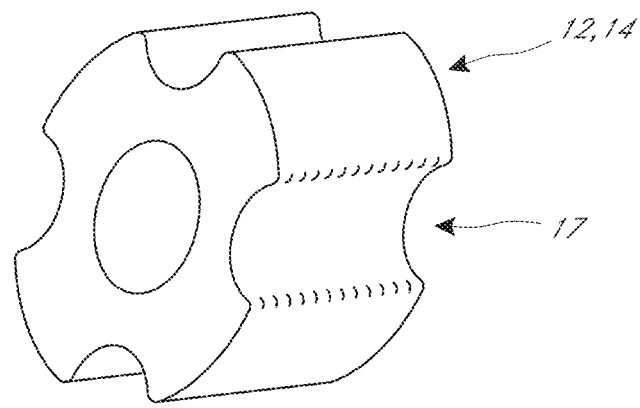
FIG. 12 is a perspective view of a ring.

FIG. 12, illustrates another embodiment of the ring 12, 14. Here, the ring 12, 14 can include a plurality of indentations or grooves 17. The grooves 17 can have a width that can accommodate the width of the distal end of strip 16. An end of a strip can be attached to the ring 12, 14 in the grooves 17 through the use of adhesive, mechanical coupling, wrapping heat shrink material around the ring, etc. In some embodiments, the strip 16 of FIG. 11 can be placed in the ring 12, 14 of FIG. 12 so that the indentations are engaged with each other.

Figure 13A:
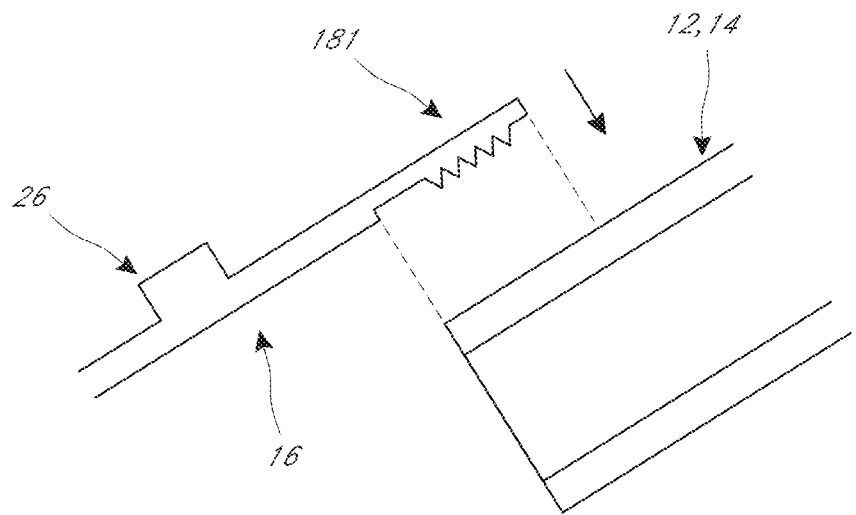
FIG. 13A shows a strip with a hook feature and ring.
Figure 13B:
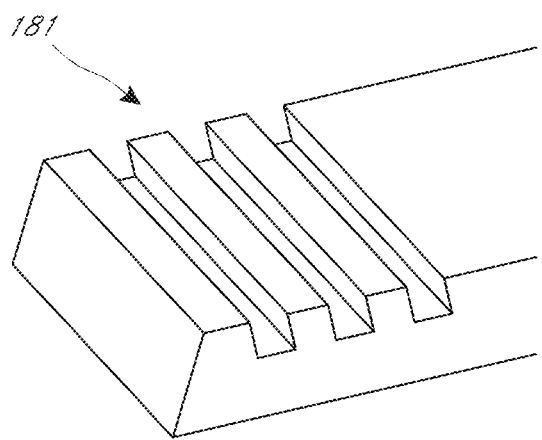
FIG. 13B is an end view of strip with a ridged hook feature.
Figure 13C:
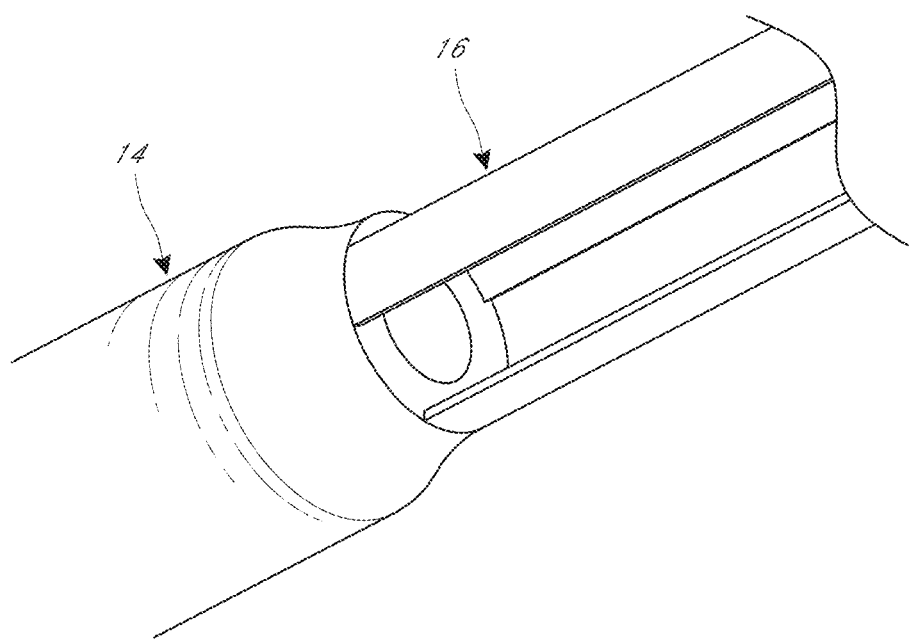
FIG. 13C shows a perspective view of a portion of a cage.

FIGS. 13A-C illustrate examples of a strip 16 that includes an securement feature 181 that improves the hold of the strips 16 to the rings 12, 14. In some variants, the securement feature 181 forms a section of the strip 16 with a higher surface roughness. This can be in the form of the illustrated ridges or other teeth-like elements that aid in the imbedding of the strip 16 into or holding the strip on the ring.

When the ring 12, 14 is a polymeric material, the securement feature 181 can be formed as narrow sections of the strip 16 at the ends (as illustrated in FIG. 13A-B), or placed strategically along the strip length (such as where three or more rings are used). The securement feature 181 can be aligned with the rings 12, 14. During fabrication, the securement feature 181 can be pressed into the polymeric material as illustrated in FIG. 13A at a high temperature where the polymeric material is near or greater than the glass transition temperature of the material. In so doing the securement feature 181 can be used to engage or connect the strips 16 to the rings 12, 14 as illustrated in FIG. 13C.

In FIG. 13A the ring 12, 14 is shown to incorporate the securement feature 181 into the body of the ring material. FIG. 13A shows the strip 16 with a ridged hook feature 181 before it is pressed into the ring material. FIG. 13B shows a perspective view of another embodiment of securement feature 181. In some examples, the securement feature 181 can be significantly longer than the ring 12, 14 is wide and be designed to provide tension on the cage 10.

When the ring 12, 14 is made from an elastic material, such as rubber or polymer, or metallic alloy or a design with elastic properties like a spring, the ring 12, 14 can be used to provide tension on the cage 10 to enable the cage 10 to return to the relaxed, deflated balloon 20 position. Furthermore, the portion of the strips 16 without a wedge dissector is the thinnest and the most flexible. This can allow the strip 16 to be the most flexible at the edge of the balloon 20 where the forces are the highest.

Figure 13D:
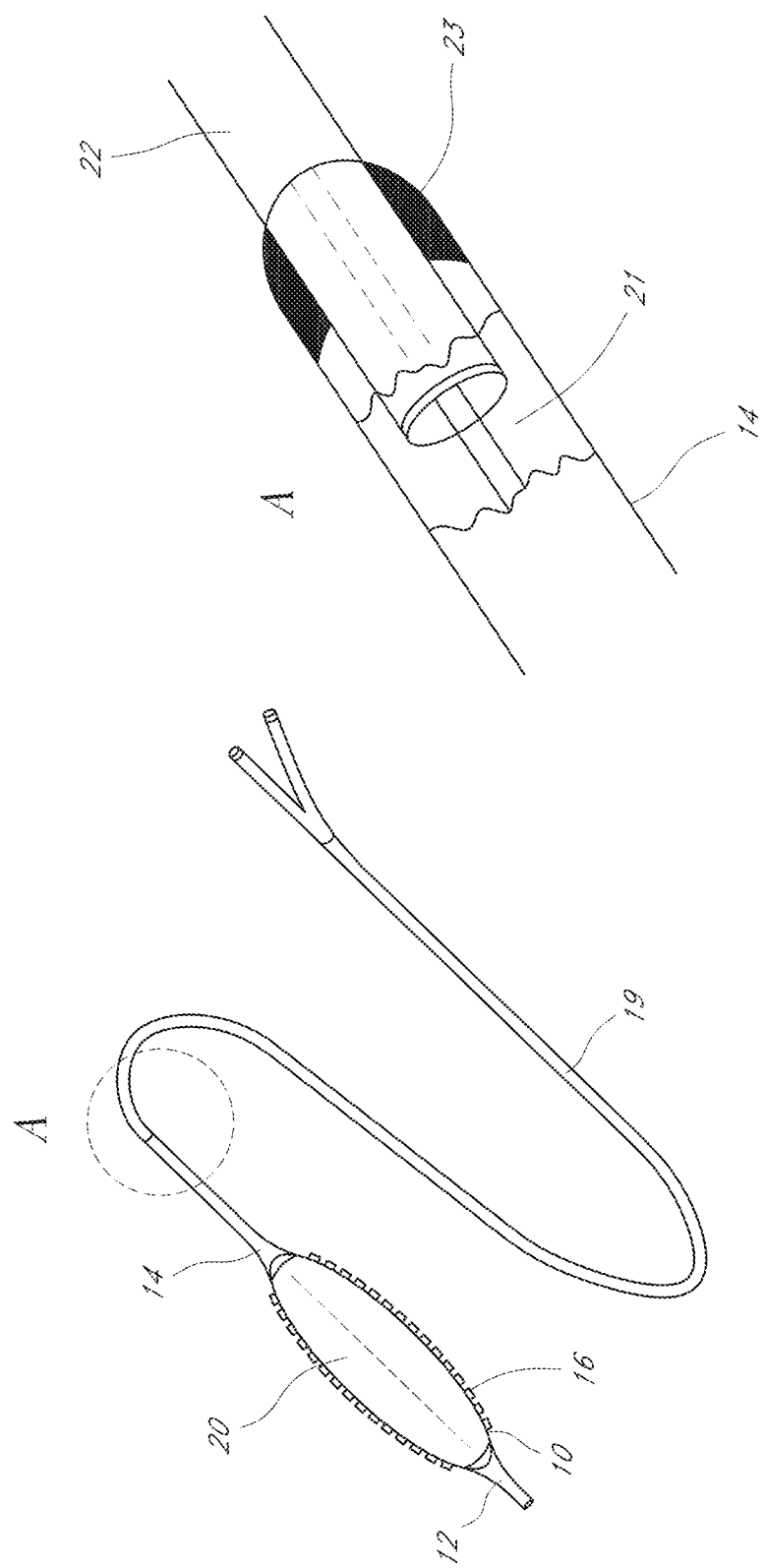
FIG. 13D illustrates a view of a conical distal ring retaining a plurality of strips.
Figure 13E:
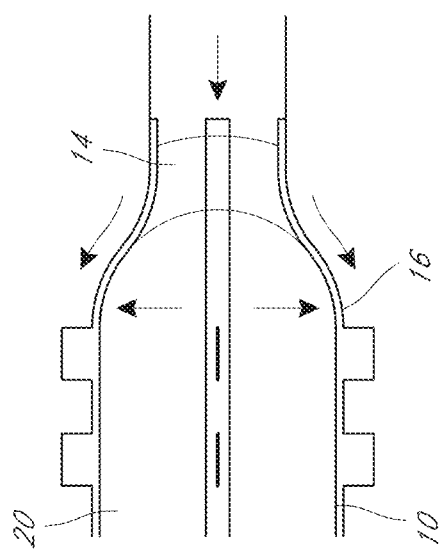
FIGS. 13E-F show a view of one end of a balloon with a cage disposed about the balloon and the forces applied to the balloon during inflation and deflation.
Figure 13F:
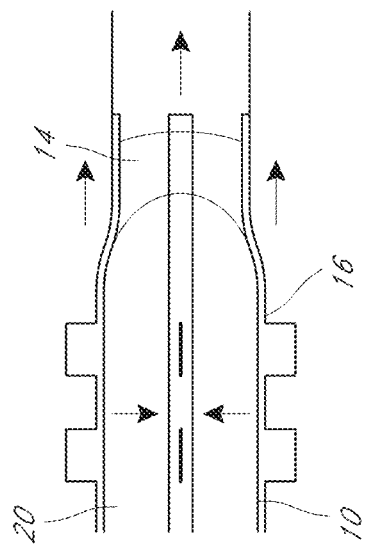

FIGS. 13D-F illustrate an example where the elastic material of a ring can provide tension on a cage during expansion and to then assist in deflating the balloon as the tension is released. Turning first to FIG. 13D, the cage 10 is disposed about the balloon 20. The cage 10 can be composed of a plurality of strips 16 that are secured to the balloon by rings 12, 14. In some examples, the rings 12, 14 can be made from long elastic material that can aid in pulling the strips 16 down into a linear position such that the wedge dissectors are perpendicular to the surface of the balloon 20. Callout "A" provides a schematic, see-through view of the proximal end of ring 14. As shown, ring 14 is secured about the outer catheter shaft 22 by an adhesive 23. As well, an inner guidewire shaft 21 can run concentric to the balloon 20. The guidewire shaft 21 can be secured with relationship to the catheter shaft 22. For example, the guidewire shaft 21 and the catheter shaft 22 can both be connected to different ports on a hub, such as the illustrated bifurcated luer at the proximal end of the balloon catheter. The balloon can be inflated by injecting a fluid into the catheter shaft. It will be understood that in some embodiments the catheter shaft 22 open directly inside the balloon 20, rather than opening at the ring 14 as shown. The ring can be attached to the catheter shaft 22 and/or the balloon 20.

FIGS. 13E-F illustrate a balloon 20 and cage 10 as the balloon 20 is inflated and subsequently deflated. As noted above, in some examples, the elastic material of the rings 12, 14 can stretch to allow the cage 10 to expand as the balloon 20 is inflated. In some embodiments such as the shown in FIGS. 13E-F, the rings can be made of an elastic polymer and the strips can be made of metal or an inelastic polymer. As shown in FIG. 13E, as the balloon 20 is inflated, the strips 16 of the cage 10 begin to move apart. In order to push each of the strips 16 outward, force is exerted radially outwards (as illustrated by the arrows) on the balloon 20—and by extension the cage 10—as the balloon 20 is inflated. As the balloon 20 expands, the rings 12, 14 are under tension and able to stretch enough to allow the strips 16 to maintain alignment while expanding with the balloon 20.

This tension can also help the balloon 20 to deflate. During balloon deflation, as illustrated in FIG. 13F, the tension on the strips 16 exerts a force radially inward as the strips 16 and the rings 12, 14 tend to want to return to a relaxed state. This force pulls on the strips 16 and allowing them to flatten, thereby providing a narrowed profile for catheter retraction.

Figure 14A:
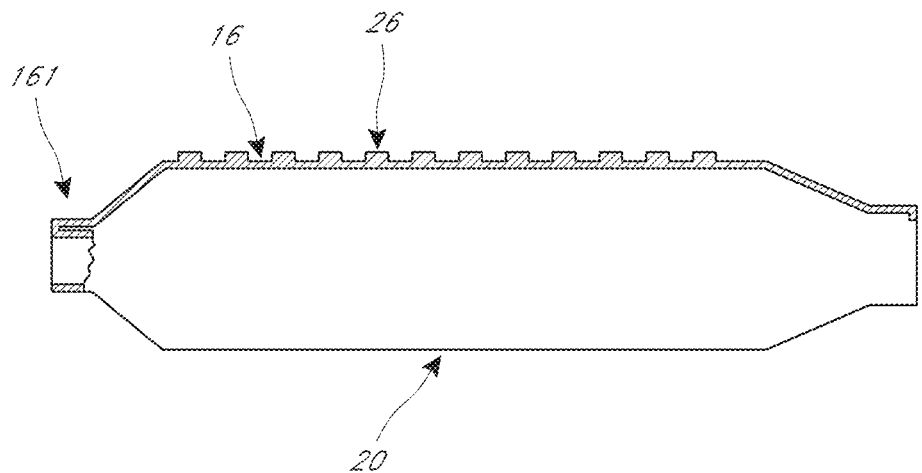
FIG. 14A illustrates a side view of an embodiment of a cage having strips with hooks that can attach to the inside of a balloon neck.
Figure 14B:
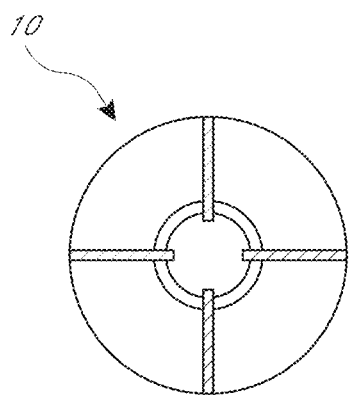
FIG. 14B shows an end view of a cage attached to a balloon as illustrated in FIG. 14A.

Looking now to FIGS. 14A-D another embodiment of strip 16 is shown with various types of rings. As illustrated in FIGS. 14A-B, in some examples, the ring can be fabricated from the lip on the neck of the balloon 20 and the portion of the catheter body used to bond the catheter to the balloon 20. The catheter can provide a pathway for gas or liquid inflation of the balloon 20. Additional components such as an over mold or heat shrink can be added to the bond joint, as can additive glue or polymeric material. In some examples, this can serve to prevent pressure from leaking out of the balloon 20 along the length of the strips 16 forming the cage 10.

As illustrated in FIGS. 14A-D, a hook 161 at the strip end can enable the strip to be easily aligned along the balloon surface and can aid in orienting the strip in a longitudinal orientation relative to the axis of the balloon 20. The hook 161 can be integrated into each end of the strip 16. The hook 161 can be wrapped around the lip of the neck of the balloon 20 from the outer diameter ("OD") of the balloon 20 neck around the opening and into the neck where the end of the hook 161 rests within the inner diameter ("ID") of the balloon 20 neck.

Both ends of the strip 16 can have a hook 161, or just one end can have the hook. In addition, the ends can be attached to the balloon catheter in the same or in different ways. For example, heat shrink can be wrapped around the ends of the strips and balloon. In some embodiment, heat shrink is wrapped around one end and a rigid ring, such as those discussed with respect to FIGS. 8-12 can be used at the other end, which may also include a heat shrink layer.

The strip may or may not be attached to the balloon at other locations. As shown, the strip 16 can also have hinges or pre-bent regions that correspond with the shape of the balloon. Thus, the strip in the expanded state can have a main portion having wedge dissectors 26 that is parallel with the axis of the balloon. Angled sections can extend from the main portion to the hooks 161. The angled sections can form an angle when the balloon is expanded as shown, but can be flat when the balloon is deflated. In some embodiments, hinges between the sections can be formed with thinner sections of material.

As shown in FIG. 14A the strip can attach to the balloon without a separate ring by use of the hooks 161. The balloon can be glued to a catheter (for example an elongated tube with one or more lumen) which can also secure the hook in place. FIG. 14A shows one strip for simplicity, though it will be understood that 2, 3, 4 (FIG. 14B), 5, or more strips could be used.

Figure 14C:
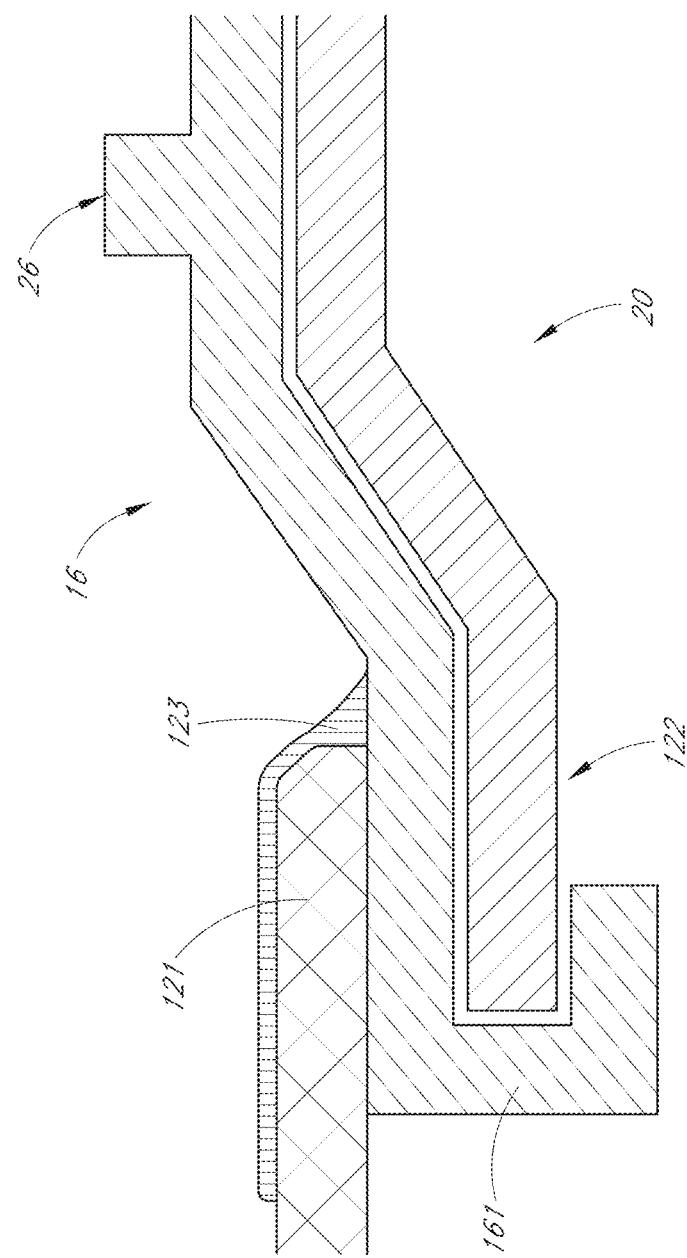
FIG. 14C is a cross sectional schematic view of the strip with hook locked into the balloon neck.

FIG. 14C shows a detail view of the hook 161 attaching to a balloon 20. As can be seen the balloon can serve as a base layer 122 of the ring and a top layer 122 is also shown. Adhesive 123 is also shown securing the top layer 121 to the balloon. In some embodiments, the top layer 121 can be the tube of the catheter.

Figure 14D:
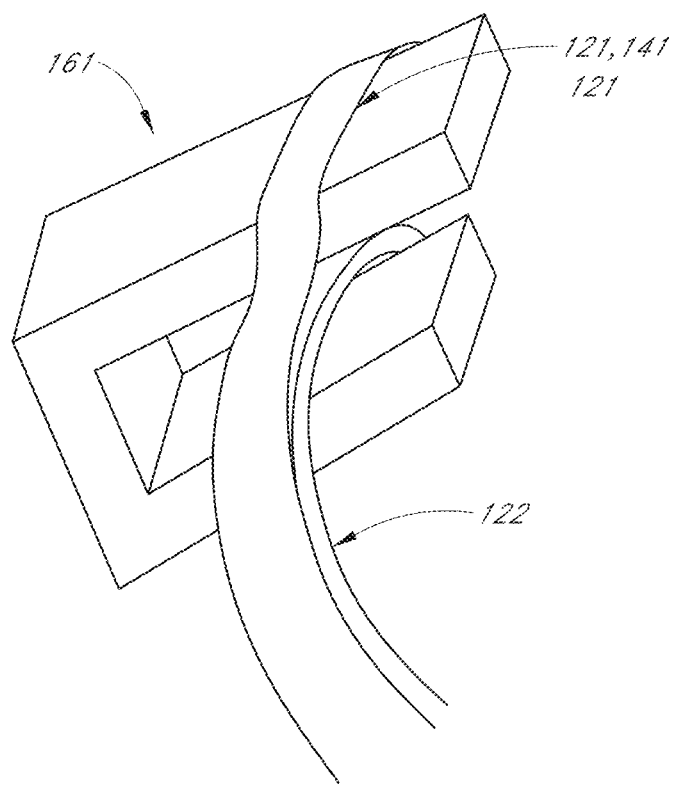
FIG. 14D is an alternative embodiment of the end of a strip with a multi-layer ring to form an end of the cage.

FIG. 14D shows a two layer 121, 122 ring. The two-layer ring can include two layers of heat shrink material. As discussed for FIGS. 10-11, the ring illustrated in FIG. 14D can be a multi-layer ring where the base layer 122 is less compressible or elastic than the top layer 121 and where energy is added to the top layer producing a reduction in the top layer's diameter until the top layer compresses and captures the strips between the base layer 122 and the top layer 121 to produce the cage 10.

Figure 14E:
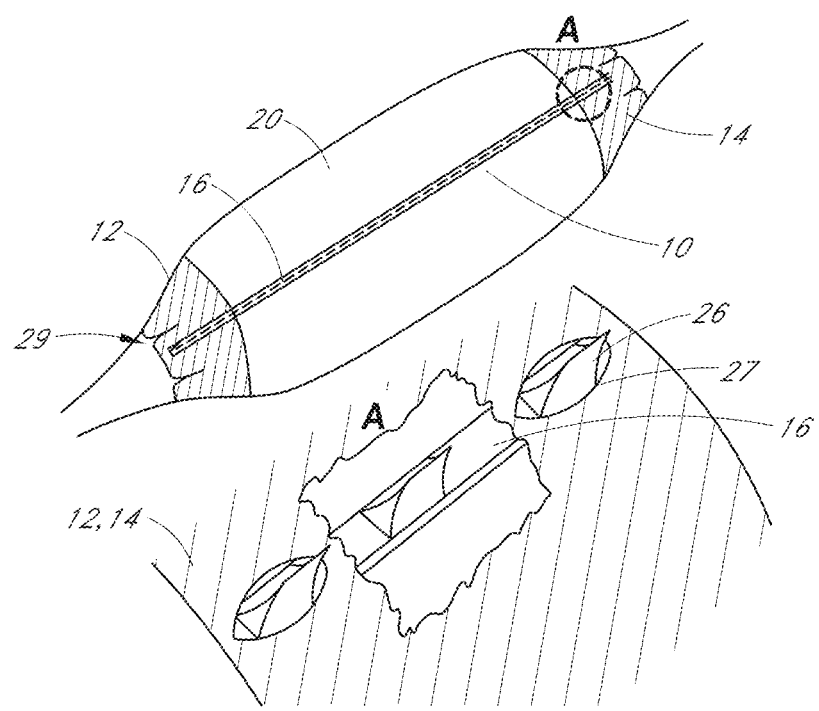
FIG. 14E shows an embodiment of a strip retained by a plurality of rings with the wedge dissectors protruding from the plurality of rings.

FIG. 14E illustrates another embodiment of the rings 12, 14 that secure the strips 16 on the surface of the balloon 20. As shown in callout "A," the rings 12, 14 can be secured to the balloon 20 such that the wedge dissectors protrude through the surface of the rings 12, 14. Callout "A" includes a cut away of the ring 12, 14 in the center in order to show the strip 16 below. The wedge dissectors can protrude through the rings 12, 14 in a variety of ways. For example, the shape of the wedge dissector can cut through the material of the rings 12, 14 as the rings 12, 14 are secured to the strips 16. This can form a hole 27. The rings 12, 14 can also have a plurality of holes 27 pre-cut into the rings 12, 14 to allow the wedge dissectors to extend through.

It can also be seen that the rings 12, 14 can be shaped to correspond with the taper of the balloon 20. For example, cutouts 29 of material in the rings can help a ring made of heat shrink material to shrink to the shape of the balloon.

As discussed above, each of the strips 16 can extend between one or two rings, though additional rings can be used as needed. For example, three, four, five, six, seven, eight, nine, or ten, or more rings can be used, especially with longer balloons. As one example, an angioplasty balloon 20 having a length of 300 mm can be fitted with a cage 10 having two rings 12 and 14 at either end. In addition to the rings 12, 14, the cage 10 can include rings 13 or other similar controlling elements that can aid the strips 16 in maintaining alignment and orientation as the balloon 20 expands towards the artery wall.

Figure 15A:
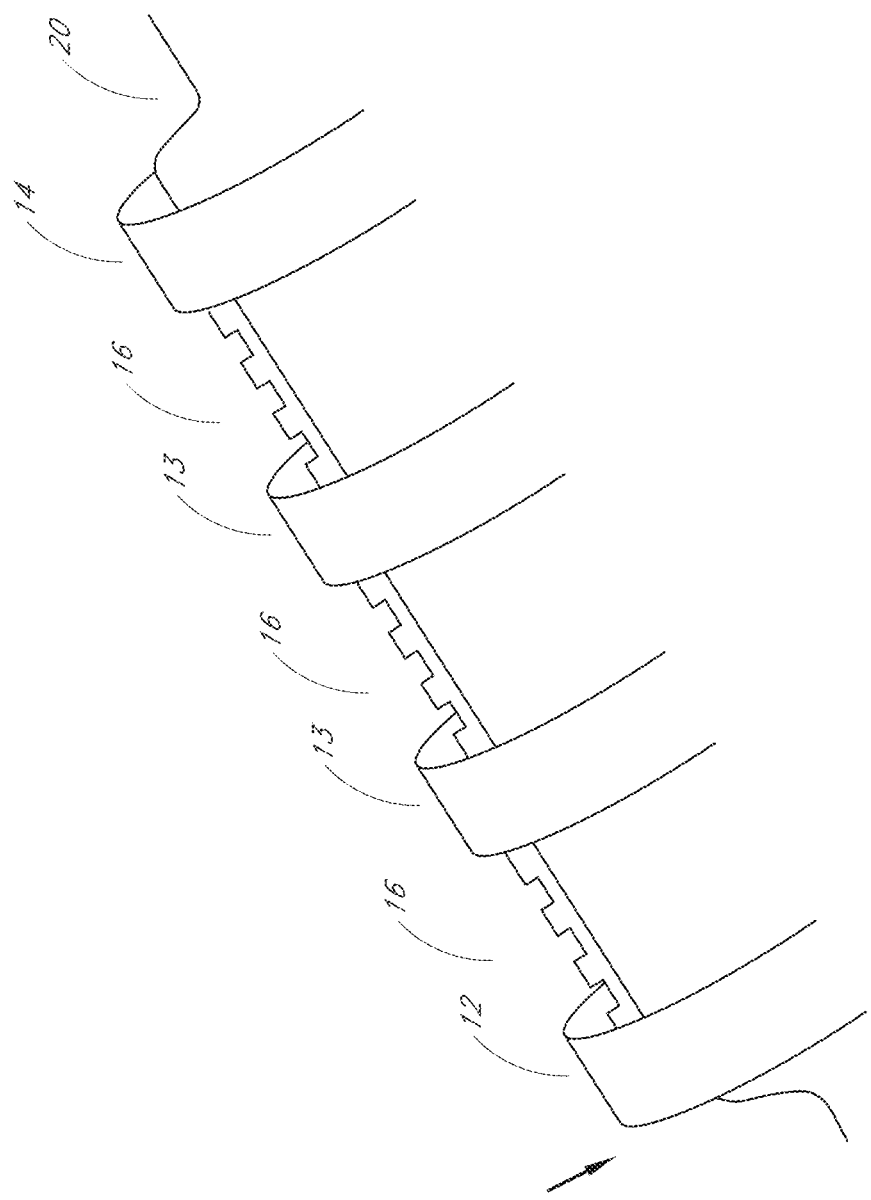
FIG. 15A illustrates a partial view of an embodiment of an angioplasty balloon with an embodiment of a strip bound to the angioplasty balloon with a plurality of ringed material to form a cage.

As illustrated in FIG. 15A, the rings 13 can be a fraction of the overall length of the balloon 20. Some ring 13 designs are less than one and a half times the length of the balloon 20. In other examples, the rings are between 1.0-0.5 times the balloon 20 length. More commonly the length of the rings 13 are between 2.5 and 1.5 times the balloon 20 diameter and typically between 1.5 and 0.5 times the balloon 20 diameter. Each ring 12, 13, 14 can be made from a different material so at to provide more than one advantage and function of the rings 12, 13, 14.

The rings 13 can be placed on the outer surface of the body of the balloon 20. In some examples, the rings 13 can be designed to retain the body of the strips 16 such that the position and orientation of the strips 16 are maintained. It can also be seen, that the strip 16 does not extend along the shoulders of the balloon. Thus, the strip can be elongated and can extend parallel with the axis of the balloon. FIG.

15A shows one strip 16 for simplicity, though it will be understood that 2, 3, 4, 5, or more strips could be used.

These rings 13 can be positioned over the expanded balloon 20 area and may have different properties than the rings 12, 14 on either end of the balloon 20. As illustrated in FIG. 15A, in some embodiments, the rings 13 positioned over the balloon 20 surface may be more elastic in property than those located on the ends of the balloon 20. This can allow the rings to accommodate the expansion and refolding of the balloon 20. In some examples, the rings used on the outer diameter of the balloon 20 are placed over the two ends of each separated strip. The strips 16 may also be glued, welded, restrained by friction fit, or otherwise attached to any of the rings described above.

In some embodiments, rows of strips and/or strip segments can be placed around the balloon 20. Some rows may extend over the entire length of the balloon 20 and other rows may not. In some examples, a row may include a plurality of strips in series that are separated by gaps. Placing strips in a series on the balloon can provide greater flexibility which can improve deliverability through tortuous anatomy.

As described previously, rings 12, 14, 13 can be used to retain the strip on the surface of the balloon 20. The rings can be connected to the strips in any number of different ways, as described in the various embodiments herein. In some embodiments, the ends of the strips 16 with no wedge dissectors can be used to attach to the rings. In other embodiments, the ends with wedge dissectors can attach to the rings.

Figure 15B:
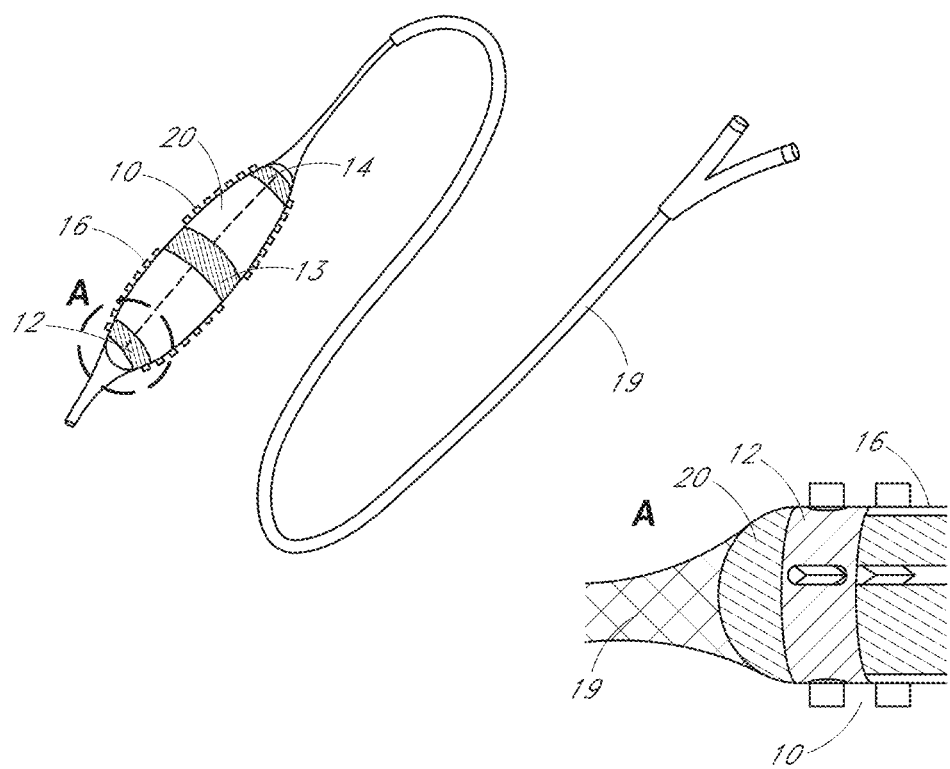
FIG. 15B is an angioplasty balloon with a cage having a plurality of segmented strips that are bound to the surface of the balloon by a plurality of rings.

FIG. 15B illustrates another embodiment of balloon catheter. A balloon 20 is shown with a cage 10 with four equally spaced rows of strips 16. Each row has two strips 16 that are laid in series. A ring 13 attaches the adjacent strips 16 to properly secure and orient the strips 16 across the surface of the balloon 20. Rings 12, 14 hold down the other ends of the strips.

The callout "A" provides an enlarged view of the distal end of the balloon 20 with cage 10. The hatching illustrated in callout "A" is provided to help visualize and delineate the different parts of the device. As shown, the end of the balloon 20 includes a ring 12 that secures a plurality of strips 16 to the surface of the balloon 20. The balloon 20 is disposed about a catheter 19. The ring 12 can be a heat shrink material. A wedge dissector is also shown extending through the ring. The placement of the strips is further clarified in FIG. 15C which shows how a pair of strips 16 which are laid in series such that the strips 16 span the length of the balloon 20.

Figure 15C:
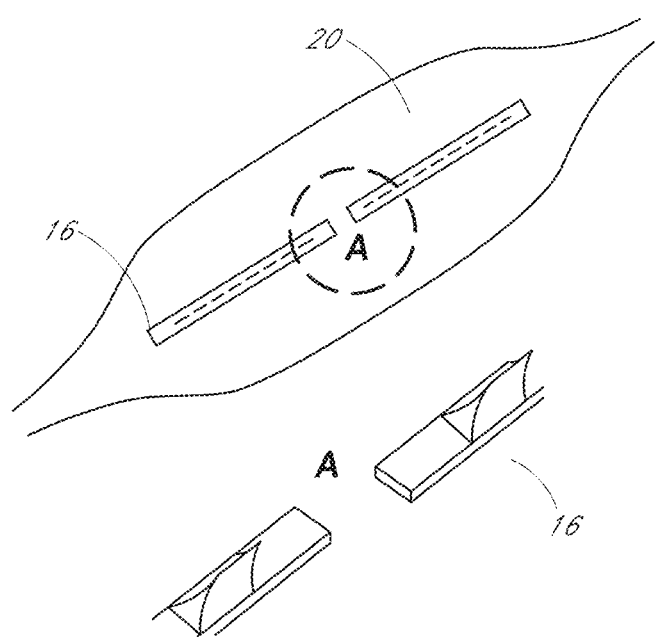
FIG. 15C shows an example of the placement of the segmented strips on the surface of the balloon.
Figure 15D:
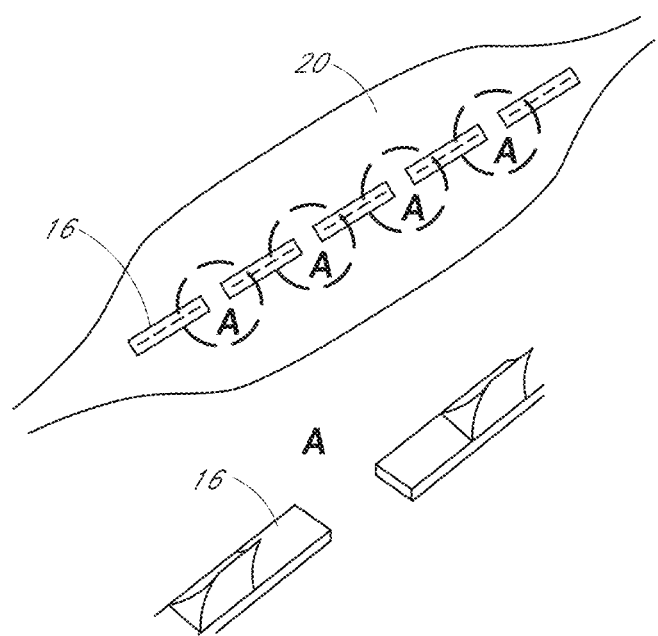
FIG. 15D is another example of the placement of a plurality of segmented strips onto the surface of an angioplasty balloon.
Figure 15E:
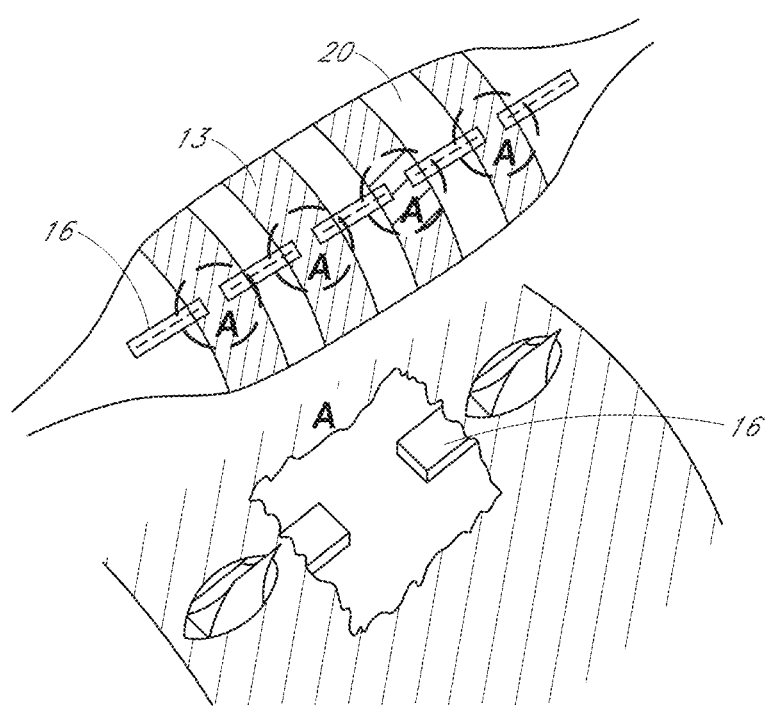
FIG. 15E illustrates an example of a plurality of segmented strips bound to the surface of a balloon by a plurality of rings.

To improve flexibility, the cage 10 can have rows that are made up of a greater number of strips 16 than illustrated in FIGS. 15B and 15C. FIGS. 15D-15E illustrate an example where five strips 16 are laid across the surface of the balloon 20 in series. As noted previously, each of these strips 16 can be secured on the surface of the balloon 20 by a plurality of rings 13. Callout "A" provides a cut away of the ring 13 to show the gap between the two strips 16 that are in series. As described above with reference to FIG. 14E, the wedge dissector can protrude through the ring 13 in a variety of ways. For example, the shape of the wedge dissector can cause the wedge dissector to poke through the material of the ring 13. As well, the ring 13 can have a plurality of holes cut into the rings 13 to allow the wedge dissectors to poke through.

In addition to having multiple strips in rows, the gap between the strips in a row can also be adjusted to increase flexibility. To ease manufacturing the linear alignment in the theta direction around the radius (angle drift) and the spacing alignment between the strips 16 (gap) can have a relatively broad tolerance creating greater options in developing the manufacturing process and choosing tools. In some cases, the gap tolerance can be ±5 mm and the angle drift±25 degrees; ±3 mm and the angle drift±10 degrees; and ±2 mm and the angle drift±5 degrees. Cage designs that require greater tortuosity can utilize the periodic strip placements in a linear sequence with spaced apart strips. This can enable the balloon to manage bends and turns in anatomical spaces with less stress on the strips and more effective pushability of the entire system.

As shown herein many of the strips 16 have a flat bottom. This can help the strips 16 sit on the surface of the balloon and to maintain the orientation of the wedge dissectors. This can prevent rotational movement of the strips 16 on the surface of the balloon 20.

Three unique features that all strip and ring configurations can work to achieve are 1) perpendicularity of the wedge dissectors to the balloon surface, 2) maintaining flat and low profile of the strips on the balloon, aiding in limiting the wedge dissectors from damaging tissue on its journey, and 3) either assisting in deflation of the balloon or producing a minimal burden on the typical balloon deflation characteristics. To achieve these features strips typically have a flat bottom, are bounding to the balloon with rings on either end of the strip, are folded to limit wedge dissector interaction with tissue on its journey, and when a ring lays over the wedge dissectors the wedge dissectors poke through the rings and the majority of the wedge dissector height is still available for penetration into the vessel. Although some designs utilize rings to produce forces on the balloon enabling more effective balloon deflation by either pulling on the strips end to end or by applying radial compression, in most designs the rings can support the strips by limiting strip movement, aiding in wedge dissector orientation, and preventing the strips from separating from the balloon. Design features that contribute to these functional characteristics include: strips that have flat bottoms enabling stable orientation of the wedge dissectors but are thin enough to be laid down tangential to the balloon or contained in a fold of the balloon during folding, spacing between the wedge dissectors does not have a cutting edge enabling rings to lay in the spacing and support strip retention, and the ends of the strips can be thinnest with no wedge dissectors enabling greater surface area for rings to bond to the strip and enabling the strip to be most flexible at the edge of the balloon where forces are highest during catheter migration to and from site of deployment. It will be understood that other benefits and advantages can also be provided.

The rings 12, 13, 14 can be attached to the strips 16 in a variety of ways. FIGS. 16A-C shows examples of the rings 12, 13, 14 secured to the strips 16. FIG. 16A shows a material wrapped around the balloon to form rings 12, 13, 14 such that the material of the ring can be secured to more than one strip. In some examples, as illustrated in FIG. 16B, the ring 12, 13, 14 can be wrapped about a portion of each strip. This can be accomplished in the same way as illustrated in FIG. 10, where each of the rings can have an upper layer and bottom layer that wraps around a portion of the strip 16. FIG. 16C illustrates a solid ring 12, 13, 14 that can be attached to a portion of the balloon. A portion of the strip can be secured to the ring.

As discussed herein, many of the embodiments can use a heat shrink material for part of, or the entire ring 12, 13, 14. Heat shrink material generally starts from an extruded tube that is cross-linked using a form of radiation. The tube can be stretched or otherwise formed to the desired thickness. For example, it can be stretched to a flexible microscopically-thin-wall tubing, it can be made rigid from a heavy-wall tubing, or it can be somewhere in-between. Cross-linking can create a diameter memory and can be designed with a shrink ratio from 2:1 up to 10:1. Heat shrink typically shrinks only in the radial direction but can also shrink in length.

Heat shrink material can be manufactured from a thermoplastic material, such as polyolefin, fluoropolymer (including fluorinated ethylene-propylene (FEP), polytetrafluoroethylene (PTFE) or polyvinylidene fluoride (PVDF)(e.g. KYNAR)), polyvinyl chloride (PVC), neoprene, silicone, elastomer or synthetic rubber and fluoropolymer elastomer (e.g. VITON). When a flexible material is desired, such as one that expands with a balloon, the heat shrink material can include one or more of polyolefin, silicone, elastomer or VITON (synthetic rubber and fluoropolymer elastomer).

Heat shrink material in the form of a tube can be used to slide onto or over the strips 16. The tube can have a shrink ratio of 3:1 or higher (e.g. 3.5:1, 4:1, 4.5:1, 5:1, 6:1) and allow for gentle heat shrinking to prevent any balloon deformation or other changing of the balloon's properties. The material can be flexible enough to conform to the balloon through a range of balloon diameters (such as typical with semi-compliant balloon technology ~0.5 mm diameter range), and may have an adhesive or other coating to support the bonding of the heat shrink material and balloon. The heat shrink material can be a thin film. The heat shrink material may also be in the form of a sheet or multiple sheets instead of a tube.

A method of retrofitting a balloon catheter with a cage can include any of the following steps. Positioning strips around an inflated balloon. The strips may include wedge dissectors. The strips can be positioned equally spaced around the inflated balloon. The strips can extend primarily longitudinally. The strips may be positioned serially in rows, such as 2-6 rows, each with 2-6 strips. The strips can be attached either permanently or temporarily to the balloon with an adhesive. Heat shrink material can be positioned around the ends of the strips as a ring. Individual rings of heat shrink material can connect to or cover ends of multiple strips positioned circumferentially around the balloon. Individual rings of heat shrink material can also connect to or cover ends of adjacent strips positioned serially in a row. Heat can then be applied to shrink the heat shrink material. The balloon can be deflated and then sterilized in preparation for use.

Turning now to FIG. 17, a schematic view is illustrated showing a detail of a cage 10. In some embodiments, the strip 16 is shown having a section 34 composed of a spring zone. The spring section of the strip 16 can provide a plurality of benefits. For example, the spring section 34 can increase the flexibility of the cage 10. Increasing the flexibility of the cage 10 can allow the cage 10 to more easily pass through the tortuous geometry of a blood vessel. The spring section 34 can also provide a wider base for the wedge dissectors 26, to help the wedge dissectors 26 remain in the desired orientation.

In some embodiments, the spring section 34 can interface with a surface of the balloon 20. The spring section can help the strip 16 to remain in the correct position with the wedge dissectors 26 in an outwardly projecting orientation. In some examples, the spring section can counteract a sideways bending moment on the spike such that the wedge dissectors 26 do not bend, flex, or change position an undesirable amount. In some embodiments, the spring section 34 can also provide the benefit of assisting the balloon 20 in refolding post inflation. The spring can add mechanical tension on the balloon 20 to return it to a compressed state and further aid the rings in compressing the balloon 20 during deflation cycles.

Figure 18:
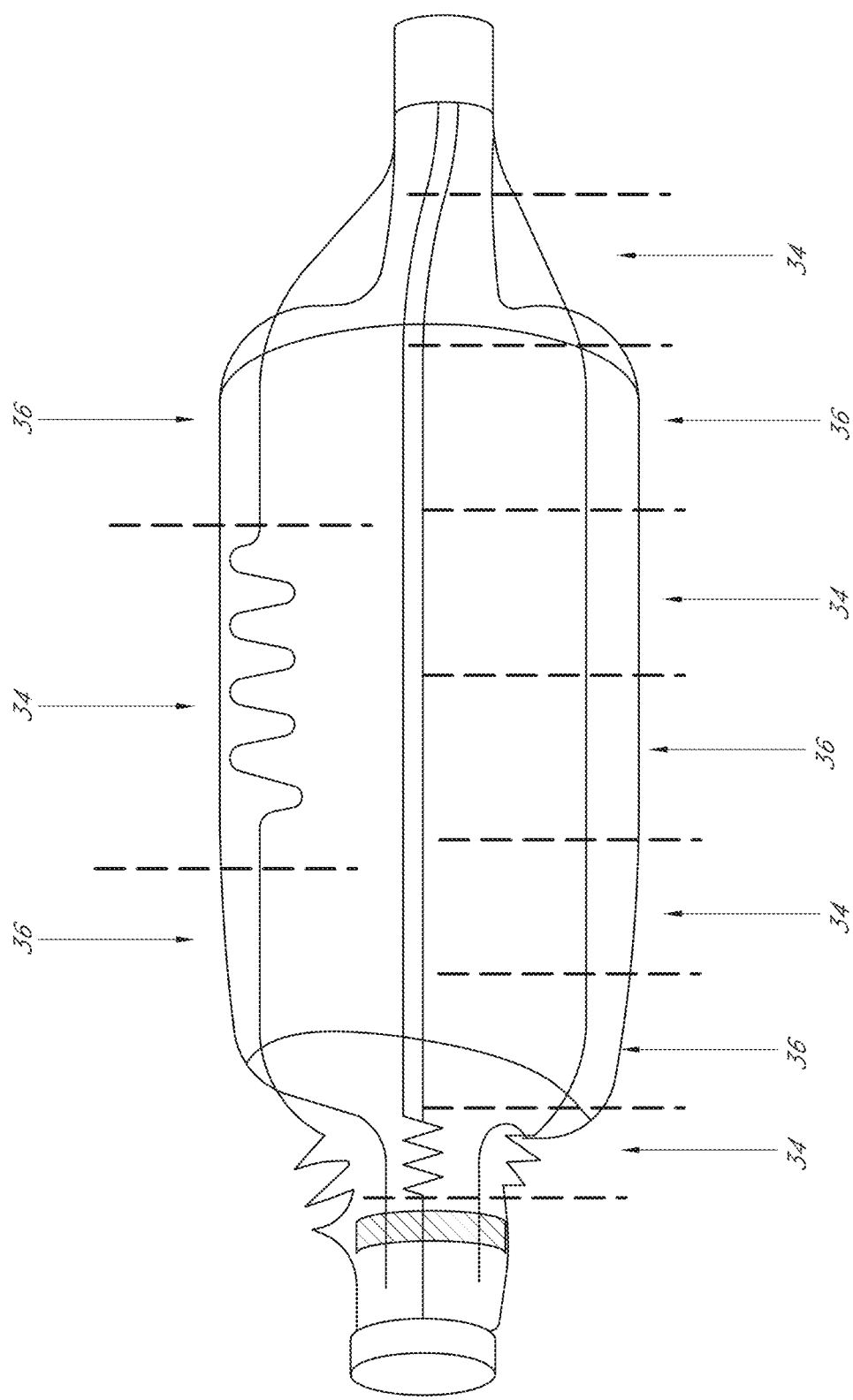
FIG. 18 illustrates various an embodiments of a cage utilizing aspects of the spring detail of FIG. 18.

The spring section 34 can have an undulating configuration and be connected to a straight section 36. In some examples, the wedge dissectors 26 can be located on the straight section. In other embodiments, the spring section can be sinusoidal. As illustrated in FIG. 18, the spring section is shown having a larger amplitude at the proximal end as compared to the distal end. The amplitude can decrease while the period increases along the spring section towards the straight section in a distal direction. In some embodiments, one side of the spring section can have a larger amplitude than the opposite side. In some embodiments, the spring section can be symmetrical.

Figure 19:
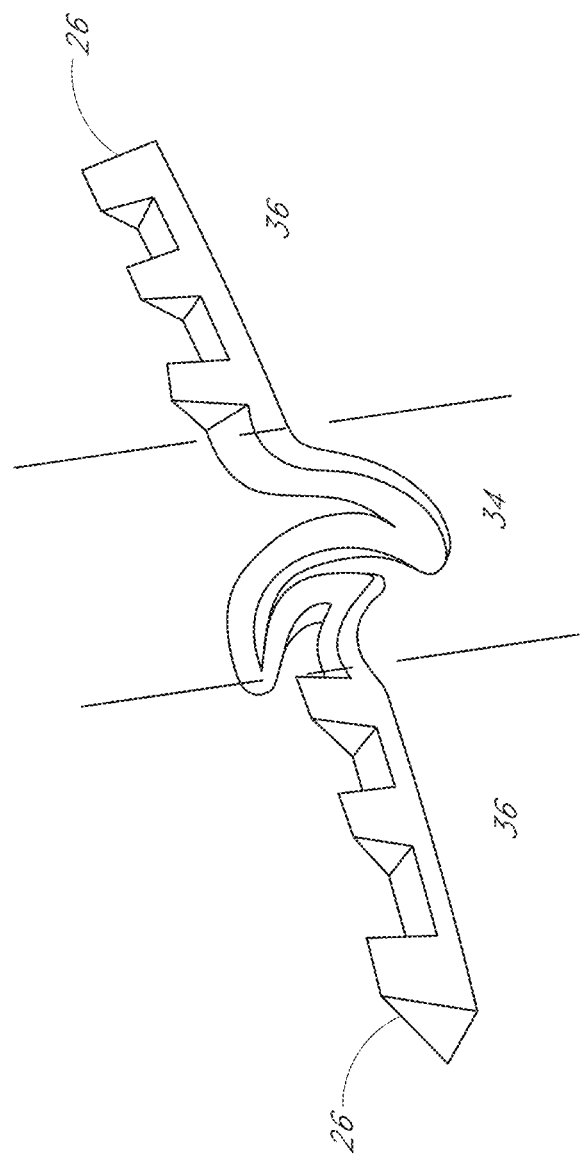
FIG. 19 shows a portion of a cage including a spring strip and spike configuration.

FIG. 18 illustrates various embodiments of the cage 10 utilizing the spring section 34 and straight section 36. Any number of different patterns can be used. FIG. 19 shows a detail of wedge dissectors 26 on straight sections 36.

Systems and methods as disclosed herein can deploy the cages and wedge dissectors in any body lumen, including vascular lumens such as arteries and veins. The arteries could be coronary arteries, peripheral arteries, or carotid or other cerebral arteries, for example, or iliac, femoral, superficial femoral, iliac, or other peripheral vasculature, for example. The device may also be used in any lumen or transportation vessel found in any of the respiratory, digestive, urinary, reproductive, lymphatic, auditory, optical, or endocrine systems. It is understood that a device for generating serrations in any one, two, or more of these systems may take slightly different forms. Independent of the location the device might be used, some embodiments of devices include spikes (also herein referred to as wedge dissectors, or serrating elements on a spline and an expandable mechanism to increase and decrease the diameter of the spike features (such as a balloon) with both attached to a base catheter-like device.

Figure 20:
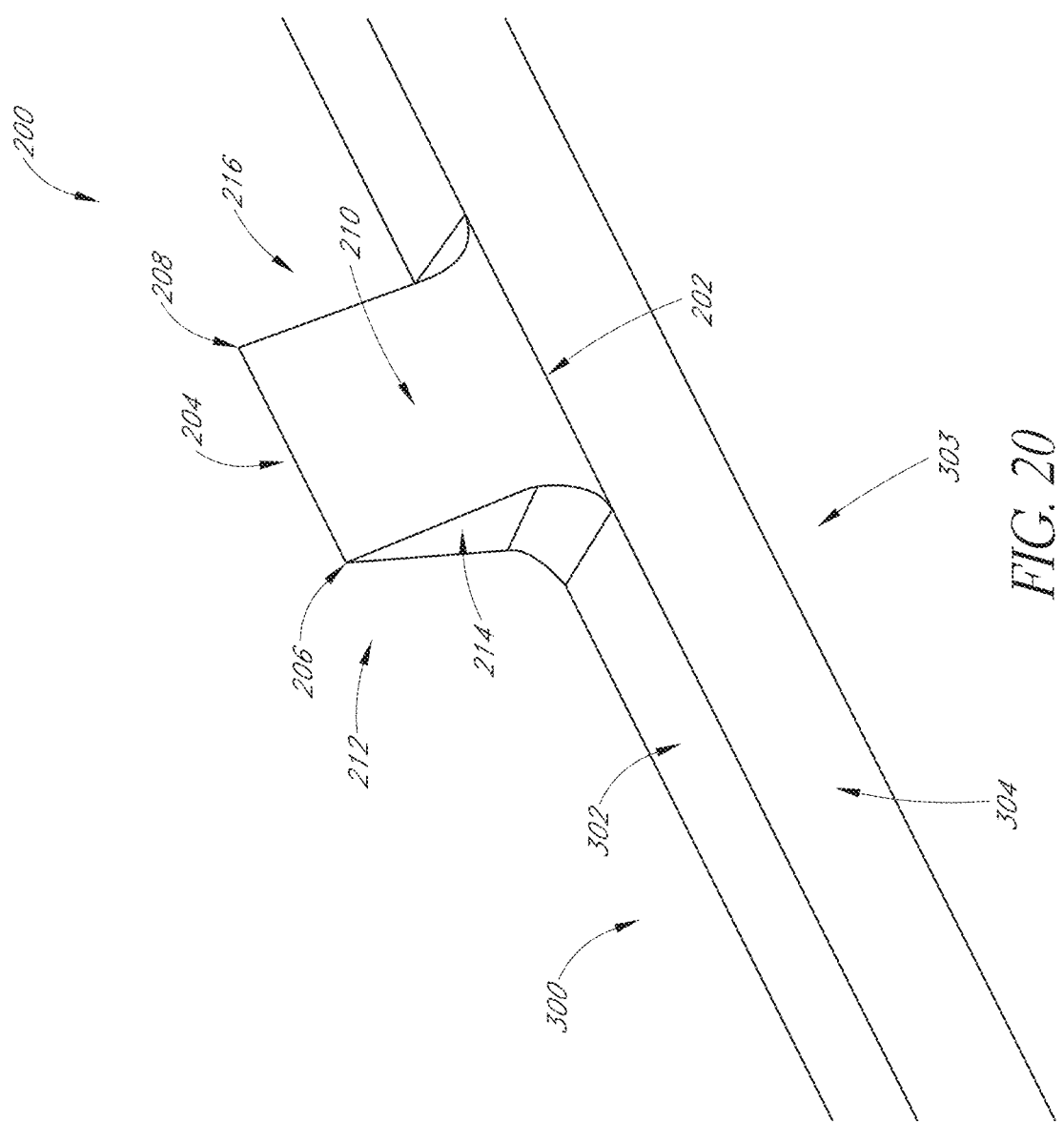
FIG. 20 is a close-up detail view of an embodiment of a wedge dissector on its associated strip.

In some embodiments, as illustrated for example in FIG. 20 which is a close-up detail view of an embodiment of a wedge dissector 200 on its associated strip 300, a wedge dissector 200 can include a strip-facing base surface 202 (which may also be referred to herein as a bounded surface). The strip-facing base surface 202 of the wedge dissector 200 can be defined by the base where the wedges 200 protrude outward and directly continuous with a surface of the strip at the interface between the wedge dissectors and the balloon. The strip could be a spline 300 or other strip-like structure. In some embodiments, this strip-facing base surface 202 has a relatively narrow width made of a hard material capable of holding a sharp edge. In some embodiments, the preferred material is martensitic stainless steel, with a hardness of 52 to 64 on the Rockwell C-scale (HRC) although other materials including a polymer or co-polymer including but not limited to polyolefin, fluoropolymer (including fluorinated ethylene-propylene (FEP), polytetrafluoroethylene (PTFE) or polyvinylidene fluoride (PVDF)(e.g. KYNAR)), polyvinyl chloride (PVC), neoprene, silicone, elastomer or synthetic rubber and fluoropolymer elastomer (e.g. VITON), or a combination thereof can be utilized. In some embodiments, the strip is about or no more than about 0.008", 0.010", or 0.012" wide (oriented circumferentially). In some cases, the width can be between about 0.006" and about 0.020" or between about 0.004" and about 0.030". In some embodiments, the strip 300 typically runs longitudinally the length of the working balloon edge, but can also be oriented in angles up to and including 90 degrees from the longitudinal axis of the balloon (or other expandable structure), or in a helical fashion at varying pitches. In some embodiments, the height of the base strip 300 can be between about 0.004" and about 0.010", or between about 0.002". and about 0.020" in some embodiments.

Still referring to FIG. 20, a wedge dissector 200 can also include a radially outwardly facing surface 204 (which may be referred to herein as an unbounded surface) that can define a top surface of the wedge dissector 200 from first (e.g., proximal) edge 206 to second (e.g., distal) edge 208 and be configured to contact tissue, plaques, or other structures within the body. Also shown are anterior surface 210, posterior surface 212, and opposing lateral surfaces 214 and 216. In some embodiments, the lateral surfaces 214, 216 extend upward generally perpendicular to the longitudinal axes of the strips, and the radially outward facing surface extends between the lateral surfaces as a linear, curved, or other geometry as described elsewhere herein at an angle to the lateral surface/lateral surface axis. Also illustrates are strips or splines 300 having an unbounded (e.g., superior-facing) surface 302 that can be coextensive with the strip-facing surface or boundary 202 of the wedge dissector 200, as well as side surfaces (e.g., 304), and inferior-facing surface 303.

Figure 21:
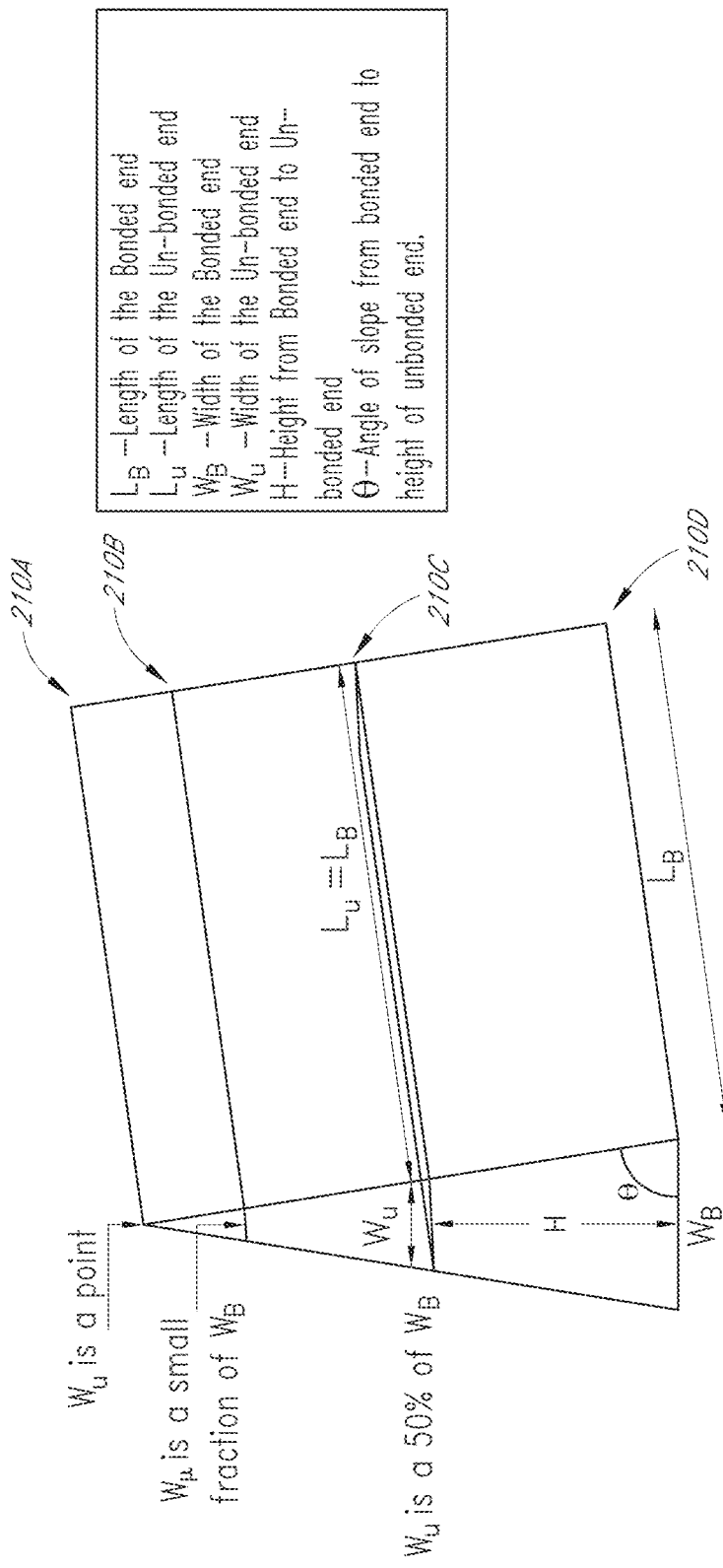
FIG. 21 illustrates a schematic perspective view of various dimensions and terminology of a wedge dissector, according to some embodiments.

FIG. 21 is a schematic illustrating several possible non-limiting embodiments of a wedge dissector. In some embodiments, the length of the radially outwardly facing surface $L_U$ (e.g., radially outwardly facing surface 204 between first edge 206 and second edge 208 of FIG. 20) is between about 30%, 20%, or 10% less than the total length of the strip-facing surface $L_B$ (of strip-facing surface 202 in FIG. 20). In some embodiments, the radially outwardly facing surface length $L_U$ can be from about 50% to about 20% less than the strip-facing surface length $L_B$, and sometimes as large as the strip-facing surface length $L_B$. The radially outwardly facing surface width $W_U$ is in some cases equal to or less than the strip-facing surface width $W_B$, and typically between or less than about 10%, 20%, 30%, 40%, or 50% of the strip-facing surface width $W_B$, or between about 20% and about to 50% less than the strip-facing surface width $W_B$, and sometimes about or up to about 50%, 60%, 70%, 75%, or 80% of the strip-facing surface width $W_B$. Therefore, in some embodiments there is an angle θ that is equal to or less than about 90 degrees that defines the slope from the strip-facing surface width $W_B$ to the radially outwardly facing surface width $W_U$ on at least one of the strip-facing surface width $W_B$ edges. While in some embodiments the radially outwardly facing surface width $W_U$ is constant from edge to edge, in some embodiments the radially outwardly facing surface width $W_U$ varies along the radially outwardly facing surface length $L_U$ as described elsewhere herein, such as decreasing from a first lateral edge to a point or segment in between the first lateral edge and the second lateral edge of the radially outwardly facing surface segment, and then increasing, from the point or segment in between the proximal edge and the distal edge, to the distal edge. In some embodiments, the relatively central segment in between the proximal edge and the distal edge has a constant width, while the lateral segments surrounding relatively central segment have variable, such as tapered widths.

Figure 22A:
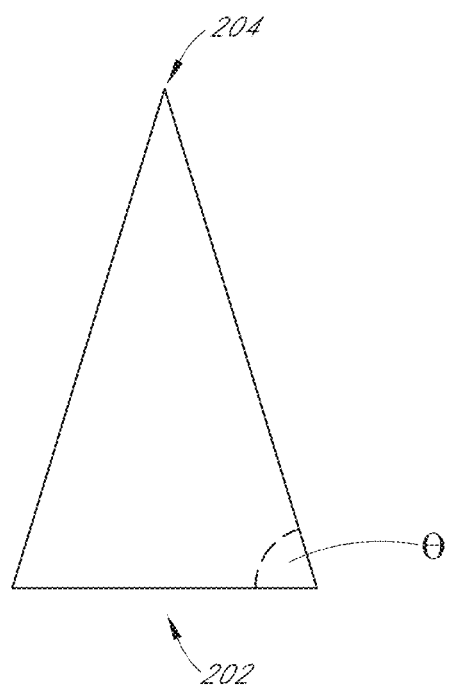
FIGS. 22A-22F illustrate respective end and isometric views of various wedge dissector geometries, according to some embodiments.
Figure 22B:
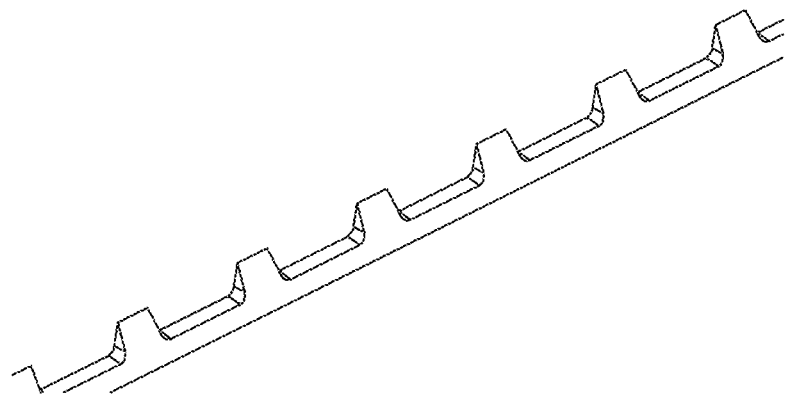
Figure 22C:
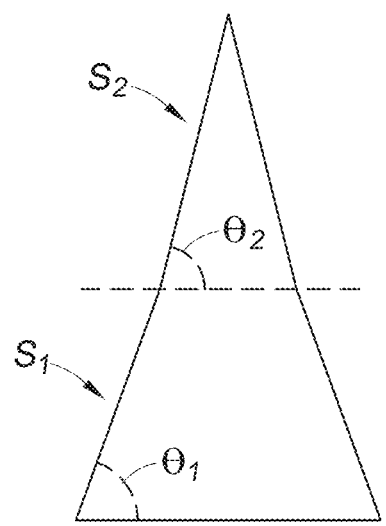
Figure 22D:
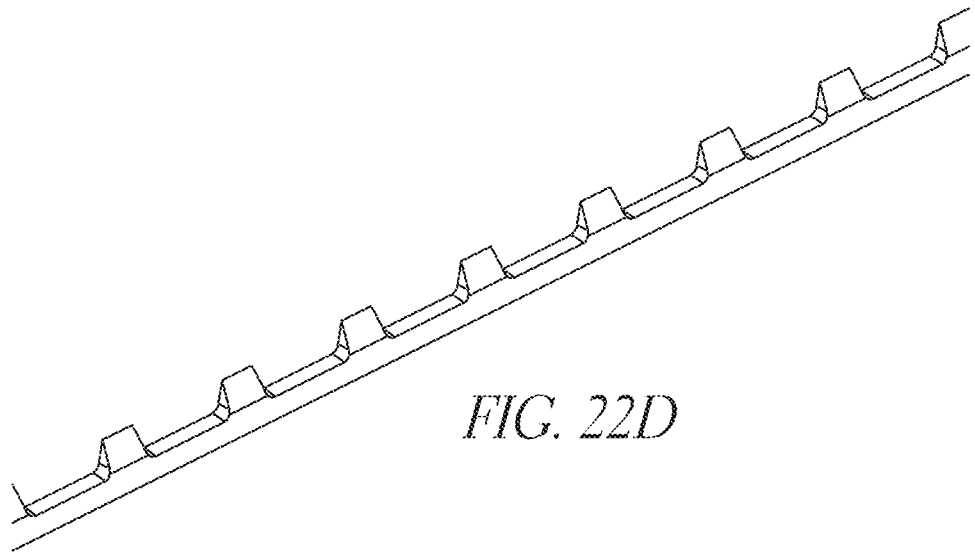
Figure 22E:
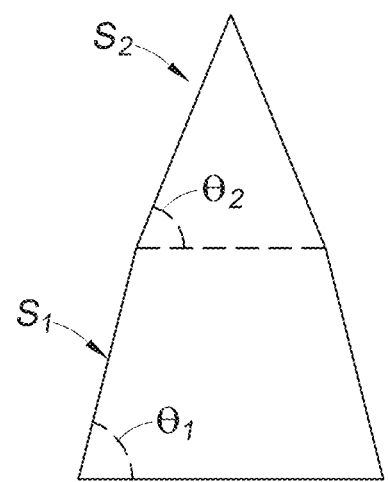
Figure 22F:
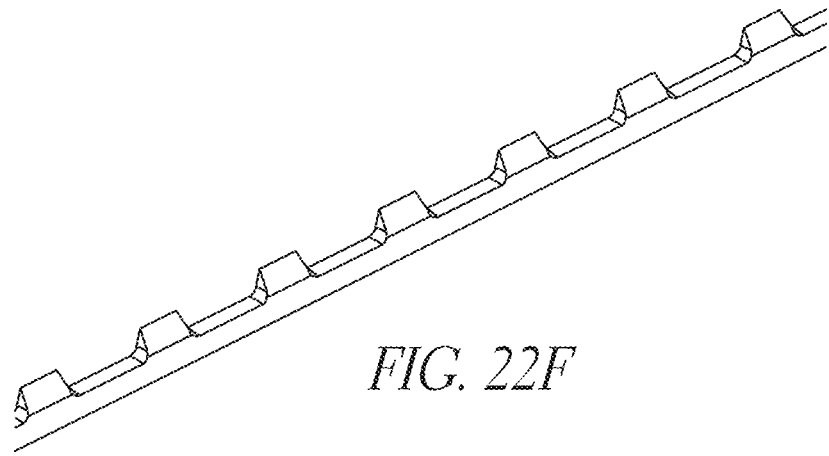

Although the radially outward facing width $W_U$ can come to a point, sloping from the strip-facing base width $W_B$ of the strip-facing base surface 202 to the radially outward facing width $W_U$ of the radially outward facing surface 204 in a single, constant sloped angle θ or bevel such as shown in FIG. 22A (end view resembling an isosceles triangle) and FIG. 22B (isometric view), it can also in some embodiments include a plurality of different angles, such as more than a single slope angle such as a double, triple or more bevel (e.g., a first angle for a first segment of the height, a second angle for a second part of the height that can be less than or greater than the first angle, and in some cases a third angle for a third part of the height that can be less than or greater than the first angle, and less than or greater than the second angle). FIG. 22C illustrates an end view and FIG. 22D illustrates an isometric view of a wedge dissector with a plurality of differing slopes and associated angles from the strip-facing base surface to the radially outward facing surface, where the angle θ2 between horizontal and an upward slope after a transition point is greater than an angle θ1 between the horizontal strip-facing base edge and the intersecting upward slope (in other words, the first slope S1 from the strip-facing base edge base is less steep than a second slope S2 higher up after a transition point). FIGS. 22E and 22F illustrate an embodiment similar to FIGS. 22C and 22D except the angle θ2 is less than the angle θ1 (in other words, the first slope S1 from the strip-facing base edge base is steeper than a second slope S2 higher up after a transition point).

Alternately, some embodiments may also include a series of steps at different heights where the width transitions to a narrower width and then continues to climb in height. When a series of steps is used in place of the bevel it can sometimes be due to fabrication limitation when methods other than a reel of stainless steel is honed to an edge.

The shapes of the radially outward facing edge or surface (e.g., radially outward facing surface 204 of FIG. 20) can in some embodiments be the same height from one edge 206 of the radially outward facing length or width to the other edge 208. In some embodiments, the height along the radially outward facing surface 204 can vary from one edge 206 to the other edge 208. When the radially outward facing edge or surface 204 varies, typically the radially outward facing edge has a series of raised features herein referred to as wedge dissectors, spikes, or serrating elements 200. In some embodiments, the midpoint of these raised features along the radially outward facing length 204 between edges 206, 208 is the highest point of the radially outward facing surface. However, in some embodiments, the highest point is offset from the midpoint, and there may be a plurality of highest points interspersed by lower point relative to the bounded/base surface 202. The maximal variation of height between edges 206, 208 of the radially outward facing surface 204 of the wedge dissectors 200 and the radially outward facing surface 302 of the base strip 300 between the wedge dissectors 200 can in some embodiments be less than about 80%, 70%, 60%, 50%, 40%, 30%, 20%, 10%, or less than the total height of the wedge dissector 200.

In some embodiments, the base strip 300 has a roughened or otherwise textured inferior surface to aid in adhesion to an outer surface of the underlying balloon. The base strip can have any desired geometry such as square, rectangular, or in some embodiments trapezoidal with the bottom surface having a greater width, such as about or at least about 10%, 20%, 30%, 40%, 50%, 60%, 70%, 80%, 90%, 100%, or more of the top surface. In some embodiments between about ⅓ and ½ of the top surface of the strip 300 is covered by wedge dissectors 200, while between about ½ and ⅔ of the top surface are free of wedge dissectors 200.

Referring to FIG. 21, in some embodiments, the radially outward facing surface viewed from the top can be seen as a line extending from one edge of the radially outward facing length to the other edge of the radially outward facing length (e.g., where $W_U$ is a point assuming 210A is the radially outward facing surface of the device). This would be analogous to a honed or "razor-sharpened" edge with no apparent width. In other embodiments, the top view appears as an unhoned surface that is slightly blunt resembling a rectangle (e.g., if 210B or 210C is the top of the device, and assuming everything above those lines were cut off) with the width of the radially outward facing surface $W_U$ being less than the strip-facing base surface $W_B$ but directly correlated with the slope or slopes between the width edge and height from the strip-facing base surface to the radially outward facing surface. In some embodiments, the top or the radially outward facing surface can be a line, a flat rectangle, a rounded or mounded surface (that might appear to be a rectangle or square in a 2-dimension point of view), or take a pyramidal, wedge, trapezoidal, or other polygonal shape.

In some embodiments, an unhoned width can be a width, for example, that is about or greater than about 1 nm, 5 nm, 10 nm, 50 nm, 100 nm, 500 nm, 1 μm, 2 μm, 5 μm, or 10 μm measured at the radially outward facing edge or surface. In some embodiments, unhoned radially outward facing surfaces of wedge dissectors can be advantageous as being slightly blunt/relatively less sharp than honed edges, in situations for example where creating serrations, indentations, and/or microperforations in a wedge dissector target, for example, is desirable rather than making cuts through the entire luminal wall. In some embodiments, the entire radially outward facing wedge dissector surface has an unhoned width.

Figure 21A:
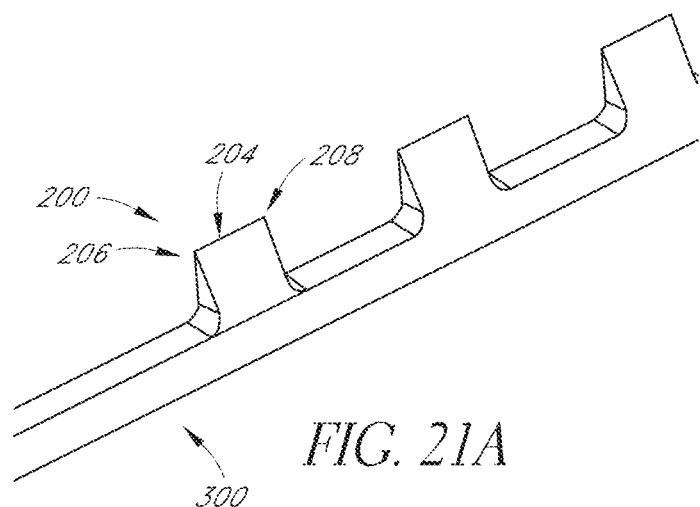
FIGS. 21A-G illustrate various embodiments of wedge dissector geometries.
Figure 21B:
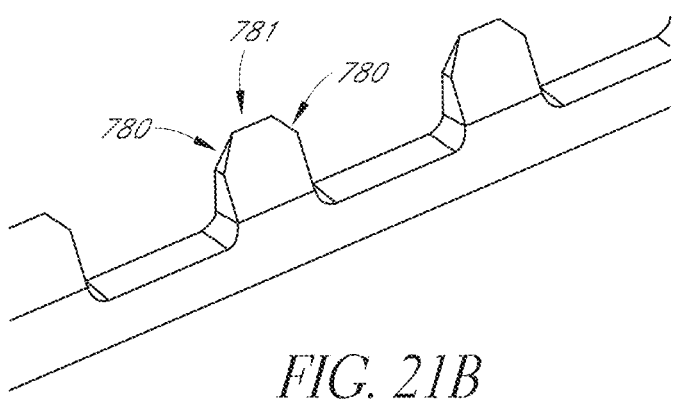
Figure 21C:
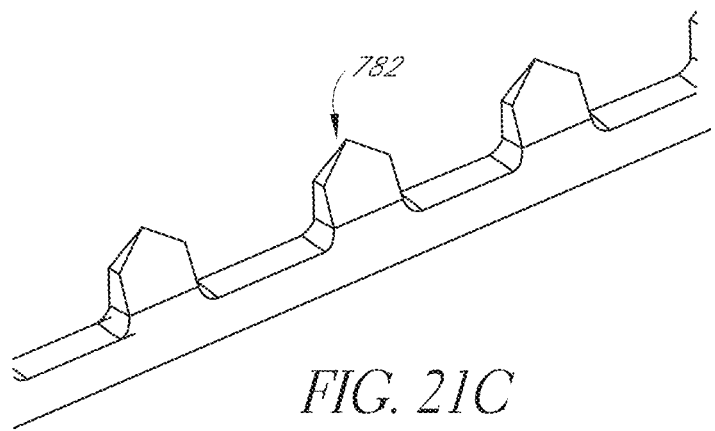
Figure 21D:
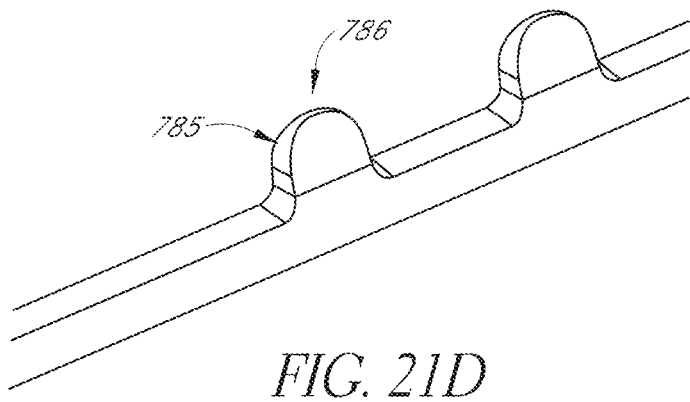

The shape of the wedge dissectors can take many forms, including further non-limiting embodiments as those shown in FIGS. 21A-G. For example, FIG. 21A illustrates wedge dissectors 200 rising from a base strip 300 with a honed/sharp radially outward facing surface 204 from edge 206 to edge 208. FIG. 21B-21C illustrates wedge dissectors with chamfered segments 780 of a radially outward facing surface on both lateral edges that slope or otherwise ramp upward to a honed central single point 782 or edge having a length 781. The slope could be a straight line ramp, or follow a curve as seen in FIG. 21D below. As illustrated in FIG. 21B, the wedge dissector includes lateral segments 780 of radially outward facing surface that increases in height, but decreases in width from a first edge to a central mid-portion 781 having a length with minimal/negligible width, and then increases in width and decreases in width from the midpoint to the second edge. FIG. 21C illustrates a wedge dissector similar to FIG. 21B except that the mid-portion is a single honed apex point 782.

FIG. 21D illustrates a wedge dissector with a radiused radially outward facing surface 785 that increases in height from an edge along a first curved length but decreases in width from a first edge to a central zone such as a midpoint 786, then decreases in height and increases in width along a second curved length to another edge.

Figure 21E:
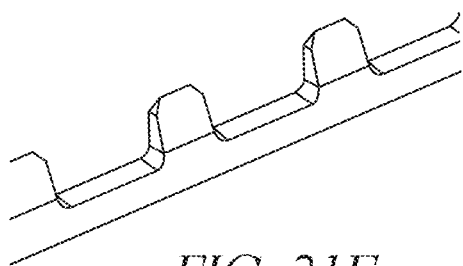
Figure 21F:
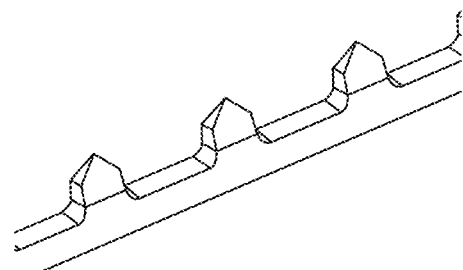
Figure 21G:
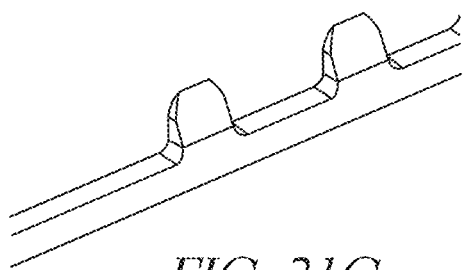

FIGS. 21E-21G illustrate embodiments of wedge dissectors with an unhoned, radially outward facing surface that do not include a sharp honed point or edge (e.g., having a width that is larger than that of a honed edge). FIG. 21E illustrates an embodiment of a wedge dissector somewhat similar to that of FIG. 21B, except the radially outward facing surface is completely unhoned along its length. FIG. 21F illustrates an embodiment of a wedge dissector somewhat similar to that of FIG. 21C, except the radially outward facing surface is completely unhoned along its length. FIG. 21G illustrates an embodiment of a wedge dissector somewhat similar to that of FIG. 21D, except the radially outward facing surface is completely unhoned along its length.

One commonality of the embodiments of FIGS. 21B-21G is that the widths of the radially outward facing surfaces are greater (wider) at the lateral edges, and narrower/less wide more centrally, either at a central point or longer central segment. The height of the radially outward facing surface from one edge to the other edge can be arched or otherwise variable, e.g., with a highest point more centrally and the shortest height at one or more edges when viewed from the side. In these embodiments, the orientation of the narrowest or thinnest (least wide) section of the radially outward facing surface can be along the longitudinal axis of the strip, which may or may not be aligned with the longitudinal axis of the balloon.

In other embodiments, the narrower point or segment need not be symmetric about the midpoint of the length of the radially outward facing surface, but can be asymmetrical/offset from the midpoint of the length in some cases.

Independent of the geometry of the wedge dissectors, some embodiments are characterized by having a bounded end 202 or base (e.g., the spikes have a base the spikes are "attached" to, whether it is a spline (or strip), a balloon, or a molded element of some sort) with a length and width and an radially outward facing surface 204, end or tip with a length and width. In some embodiments, the width of the radially outward facing end is about, or less than about 90%, 85%, 80%, 75%, 70%, 65%, 60%, 55%, 50%, 45%, 40%, 35%, 30%, 25%, 20%, or less than the width of the strip-facing base end, or ranges incorporating any of two of the foregoing values. The width of the strip-facing base end of the wedge dissector (as well as the spline/strip) can be fixed/constant, or alternatively variable in some embodiments.

The wedge dissectors can be a number of different sizes and shapes. In some embodiments, the wedge dissectors are about or less than about, for example, 0.10", 0.09", 0.08", 0.07", 0.06", 0.05", 0.04", 0.03", 0.02", or 0.01" in length at the strip-facing base end or ranges incorporating any of two of the foregoing values, or between about 0.01" and about 0.06", or between about 0.01" and about 0.04" in length. In some embodiments, the wedge dissectors can be about or less than about 0.05", 0.04", 0.03", 0.025", 0.02", 0.015", 0.01", or 0.005" in height as measured from the unbonded edge of the base strip, or between about 0.005" and about 0.025" or between about 0.01" and about 0.025", or between about 0.005" and about 0.015" in some embodiments.

The wedge dissectors can, in some embodiments, have a wedge strip-facing base length of about, or less than about 25 mm, 20 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm long, or ranges incorporating any two or more of the foregoing values. In some embodiments the wedge dissectors have a wedge strip-facing base length of 2 mm, 2.5 mm, or 3 mm long, or between about 1 mm and about 5 mm long, or between about 1.5 mm and about 3.5 mm long. The wedge dissectors can be spaced apart in a regular or irregular fashion to increase the flexibility of the device. For example, the space between adjacent wedge dissectors can be, for example, between about 2 times to about 10 times the wedge strip-facing base length of the wedge dissectors, with the wedge dissectors positioned lengthwise. For example, in some embodiments, wedge dissectors with a wedge strip-facing base length about 2.5 mm long can have about 5 mm spaces between them, or about 25 mm spaces between them. In some embodiments, groups of wedge dissectors can be spaced apart with a first smaller ratio of, for example, about 1-4 times the strip-facing base length of the wedge dissectors and then a group can be spaced apart by a second larger ratio, for example, about 8-10 times the strip-facing base length of the wedge dissectors. For example, a first group of wedge dissectors with a strip-facing base length of 2.5 mm can have 5 mm spaces between them and then a second group of wedge dissectors can be spaced 20 mm from first group. The second group can have the same or a different size, shape, and or spacing as the first group.

The location of the radially outward facing surface relative to the strip-facing base surface is not always centered or symmetric in some embodiments. In other words, the midpoint of the radially outward facing surface can be offset from the midpoint of the strip-facing base surface. FIGS. 23A-B and 24 illustrate an asymmetric radially outward facing surface as an alternate embodiment of the spikes. An asymmetric radially outward facing surface can be off center with respect to the alignment of a radially outward facing width edge directly over the strip-facing base width edge. In this configuration only one of the strip-facing base width edges has a tilted edge 440 climbing in height off of the radially outward facing surface while the other height edge 442 is perpendicular, at a 90 degree (right) angle RA to the strip-facing base surface 444, seen best in FIG. 23A. In addition, the edges of the radially outward facing surface in one or both of the width ends and/or in one or both of the length ends can be chamfered or beveled or have a radius. In some variations, the radially outward facing surface location is limited to the area projected upward over the strip-facing base surface. The radially outward facing surface can be a sharp line (e.g., honed edge) or any of the described unhoned edge variations for example. FIG. 23C-D illustrates an embodiment where the total volume or substantially the total volume of the wedge dissector rises/is present over less than the entire width (or surface area) of the base of the strip, such as about or less than about 70%, 60%, 50%, 40%, or 30% of the width or surface area of the strip, for example, and are thus the wedge dissectors are asymmetrically offset either anteriorly or posteriorly from the longitudinal axis of the strip.

FIG. 24 illustrates an embodiment illustrating how the radially outward facing surface 204 may have a varying height (increasing from first height 24H1 at first edge 206 to second height 24H2 at second edge 208) from the strip-facing base surface 202 and may include edge profiles that are rounded with a radius of curvature of the radially outward facing length edges 206, 208. Here we see a wider radius of curvature at one edge 206 that has a shallow height 24H1 measured from the strip-facing base surface 202 while the radius of curvature of the opposite edge 208 is narrower and has a longer height 24H2 measured from the strip-facing base surface 202.

In some embodiments, the various wedge dissector features described herein can offer unique advantages to aid in delivery of the device, including but not limited to reducing vessel trauma if the radially outward facing surface is positioned outside of the delivery apparatus and/or can contact the luminal wall and has the potential to scrape the vessel wall during movement through the artery. This can be the case, for example, in embodiments with wedge dissectors with unhoned, radially outward facing surfaces.

In addition, not to be limited by theory, certain shapes may offer more effective penetration into the tissue. For instance, wedge dissectors that include chamfered or rounded radially outward facing edges can potentially enter the vessel wall with less force (requires less pressure to penetrate tissue) while still maintaining an effective micro channel 5100 to weaken the tissue and enable tissue expansion with minimal vessel trauma and cellular injury.

Furthermore, while there have been prior proposals for providing blades or sharp edges or scoring wire on a balloon during angioplasty or other procedure for cutting or scoring the plaque in conjunction with balloon expansion, these prior methods are deemed to have problems or disadvantages which are eliminated or avoided by systems and methods as disclosed herein. Cutting or scoring a luminal wall, such as, for example, the plaque during angioplasty can be performed at high pressures that can result in high injury to the blood vessel. The cutting blades, edges or scoring wire can be forced into the wall of the blood vessel at the same time that the angioplasty balloon is expanded to dilate the plaque. During this process the cutting blades, edges, or scoring wire can be forced into the vessel wall at oblique angles and can plow up the plaque potentially increasing the tendency for dissections. In contrast, in some embodiments, wedge dissectors employ can be expanded into the plaque at low pressures so as to form precise microperforations, serrations, and/or indentations in a radially outward direction that form precise indentations, cleavage lines or planes in the plaque or other location in the luminal wall, or other target. The radially outward facing surface of the wedge dissector can push into the plaque or other luminal surface in small surface areas, thereby being much less likely to plow up the plaque or luminal surface.

Wedge dissectors can be designed, in some embodiments, to provide a series of oriented punctures or serrations into (but not completely through in some cases) a diseased vessel wall, which can create in some cases predictable and controlled lumen expansion along the serrated lines with minimal injury, and without cutting with blades with honed/sharp edges. The perforations can serve as a pathway such as micro-channels for pharmaceutical or other agents as shown in FIG. 23E. The pharmaceutical or other agents could be delivered using a drug-coated balloon, incorporated either with the device disclosed herein, or on a separate device that is used following the usage of the disclosed device. In some embodiments, the wedge dissectors can be detachable from the base strip, and/or be coated or otherwise impregnated with one or more pharmaceutical agents for drug delivery. The wedge dissectors can produce a linear line of weakness or perforations without cutting a continuous axial segment of the vessel wall that can enable more effective and gentler vessel lumen expansion 5110 as shown in FIGS. 23F and 23F.1. One can see the examples of stages of gradual expansion and serration in 5110, 5130, 5140, 5150. The balloon can be inflated and while the pressure in the balloon increases the following series of events can occur: the balloon unfolds in the artery and the strips are exposed from their resting place within the folds; the tips (e.g., radially outward facing surface) of the wedge dissectors on the strips contact the wall; the tips' relatively narrow profile penetrate the wall generating nucleation sites for the fissuring event; the fissures quickly produce cracking along the intra-luminal surface; due to the proximity and alignment of the cracks, the cracks join to become a long crack along the intra-luminal surface that can extend along the entire length of the strip, or less of the strip length, or greater than the strip length; the depth of the penetration of the crack has been found to be typically similar to the depth of medial tissue.

To reduce potential rigidity of the spline, or base strip, it is envisioned that a series of reliefs on the spline can be added in some embodiments, as illustrated in FIGS. 25 and 26. The relief elements can be produced in many different ways with the intent to have material removed and offer a more pliable spline for the wedges to be strip-facing base to. Relief can be made in the base of the spline opposite the wedge dissector strip-facing base surface, at the top of the spline directly adjacent the wedge dissector strip-facing base surface, or in both locations, e.g., a combination of top and bottom. The relief can also be made on the side of the spline, or apertures strip-facing base by other areas of the spline can be added to the spline. Any combination of top, bottom, side or through apertures can be added to the spline to offer relief.

In some embodiments, as illustrated in FIGS. 25 and 26, the strip 300 can have relief holes or slits located at the top, bottom, centered or off center that are either circular, rectangular, linear, triangular, or elliptical or combinations thereof (See FIGS. 25 and 26). The strips offer a supporting base infrastructure, intended to be flexible and follow the movement of the balloon, for the wedges to be oriented correctly.

The relief holes illustrations as shown in FIGS. 25 and 26 can be specifically designed to offer a pathway for balloon-based pharmacological agents to migrate through; in addition, they offer strain relief in the surface to enhance the deliverability of the device in tortuous anatomy. FIGS. 25A-C illustrate embodiments of wedge dissectors with reliefs 502 on the inferior surface 500 of the strips 300 opposite the bounded surface of the wedge dissectors 200. FIG. 25A illustrates an embodiment where the reliefs 502 are regularly spaced apart approximately a length of the bounded surface of each wedge dissector 200. FIG. 25B illustrates an embodiment where the reliefs 502 are regularly spaced apart 50% or less of the length of the bounded surface of each wedge dissector 200. FIG. 25C illustrates an embodiment where each relief 502 is spaced apart 50% or less of the length of the bounded surface of each wedge dissector 200, but the reliefs 502 are grouped only under the wedge dissectors and are not present under the strip sections in between the wedge dissectors. In other embodiments, the reliefs 502 are grouped only under the strip sections in between the wedge dissectors, but not under the strip sections directly below the wedge dissectors.

FIGS. 25D-25E illustrates an embodiment where the reliefs 502 are present on the top (bounded or superior-facing surface 302) of the strip in between the wedge dissectors. In FIGS. 25D and 25E, the reliefs form depressions in the superior-facing surface 302 of the strips in between wedge dissectors with a generally curved based as illustrated in FIG. 25D, and a relatively more square or rectangular base as illustrated in FIG. 25E, with or without rounded edges. FIG. 25F is an embodiment combining two different kinds of reliefs 502 found in the embodiments of FIGS. 25C and 25D. Other permutations of combinations are also possible, depending on the desired clinical result. FIGS. 25G and 25H illustrate other embodiments where the reliefs 502 are on an anterior 304 and/or posterior side surface of the strip 300. FIG. 25G illustrates generally pyramidal-shaped reliefs 502, while FIG. 25H illustrates generally arcuate reliefs 502. The reliefs can be spaced axially apart from the wedge dissectors as shown, and/or spaced axially aligned with wedge dissectors in other embodiments. FIGS. 25I and 25J illustrate embodiments where the reliefs 502 take the form of vertically (FIG. 25I) or horizontally (FIG. 25J) oriented through-channels, which can be spaced axially apart from the wedge dissectors as shown, or in another configuration. In some embodiments, the reliefs can be oriented at an oblique angle to the longitudinal axis of the strip. FIG. 25K illustrates an embodiment where the reliefs 502 take the form of slots on the anterior and/or posterior side surfaces, bounded base surface, and/or other locations.

To aid in removal of material fabrication from the initial blade, the strips can include tabs along the base or bonded surface in some embodiments. The tabs can aid in controlling long strips from vibration or movement during the material removal. Once fabrication is completed, the tabs are then removed. In some embodiments, the tabs have an inset that they sit at the base of the strip. In some embodiments, inset reliefs can serve as the tabs, and be advantageous during the manufacturing process, when several strips are, for example, laser cut from the same sheet of source material. In some embodiments, a complementary protrusion (e.g., a tab or related structure) on or connected to an adjacent area of the source material to be laser cut can fit into an inset relief of a strip adjacent to the source material to maintain proper alignment of the strips during laser cutting/manufacturing. This can keep the strips in place during laser cutting, and prevent undesired migration and misalignment of a strip relative to an adjacent material area due to, for example, laser vibrations, which can decrease product yields. In some embodiments, reliefs for manufacturing stability purposes need not be inset and can take the form of tabs that protrude outwardly from the base of the tab. In some embodiments, these tabs are later removed by laser cutting or other methods prior to bonding or other attachment to the outer surface of the balloon, to prevent inadvertent puncture of the balloon. Some embodiments are illustrated in FIGS. 25L and 25M, which schematically illustrate strips 300 with wedge dissectors 200 during the strip and manufacturing process. Also shown is tab 580, which can be laser cut out of the source material, and be connected with one end at an adjacent area of the source material 581 and the other end inset in an inset relief 502 in, for example, an inferior surface of the strip 300. The inset relief 502 can be any pattern as previously described, for example, in FIG. 25A-25K or others, and in some embodiments are shown underneath the wedge dissector 200. FIG. 25M illustrates the tab 580 which can be cut into segments 588, 589 following the manufacturing process when it is no longer required to hold the strip 300 in place with respect to adjacent source material 581, and the strip 300 can then be separated for attachment to a balloon or other device. The inset can allow for the tab to be removed while minimizing that amount of material that could potentially hang below the base of the strip which might interfere with the bonding of the strip to the balloon or other expansion device.

In some embodiments, balloons can be pleated and crimped down to the very narrow profile allowing the device to be delivered through and introducer sheath with a narrow diameter. Once the balloon has been deployed and deflated, the post-inflated balloon profile can be larger than its original pleated and crimped down diameter. This new profile may have strips that sit proud of the balloon profile potentially scraping the arterial wall or snagging on the opening of an accessory device such as an introducer sheath. The following elements, which are in general described as ramps, can address this potential issue, according to some embodiments.

FIG. 25N illustrates schematically an embodiment of a ramp 680 of adhesive or other material is placed at (e.g., over) one, as shown, or both lateral ends 333 of some or all of the strips 300. This can be, in some cases, in addition to adhesive placed at other locations such as under the strips (e.g., on the inferior surface of the strips 300) to attach the strips 300 to the balloon. The ramp 680 can offer an effective flexible interface between the edge of the flexible balloon (not shown) and the semi-rigid strip 300, as the ramp 680 can be made of a material (e.g., an adhesive) that is relatively more flexible than that of the strip 300. The ramp 680 can be designed in some embodiments to gently slope from the balloon surface (not shown) to the edge of strip. In some embodiments, the adhesive ramps 680 can advantageously both retain strips and offer protection from undesired strip interaction 300 with ancillary devices during a procedure.

In some embodiments, the lateral edges of the strips can include glue ramps 680 to retain strips 300 and offer protection from strip interaction with ancillary devices during a procedure. Ramps may be produced with UV glues using repeat deposition and curing steps in a series of laying down and building up layers until a ramp is produced as seen in FIG. 25N.1. Alternatively, ramps may be prefabricated into the desired shape and then bonded to the surface with cyanoacrylate, UV glue, or other material or method offering a chemical, mechanical, or electromagnetic bond between the prefabricated ramps to the balloon surface. Note that this embodiment, the top of the adhesive layer is near crest of strip projection (wedge dissector tip) 681. In some embodiments, the ramp can extend laterally past the later edge of the strip a distance of between about 0.008" and about 0.040", between about 0.008" to about 0.012", between about 0.010" and about 0.040", between about 0.020" and about 0.030", or other dimensions depending on the desired result.

In some embodiments, a feature that can be incorporated into the balloon element is a cone ramp. The cone ramp feature can be implemented in several ways. In one embodiment, the cone ramp is fabricated by taking a cone configuration for a larger balloon, for example taking a cone for a 6 mm balloon, or 5.5 mm balloon and incorporating it using known methods to be attached to a 5 mm balloon. One such embodiment is shown schematically in FIG. 25O. The cone 970 can have in some cases an outer diameter that is larger than that of the outer diameter of the balloon 960, such as about or at least about 5%, 10%, 15%, 20%, or more than that of the outer diameter of the balloon 960, or between about 5% and about 20% larger than that of the outer diameter of the balloon 960 in some embodiments. The relatively larger cone 970 will sit proud of the balloon 960 generating a lip 972 at the intersection of the balloon body. The lip 972 can be beneficial in reducing the potential of the metal strip edges to be snagged or lifted off when the balloon is deflated and retracted through the introducer catheter.

In some embodiments, illustrated in FIG. 25P, included are a series of rails 980 along the cone 970 to serve as support or stiffening structures, and assist in collapsing the balloon 960 as it enters an introducer catheter (not shown). In some embodiments, the rails 980 are oriented/align with the longitudinal axes of the strips, furthering enhancing the function of pushing the strips toward the middle of the balloon as the cone is pulled through the introducer.

In some embodiments, also disclosed herein are balloons that can have depressions in the outer surface of the balloon for strip attachment. A series of depressions can be produced on the surface of the balloon. The depressions can, in some embodiments, configured to be wide enough and long enough to allow the strips to be placed within, such as entirely within the depression. The depths of the depressions can be sized to limit the likelihood that the strips could get caught on the distal opening of the introducer during balloon retraction.

The use of the through-holes or microchannels 5100, as shown in FIG. 23E, either in the spline or on the spline sides can offer a mechanism for a therapeutic agent such as, for example, one or more drugs, nanoparticles, and/or stem cell transport from the balloon surface into the diseased luminal surface through capillary or diffusion action and/or utilization of the balloon pressure forcing the drug, nanoparticles, and/or stem cells through the micro channels 5100 on to the surface or into the diseased site. Alternatively, the microchannels 5100 or modified surfaces can provide a reservoir for drug, nanoparticles, or stem cells or other therapeutics to be placed and protected during transport to the diseased site. In some embodiments, the drug may be any drug known in the art. In some embodiments, examples of drugs that may be suitable for use in the methods and devices of this invention depending, on the specific disease being treated, and with consideration of the physical properties of the drug, include, without limitation, anti-restenosis, pro- or antiproliferative, anti-inflammatory, anti-neoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective drugs.

Examples of antiproliferative drugs include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy]ethyl-rapamycin (a structural derivative of rapamycin), 40-O-tetrazole-rapamycin (a structural derivative of rapamycin), 40-O-tetrazolylrapamycin, 40-epi-(N-1-tetrazole)-rapamycin, and pirfenidone.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin, from Biogen), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative drugs include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril.

Examples of angiotensin II receptor antagonists include, without limitation, irbesartan and losartan.

Other therapeutic drugs that may find beneficial use herein include, again without limitation, alpha-interferon, genetically engineered endothelial cells, dexamethasone, antisense molecules which bind to complementary DNA to inhibit transcription, and ribozymes, antibodies, receptor ligands such as the nuclear receptor ligands estradiol and the retinoids, thiazolidinediones (glitazones), enzymes, adhesion peptides, blood clotting factors, inhibitors or clot dissolving drugs such as streptokinase and tissue plasminogen activator, antigens for immunization, hormones and growth factors, oligonucleotides such as antisense oligonucleotides and ribozymes and retroviral vectors for use in gene therapy, antiviral drugs and diuretics.

In other embodiments, a combination of any two, three, or other number of the foregoing drugs or other therapeutic agents can be utilized depending on the desired clinical result.

One method for laying down drugs, nanoparticles, stem cells or other therapeutics in specific regions such as the relief holes is the use of a direct write process, e.g., MICROPENNING (MICROPEN Technologies, Honeoye Falls, N.Y.), to deposit material onto a surface. In general, the term "direct write" describes a printing or patterning method that employs a computerized, motion-controlled stage with a motionless pattern generating device to dispense flowable materials in a designed pattern onto a surface. MICROPENNING is a flow-based micro-dispensing technique in which printed materials are extruded with a high degree of control through a syringe and a precision pen tip. The pen tip "rides" on the surface of the material, not touching the substrate surface and is capable of place precise amount of materials in precise locations.

FIG. 26 illustrates an embodiment of a strip 500 with reliefs 502 on the inferior surface of the strips 300 opposite the bounded surface of the wedge dissectors 200, with additional relatively larger apertures 503 in between wedge dissectors 200 which can be configured to facilitate bonding of the strip 300 to the underlying balloon, which can be as disclosed, for example in PCT Pub. No. WO 2016/073490 published on May 12, 2016 and hereby incorporated by reference in its entirety. The apertures 503 can be relatively oval shaped, circular, or any other shape depending on the desired clinical result.

In some embodiments, the longitudinal axis of the strips are longitudinally oriented along the balloon and spaced apart from each other. In some embodiments, the strips do not completely cover the length of the balloon. For example, in one embodiment an 80 mm long balloon can have strips that measure 76.6 mm. While the length of the strip can be the same as the defined working balloon length, in some embodiments the length of the strip is shorter than the defined working balloon length to allow for balloon contraction that is typically observed when a balloon goes to rated burst pressure. The length of each strip can in some cases be no more than about 15%, 10%, 9%, 8%, 7%, 6%, 5%, 4%, 3%, 2%, or 1%, or between about 1% and about 7%, between about 1% and about 5%, or between about 1% and about 4% shorter than the overall working balloon length. In some embodiments, the working balloon length does not include the lengths of the cones.

In some embodiments, part of the strip, e.g., the base of the strip (e.g., the inferior most surface configured to be attached to the outer surface of the balloon) can be roughened to aid in adhesion.

Spikes (e.g., serrating elements or wedge dissectors) can be fabricated in many different manufacturing methods and in a large range of shapes. Regarding the manufacturing processes, the devices may be fabricated using one or more additive or subtractive processes. Additive processes such as high energy vapor deposition, for instance laser chemical vapor deposition, self-assembly techniques, polymer/metal 3D printing, selective laser sintering, powder printers, or other stereo lithographic are a few such options but other additive processes may be used. Alternatively, subtractive processes such as etching, CNC milling, laser cutting, water jet, or electrical discharge machining are just a few examples but other subtractive processes may be used.

In some embodiments, a method of fabrication includes the use of a reel of martensitic stainless steel, such as for example a 300 or 400 series stainless steel with a hardness of about 52 to about 64 on the Rockwell C-scale (HRC) although other materials can be used. The reel is either honed or precisely unhoned on one or both sides of one edge of the steel. In some embodiments, the steel is in the form of a thin reel strip between about 0.005" and about 0.020" thick or between about 0.007" to about 0.015" thick, and/or between about 0.25" to about 0.75" wide, but can range between 0.005" and about 0.005" and 0.020" and between 0.15" and 1" wide. In some embodiments, the tolerance of the thickness and width of the reel is greater on the higher end and can have a thickness greater than about 0.005" and a width greater than about 0.5". The edge that is either honed or unhoned can be a single hone or two or more honed angles (as illustrated, for example in FIGS. 21 and 22). In some embodiments, when the angle of a honed edge is measured as the slope from the bounded end to the height of the unbounded end shown in FIG. 21, the angle of the honed edge can be, for example, greater than about 75 degrees. But when more than one honed angle is used, then the tip angle is can be less than, for example, about 75 degrees. In some embodiments, a honed edge has an angle of about or at least about 70, 75, 80, 85, 90 degrees or greater as it moves toward the honed edge in a series of bevels. In addition to the honed edge, independent of the number of honed angles, in some embodiments a separate and additional edge is generated at the very tip of the unbound edge of the strips. When added, the additional tip edge height from the honed edge to the unbounded edge is often very short and typically has a much larger angle than the overall honed edge. Independent of the number of honed angles used, the unbounded tip width, $W_u$, can be described as the radius of the tip. The unbounded tip width, Wu is the penetrating edge into the lesion, when the width is, in some cases, less than about 0.015" or 0.006", the surface area is minimized to have a less pronounced contact surface with the vessel enabling a reduced amount of energy requirement for penetration. When the tip is configured for penetration into harder surfaces such as calcium beds, in some cases either a more obtuse angle or the removal of the unbound tip at a greater distance from the unbounded surface can produce a wider tip edge (see FIG. 21, Wu). Not to be limited by theory, this wider edge distributes the load across the larger surface area generating a more effective resistance to tip deformation when the tip is pressured into rigid tissue surfaces. Once the reel is sharpened it is stamped to a desired length of blades. In some embodiments, the reel is hardened and then stamped to the desired length. Independent of when the stamping occurs, the blades can in some cases be passivated and hardened above, e.g., about HRC 45. but more typically in a range of from about HRC 58 to about HRC 62. The hardened blade can then be laser cut, stamped, EDM'ed or another precise metal shaping technology with spikes, serrating elements or wedge dissectors utilized. In some cases, the serrated elements are processed on the reel and then hardened and passivated. In some embodiments of strips where the tip is not a sharpened honed edge, the tip of the blade, that was produced during the reel sharpening step, is removed during the wedge dissector and strip manufacturing step. In some cases, the material removal is design to start a distance, such as from about 0.0001" to about 0.003" below the honed edge, or from about 0.0001" to about 0.0005" is removed from the honed edge, producing a flat top as illustrated in FIG. 21. The thinnest edge remaining (now a flat top in some cases) on the previously honed edge side is what will become the unbounded surface of the strip.

To aid in removal of material fabrication from the initial blade, the strips typically are designed with tabs along the base or bonded surface as illustrated in FIG. 25L and FIG. 25M. The tabs aid in controlling long strips from vibration or movement during the material removal. Once fabrication is completed, the tabs are then removed. In one preferred embodiment the tabs have an inset that they sit at the base of the strip. The inset allows for the tab to be removed while minimizing that amount of material that could potentially hang below the base of the strip which might interfere with the bonding of the strip to the balloon or other expansion device.

In some embodiments, disclosed are methods for attaching the strips. The methods can include any number of processing steps that provides effective strip retention, perpendicular orientation, and structural stability during the fabrication and use. In one embodiment the bounded surface is typically coated with a base coat of an appropriate material, such as a polymer, e.g., polyurethane through a controlled dipping process producing a uniform layer of polyurethane. The coating is dried and typically 3 or 4 strips are aligned with a strip alignment mechanism or jig and glued with a medical grade cyanoacrylate into place at predetermined orientations. The number of strips and the periodicity can vary from, for example, 1 to 8 and is typically associated with the same number of balloon folds but can be less than the number of folds and the periodicity can be non-sequential. Once the strips are bonded to the balloon surface, a single or series of multiple top coats or retention layers, are placed over the metal interrupted scoring elements or wedge dissectors to retain the strips and protect the balloon from the thin tips of the scoring elements. In some embodiments, these layers follow a similar process as the base or pre coat using a controlled dipping process producing one or more uniform layers of urethane or polyurethane. In some embodiments there is no base coat and only 1 top coat. Variations in the numbers of base coats and top coats can be between 0-4 on either base or top coats. Once the retention layer or layers are cured a layer of hydrophilic or other coating may be apply to decrease balloon friction and increase the balloons deliverability and retrievability. When incorporated, the outer slip coating as can increase the functionality of the balloon by reducing the force to insert and retract the device.

FIG. 27 illustrates a schematic cross-sectional view of a strip and wedge dissector operably attached to the outer surface of a balloon, according to some embodiments of the invention. A polymer layer, typically thin (e.g., from 0.0001" to 0.0009"), or about or less than about 0.001" in some embodiments, such as to limit increasing the balloon diameter profile, can be used as a base coat (layer 270A) covering the outer balloon surface. This base coat 270A offers an interface bonding layer for the interrupted scoring element to the balloon surface. This layer 270A can be made of the same or similar polymer chemistry as other layers while offering a chemical, mechanical, or electromagnetic bond to the balloon surface. This base coat layer 270A can be configured to and potentially capable of reducing the interface strain between the balloon outer surface and the bonding surface of the metal scoring element. Strain between the two surfaces is reduced by allowing an adhesive layer 270E and the scoring element 200 to be sandwiched within a polymer matrix independent and somewhat isolated from the balloon strain during balloon expansion and pressure. Although typical base coats 270A are polymers, e.g., urethane or polyurethane this layer can be a variety of other materials. In some embodiments, the coating could include silicone and hydrophilic coatings involving hydrogel polymers or the like, such as polymer networks of a vinyl polymer and an uncrosslinked hydrogel, for example. Polyethylene oxide (PEO) is an example of a hydrogel. An example of a vinyl polymer is neopentyl glycol diacrylate (NPG). The deposition of the layer can be done by single or a series of dips of a balloon or matrix of balloons into a polymer bath under controlled insertion and extraction conditions at controlled rates in both or in one direction. Alternately, layers can be deposited at Angstrom layers through self-assembly of monolayers using known and practiced self-assembly techniques, typically employing surface ionic charging.

Still referring to FIG. 27, a bonding layer 270E between the metal scoring element and the basecoat can typically be thin (0.0001" to 0.0005") but can be as thick as 0.001" in some embodiments and thin enough such as to limit increasing the balloon diameter profile. The adhesive layer 270E can be a cyanoacrylate but can be made from other bonding materials, such as UV cure glue, that offer a chemical, mechanical, or electromagnetic bond between the basecoat 270A and the bonding surface of the metal scoring element. This layer 270E can be seen as the functional layer at joining the bonding surface of the metal scoring element to the balloon and sometimes is the only layer between the bonding surface of the metal scoring element and the outer balloon surface. This layer 270E can be one or more adhesive products. In one preferred embodiment the adhesive layer 270E is a single adhesive with the low viscosity allowing a wicking of the adhesive along the interface of the bonded surface of the metal scoring element and the base coat. In some embodiments, an adhesive dries quickly, allowing successive layers to be applied on the top of the adhesive layer with minimal curing delay. In other methods of fabrication, a more viscous adhesive layer can be placed at both ends of the bottom of the strips or periodically between the bonding surface of the metal scoring element and the base layer allowing non-glued sections to be free or unbonded. In still another method more than one adhesive can be used. For instance, a more viscous adhesive can be used on either end of the bonding surface of the metal interrupted scoring elements and then followed by wicking adhesive on some or all of the unbonded sections. In some embodiments, one (e.g., a single layer) two, or more retention layers (two layers shown in FIG. 27) 270B, 270C can be present over the base layer 270A as well as the scoring element. A polymer retention layer can in some embodiments be similar to, and have dimensions as described above for the base layer with enough properties such that the base 270A and retention 270B, 270C layers produce an effective bond between the layers. In some cases, the retention layer(s) can be designed to offer a similar thickness as the base layer while other times it may be useful to have the retention layers slightly thicker than the base layer. Thicker base and/or retention layers can in some circumstances offer greater puncture resistance and increased durability of the balloon against potential puncturing from the metal interrupted scoring elements, any sharp edges from implants left in the body, or from sharp edges found in severely calcified disease vessels for example. In some embodiments, an outer slip layer 270D can also be present, above the retention layer(s) over the balloon and/or scoring elements. A variety of hydrophilic coatings are commercially available to reduce friction and offer increased navigation of balloons through tortuous and narrow anatomical features. In some embodiments, the balloon surface can be fully encased in a hydrophilic coating while in other embodiments the balloon can be coated after pleating or after pleating and crimping and therefore only surfaces that will typically be exposed during delivery are coated with the hydrophilic coat. Typical hydrophilic coats are a few microns thick and can be as thin as about 10 Angstroms in some embodiments.

In some embodiments, the adhesive can be applied separately to the balloon and to the strips and then both components are then bonded together. A template can be used to ensure proper positioning of the scoring elements along the surface of the balloon.

A retention polymer layer 270B, 270C can be typically similar to the base layer with enough properties such that the base and retention layers produce an effective bond between the layers. Sometimes the retention layer(s) can be designed to offer a similar thickness as the base layer while other times it may be useful to have the retention layers slightly thicker than the base layer, such as about or no more than about 20%, 15%, 10%, or 5% thicker in some cases. Thicker base and/or retention layers offer greater puncture resistance and increased durability of the balloon against potential puncturing from the metal interrupted scoring elements, any sharp edges from implants left in the body, or from sharp edges found in severely calcified disease vessels. In some embodiments with a plurality of retention layers 270B, 270C, the layers can be made of the same or differing materials.

A variety of hydrophilic coatings are commercially available to reduce friction and offer increased navigation of balloons through tortuous and narrow anatomical features. In some embodiments, layer 270D of FIG. 27 can be a hydrophilic slip layer. In one preferred embodiment the balloon surface can be fully incased in a hydrophilic coating while in other embodiments the balloon can be coated after pleating or after pleating and crimping and therefore only surfaces that will typically be exposed during delivery are coated with the hydrophilic coat. Typical hydrophilic coats are a few microns thick and can be as thin as, for example 10 Angstroms.

The height of the wedge dissectors, strips, and layers of the outer balloon encapsulation process can be viewed as a cage for use with an expandable member such as a medical balloon, such as an angioplasty balloon or as part of a medical procedure involving a medical balloon or other expandable member. In order to effectively perform key hole or catheter based surgery, the ability to fold the balloon to a fraction of the diameter of the intended inflation diameter can be of value. Therefore the balloon and in some cases the cage are typically folded where the profile of the folded balloon can be effectively used. In one such embodiment the cage is folded in a manner that offers orientation of the spikes such as to avoid puncturing the balloon or scraping the intima of the lumen during delivery and removal, as illustrated in FIG. 28. FIG. 28 illustrates the balloon 1000 with a plurality of pleats 1002, and strips 300 and associated wedge dissectors 200 in between the pleats, thus allowing a single strip 300 with its plurality of wedge dissectors 200 to lie between two pleats 1002. A pleating tool was designed that offers effective orientation of the spikes and splines. The pleating tool can have a series of pleating wedges where each wedge offers the ability of the crimp the balloon between the wedges as the wedge elements are closed down onto the balloon. Due to the bulk of the spline elements and desire to minimize contact, and potential damage to the wedge heads, the wedges are designed with a series of pockets that run the length of the wedge heads. The pockets in the wedge heads offer the ability of the spline features to rest within said pockets and limits the spline to wedge contact. The pockets can also offer the ability to aid in orientation of the spline and spike features such that the orientation of the features limits contact with the balloon, such as over folding, and limits orientation, such as perpendicular orientation to the balloon, that might produce scraping of the intima of the vessel during transport of the device on said balloon. One such orientation of the spikes might be at a tangential orientation, an apparent lying down, to the balloon surface as illustrated in FIG. 28.

In some embodiments, disclosed herein are systems and methods that produces linear incision through serration preparation in tissue. It is well understood in cardiovascular disease that applying interventional methods to increase lumen size in occluded lesions aids in blood flow and increases the likelihood that the vessel will remain patent longer than when minimal lumen gain is achieved post-procedurally. Methods for increasing lumen diameter have a range of options. On the basic end, Plain Old Balloon Angioplasty (POBA) or the use of percutaneous transluminal angioplasty (PTA) or similar approaches are often used to open the diseased lesion. In addition, more specialty devices such as the cutting balloon, AngioSculpt (Spectranetics), Chocolate (Cordis), and others that provide a mechanism to aid or control the balloon energy. Often products in this general category provide external structures on the surface of the balloon (either attached or not) that are designed to contact the wall first and be pressed into the wall surface with the balloon pressure. The theory is that the structures on the outer surface produce a localized increase in the force on the lumen which in turn is intended to aid in allowing the surface to be incised and along with the balloon expansion enables arterial expansion. While these designs some offer advantages over POBA or balloons alone they all have limitations on their effectiveness and their ability to facilitate lumen expansion especially in the complexity of diseases they might be used in.

An alternative to external structures that produce lines of compression along the intima is producing lines of serration along the lumen. The effectiveness of serration to aid in separation of materials (such as paper, stamps, cardboard, granite stone, marble, etc.) is well understood and since disease morphology often involves both soft and hard materials, serration technology can be advantageous to effectively aid in vessel expansion. There are several ways to produce serrations, including those described in U.S. Pat. No. 9,480,826 issued on Nov. 1, 2016, PCT Pub. No. WO 2015/187872 published on Dec. 10, 2015, PCT Pub. No. WO 2016/073511 published on May 12, 2016, PCT Pub. No. WO 2016/073490 published on May 12, 2016, and U.S. patent application Ser. No. 15/268,407 filed on Sep. 16, 2016, each of which is hereby incorporated by reference in its entirety. For example, a series of serration elements can offer features configured to produce serrations or linear serrated scoring at the deployment site.

In some embodiments, the inclusion of serration technology can offer advantages to balloons, not only for the preparation of tissue prior to or concurrent with the use of drug coated balloons, but also as a single step drug delivery mechanism. The inclusion of drug coatings on, around, and/or within reservoirs or regions neighboring serration features on a balloon can facilitate the serrations of a serrated balloon to delivery of the desired drug or other therapeutic agent(s) deeper into the desired target location, such as for example the intima, media, or adventitial surface of a luminal wall.

Typically drug coated balloons are coated on their surface. When the non-serrated drug coated balloon expands it contacts the intima and begins to elude the drug residing on its surface which inhibits the ability of the surface of the balloon to provide drug delivery into the deep tissue spaces. The following disclosure includes, in some embodiments, components and methods to use the components that can effectively deliver drug into tissue with the use of serrations independent of design elements, including but not limited to any number of the following:

1) a surface capable of radial expansion (e.g., a compliant or semi-compliant balloon);

2) a series of drug coated strips including a plurality of wedge dissectors spaced apart along a surface of each strip (in some embodiments, spaces between each wedge dissector are not as long as the length of the wedge dissectors themselves, and/or the height of wedge dissectors are a small fraction of the balloon diameter);

3) the protrusions can be in some cases be an A-framed structure angled from their base to their tip and where long wells or spaces within the A-framed structure becomes a drug reservoir region;

4) the side walls of the wedge dissectors on the A-frame can include a series of holes and/or microchannels to allow for drug migration to the interrupted surface directly beneath the serrations;

5) a single or series of wells where drugs, stem cells, or other therapeutics can be placed within each A-frame structure of the strips;

6a) the wells can include either a depression into the balloon surface, or a separate catheter-like channel along the balloon body, that may include finely defined holes (made through laser drilling or other precision method) offering a greater volume of therapeutics to reside;

6a.1) in some cases the catheter channels are incorporated into the inner diameter of the catheter shaft and can run the entire length of the shaft back to the hub, allowing for drug delivery from a port on the hub through channels to the balloon surface;

6b) during balloon inflation the outward balloon pressure can either a) apply a force on the depressed wells thereby displacing the volume where the therapeutics reside or b) expand the finely defined holes and allow for drug to pass through the holes; this in turn displaces the therapeutics outwardly and encourage the therapeutics to be released into the disrupted tissue;

6c) typically upon balloon delivery the wells, strips, elevating elements and the A-frames are captured within folds of the balloon minimizing therapeutic from leaching systemically into tissue;

7) upon expansion of the balloon, the serrated A-frames separate the intima tissue layer exposing the media, and in some cases open the media layer and the adventitia layer allowing for the therapeutic agents, captured within the balloon folds, to be expelled primarily deep into the vessel wall; and/or exposed;

8) allowing therapeutic agents and drugs to elute from the surface of the serrated drug eluting balloon into the incisions and micro fissures generated by the serrated A-frames, through the intima and into the media or adventitia.

The invention relates, in some embodiments, to the use of serration technology in conjunction with endovascular procedures, where the design of the serration technologies includes a novel drug delivery design in combination with: selectively placed drugs on the balloon, with wells of drug contained near or beneath the serrated elements, or with pathways where drugs can travel from a more proximal section of the delivery system to the balloon surface and out into the tissue through access created by the serrated elements.

In some embodiments serration elements can be combined with a multilayer, such as a bi-layer or tri-layer of polymer previously disclosed, for example, in U.S. patent application Ser. No. 15/268,407, where the space between the base polymer and the top layer or layers can be used as a drug reservoir space. In some embodiments the bottom polymer is removed and the space between the surface of the balloon and the top layer or layers can be used as the drug reservoir space. Depositing the drug in this space can be facilitated, for example, by a spray coating, dipping, or utilizing nanotechnology self-assembly techniques where the drug becomes encapsulated between a base and top layers of polymers. The drug reservoir layer is not, in some embodiments, exposed to the environment due to its encapsulation of the top layer(s) thereby limiting the exposure to the body or to the intima layers that are not perforated. The inclusion of drug coating on, around, and/or within the encapsulated layers facilitates the serrations of a serrated balloon to delivery drug primarily into the sub-intima.

Methods of producing linear serrations are also disclosed. In some embodiments, this can be achieved through the inclusion on a wedge dissector of a series of elevated elements, typically with the radially-outward facing surface having a narrow section circumferentially oriented and a longer section longitudinally oriented, but can be oriented helically or otherwise. Such elevated elements can be designed such that as the deflated, pleated, and crimped balloon, containing the elevating elements there within, expands at the site of repair the elevated elements are unfolded. The elevated elements contact the wall, in some cases perpendicular, parallel, or oblique to the longitudinal axis of the sidewall of the vessel, and break though the diseased vessel's intima. Each of the rows of wedge dissectors micro pierce tissue with broken intima spaced apart by unbroken intima can be in-effect lines of serration in the tissue. This process can be referred to herein as a serratoplasty.

In some embodiments, about or at least about one, two, three, four, or more lines of serrations along the surface of the tissue can effectively produce linear serration with minimal tissue injury. These lines of serration collectively generate a series of lines of weakness in the serrated surface. When serration technology is adopted to existing balloon angioplasty, this can be referred to herein as serratoplasty. Orientation of lines of serration can be aligned with one of the layers of cellular matrix or aligned with other biological purposes in mind. In leg arteries, for example, the orientation of the medial tissue is longitudinally oriented, along the axis of artery, and as such serratoplasty designs can in some embodiments have longitudinally oriented rows of elevating elements for producing serratoplasty but in some cases the design can be made to align perpendicular or at some acute angle off the longitudinal axis of the artery.

The depth of penetration of the elevating elements is a factor that can be configured in the design of the serratoplasty device. First, the ability to penetrate the surface of the target tissue or wall can be directly a function of the height of the individual serrating elements (or wedge dissectors) that sit proud of the carrier. Secondly, the depth can be limited to the expandable diameter of the carrier, typically a balloon. Once the serrations features penetrate the surface, the depth of penetration can extend past the height of the wedge dissector since the crack depth can be influenced by the strain forces produced by the balloon. As the balloon expands it opens the serration and can influence the propagation of the crack into deeper tissue than the original wedge dissector contacted. Therefore the tip of the wedge dissector only produces the initial micro perforation after which the tip does not contact the tissue it is penetrating. Once the tip has penetrated the intima, the side walls of the wedge dissector generate cleaving stress that exerts a prying force on the side walls of the penetrated tissue. The cleaving stress adds to the strain that the expanding balloon exerts on the wall and together the stress is magnified enabling serratoplasty to open hard and soft calcified plaque ridden vessels with less pressure than using a balloon alone or with balloons that use linear raised features to score the intima.

In some embodiments, a serranator device can be used with both surface expansion and fissure assist for use of DEB. Not to be limited by theory, the serratoplasty design can produce two effects, one mechanical and one biological. Serratoplasty can create a mechanical aid to arterial expansion through the line of elongated micropunctures along the overall surface of the plaque to aid in surface expansion though fissure mechanics. In addition, serratoplasty can produce mini-wells or punctures through the intima and into the media along with micro channels 5100 to aid in drug capture and retention when a pharmaceutical agent is introduced in conjunction with a serranator device. The method for producing serratoplasty can include inflating a balloon comprised with a series of strips where the strips can include a plurality of wedge dissectors spaced equally apart along a surface of each strip. Alternately, the spacing of the wedge dissectors can vary with periodic larger spaces between the shorter spaces. In addition, some methods utilize strips where either the spacing or the length of the wedge dissectors varies. In some embodiments, the serration pattern, during the initial penetration of the strips, can be a cut-along-dotted-line 300 to 100 micron "dashes" and 200 to 50 micron "dots", or a combination of "dashes" and "dots" in some embodiments. The length of "dash" like features, which represent the spaces where the intima was not initially effected by the strip, can vary but are typically between 100 to 600 micron long. The length of "dot" like features, which represent the areas where the intima was initially penetrated by the strip, can vary but are typically between 10 to 500 micron long.

In some embodiments, serratoplasty can advantageously reduce dissection rates. In some embodiments, a pre-serratoplasty increase in surface area can be provided for DEB, reducing the pressure needed for dilatation of an atherosclerotic plaque, especially when the plaque contains a large amount of calcium.

Examining the mechanics of plaque fracturing with no preparation versus the mechanics with preparation is necessary in understanding the value provided by the microperforations. The basic steps for material fracture include, void formation, void coalescence (also known as crack formation), crack propagation, and finally failure. This phenomenon can be examined further, mathematically, with a fracture mechanics approach. Assuming the surface is isotropic and a surface crack in the arterial lumen is semi-elliptically shaped, the maximum crack opening displacement $COD_{max}$, is:

$$COD_{max} = \frac{4\sigma d}{E}$$

Where σ=applied strain, d=depth of crack, and E=elastic modulus. Assuming the area is a perfect triangle with a variation in crack opening displacement then the total surface area of the crack, Ac is $$A_c = 1/2 db \Sigma COD/(b+1)$$

Where b is the crack length and ΣCOD is the sum of the Crack Opening Displacements. To simplify the equation, we assume the $\Sigma COD/(b+1)$ is equal to ½ $COD_{max}$.

Therefore $A_c$, related to the material becomes $$A_c = \frac{\sigma b d^2}{E}$$

This equation states that the total surface area of the crack, $A_c$, t will increase with the applied strain, σ, and grows exponentially with increase in depth d. The strain energy release rate (or energy release rate) is the energy dissipated during fracture per unit of newly created fracture surface area. While the d is directly associated with the ability to effectively penetrate the tissue. With micro perforations or serrations, the ability of individual elevated elements or wedge dissectors to penetrate more deeply is greatly enhanced.

In the case of traditional balloon angioplasty, the amount of energy required to initiate crack formation (starting with void formation) then produce crack propagation, and finally failure can be very high. The initiation of void formation without the introduction of nucleation sites (d in the formula above) requires much higher initial strain (σ in the formula above) and once the crack begins the energy dissipates quickly over the newly formed cracked surface areas thus leading to the unpredictable nature of plaque ripping, or dissecting during the angioplasty procedure. Individual elevated elements or wedge dissectors on the outside of a balloon can penetrate first (forming voids) and provide preparation for the Serranator balloon's pressure to more effectively open the artery with less pressure. Through the use of plaque preparation devices and techniques as disclosed herein (including but not limited to the Serranator family of products), the stress concentration and thereby the strain release is assisted by the series of voids designed to offer relief more uniformly across the overall surface of the plaque. The objective can be in some cases to penetrate deeply into the tissue bed. The equation derived for the total surface area of the crack, $A_c$, offers some insight into certain advantages serration technology can offer in some cases over existing technologies. Through the creation of microperforations in the surface of the plaque the device can permit relaxation of the plaque and dilatation at low angioplasty pressures. In clinical trials pressures as low as 3 ATM have been effective at opening diseased arteries using Serratoplasty technology. Low-pressure angioplasty minimizes acute injury and enables smoother post-angioplasty surfaces in some cases.

TABLE 1

Serranator prepped angioplasty vs traditional and DEB angioplasty: comparison

| Factors for Comparison | Traditional Angioplasty | DEB Angioplasty | Serratoplasty |
|---|---|---|---|
| Injury/Plaque Disruption | Severe | Severe | Minimal |
| Pressure on Artery | Severe | Severe | Minimal |
| Stimulates Growth of Re-stenosis | Moderate | Anticipated minimal | Anticipated minimal |
| Cost | Low but high need for stents | High and more need for stents | Minimal and less need for stents |

In some embodiments, systems and methods can be used as a device aid to atherectomy. To provide effective atherectomy of plaque or removal of other diseased outcroppings that are found in vessels throughout the body, it is sometimes advisable to prep the vessel to aid in effective extravasation of the diseased tissue. Alternately, it is sometimes advisable to follow atherectomy with angioplasty. When angioplasty is used pre and/or post atherectomy it is anticipated that Serrating the surface to enable effective preparation or post atherectomy lumen enhancement a Serratoplasty device might offer a method to weaken the cellular or molecular bonds that, in a fashion, provides more effective atherectomy.

In some embodiments, an atherectomy enhancement tool can include one or more of the following features, not necessarily in the order presented:

The serratoplasty device expands allowing the serration elements to penetrate the vessel wall;

The serration elements pierce through the intimal layers of the wall and disrupt the tissue producing serrated marks;

The device expansion continues and induces a stress on the wall of the vessel;

The stress builds seeking weakened areas to release the strain;

Linear incision is then produced;

The linear serrated marks produce the region for the strain to release (line of weakness);

The strain is quickly dispersed along the line;

The sub intimal layers of the vessel enable continued expansion without tearing through all the tissue layers;

While the serration elements sit proud of the expansion device the ability of the serration elements to continue the depth of penetration all the way through the vessel is limited by numerous factors;

If the vessel is healthy the tissue expands and thins around the region of the expansion event while the absolute depth of penetration is controlled by the limit of the expansion device diameter which is pre-measured to not exceed the relative vessel diameter;

If the vessel is diseased the depth of penetration can be limited by not only the balloon diameter but also by the limit of the artery to expand (diseased tension), the thickness of the disease (hardened vessel), and/or the limit of the energy used to expand the balloon;

The artery (vessel) is prepared for the atherectomy;

The atherectomy tool is able to navigate and collect the diseased tissue more effectively due to concentric oriented plaque fractured into manageable segments that require less rotary energy to remove from the cellular matrix and are more easily passed through the atherectomy tool into the collection cup;

Non-concentric (eccentric) plaque may not directly be fractured due to the nature of balloon energy being dispersed more effectively into arterial sections that have the higher elastic modules. Therefore the tissue might expand more on the side of the vessel wall that is healthy and expand less on the side of the vessel that is diseased. In this case the effect might be that the healthy vessel is expanded or out of the way of the atherectomy rotor. The rotor can more easily find and bear down on the disease tissue limiting or reducing the interaction of the rotor head with the healthy tissue.

Continuous disease either concentric or eccentric offers additional challenges to the atherectomy tool and this disease morphology can produce very high strains (due to the pushing of the vessel) in the vessel wall both in front of the rotter head and in the area just passed where the rotor head (due to tug or pulling and torqueing) of the tissue in regions very near where the rotor head recently passed. To minimize the pushing and pulling the artery experiences it can be advisable to prep the vessel effectively. A very effective preparation one can do in some embodiments is to release the diseased binding energy that the diseased morphology produces prior to atherectomy. Serration and linear fissuring can be a very effective tool in this regard.

Non-continuous disease behaves similar to continuous disease but adds the challenge of the healthy artery being interwoven throughout the diseased region. Due to this unique challenge it would be best to fracture the diseased sections as described in the non-concentric and concentric plaque modification previously described but also to push the healthy tissue out of the same plane where the disease is. By pushing the diseased tissue out of the way the atherectomy rotor head can be able to cut away the diseased tissue and reduce the tendency for the rotter head to tear into and cut less of the healthy intima or healthy medial tissues.

Drug-coated or drug-eluting balloons (DCB or DEB) are designed to treat atherosclerotic occlusive disease. The preliminary results of clinical trials appear to show that DCB's offer a new advancement in endovascular therapy. The existing designs of drug-eluting or drug-coated balloons can produce long term arterial patency based on the localized delivery of therapeutics that limits cellular growth. Most DCBs available today utilize paclitaxel or another agent in combination with different carriers and excipients offering balloon adhesion and drug delivery. When DEB angioplasty is performed, medication is transferred to the wall of the blood vessel and transported by diffusive and convective transfer into the cellular matrix and if the drug is crystalline can reside in the tissue for many days. The medication used and the method of coating can be engineered to achieve a variety of effects. Independent of the coating used, the mechanism for delivery, an angioplasty balloon, has not been changed significantly from original balloon angioplasty. The balloon angioplasty approach, by which these devices function, is a blunt, strain loading, unpredictable tissue damaging event that often produces a fractured, irregular blood vessel surface. The blunt, high pressure nature of the mechanism of balloon angioplasty can be traumatic to arterial tissue. Pressurizing and expanding the angioplasty balloon within a hardened, calcified atherosclerotic lesion usually leads to plaque tearing or disruption that often requires restoration of the arterial lumen which is often achieved through tissue compression by a follow-on therapy of an implantable stent. Once the pressure in the tissue has exceeded the strain limit of the diseased morphology plaque disruption followed by crack propagation quickly follows. Dissection, secondary to the cracking, is a form of balloon angioplasty-induced arterial trauma where sections of tissue are no longer bound and wave freely in the artery stream. The degree of dissection can serve as an important predictor of clinical outcome. Because the dissection creates an irregular and potentially unstable luminal flow surface, a stent is often placed to create a smooth surface and stabilize the plaque and treat the angioplasty-induced dissection. The need to place a stent arises with acute post-angioplasty dissections, which occurs in 25% to 50% of cases after standard balloon angioplasty. Since the intent of DEB angioplasty is to minimize the need for stenting, dissections defeat the purpose of a drug-coated or drug-eluting balloon, since a stent will be required. The use of coatings on these balloons may add nothing to provide control for these dissections and thereby may not reduce the need for stenting.

If standard DEB angioplasty is used without the plaque-preparation step, the amount of initial surface contact is defined by the morphology of the lumen. A better efficacy of medication delivery has been observed in porcine studies using serratoplasty vs. POBA prior to DEB, as shown in FIGS. 28A and 28B below.

FIG. 28A is a chart that shows the amount of paclitaxel (PTX) drug retained in the tissue wall in an experiment after 7 days post Serranator followed by DCB (263.5 µg/mg) vs. POBA followed by DCB (181.8 µg/mg) when the inflation was 1.2 times the reference vessel diameter. As shown, the Serranator device surprisingly and advantageously was able to cause over 1.5× the amount drug retained in the tissue wall compared with POBA.

FIG. 28B is a chart that shows the amount of PTX drug retained in the tissue wall after 7 days post Serranator followed by DCB (479.2 µg/mg) vs. POBA followed by DCB (178.7 µg/mg). As shown, the Serranator device surprisingly and advantageously was able to cause over 2.7× the amount drug retained in the tissue wall compared with POBA.

The method used to achieve the enhancing drug uptake shown in the graphs (data collected at 7 days post treatment) above where data was collected comparing pretreatment of the porcine vessel with either a Serranator device or a POBA followed by a drug eluting balloon can include any number of the following steps:

Pretreating a site in a vessel by expanding a pretreatment balloon at the site to create a plurality of micro fissures in the vessel wall, the pretreatment balloon comprising a plurality of strips, each strip of the plurality of strips including a plurality of wedge dissectors spaced apart along a surface of each strip, each strip extending longitudinally along an outer surface of the pretreatment balloon;

Removing the pretreatment balloon from the site;

Positioning a drug eluting balloon at the site; and

Expanding the drug eluting balloon to bring the balloon into contact with the vessel wall and allowing drug to elute from the surface of the drug eluting balloon into the micro fissures, through the intima and into the media. In some embodiments, the quantity of drug or other therapeutic agents eluted is sufficient to prevent or reduce restenosis.

In some embodiments, the pre-treatment balloon can be the same balloon as the drug-eluting balloon (e.g., a pretreatment balloon that can be drug-coated or drug-eluting) as such that removing the pre-treatment balloon step is not needed. However, in some embodiments, the drug-eluting balloon is discrete from the pre-treatment balloon.

In addition to showing a 1.5 to 2.7 times increase in drug uptake of the Serranator vs. POBA as the pretreatment after 7 days it was observed that the uniformity of the distribution of the drug in the tissue at the proximal, middle and distal sections were more uniformly distributed in the Serranator arm when compared to the POBA arm in the study.

The method of generating micro fissure planes can include the rotation of the Serratoplasty balloon and reinflation. At each consecutive inflation, a new set of micro fissure planes are generated. With increased fissure planes increase the number and depth of nucleation sites which in turn offers more mechanical effect to reduce the need of abundant strain to be built up during the increase in atmospheric pressure in the balloon. In addition, the increased fissure planes offer increased micro wells for pharmacokinetics to be captured, collected and evenly distributed throughout the tissue when used in conjunction with a DEB. In one such method the serranator device could be inflated, producing micro fissure planes, then deflating the balloon, rotating it between a fraction of an angle, e.g., up to about half of the angle between adjacent spike strips, and reinflating it. With the addition of an increased number of micro fissures some embodiments of methods can further increase drug uptake significantly, such as at least about 1.5×, 2×, 2.5×, 3×, or even more.

In some embodiments, the pre-treatment balloon (such as serratoplasty balloons) can increase the effectiveness of the drug-eluting balloon (e.g., a pre-treatment balloon can increase surface area and enable access to deeper tissue in the tissue wall) as such the pre-treatment balloon may reduce the volume of drug required from the drug-eluting balloon.

DEB can in some cases contact new surface areas for drug delivery. An additional advantage of Serratoplasty in some embodiments is the mechanical effect of allowing the tissue to relax. The Serratoplasty pre-DEB angioplasty preparation of the calcified or thrombotic tissue can reduce the rigid and constrained or bound behavior of the tissue surface. The ability of the atherosclerotic surface to retain a more open structure, accessible to the DEB surface as it expands is achievable by pre-perforation with Serratoplasty. The result is plaque relaxation, opening numerous micro fissure planes, allowing the plaque surface to generate a more uniform intraluminal surface roughness while minimizing the typical tearing associated with angioplasty that generates unpredictable intraluminal surface roughness.

In some embodiments, a method of generating a line of serration by a series of events is disclosed. A method can produce a line of serration inside a vessel, including treating a site in a vessel by expanding a treatment balloon at the site to create a plurality of micro fissures in the vessel wall, the treatment balloon comprising a plurality of strips, each strip of the plurality of strips including a plurality of wedge dissectors spaced apart along a surface of each strip, each strip extending longitudinally along an outer surface of the pretreatment balloon. In addition, in some embodiments the method for serratoplasty can include one or more of the following features:
1. The device can expand, allowing the plurality of strips including a plurality of wedge dissectors or elevating elements to penetrate the vessel wall.
2. The plurality of wedge dissectors can pierce through the intimal layers of the wall and disrupt the tissue producing serrated marks
3. The device expansion can continue typically through an increase in balloon carrier pressure and induces a strain on the wall of the vessel
4. As the pressure builds the tissue seeks weakened areas to release the strain
    a. Linear incisions are produced through the release of strain energy propagating along the serrated line.
    b. The strain is quickly dispersed along the serrated line
    c. The linear serrated marks produce the region for the strain to release (line of weakness)
5. The sub intimal layers of the vessel can enable continued effective expansion
6. While the wedge dissectors or serrating elements sit proud of the expansion device the ability of the serration elements to continue the depth of penetration is limited by numerous factors.
    a. If the vessel is healthy the tissue expands and thins around the region of the expansion event while the absolute depth of penetration is controlled by the operator by limiting the expansion devices diameter.
    b. If the vessel is diseased the depth of penetration can be limited by not only the balloon diameter but also by the limit of the artery to expand (diseased tension), the thickness of the disease (hardened vessel), and the limit of the energy the expansion device can accommodate (I.e. The limit of the pressure the balloon can hold).

Fracture is the propagation of cracks through materials. There are in some cases 3 modes of fracture mechanics including an opening mode generated by tensile stress normal to the plane of the crack, sliding mode where shear stress acting parallel to the plane of the crack and perpendicular to the crack front, and tearing mode where the shear stress is acting parallel to the plane of the crack and parallel to the crack front.

Fracture mechanics was developed during World War I by English aeronautical engineer, A. A. Griffith, to explain the failure of brittle materials. Griffith's work was motivated by two contradictory facts: (1) the stress needed to fracture bulk glass is measured around 100 MPa (15,000 psi), while (2) the theoretical stress needed for breaking atomic bonds is approximately 10,000 MPa (1,500,000 psi). A theory was needed to reconcile these conflicting observations. Through a series of experiments on glass fibers, Griffith's observations suggested that the low fracture strength observed in experiments, as well as the size-dependence of strength, was due to the presence of microscopic flaws in the bulk material.

To verify the flaw hypothesis, Griffith introduced an artificial flaw in his experimental glass specimens. The artificial flaw was in the form of a surface crack which was much larger than other flaws in a specimen. The experiments showed that the product of the square root of the flaw depth (a) and the stress at fracture ($\sigma_f$) was nearly constant, $C_F$ (constant with flaw) which is expressed by the equation:

$$\sigma_f \sqrt{a} \approx C_F$$

From this understanding it can be derived that the introduction of artificial flaws in a diseased vessel in the form of micro punctures or serrations will reduce the required energy need to expand the lumen of the diseased vessel. Therefore, a rewriting of the Griffith formula might be:

$$\sigma_s \sqrt{\sum_0^n a} \approx C_S$$

where it is understood that the square root of the sum of the product of the flaw depths (a) from 0 to n and the stress at fracture ($\sigma_f$) is nearly constant $C_S$ (constant with serration).

From these two equations we can hypothesize that increasing the number of artificial flaws, $C_S$ would inherently produce a lower constant than might be observed with a constant with a flaw. $C_F$. Expressed mathematically:

$$C_S < C_F$$

Therefore, if $C_S$ is less than $C_F$ then the stress at fracture ($\sigma_f$) must also be less. When predicting small crack propagations, it has been noted through experimentation that the generation of linear serration offers a line of weakness in the luminal surface thereby allowing crack propagation along the line of weakness at lower balloon expansion pressures. This phenomena is well understood in mechanical engineering and in general the science is typically applied to limit and prevent crack formation and propagation. In some applications the use of serration is applied to aid in the ease of the separation of materials along a predictable line, such as FedEx packages, or stamps, or perforated paper, etc.

Discussed herein is in some cases the correlation between the pressure in a cylindrical balloon and the effect of the pressure exerted on the artery wall with serrations of a certain depth.

Through an examination of Laplace's formula for estimating hoop stress created by internal pressure of a thin walled cylinder, in some cases a serrated balloon:

$$\alpha = \frac{PR}{t}$$

where $\alpha$ is the hoop stress, t is the thickness of the balloon, P is the pressure, and R is the radius of the of the balloon. This principle of fluid dynamics also defines how pressure is disbursed along the balloon when sections of the balloon become enlarged into a spherical shape while other sections remain cylindrical. Pascal's principle states the surface tension reduces to half in the engorged spherical region while the tension remains the same multiple of pressure times radius in the cylindrical region.

Applying new variables based on the dynamics of a diseased vessel, we assign t to the thickness of the diseased region, a applied strain in our previous equation, $\sigma$, while R and P remain the same.

From our previously defined equations $COD_{max}$ we can solve for the applied strain, $\sigma$, and substituting this strain in place of the hoop stress from Laplace's equation we derive a new formula for pressure:

$$P = \frac{COD_{max} E t}{4 d R}$$

This equation indicates that Crack Opening Displacement (COD) is directly related to the pressure (P), depth of the cracks (d), the radius of the balloon (R), and inversely related to the thickness of the disease (t).

According to LaPlace's law, the wall tension will be twice as large for a balloon of twice the radius. If it takes a certain applied pressure to overcome the elasticity of the large balloon and cause it to expand further, it will take twice as much pressure to start to expand the smaller balloon. According to the equation above a serration device can alter this dynamic and provides a mechanism to reduce the pressure needed to start the balloon expansion with the product of pressure, crack depth, and balloon radius.

The tension in the walls of arteries and veins in the human body is a classic example of LaPlace's law. This geometrical law applied to a tube or pipe says that for a given internal fluid pressure, the wall tension will be proportional to the radius of the vessel. The implication of this law for the large arteries, which have comparable blood pressures, is that the larger arteries should have stronger walls since an artery of twice the radius should be able to withstand twice the wall tension. Arteries are reinforced by fibrous bands to strengthen them against the risks of an aneurysm. While, tiny capillaries rely on their small size. The walls of the capillaries of the human circulatory system are so thin as to appear transparent under a microscope, yet they withstand a pressure up to about half of the full blood pressure. LaPlace's law gives insight into how they are able to withstand such pressures: their small size implies that the wall tension for a given internal pressure is much smaller than that of the larger arteries. Given a peak blood pressure of about 120 mmHg at the left ventricle, the pressure at the beginning of the capillary system may be on the order of 50 mmHg. The large radii of the large arteries imply that for pressures in that range they should have strong walls to withstand the large resulting wall tension. The larger arteries provide much less resistance to flow than the smaller vessels according to Poiseuille's law, and thus the drop in pressure across them is only about half the total drop. The capillaries offer large resistances to flow, but don't require much strength in their walls. The larger arteries of the body are subject to higher wall tensions than the smaller arteries and capillaries. This wall tension follows the dictates of LaPlace's law, a geometrical relationship which shows that the wall tension is proportional to the radius for a given blood pressure. If an artery wall develops a weak spot and expands as a result, it might seem that the expansion would provide some relief, but in fact the opposite is true. In a classic "vicious cycle", the expansion subjects the weakened wall to even more tension. The weakened vessel may continue to expand in what is called an aneurysm. Unchecked, this condition will lead to rupture of the vessel, so aneurysms require prompt medical attention. A localized weak spot in an artery might gain some temporary tension relief by expanding toward a spherical shape, since a spherical membrane has half the wall tension for a given radius. By introducing areas of serrated weakness in the artery through penetration of wedge dissectors into the diseased vessel segments, serration technology aids in vessel expansion at lower pressures and kicks off the "vicious cycle" by reducing the wall thickness in several locations and generating regional increases in wall tension as the internal diameter of the artery expands.

The tension on wall can be directly proportional to pressure in balloon. The wall stress can be indirectly proportional to wall thickness, as schematically illustrated in FIG. 29. FIG. 29 is an illustration of Tangential Stress of a cylinder with a known wall thickness and the simplified equation of Tangential Tension of a cylinder assuming no wall thickness.

In some cases, the pressure in the balloon can be indirectly proportional to balloon radius.

In some cases, balloon dilation can lead to uncontrolled dissection. Radial force of the angioplasty balloon causes plaque fracture at an area of the fixed stenosis. There is often evidence of dissection on completion images immediately following the angioplasty, where contrast fills the flaps in the plaque. Prediction of the location for nucleation of micro-tears within the region of the balloon angioplasty and the behavior of the cracked body can be difficult, and can be easy to interpret as uncontrolled.

Excessive tension on the balloon surface can produce micro-tears which then produce dissections or tearing along the artery. The control of the energy transferred from the balloon into the diseased or the elevating element can be modeled and designs of the wedging element can be optimized for disease morphology, lumen sizes and shape, or a variety of other factors. The model shown in FIG. 30 shows four distinct zones that can be a signature of balloon angioplasty. Zone 1 occurs as the balloon is inflating but before the balloon contacts the surface, Zone 2 is the settling zone when the balloon (and any external features on the balloon) align with the surface topography and achieve a "snug" relationship and balloon pressure begins to increase rapidly. Zone 3 is the work phase of the balloon expansion as the balloon increases outward pressure against the disease morphology. Zone 4 is the post yield phase, which begins at an inflection point where the yield event can occur because of a dissection event in the endothelium or an expansion of the adventitia.

Zone 1 is the initial inflation zone where the prevailing pressure is driving the balloon expansion. In this zone frictional forces between the anatomical features and the balloon catheter will show up also any torque in the catheter and the friction from unfolding of the balloon and any catheter imperfections such as kinks or glue anomalies are present in this zone.

Zone 2 is the balloon alignment or snugging zone where the balloon mates with the endothelium and any mechanical features on the outside of the balloon come into contact and align themselves with the wall. This zone is nonlinear as it is a complex function of the pairing of complex geometry of the disease with the unfolding balloon and any surface modifying features. This zone contains the beginning effects that are displayed as both a macro effect related to the alignment of the modifying features and micro effects including the stress-induced deformations of the mechanical modified surface, the local surface roughness, and the orientation of entry of the mechanical component.

Zone 3 is the semi-elastic expansion zone, wherein the slope of the force-diameter signature curve is constant. The semi-elastic expansion zone force-diameter slope is important characteristic of each balloon. The steeper sloped curves are generating higher strain and tension on the healthy and diseased tissue collectively. This imparted tensile stress can produce unwanted and uncontrolled tearing or dissection planes.

Zone 4 is the post yield phase, which begins at an inflection point where the yield event can occur because of a dissection event in the endothelium or an expansion of the adventitia. FIG. 30 illustrates balloon pressure vs. diameter enlargement. FIG. 30 shows four zones as the vessel enlarges in diameter for a POBA balloon and a Serranator balloon.

The equations above and otherwise disclosed herein provide non-limiting possible models of mechanisms of action on tissue of certain systems and methods as disclosed herein, and the invention is not intended to be limited by any particular theories.

In some embodiments, a serranator system includes one or more of: a wire on outside of balloon; a blade; and a serrated strip. FIG. 31A below illustrates schematically strain produced by balloon expansion and the penetration of the serrating element into the tissue bed:

FIG. 31A illustrates that once the initial penetration of the tip 3110 into the tissue 3140, cleaving stress overcomes the need for tip penetration. The further expansion of the tissue through the advancing of the crack 3120 into deeper tissue 3140 provides a tissue wake for the serrating elements 3150. As the serrating elements 3150 penetrate the tissue the tip 3110 does not contact the tissue 3140 and the crack generation 3120 is aided by the sidewalls 3130 of the serrating element 3150 and the strain 3100 produced by the balloon expansion. Due to the design and nature of the strain 3100 induced by the balloon expansion the tip 3110 and advancing crack 3120 plane quickly migrates into spaces beyond the tip surface such that the tip (e.g., radially outward facing surface of wedge dissectors in some cases) no longer is in direct contact with the leading edge 3120 of the crack/cleavage plane.

FIG. 31B is a chart that illustrates the serrations were able to successfully penetrate into the medial tissue layer of the vessel wall in each patient that was examined with OCT imaging. In some embodiments, a method of creating serrations at a treatment site in a vessel can include providing a serration balloon comprising a plurality of strips. Each strip of the plurality of strips can include a plurality of wedge dissectors spaced apart along a surface of each strip. Each strip can extending longitudinally along an outer surface of the serration balloon. Each wedge dissector can include radially outward facing surfaces and lateral surfaces. The serration balloon can then be expanded at the site such that the radially outward facing surfaces of the plurality of wedge dissectors directly contact tissue of the intima layer of the vessel wall creating cleavage planes into a media layer of the vessel wall. The serration balloon can continue to be expanded, such that radially outward facing surfaces of the plurality of wedge dissectors no longer contact tissue of the media layer of the vessel wall, and the lateral surfaces of the wedge dissector contact tissue of the media layer of the vessel wall to expand the cleavage planes. In some embodiments, the cleavage planes created can have a total depth, or depth within the media layer, of between about 0.2 mm and about 2.0 mm, such as between about 0.3 mm and about 1.5 mm, or between about 0.5 mm and about 1.2 mm. In some embodiments, the cleavage planes can have a total depth, or depth within the media layer, of about 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, or ranges including any two of the aforementioned values. In some embodiments, the cleavage planes do not intersect other cleavage planes.

The use of a single or multi (bi or tri layer) coatings on top of the strips and/or balloon has been described in previous applications. In some cases it is envisioned that there would be an advantage to have the tips of the strips free of the top coats. The removal of the top coats can be achieved through a variety of processes, including but not limited to a laser ablation step to selectively remove the top coat, either completely or nearly completely (leaving a very thin film) where the remaining thickness is around, or less than about, in some cases 20 µm, 10 µm, 5 µm, 3 µm, 1 µm, or less. Alternatively, in some embodiments, the coating can be sprayed on the balloon surface over all the surface but carefully avoiding the tips of the strips.

The large variety of designs of the strips can in some cases offer not only features that might be advantageous for drug delivery, but also can aid more effective tissue penetration in a variety of cellular and diseased morphologies. For instance, tip designs with more than one contact surface could be advantageous for providing effective penetration into thick calcium or fibrotic laden tissue. In addition, tip designs with steeper angles, such as in some cases less than 15 degrees, could be advantageous to penetrating deeper into the disease vessel offering better nucleation sites for crack propagation. As discussed above depth of penetration can aid in reducing the pressure needed to initiate the crack and allow for increase in crack opening displacement. In some cases, broader angles, like those above 20 degrees, might be effective at cracking hard, calcium rich, diseased vessels.

The design of the serratoplasty balloon can vary based on the type of disease being treated. In some cases the design of the strips and the elevated elements (e.g., wedge dissectors) can be effective over a large range of heterogeneous plaque morphologies including circumferential and non-circumferential plaques. For instance the use of a rounded elevated element with a narrow tip can in some cases effectively penetrate both hard and soft tissue and limit trauma to the underlying cellular matrix by minimizing the necessary pressure required to initiate nucleation sites for crack formation and eventually lumen expansion 5100.

The design of some embodiments of serration balloons can offer the unique advantage of enabling low pressure dilatation (e.g., about or less than about 9, 8, 7, 6, 5, 4, 3.5, 3, 2.5, 2, or less ATM in some cases) in a variety of disease morphologies. We observed low pressure (3 ATM) angioplasty during the PRELUDE study. During the PRELUDE trial physicians routinely inflated a Serranator device up to about 3 or about 4 ATM and held the pressure for 30 seconds. It was observed that when the balloon would inflate, it would do so often with a waist, where the middle of the balloon was less inflated that the ends of the balloon (often referred to as a dog bone shape). Without increasing the pressure the physician would hold the pressure at wither 3 or 4 ATM for 30 seconds. After the 30 seconds, the physician would take an angiographic image and typically the waist was gone and the balloon was fully inflated and apposed and the artery appeared to have expanded (FIG. 3A). This phenomenon is believed to be unique and is typically not seen at low pressure angioplasty.

FIG. 31C illustrates fluoroscopic images of a serration balloon inflation procedure. The leftmost image illustrates an arterial stenosis seen with the absence of contrast along a length of the vessel. As shown, a waist can be seen when the balloon is inflated to 4 ATM in the left middle image. In the right middle image, with the same 4 ATM, taken only 30 seconds after the first, a fully inflated balloon can be seen. The rightmost image illustrates successful revascularization following the procedure.

FIG. 31D shows an OCT image on the left showing intima dissection. IVUS image on the right showing calcium cracking and disruption into the media exposure, to allow for advantageous drug delivery in some cases.

FIG. 32 illustrates an embodiment of a modified cutting balloon to produce serrations. In some embodiments, serration or serration-like advantageous effects could be achieved by modifying a cutting balloon catheter as described, for example, in U.S. Pub. No. 2006/0184191 to O'Brien, which is hereby incorporated by reference in its entirety. The balloon catheter can include a catheter shaft having a balloon coupled thereto. One or more cutting members or blades may be coupled to the balloon. The balloon may include one or more discrete points or areas of flexibility 3200 to enhance flexibility of the cutting balloon catheter. A break in the one or more cutting members may be aligned with the one or more discrete points of flexibility in the balloon. In some embodiments, flexpoints can be located every 5 mm on 10 mm and 15 mm lengths (6 mm length=0, 10 mm length=1, 15 mm length=2). Atherotomes with flexpoints can in some cases assist in tracking to lesions that may have been previously out of reach.

FIG. 33 shows an illustration of a modified cutting balloon where flexibility is further enhanced and the cutting is either completely or partially replaced with a serrated blade 3350 pattern. As shown in FIG. 32, cutting members 3320 may vary in number, position, and arrangement about balloon 3316. For example, catheter 3310 may include one, two, three, four, five, six, or more cutting members 3320 that are disposed at any position along balloon 3316 and in a regular, irregular, or any other suitable pattern. The pattern can include a generally helical orientation of the cutting members 3320. Catheter 3310 may include a plurality of cutting members 3320 placed equidistantly about balloon 3316 extending generally longitudinally. In general, cutting members 3320 may be configured to provide variable flexibility or otherwise vary the flexibility of catheter 3310. Increasing the flexibility of cutting members 3320, balloon 3316, and/or catheter 3310 may be desirable, for example, because it may improve the tracking ability and general deliverability of catheter 3310 through the often tortuous anatomy. Additionally, increasing the flexibility may allow catheter 3310 to be navigable to a larger number of intravascular locations, including some that may not be readily reachable by other, less flexible, cutting balloon catheters. In general, the enhanced flexibility may be the result of a structural feature of cutting members 3320, a structural modification to cutting members 3320, and/or a structural feature of the cutting balloon 3316. For example, cutting members 3320 may include a first section 3344a, a second section 3344b, and a gap or break 3346 disposed between first section 3344 a and second section 3344b. Break 3346 may be configured to provide a region of flexibility such as a space between first section 3344a and second section 3344b. In some embodiments, break 3346 may be defined by a downward deflection or slot that is formed in the cutting surface of cutting member 3320. Alternatively, break 3346 may not be a physical gap between first section 3344a and second section 3344b, but rather break 3346 may be a region of cutting member 3320 having a reduced wall thickness or may comprise a material having an increased flexibility relative to the material of first and second sections 3344a, 3344b. Break 3346 also may comprise an exogenous connector that is connected to both first section 3344a and second section 3344b in order to bridge sections 3344a, 3344b. Separation of sections 3344a, 3344b can increase the flexibility of cutting member 3320 and/or the overall flexibility of catheter 3310.

In some embodiments, a series of cutting elements (or micro atherotomes) as described above can be placed linearly along the surface of the balloon spaced apart by a gap in the upper surface of the blade. In the above schematic illustration, the gap length is approximately one tenth of the length of an individual blade length. In some embodiments, the gap length to blade length ratio can be, for example, between about 1/15 and about 1/1, between about 1/10 and about 1/1, between about 1/5 and about 1/1, between about 1/5 and about 1/2, or about 1/1, 1/14, 1/13, 1/12, 1/11, 1/10, 1/9, 1/8, 1/7, 1/6, 1/5, 1/4, 1/3, 1/2, 1/1, 1/1.5, 2/1, or ranges including any two of the aforementioned values.

A modified cutting member with dimensions that provide for a more flexible, more stable design and that can serrate or approximates serrations in the tissue are described herein. A modified cutting member embodiment can offer, for example, about or greater than about 8, 9, 10, 11, 12, 13, 14, 15, 20, or more degrees lateral flexion with or without sections where the cutting surface is less or not serrated. Some embodiments can include a series of cutting members, either in tandem or with periods of serrated features as described elsewhere herein (for instance elevated elements) between or on the ends of the cutting members. The cutting members (X) when divided into multiple discrete sections can have a length, for example, in the range of 0.01" to about 0.10" in separated by spaces (Y) of, for example, about 0.01" to about 0.08". The entire cutting blade may have discrete sections at any one or any number of locations along the blade. Once pressure is applied by the balloon into tissue the resulting tissue disruption may appear to be a series of dots and dashes or any combination of dots and dashes, produced by the bonded modified cutting members, piercing the tissue only in narrow regions where the discrete cutting members (X) are located. The effect of this discrete localized penetration is that the balloon with modified cutting blades produces a new angioplasty effect, referred to as serratoplasty. For instance, one such serratoplasty design might be small raised features, able to produce dot like effects (or serration like features) in tissue, on the ends of the cutting blade, then longer raised features, able to produce dashes in the center portion of the blade. Other serratoplasty designs might mix small and longer raised features in alternating patterns, or a series of dots spaced by one or more dashes with a repeated pattern or a non-repeated pattern. The embodiment might have 1, 3, 4, 5, 6, or 8 members, e.g., blades (or a combination of these number of members, e.g., blades) on the outside of a balloon with the blade being typically less than the balloon body length. This device, configured for serratoplasty, can be used as a stand alone angioplasty balloon or as a preparation device prior to a follow-on therapy. Follow-on therapies would include but are not limited to: stenting, placing a drug eluting stent, performing atherectomy, high pressure ballooning or drug coated balloon treatment. Whether or not the device is used as a preparation device for follow-on therapy or a stand-alone therapy, through the use of modified atherotomes as disclosed herein, the device effectively manages plaque or calcium by weakening the bonds, initiating cellular or structural disassociation and minimizing cellular or structural compression, typically generated by angioplasty alone. Serratoplasty allows for the diseased lumen to be safely expanded and accurately dilated and stretched, using low pressure, to a desired diameter without creating numerous and substantial dissections and elevated flaps. The serrations can enable the plaque to be dilated more evenly and smoothly and avoid forming random cracks that may lead to dissection and residual stenosis. The plaque, after it has been pre-treated with serration, in some cases, may also be dilated with lower pressure than that which is used in standard balloon angioplasty. The lower intra-balloon pressure (e.g., less than or equal to 4, 3.5, 3, 2.5, 2 atm, or less) applied by the balloon, bonded with modified cutting members, causes less disruption of the plaque, fewer dissections, and less injury to the artery wall. This "low pressure" or "minimal injury" serratoplasty is less likely to cause the biological reaction that often follows balloon angioplasty with neointimal hyperplasia or smooth muscle cell replication. In addition, serration can permit the plaque to expand with less fracturing or disruption of the plaque during balloon angioplasty. By preparing the plaque using a balloon with serrations, the number and severity of dissections can be reduced. This decreases the need for stent placement to be used to treat dissection or residual stenosis after balloon angioplasty with serration. In some cases, a subsequent balloon angioplasty may be performed, at low balloon pressures of about 4 atmospheres or less due to preparation of the plaque with perforations, so as to avoid injury to the arterial wall or its sub-intimal tissues. By performing plaque preparation and then low-pressure angioplasty, there is less likelihood of a dissection occurring that generates deep tissue tearing while still potentially exposing the media layer of the artery. Exposure of deep tissue from within the artery wall can in some cases stimulate thrombus formation by collagen exposure and also stimulates smooth muscle cell growth which later causes neointimal hyperplastic occlusion of the artery. This decrease in number and also decrease in severity of dissection can in some cases be an advantageous differentiating factor in comparison to conventional cutting or scoring devices.

Entrapment Coil Designs

Incorporation of materials to increase device pushability can be advantageous. When a physician encounters a lesion such as a chronic total occlusion (CTO) the ability to cross the lesion can be challenging with conventional catheters. To increase pushability, the catheter might include fiber, high-density polymer, and/or a metal component. These materials can be incorporated into the polymer matrix of the main shaft, the inner member, or as a separate component. When included as a separate component the added component typically is captured between the outer sheath in the inner member. In one embodiment it is envisioned a coil, such as a metal coil for example can be inserted between the inner member and the outer sheath. The coil pitch can be, for example, between close-wound to 35 degrees in angle and the coil pitch may or may not change along the entire length of the catheter. The coil typically includes a segment that tapers from a first diameter to a second diameter that is smaller than the first diameter. The catheter shaft typically is designed with a tapering segment designed to follow the coil tapering segment maintaining an entrapment of the coil tightly between an inner member and outer sheath of the catheter. In some embodiments, the reduction of the outer diameter can occur or start proximal of the balloon. For example, in some embodiments the tapered segment or segments can be entirely proximal to the proximal end of the balloon, or the distal end of the balloon In some embodiments, the tapered segment or segments can be within the insertable working length of the catheter (e.g., positionable within a body lumen). In some embodiments, the start (e.g., proximal end) of the tapering segment can be distal to a strain relief element, such as within about 10, 9, 8, 7, 6, 5, 4, 3, 2, 1 cm, or less, or ranges including two of the foregoing values.

Illustrated in FIG. 34 is an embodiment of a catheter 3310 that can include a coil 3400 in the space between the outer catheter shaft 3410 and the inner member (guide wire shaft) 3420. Typically, the coil can be made of a metal or alloy, such as stainless steel, but also could be a polymer material. The coil 3400 can be designed with one or more taper(s) from a larger diameter 3430 to a smaller diameter 3440. The taper of the coil can be fabricated between, for example, a 0-degree pitch and a 15-degree pitch in the wind. Lower pitches can offer greater pushability while higher pitches can offer greater flexibility. In some embodiments, the pitch angle can be about 0, 1, 2, 3, 4, 5, 6, 7, 8, 9, 10, 11, 12, 13, 14, 15, 16, 17, 18, 19, 20, 21, 22, 23, 24, 25, 30, 35, or more degrees, or ranges including any two of the aforementioned values. In some embodiments with multiple tapers (e.g., 2, 3, 4, 5, 6, 7, 8, 9, 10, or more tapers, or ranges including any two of the foregoing values), each taper, or one or more of the tapers could have the same, or a different pitch to it. The coil can typically lie within the space that lies between the inner diameter of the outer shaft of the catheter and the outer diameter of the inner member, where the guidewire passes through. In some embodiments, the coil's outer diameter matches or substantially matches the inner diameter of the outer shaft through at least a portion of the axial length of the coil and the outer shaft, such that the outer diameter of the coil is no more than about 15%, 10%, 5%, 4%, 3%, 2%, 1%, or more or less than that of the outer shaft. In embodiments where the surfaces (e.g., coil outer diameter surface and outer shaft inner diameter surface) touch or nearly touch the device can provide greater stability and greater effective pushability in tortuous anatomy. In some embodiments, the taper of the coil matches up to a similar taper of the outer shaft, therefore when the coil tapers down from one outer diameter to another smaller outer diameter the outer shaft can follow with a matching or substantially matching taper. In addition to the coil following the taper of the outer shaft, the coil can reduce further in dimension and follow the outer diameter of the inner member or radio-opaque markers that typically reside integral with the inner member(s). The support of the inner member on the smaller coil diameter and support of the outer shaft at the taper and on the larger coil diameter collectively increases the stability of the coil in some cases. In embodiments when the coil is supported along its entire length, the coil is less able to become uncoiled or unwind. The combination of one or more coils and adjacent shafts can advantageously increase the robustness of the device and its ability to translate energy to the tip of the catheter especially when the catheter body has bent through tortuous anatomy.

In some embodiments, the taper of the coil matches up to a similar taper of the outer shaft, therefore when the coil tapers down from one outer diameter to another the outer shaft can bump with a matching taper. The outer dimensions of the largest region of the coil can be in some cases between about 0.030 inches and about 0.150 inches, such as between about 0.070 inches and about 0.050 inches. The outer diameter of the smallest diameter section of the coil can be, for example, between about 0.025 inches and about 0.045 inches, or between about 0.030 inches and about 0.040 inches. There may be a single transient taper from the larger diameter to the smaller diameter but there may be as many as 2, 3, 4, 5, or more tapered sections with varying degrees of diameters in some embodiments. The outer shaft can be similar in design with 1 to 5 or more tapering segments, e.g., bumps down from one diameter to another. In some embodiments, the outer dimensions of the largest region of the outer shaft is between about 0.030 inches to about 0.150 inches, or between about 0.050 inches and about 0.075 inches. In some embodiments, the outer diameter of the smallest diameter section of the outer shaft can be, for example, between about 0.020 inches and about 0.080 inches, or between about 0.0030 inches and about 0.065 inches. In some embodiments, the coil thickness can range from between about 0.0001 inches and about 0.0010 inches thick, or between about 0.0002 inches thick and about 0.0005 inches thick. The width of the coil can range, for example, from between about 0.006 inches to about 0.040 inches thick, between about 0.040 inches and about 0.008 inches thick, or between about 0.020 inches and about 0.010 inches thick. The coil can in some cases run the entire length or substantially the entire length of the catheter from the hub to the tip, or at least about 50%, 60%, 70%, 80%, 90%, 95%, or more or the entire axial length of the catheter, or ranges incorporating any two of the aforementioned values. The length of the system (and/or the coil) could range, for example, from about 20 cm to about 250 cm in length, such as about 20, 30, 40, 50, 60, 70, 80, 90, 100, 110, 120, 130, 140, 150, 160, 170, 180, 190, 200, 210, 220, 230, 240, 250 cm, or more or less, or ranges incorporating any two of the aforementioned values. The length of the tapering from the larger diameter coil to the smaller diameter can occur in some cases over a narrow length of the entire coil, such as, for example, about or less than about 50%, 40%, 30%, 25%, 20%, 15%, 10%, 5%, or less of the entire axial length of the coil, such as between about 10% and about 40%, or between about 15% and about 30% of the entire axial length of the coil. The axial length of the tapered segment of the shaft from the larger diameter shaft to the smaller diameter shaft configured to match or substantially match the tapered segment of the coil can occur in some cases over a narrow length of the entire shaft, such as, for example, about or less than about 50%, 40%, 30%, 25%, 20%, 15%, 10%, 5%, or less of the entire axial length of the shaft, such as between about 10% and about 40%, or between about 15% and about 30% of the entire axial length of the shaft. The tapering segment length can be, for example, between about 0.01 cm and about 10 cm, between about 0.03 cm about 10 cm, between about 0.05 cm and about 10 cm, between about 0.3 cm and about 5 cm, between about 0.5 cm and about 5 cm, and other ranges incorporating any two of the aforementioned values. In some case, the location where the tapering length ends and the smaller diameter coil begins can be, for example, on or proximate the distal end of the catheter and is typically between about 5 cm and about 50 cm measured from the tip of the catheter or can be measured from the proximal leg of the balloon. In some embodiments, the coil can be fused or otherwise connected into the outer sheath on the proximal end prior to being bonded to the hub typically with a UV adhesion agent but other commonly used bonding methods could be used. In other embodiments the coil is bonded directly to the hub at the same time or at separate bonds of the outer sheath and/or inner member to the hub. While on the distal end the coil can be fused to the tip, balloon, balloon assembly, and, or the inner member collectively creating a joint created using heat for example to allow all or some polymer layers to reflow and solidify into a single fused joint, although other commonly used bonding methods could be used.

FIG. 34A illustrates an embodiment of a catheter including a shaft comprising an insertable axial length 34L and a coil extending axially substantially along the entire length of the shaft. The catheter can include a strain relief element 3470 with a distal end 3472 that is spaced apart from a tapered segment 3471, which can in turn be spaced apart from the proximal end 3475 of a balloon 3477 in some embodiments.

FIG. 34B illustrates a cross-section of a shaft through line A-A of FIG. 34A (coil removed for clarity). FIG. 34C illustrates a cross-section of a shaft through line B-B of FIG. 34A (coil removed for clarity). FIG. 34D illustrates a schematic sectional view illustrating a taper of coil A within a taper of the main shaft B, and FIG. 34E also schematically illustrates the taper region. FIG. 34F illustrates a schematic view of a balloon catheter including a coil 3488 extending within an inner surface of balloon 3490 with wedge dissectors 3492 on an outer surface of the balloon. As shown, the coil 3488 commonly extends (not shown) proximally through shaft 3486 and in some designs the coil extends distally if the shaft were also distal the balloon. In some embodiments the coil runs in the interstitial space between the main shaft of the catheter and the inner member from the hub to the tip. FIG. 34G illustrates an embodiment of a coil 3488 extending through a balloon as previously described, with one or more gap or coil separation portions 3489 within the balloon configured to aid visibility of radiopaque markers typically imbedded in or locked onto an inner member running the entire length of the catheter from hub to the tip. In some embodiments, the coil separation portions 3489 can be outside the balloon, such as at the distal tip or within the catheter shaft, alternatively or in addition. In other embodiments, the coil could remain continuous and a radiopaque coating applied to a portion of the coil. In other embodiments, the coil itself may be made of more than one material, with part of the coil being more radiopaque than other portions of the coil. Designs where more than one material is used the more radiopaque region might be used to define working zones of the device. The working zone would be interpreted by the physician as the area to place the device aligned with the desired treatment zone. FIG. 34H schematically illustrates an embodiment of the coil 3488 running through the length of the catheter between an outer sheath 3498 and inner member 3497. FIG. 34I schematically illustrates the coil 3488 running inside the entire length of the balloon 3490, and extending proximally as well as distally. FIGS. 34J-34K illustrate views of the distal end 3481 of the coil 3488 fused or otherwise bonded to a distal tip portion 3471 of the catheter as previously described. FIG. 34L schematically illustrates an embodiment of a proximal bond region of the balloon, illustrating coil 3488, outer sheath 3498, and inner member 3497. FIG. 34M illustrates a schematic sectional view through a proximal hub of a catheter system, illustrating coil 3488, outer sheath 3498, and inner member 3497, which can be bonded or otherwise attached together as previously described.

Some non-limiting features of the coil are also described. (1) Tolerance stacking—the coil thickness preferably can accommodate the system's profile needs. Therefore, a 5F system can be, for example less than about 0.08, 0.075, 0.07, 0.066, 0.063, 0.060, or less inches (or ranges including any two of the aforementioned values) for the outer diameter of the catheter shaft. The catheter shaft tolerances can match up to the coil tolerances which in turn can match up to the radiopaque markers (if needed in the system), which then can match up to the tolerance stack of the inner member. This stack can require precision fabrication; in some embodiments catheter designs that include coils can choose to combine more than one material together. (2) Addressing torturous bends—the need of a more effective design has become more relevant as physicians address complex diseases in the most distal areas of the body. Presently few devices are capable of tracking over a guide wire to regions of disease below the popliteal and especially below the ankle. The main difficulty in tracking to these most distal vessels are driven by the complexity of the disease and the anatomical tortuosity of the vessels in these arterial paths. The anterior tibial for instance typically displays two 90 degree bends within a short 5 cm length. The ability of extruded polymer materials alone, that is without coils, to manage effectively navigating these bends and still enabling effective pushability has proven to be poor. The inclusion of coil designs offers an effective ability of the system to increase column strength while not reducing the ability to manage tortuous anatomy. (3) Effect translation of system control—in some catheter-based devices the physician would prefer to be able to control the orientation of the entire system by changing the orientation of the hub or handle that remains outside the patient. If the devices is laying freely on a table with no constraints on it and the physician rotates the handle, the entire device typically rotates. However, when the device is introduced into the patient it typically has to travel through a series of bends, and can be twisted while it is pushed to the site the device will be used. Once at the location, the ability of the physician to rotate the device is very limited due in great part to the friction of all the bends and the inability of the device to effectively translate the rotational energy at the handle to the distal end of the catheter. The use of entrapped coil technologies offers the ability of the coil to more effectively translate the rotational energy down the device. (4) The use of periodic tack bonds—in some embodiments the use of periodic tack bonds can be used to aid in the translation of the system control. These embodiments include a single or a set of regions where the coil and the outer sheath are "tacked" together. The use of tacking regions of catheters can be used to aid in the translation of energy along the catheter body. Although tapering the coil and the outer shaft and the use of different pitches in the coil design can effectively provide increased system controls, to the physician some embodiments include one, two, or more tack bonds to further enhance the system's control. (5) Materials and processes to make coils—in tests performed to date, a series of stainless steel materials with varying thickness, width, tapers, and lengths have shown effective. Other materials with similar geometries can also be effective. Plastic materials such as polymers or copolymers can be extruded and then cut to form a coil, or might start as a flat ribbon and be heated and wrapped around a mandrel to form the coil shape and then cooled to retain its shape. For metals, such as stainless steel, the material might start as a tube and then be cut to form a coil, or might start in flat ribbon and be heated, if needed, and wrapped around a mandrel to form the coil shape and then cooled, if needed, to retain its shape. Other manufacturing methods typically known in the industry to form coils might also be used. (6) Pushability of the distal tapered region—the effective inclusion of the taper can offer increase in pushability in the distal section, where the device has the least linear translation of energy. Again, in the case of the lower extremity tibial disease for example, the distal section of the device can successfully track over two right angle bends only about 5 cm apart, such as tibial arterial branching segments as schematically shown in FIG. 34N. In contrast, the linear pushability of a conventional system can be compromised in each additional turn. The reduction in diameter can advantageously and effectively tightens the column strength and enables greater translation of momentum through the bends and to the tip of the system.

Balloon in Balloon Designs

In some embodiments, the use of a single pre-fabricated covering or top balloon in place of the top coats (as described herein as well as, for example, U.S. Pub. No. 2017/0333686 to Schneider et al. and U.S. Pub. No. 2017/0080192 to Giasolli et al., both of which are hereby incorporated by reference in their entireties), can be preferable. The use of a prefabricated covering can provide a series of additional values such as, for example, ease in manufacturing, precise control of the thickness, increase retention of the strips, uniformity of the outer layer, and/or the ability to use a wider range of materials on the outermost surface. The range of materials can include nearly any material that is both extrudable and can be blown into a balloon mold. In some embodiments, the pre-fabricated coatings might be made of more than a single material or more than a single layer but is typically made from a more stretchable or pliable material than the base balloon. Since the functional characteristics of the pre-fabricated covering or outer balloon are different from the inner balloon the materials used to build it are typically different. In the case of the outer balloon the main requirement of the balloon can be to allow the elevating elements (e.g., wedge dissectors/serrations for example) to penetrate effectively but not to tear along the spaces between the elevating elements under high loading during a high-pressure expansion of the base balloon. Independent of the material used to build the outer balloon, the dimension of the balloon can be the same or different than that of the base balloon. In some embodiments, both the length and the diameter of the outer balloon are larger than the length and diameter of the base balloon. Due to the Laplace formula described above we note that the tangential stress on the balloon surface is directly proportional to the radius of the balloon and the pressure inside the balloon. Therefore, the material of choice and the dimensions of the inner and outer balloon may need to vary at different diameters of balloons. Therefore, a 2.5 mm diameter balloon may need a more stretchable material as a 5.0 mm diameter balloon since the tension on the surface of the balloon are ½ as high at the same pressure. In addition to the length and diameter difference between the two balloons, the angle and length of cone on the ends of the two balloons may be different. Balloons can be designed to stretch or be compliant to the pressure being delivered. When this occurs, both the diameter and the length of the balloon typically increases, and the pre-fabricated covering or outer balloon is designed to accommodate this expansion. In some embodiments, the pre-fabricated coating has a length that is less than the base balloon, such as about, at least about, or no more than about 1%, 2%, 3%, 4%, 5%, 6%, 7%, 8%, 9%, 10%, 11%, 12%, 13%, 14%, 15%, 16%, 17%, 18%, 19%, 20% or more, less than that of a length of the base balloon, or ranges including any two of the foregoing values. In some embodiments, the pre-fabricated covering or outer balloon has a length that is about 5 mm, 4 mm, 3 mm, 2.5 mm, 2 mm, 1.5 mm, or 1 mm less than that of the base balloon, or ranges including any two of the foregoing values. In some embodiments, the pre-fabricated coating has a diameter that is greater than the base balloon, such as about, at least about, or no more than about 1%, 2%, 3%, 4%, 5%, 6%, 7%, 8%, 9%, 10%, 11%, 12%, 13%, 14%, 15%, 16%, 17%, 18%, 19%, 20% or more greater than that of a length of the base balloon, or ranges including any two of the foregoing values. In some embodiments, the pre-fabricated covering or outer balloon has a diameter that is about 0.05 mm, 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 2 mm, or more greater than that of the base balloon, or ranges including any two of the foregoing values.

The dimensions of the outer balloon (or pre-fabricated covering) can in some cases be larger than the inner balloon to aid in fabrication. In some embodiments, an outer balloon can have a length, diameter, and/or thickness that is about, at least about, or no more than about 1%, 2%, 3%, 4%, 5%, 6%, 7%, 8%, 9%, 10%, 15%, 20%, 25%, 30%, 35%, 40%, 45%, 50%, or more or less relative to that of the base (inner) balloon, or ranges incorporating any two of the aforementioned values. In some embodiments, a balloon with serrations bonded to the surface is inflated inside the pre-fabricated covering. FIG. 34O illustrates schematically an embodiment of a method for producing a balloon-in-balloon design. As shown in panel 1, a Plain Old Balloon Angioplasty (POBA) base balloon 5100 that provides the desired support typically on a short catheter can be used alone or with only a single base coat (or multiple base coats in other cases). As shown in panel 2, strips with wedge dissectors 5102 can be attached to the base balloon 5100, e.g., the outer surface of the balloon, as described for example elsewhere herein to create a serrated balloon. As shown in panel 3, the balloon 5100 with attached wedge dissectors and strips can then be pleated. As shown in panel 4, the pleated balloon 5100 with attached wedge dissectors and strips can then be inserted into a second balloon 5104 or other outer walled structure or covering that does not include any serrations/wedge dissectors on its outer surface. As shown in panel 5, the inner serrated balloon 5100 can then be inflated. In some embodiments, the entire balloon and strips are bonded to the outer pre-fabricated covering. The final balloon-in-balloon construct 5199 can be seen in panel 6. The bonding of the two layers is typically done with, for example, a UV curable glue or other adhesive that is uniformly applied to the surface of the inner balloon prior to sliding the outer pre-fabricated covering over the inner balloon. The inner balloon is then inflated, such as to high pressures (for example, above about 5, 6, 7, 8, or more ATM) and then exposed to UV light and allowed to cure. The contact of the two surfaces under the pressure loading disperses the glue uniformly allowing for uniform coating thickness on the balloon body and balloon cone surfaces prior to the curing cycle. Alternately, it is envisioned that during the balloon blowing process the strips would be incorporated in the balloon molder in some embodiments. When the strips are incorporated into the balloon fabrication it is envisioned that the inner and outer balloon may be laminated or thermally bonded with the strips incorporated within the laminate layers. When the strips are incorporated into the fabrication of the balloon pairs it is envisioned that the strips might be pressed into the outer balloon first, such as from the ID of the balloon, then the inner balloon would be expanded and fused into the outer balloon thereby producing a fusion bond of the balloons with the base of the strips captured. As is typical with other manufacturing techniques the elevating elements rise above the outer balloon surface.

Interface Bonding Between Pre-Fabricated Covering and Base Balloon.

The spacing between the elevated elements or the top surface of the base strip can be thought of as a stretchable membrane that retains the strip and stabilizes the elevated elements to the balloon surface. In some embodiments this space between the elevated elements might be bonded to the base balloon and the strip. In other embodiments the space may not be bonded to the base balloon allowing the pre-fabricated balloon to float free in the strip section while both balloons are selectively bonded elsewhere. In the embodiment where the strip region is not selectively bonded, the inner balloon can in effect fall away during the deflation event. As the system deflates, the outer balloon deflates at slightly different rate than the inner balloon since the balloon system is not completed bonded into a single unit. Due to the variation in deflation rates a regional void between the balloons is generated. The space produced by the regional void enables the serrated strip to retract into the space. As such, the elevated elements of the strip body or recessed the height or profile of the elevating elements that lies above the outer balloon is minimized and in some cases all of the elevating elements are fully recessed into the space between the balloons. Such embodiments can be advantageous to, for example, reduce the risk of the serrations catching on an undesired portion of the anatomy, such as a vessel or bifurcation other than the target treatment location, during insertion or removal of the device for example. However, in some embodiments the pre-fabricated covering or outer balloon is bonded to the base balloon into a single unit.

TAVR Indications

In some embodiments, a serration device could be used to prepare an access vessel for a large bore sheath (e.g. >12 Fr), such as that required, e.g., for endovascular aneurysm repair (EVAR), fenestrated endovascular aortic repair (FEVAR), transcatheter aortic valve replacement (TAVR), transcatheter mitral valve repair or replacement, or thoracic endovascular aortic repair (TEVAR). The placement of a large bore sheath in a severely diseased and/or calcified iliac artery or infrarenal aorta that is being used for access can create dissection or trauma to the artery. The advancement of a large bore sheath that is used for device delivery can cause injury to a small or calcified or severely diseased iliac artery if the lumen of the access artery is not adequate to accommodate the sheath. Similarly, the enlargement of a dilating sheath that is used for device delivery can cause injury as it is expands to accommodate the large diameter index procedure catheters. The serration balloon would be used to create a serration effect in the access artery (iliac or infrarenal aorta or common carotid artery or subclavian artery that may be used for access for large bore sheaths) enabling more control during the use of large bore delivery sheath. This technique would permit expansion of the access artery, creation of adequate lumen for sheath placement and decrease the potential of dissection or trauma to the access artery which can occur during the expansion of dilating sheaths.

The use of serratoplasty for access for a variety of procedures is another area of use for, e.g., 8-12 mm diameter vessels or balloons. With TEVAR and EVAR, one potential issue is access through the common femoral artery or iliac artery. A serratoplasty procedure utilizing catheters with wedge dissectors as disclosed herein can be performed before placing the sheath. This can advantageously aid healthy or diseased tissue in expanding (predilating) the tissue) prior to performing the index procedure.

FIG. 35a above illustrates an embodiment of a strip 3500 with wedge dissectors where the wedge dissector has sloped non-linear edges 3510. The wedge dissectors can include radially-outward facing peaks 3570. The strip 3500 has a top surface 3550 and side surface 3560. The sloped non-linear edge 3520 can have an upper concave or convex feature 3530 than is different from the bottom concave or convex feature 3540 along one or both slope sides. Another view can be seen in the FIG. 35b end view illustration.

In the side view shown in FIG. 35b, the bottom section 3540 is a biconcave section of the strip 3500 that has a greater thickness than the upper biconcave section 3530. The upper biconcave section 3530 shows a thinner biconcave section of the strip 3500 as the strip 3500 narrows towards the tip 3580, which can be radially outward-facing in some cases. Other designs and manufacturing techniques can produce a series of concave sections on the strip side.

As illustrated in FIG. 36, the top of the wedge dissector 3570 can have a variety of unique features 3600 on the tip (e.g., radially outward facing surface) 3580 that contacts the tissue. As shown, the wedge dissector 3510 has the appearance of a serrated tip with micro-concavities, valleys, or features 3600 near the apex of the radially-outward surface of the wedge dissector 3580, that have small, e.g., less than about 10%, 8%, 6%, 4%, 2%, or less increases or decreases in height with respect to the entire height of the wedge dissector that laterally border a central segment 3610 which can be flat-topped as shown.

FIG. 37 is another design illustrating an alternate variation of the serrated edge of the wedge dissector 3510, where the central segment can include a small depression 3700 as shown, which can have a depth of, for example, less than about 10%, 8%, 6%, 4%, 2%, or less increases or decreases in height with respect to the entire height of the wedge dissector.

In another embodiment, shown in FIG. 38, the wedge dissectors 3510 can include rounded double-hump like contacting surfaces 3800 at the tip 3580 that can provide effective tissue penetration. The effect of multiple points of contact on the surface of the wedge dissector 3510 can in some cases provide better penetration force (point source) into a variety of disease morphologies, including calcium, while still enabling serration effect across the diseased lesion and thereby facilitating arterial lumen gain with minimal balloon pressure.

FIG. 39 illustrates variations on a design that provides a relatively sharp, pointed double contacting surface at the tip 3900 of each wedge dissector 3510 that can provide effective tissue penetration. FIG. 40 also illustrates a similar design that provides a relatively sharp, pointed double contacting surface at the tip of each wedge dissector that can provide effective tissue penetration, that abut a central wider, and shallower valley/depression respectively 4000.

In some embodiments, disclosed below are a series of frames that follow to illustrate a design to provide access of one, two, or more therapeutic agents into the regions where dissection planes were produced.

As illustrated in FIG. 41A, a strip 3500 can be fabricated that includes a plurality of strips (e.g., two identical strips) touching only tip to tip 4100, in a wedge dissector frame or carrier 4110. This wedge dissector frame 4110 can be potentially created via a mechanical removal process such as chemical etching. In some embodiments, the strip 3500 can be easily and cleanly detached from the frame 4110 and mirror image strip via a mechanical force or other means without modifying the geometry of the wedge dissectors of the strip 3500. In some embodiments, the frame or carrier 4110 can remain attached to the strip 3500 until a surface of the strip opposite the base of the wedge dissectors is bonded or otherwise attached to a surface of a balloon as described elsewhere herein.

FIGS. 41B and 41C illustrate that in some embodiments, a plurality of strips 4100 can be bent or folded over into a bent form 4120 leaving the tips 4100 intact and producing an A-frame 4130 with an open gap or well within the radially-outward facing surface of the combined A-frame wedge dissector 3510 assembly.

FIGS. 41D and 41E illustrate an alternative embodiment with serrated tips 4160, that include a plurality of pointed surfaces with a central concave segment therebetween 4150 (compared with the central flat segment 4140 in FIGS. 41B and 41C). A strip 3500 with serrated tips 4160 can be bent over leaving the serrated tips 4160 intact and producing an A-frame with serrated tips 4160 with an open gap or well.

In some embodiments, the distance between adjacent base strips at the base is between about 30 µm and about 260 µm, between about 60 µm and about 190 µm, or between about 90 µm and about 130 µm. In some embodiments, a dimension, e.g., width of the gap at the apex of the "A" of the A-frame can be, for example, between about 10 µm and about 150 µm, between about 25 µm and about 100 µm, or between about 50 µm and about 75 µm. In some embodiments, the angle creating the apex of the "A" of the A-frame defined by the intersection of distal portions of the two wedge dissectors can be, for example, between about 5 degrees and about 45 degrees, such as between about 10 degrees and about 30 degrees, or between about 15 degrees and about 22 degrees.

FIG. 42 illustrates an illustration series that shows the ability to take a stack of strips 4200 connected to a blank or carrier 4300 that can be discarded at any point in the strip attachment process (prior to placement on the balloon, during balloon placement, or post gluing of the strip to the balloon). This process offers an aid to automation, picking up and placing the strip, and facilitates the precision in aligning the strip and balloon. The radial distal tips 4210 can abut against continuous free edge 4220 or other continuous or discontinuous surfaces to allow for simple detachment of the strip. In some embodiments, a carrier system for attaching wedge dissectors to a medical balloon can include a strip including a plurality of wedge dissectors spaced longitudinally apart along a surface of the strip. Each of the wedge dissectors can include a strip-facing base surface directly adjacent a first surface of the strip, an unhoned radially outward facing surface having a length between a proximal edge of the radially outward facing surface and a distal edge of the radially outward facing surface and defining a height of each wedge dissector, and lateral surfaces between the strip-facing base surface and the radially outward facing surface. The strip can also include a second surface opposing the first surface of the strip and a strip carrier that includes a free edge. The unhoned radially outward facing surface of each of the wedge dissectors can be reversibly attached to the free edge of a strip carrier at attachment zones. The areas between attachment zones can define voids, and be configured to be detached upon application of a mechanical force. In some embodiments, the second surface of the strip can be attached to a surface of the medical balloon, and the strip carrier detached from the strip after the second surface of the strip is attached to the medical balloon. In some embodiments, the strip carrier can be integrally formed with the strip, and created using a process such as chemical etching. The strip carrier can be made of the same, or a different material than that of the strips.

FIG. 43 illustrates an embodiment of a close-up drawing of the attachment of the radially outward facing surfaces 4325 of the wedge dissectors 4100 to the free edge 4220 of the blank or carrier 4300. Also shown are voids 4280 between attachment zones 4328 where the base surface of the strip does not contact the corresponding free edge 4420 of the blank or carrier. In some embodiments, each void or all of the voids 4280 have a surface area that is about, at least about, or about or more than about 110%, 120%, 130%, 140%, 150%, 160%, 170%, 180%, 190%, 200%, 250%, 300%, or more of the surface area of a wedge dissector or each of the wedge dissectors of each strip. In some embodiments, the proximal-most free edge 4420 of the blank or carrier 4300 contacts (e.g., is the only contact edge) to the distal-most edge or surface of the wedge dissector 4325 such that the intersection or points of contact between the strip/wedge dissector 4100 and the blank 4300 are along a straight line only, and there is no or substantially no overlap in a dimension, such as a height dimension as shown in FIG. 43 between any part of the strip or wedge dissector of the strip and the blank or carrier. In some embodiments, this can advantageously allow for simple detachment of the strip and associated wedge dissectors from the carrier. In other embodiments, there can be overlap in one or more dimensions between the attachment zone of the carrier and the strip and associated wedge dissectors, e.g., via a slot or groove in a free edge of the blank. In other embodiments, the attachment zone need not be along a continuous free edge of the blank or carrier, but rather at spaced apart intervals between projections of the blank or carrier and the wedge dissectors. The projections can be mirror images of the wedge dissectors, or another pattern.

FIGS. 44A and 44B shows a description of an embodiment of a fabrication process for the manufacturing of serratoplasty strips, cutting members, or wedge dissectors 3510 which utilizes a reel of an appropriate material, such as a metal, e.g., stainless steel material stock 4410. The stock 4410 can be shaped or ground with or without honed edges. The honed edge 4430 can be fabricated with a single or multiple facets on its edge and can be either ground to a fine tip (e.g., honed) or with a narrow but flat side (e.g., unhoned). The cross-sectional view of ground honed stock 4430 in some embodiments can be a triangle like shape with potentially multiple slopes on the rising side of an equilateral triangular slope.

In addition to the material grinding fabrication technique described above, the fabrication of stainless steel serrated blades can be achieved with other bulk processing techniques.

As such grinding, stamping, etching are bulk processing techniques are envisioned to achieve low cost manufacturing of serrated tips.

A description of the fabrication steps that would be included in chemical etching can in some embodiments include some or all of the following.

A mask or mask set 4400 that includes the information and design details to produce a series of serrated blades, cutting members, or wedge dissectors can be placed on top of a photo resistant layer 4420. Each mask 4400 is a series of openings to allow light to shine through the mask 4400. The mask set 4400 can be the same or can be slightly different from each other to allow partial etching through of a single side of the stainless steel material 4410.

Chemical etching of stainless steel reel or sheets 4410 using masks, photoresist, and etching materials can be advantageously applied to allow for large volumes of material to be etched at low costs.

Bulk chemical etching can allow for extremely repeatable and low cost parts to be fabricated in volume. Traditionally, chemical etching produces rounded edges with gentle slope side walls through the material at angles approximating 90 degrees. To achieve more gentle sloped angles grayscale masking was considered with poor results. In place of grayscale new masking techniques utilized relatively narrow hole along with narrow slit like patterns to control etch rates with success. By controlling the etch material flow through the resist layer, angles for blade-like structures have been achieved.

Two-sided mask exposure can enable etching through the material from both sides. With dual side exposure the edge profile produces greater control mirror imaging profiles on either side of the stainless-steel material.

FIG. 45B shows the strip 3500 can be placed over a through hole 4500 embedded in the balloon wall 4510. The through hole can be a hole that was extruded prior to the fabrication of the balloon, thus providing a conduit through which a volume of therapeutic agent(s) can be passed and delivered to the serrated tissue. Similarly in FIG. 45A, in some embodiments, the strip 3500 can be placed over a series of through holes 4520 laser cut or other method to puncture the balloon wall 4510, down to a separate conduit produced in the extrusion process thus providing a conduit through which a volume of therapeutic agent(s) can be passed and delivered to the serrated tissue.

FIG. 46 illustrates in some embodiments, a series of a plurality, such as 4 A-frame strips 3500 (or non A-frame strips with wedge dissectors as disclosed herein) can be placed over through holes 4600 embedded in the balloon wall 4610. The A-frame strips 3500 above can be spaced regularly apart as illustrated above, or irregularly in other embodiments.

In other words, in some embodiments the "A-frame" strip 3500 design includes a first strip 3510 and a second strip 3520 spaced apart at their respective bases, each strip comprising wedge dissectors 3510 having radially-outward facing surfaces having a perimeter, the wedge dissectors 3510 of the first strip 3510 and the second strip 3520 contacting each other at part of the perimeters of each of the radially-outward facing surfaces, wherein an apex gap is present at a location where the first strip 3510 of wedge dissectors 3510 and second strip 3520 of wedge dissectors 3510 do not touch each other, wherein the gap is configured to house a drug reservoir hole 4500 therethrough.

FIG. 47 illustrates an embodiment (with a closeup insert) of an array of strips 3500 on a mask 4700 set prior to chemical etching. Each array of strips 3500 can include a detachable zone 4710 between adjacent wedge dissectors 3510.

FIG. 48a shows a strip array 3500. FIG. 48b shows a detailed close up image of the adjacent wedge dissectors 3510 with detachable zones 4710. FIG. 48c shows serration strips 3500 reversibly connected to a strip carrier 4810 for alignment, control, placement, and ease of manufacturing. Three chemical etch variations of connection of a strip carrier 4810 to strips 3500 with different geometries are shown in Etch 1 4820, Etch 2 4830, and Etch 3 4840. The close-ups illustrate how the wedge dissectors 3510 on the side are connected to the strip carrier 4810. FIG. 48d illustrates another embodiment of a strip carrier 4480 reversibly attached to wedge dissectors of a strip 4890. The strip carrier 4880 can have any appropriate geometry, and in some cases have rounded or other tabs 4882, apertures 4884, lateral tabs 4886, or other features for alignment, control, placement, and ease of manufacturing. In some embodiments, the strip carrier includes projections that can be mirror images of the wedge dissectors of the strip to allow for ease of removal, such as after the strip has been bonded or otherwise secured to a balloon (not shown).

FIG. 49 above is an illustration of one embodiment of an overall system for producing serratoplasty showing a series of serrating or scoring wedge dissectors 3510 on the outer diameter of the balloon 3316 attached to a catheter 3310 with a guidewire hub 4900 and balloon inflation hub 4910. FIGS. 49A-49J illustrate additional views of one embodiment of a serratoplasty system.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "creating microperforations in an arterial plaque" includes "instructing the creating of microperforations in an arterial plaque." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A medical balloon catheter comprising:
   an elongate member comprising a lumen, the elongate member defining a longitudinal axis;
   a first expandable balloon connected to the elongate member proximate a distal end of the elongate member;
   a plurality of strips, each strip of the plurality of strips including a plurality of wedge dissectors spaced apart along a surface of each strip, each strip extending longitudinally along an outer surface of the first expandable balloon,
   wherein each wedge dissector forms a radially outward facing surface,
   a pre-fabricated cover comprising a polymer walled structure,
   an UV curable adhesive directly in contact with the first expandable balloon and the pre-fabricated cover, wherein the first expandable balloon is bonded to the pre-fabricated cover with the UV curable adhesive,
   wherein the pre-fabricated cover is positioned over the plurality of strips including the plurality of wedge dissectors, wherein the plurality of wedge dissectors rise above the polymer walled structure,
   wherein the pre-fabricated cover is configured to allow the plurality of wedge dissectors to penetrate plaque effectively but not tear along the spaces between the wedge dissectors during expansion of the first expandable balloon.

2. The medical catheter of claim 1, wherein the pre-fabricated cover comprises more than one material.

3. The medical catheter of claim 1, wherein the pre-fabricated cover comprises more than one layer.

4. The medical catheter of claim 1, wherein the pre-fabricated cover is more stretchable or pliable than the first expandable balloon.

5. The medical catheter of claim 1, wherein a length and a diameter of the pre-fabricated cover is greater than a length and a diameter of the first expandable balloon.

6. The medical catheter of claim 1, wherein the pre-fabricated cover increases the retention of the strips.

7. The medical catheter of claim 1, wherein the pre-fabricated cover provides an uniform outer layer.

8. The medical catheter of claim 1, wherein the first expandable balloon with the plurality of strips is configured to be inflated inside the pre-fabricated cover.

9. The medical catheter of claim 1, wherein the pre-fabricated cover is a balloon.

10. The medical catheter of claim 1, wherein the radially outward facing surface is unhoned.

11. The medical catheter of claim 1, wherein the widths of the radially outward facing surface are wider at the lateral edges and narrower more centrally.

12. The medical catheter of claim 1, wherein the orientation of the narrowest section of the radially outward facing surface is along the longitudinal axis of the strip.

13. A medical balloon catheter comprising:
an elongate member comprising a lumen, the elongate member defining a longitudinal axis;
a first expandable balloon connected to the elongate member proximate a distal end of the elongate member;
a plurality of strips, each strip of the plurality of strips including a plurality of wedge dissectors spaced apart along a surface of each strip, each strip extending longitudinally along an outer surface of the first expandable balloon,
wherein each wedge dissector forms a radially outward facing surface,
a pre-fabricated cover comprising a polymer walled structure,
wherein the first expandable balloon with the plurality of strips including the plurality of wedge dissectors is configured to be pleated and inserted into the pre-fabricated cover such that the pre-fabricated cover is over the plurality of strips including the plurality of wedge dissectors,
wherein the first expandable balloon with the plurality of strips including the plurality of wedge dissectors is configured to be inflated within the pre-fabricated cover such that the first expandable balloon and the pre-fabricated cover are bonded when the first expandable balloon is inflated, wherein the plurality of wedge dissectors rise above the polymer walled structure,
wherein the pre-fabricated cover is configured to allow the plurality of wedge dissectors to penetrate effectively but not tear along the spaces between the wedge dissectors during expansion of the first expandable balloon.

14. The medical catheter of claim 13, wherein the pre-fabricated cover is bonded to the first expandable balloon with a UV curable adhesive.

15. The medical catheter of claim 13, wherein the pre-fabricated cover is a singular tubular structure.

16. A medical balloon catheter comprising:
an elongate member comprising a lumen, the elongate member defining a longitudinal axis;
a first expandable balloon connected to the elongate member;
a plurality of strips, each strip of the plurality of strips including a plurality of wedge dissectors spaced apart along a surface of each strip, each strip extending along an outer surface of the first expandable balloon,
wherein each wedge dissector forms a radially outward facing surface,
a pre-fabricated cover comprising an outer walled structure,
wherein the pre-fabricated cover is positioned over the plurality of strips including the plurality of wedge dissectors, wherein the first expandable balloon is bonded to the pre-fabricated cover along less than the entire surface between the first expandable balloon and the pre-fabricated cover, wherein the plurality of wedge dissectors rise above the outer walled structure, wherein the pre-fabricated cover is configured to allow the plurality of wedge dissectors to penetrate effectively but not tear along the spaces between the wedge dissectors during expansion of the first expandable balloon.

17. The medical catheter of claim 16, wherein a length and a diameter of the pre-fabricated cover is greater than a length and a diameter of the first expandable balloon.

18. The medical catheter of claim 16, wherein the first expandable balloon is bonded to the pre-fabricated cover with a UV curable adhesive.

19. The medical catheter of claim 16, wherein the first expandable balloon with the plurality of strips including the plurality of wedge dissector is configured to be inserted into the outer walled structure.

20. The medical catheter of claim 16, wherein the pre-fabricated cover and the first expandable balloon comprise different materials.

* * * * *